United States Patent
Mumm

(10) Patent No.: US 11,613,563 B2
(45) Date of Patent: Mar. 28, 2023

(54) DUAL CYTOKINE FUSION PROTEINS COMPRISING IL-10

(71) Applicant: Deka Biosciences, Inc., Germantown, MD (US)

(72) Inventor: John Mumm, Germantown, MD (US)

(73) Assignee: DEKA BIOSCIENCES, INC., Germantown, MD (US)

(*) Notice: Subject to any disclaimer, the term of this patent is extended or adjusted under 35 U.S.C. 154(b) by 0 days.

(21) Appl. No.: 17/684,151

(22) Filed: Mar. 1, 2022

(65) Prior Publication Data

US 2022/0275039 A1 Sep. 1, 2022

Related U.S. Application Data

(60) Division of application No. 17/199,239, filed on Mar. 11, 2021, now Pat. No. 11,292,822, which is a continuation of application No. 17/110,104, filed on Dec. 2, 2020, now abandoned.

(60) Provisional application No. 63/054,208, filed on Jul. 20, 2020.

(51) Int. Cl.
| | |
|---|---|
| *C07K 14/54* | (2006.01) |
| *C07K 14/55* | (2006.01) |
| *C07K 16/28* | (2006.01) |
| *C07K 16/32* | (2006.01) |
| *C07K 16/46* | (2006.01) |
| *A61K 39/395* | (2006.01) |
| *A61K 38/00* | (2006.01) |
| *A61P 37/06* | (2006.01) |
| *A61P 35/00* | (2006.01) |
| *C07K 16/10* | (2006.01) |
| *A61K 39/00* | (2006.01) |

(52) U.S. Cl.
CPC .......... *C07K 14/5428* (2013.01); *A61P 35/00* (2018.01); *A61P 37/06* (2018.01); *C07K 14/5406* (2013.01); *C07K 14/55* (2013.01); *C07K 16/10* (2013.01); *C07K 16/1045* (2013.01); *C07K 16/2803* (2013.01); *C07K 16/2863* (2013.01); *C07K 16/2896* (2013.01); *C07K 16/32* (2013.01); *C07K 16/464* (2013.01); *A61K 38/00* (2013.01); *A61K 2039/505* (2013.01); *A61K 2039/545* (2013.01); *C07K 2317/53* (2013.01); *C07K 2317/565* (2013.01); *C07K 2317/622* (2013.01); *C07K 2317/92* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 6,617,135 B1 | 9/2003 | Gillies et al. | |
| 9,346,872 B2 | 5/2016 | Duerner et al. | |
| 10,858,412 B2 | 12/2020 | Mumm | |
| 10,975,133 B2* | 4/2021 | Mumm | .................. A61P 29/00 |
| 10,975,134 B2* | 4/2021 | Mumm | .................. C07K 16/22 |
| 10,981,965 B2* | 4/2021 | Mumm | .............. C07K 16/1045 |
| 10,981,966 B2* | 4/2021 | Mumm | .................. C07K 16/22 |
| 11,292,822 B2* | 4/2022 | Mumm | .............. C07K 14/5406 |
| 2010/0055070 A1 | 3/2010 | Mannie | |
| 2011/0256091 A1 | 10/2011 | Neri et al. | |
| 2013/0224202 A1 | 8/2013 | Ohlfest et al. | |
| 2014/0044674 A1 | 2/2014 | Duerner et al. | |
| 2015/0218244 A1 | 8/2015 | Emrich et al. | |
| 2015/0314014 A1 | 11/2015 | Lauermann | |
| 2016/0185853 A1 | 6/2016 | Gill et al. | |
| 2017/0106051 A1 | 4/2017 | Oh et al. | |
| 2019/0352384 A1 | 11/2019 | Kaspar et al. | |
| 2020/0062851 A1 | 2/2020 | Vrljic et al. | |
| 2020/0385436 A1 | 12/2020 | Mumm | |
| 2020/0399337 A1 | 12/2020 | Mumm | |
| 2021/0040168 A1 | 2/2021 | Mumm | |
| 2021/0214782 A1* | 7/2021 | Mumm | ................ C12Q 1/6869 |
| 2022/0106373 A1* | 4/2022 | Mumm | .............. C07K 14/5428 |

FOREIGN PATENT DOCUMENTS

| | | |
|---|---|---|
| WO | 01/10912 A1 | 2/2001 |
| WO | 2019/201866 A1 | 10/2019 |

OTHER PUBLICATIONS

Beasley, Matthew D., et al., "Antibodies that potently inhibit or enchance SARS-CoV-2 spike protein-ACE2 interaction isolated from synthetic single-chain antibody libaries" bioRxiv, Jul. 28, 2020.
International Search Report and Written Opinion issued by the International Search Authority corresponding to PCT/US2020/062907, dated Jun. 6, 2021.
Kalnine, N., et al.,Interleukin 10, partial [synthetic construct], Genbank entry (online), National Center of Biotechnology Information, https://www.ncbi.nlm.nih.gove/protein/AAV38450.1, Jul. 26, 2016 [retrieved on May 14, 2021].
Latifi, Samir Q., et al., "Interleukin-10 Controls the Onset of Irreversible Septic Shock", Infection and Immunity, vol. 70, No. 8, p. 4441-4446, Aug. 2002.

(Continued)

*Primary Examiner* — Ilia I Ouspenski
(74) *Attorney, Agent, or Firm* — ArentFox Schiff LLP

(57) ABSTRACT

The application relates to a dual cytokine fusion protein composition, pharmaceutical composition, and/or formulation thereof comprising IL-10 or IL-10 variant molecules fused to a single chain variable fragment scaffolding system and a second cytokine, where the second cytokine is linked in the hinge region of the scFv. The application also relates to methods of using the dual cytokine fusion protein composition for treating cancer, inflammatory diseases or disorders, and immune and immune mediated diseases or disorders.

6 Claims, 25 Drawing Sheets

Specification includes a Sequence Listing.

(56) References Cited

OTHER PUBLICATIONS

Qin, et al., Combination of localized radiation therapy and ERB-IL-10 generates abscopal effect by activating CB8+ T cells in tumor microenvironment. Int. J. Radiation Oncol. Biol. *Phys, 99 Supplement, Oct. 1, 2017, p. S162. (Year: 2017).

* cited by examiner

Macrophage Response

```
                        SEQUENCE LISTING

<160> NUMBER OF SEQ ID NOS: 63

<210> SEQ ID NO 1
<211> LENGTH: 178
<212> TYPE: PRT
<213> ORGANISM: Homo sapiens
<220> FEATURE:
<223> OTHER INFORMATION: Human IL-10 Amino Acid Sequence

<400> SEQUENCE: 1

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn

<210> SEQ ID NO 2
<211> LENGTH: 1629
<212> TYPE: DNA
<213> ORGANISM: Homo sapiens
<220> FEATURE:
<223> OTHER INFORMATION: Human IL-10 Nucleic Acid Sequence

<400> SEQUENCE: 2
acacatcagg ggcttgctct tgcaaaacca aaccacaaga cagacttgca aaagaaggca      60
tgcacagctc agcactgctc tgttgcctgg tcctcctgac tggggtgagg gccagcccag     120
gccagggcac ccagtctgag aacagctgca cccacttccc aggcaacctg cctaacatgc     180
ttcgagatct ccgagatgcc ttcagcagag tgaagacttt ctttcaaatg aaggatcagc     240
tggacaactt gttgttaaag gagtccttgc tggaggactt taagggttac ctgggttgcc     300
aagccttgtc tgagatgatc cagttttacc tggaggaggt gatgccccaa gctgagaacc     360
aagacccaga catcaaggcg catgtgaact ccctggggga gaacctgaag accctcaggc     420
tgaggctacg gcgctgtcat cgatttcttc cctgtgaaaa caagagcaag gccgtggagc     480
aggtgaagaa tgcctttaat aagctccaag agaaaggcat ctacaaagcc atgagtgagt     540
```

```
ttgacatctt catcaactac atagaagcct acatgacaat gaagatacga aactgagaca    600
tcagggtggc gactctatag actctaggac ataaattaga ggtctccaaa atcggatctg    660
gggctctggg atagctgacc cagcccttg  agaaaccta ttgtacctct cttatagaat    720
atttattacc tctgatacct caaccccat  ttctatttat ttactgagct tctctgtgaa    780
cgatttagaa agaagcccaa tattataatt tttttcaata tttattattt tcacctgttt    840
ttaagctgtt tccatagggt gacacactat ggtatttgag tgttttaaga taaattataa    900
gttacataag ggaggaaaaa aaatgttctt tggggagcca acagaagctt ccattccaag    960
cctgaccacg ctttctagct gttgagctgt tttccctgac ctccctctaa tttatcttgt   1020
ctctgggctt ggggcttcct aactgctaca atactctta  ggaagagaaa ccagggagcc   1080
cctttgatga ttaattcacc ttccagtgtc tcggagggat tcccctaacc tcattcccca   1140
accacttcat tcttgaaagc tgtggccagc ttgttattta taacaaccta aatttggttc   1200
taggccgggc gcggtggctc acgcctgtaa tcccagcact ttgggaggct gaggcgggtg   1260
gatcacttga ggtcaggagt tcctaaccag cctggtcaac atggtgaaac cccgtctcta   1320
ctaaaaatac aaaaattagc cgggcatggt ggcgcgcacc tgtaatccca gctacttggg   1380
aggctgaggc aagagaattg cttgaaccca ggagatggaa gttgcagtga gctgatatca   1440
tgcccctgta ctccagcctg ggtgacagag caagactctg tctcaaaaaa taaaaataaa   1500
aataaatttg gttctaatag aactcagttt taactagaat ttattcaatt cctctgggaa   1560
tgttacattg tttgtctgtc ttcatagcag attttaattt tgaataaata aatgtatctt   1620
attcacatc                                                          1629
```

<210> SEQ ID NO 3
<211> LENGTH: 147
<212> TYPE: PRT
<213> ORGANISM: Human gammaherpesvirus 4
<220> FEATURE:
<223> OTHER INFORMATION: EBV IL-10 Amino Acid Sequence

<400> SEQUENCE: 3

```
Thr Asp Gln Cys Asp Asn Phe Pro Gln Met Leu Arg Asp Leu Arg Asp
1               5                   10                  15

Ala Phe Ser Arg Val Lys Thr Phe Phe Gln Thr Lys Asp Glu Val Asp
            20                  25                  30

Asn Leu Leu Leu Lys Glu Ser Leu Leu Glu Asp Phe Lys Gly Tyr Leu
        35                  40                  45

Gly Cys Gln Ala Leu Ser Glu Met Ile Gln Phe Tyr Leu Glu Glu Val
    50                  55                  60

Met Pro Gln Ala Glu Asn Gln Asp Pro Glu Ala Lys Asp His Val Asn
65                  70                  75                  80

Ser Leu Gly Glu Asn Leu Lys Thr Leu Arg Leu Arg Leu Arg Arg Cys
                85                  90                  95

His Arg Phe Leu Pro Cys Glu Asn Lys Ser Lys Ala Val Glu Gln Ile
            100                 105                 110

Lys Asn Ala Phe Asn Lys Leu Gln Glu Lys Gly Ile Tyr Lys Ala Met
        115                 120                 125

Ser Glu Phe Asp Ile Phe Ile Asn Tyr Ile Glu Ala Tyr Met Thr Ile
    130                 135                 140

Lys Ala Arg
145
```

```
<210> SEQ ID NO 4
<211> LENGTH: 632
<212> TYPE: DNA
<213> ORGANISM: Human gammaherpesvirus 4
<220> FEATURE:
<223> OTHER INFORMATION: EBV IL-10 Nucleic Acid Sequence

<400> SEQUENCE: 4
tataaatcac ttccctatct caggtaggcc tgcacacctt aggtatggag cgaaggttag      60
tggtcactct gcagtgcctg gtgctgcttt acctggcacc tgagtgtgga ggtacagacc     120
aatgtgacaa ttttccccaa atgttgaggg acctaagaga tgccttcagt cgtgttaaaa     180 ccttttttcca gacaaaggac gaggtagata accttttgct caaggagtct ctgctagagg     240
actttaaggg ctaccttgga tgccaggccc tgtcagaaat gatccaattc tacctggagg     300
aagtcatgcc acaggctgaa aaccaggacc ctgaagccaa agaccatgtc aattctttgg     360
gtgaaaatct aaagacccta cggctccgcc tgcgcaggtg ccacaggttc ctgccgtgtg     420
agaacaagag taaagctgtg gaacagataa aaaatgcctt taacaagctg caggaaaaag     480
gaatttacaa agccatgagt gaatttgaca ttttttattaa ctacatagaa gcatacatga     540
caattaaagc caggtgataa ttccataccc tggaagcagg agatgggtgc atttcacccc     600
aaccccccct ttcgactgtc atttacaata aa                                    632

<210> SEQ ID NO 5
<211> LENGTH: 177
<212> TYPE: PRT
<213> ORGANISM: Human betaherpesvirus 5
<220> FEATURE:
<223> OTHER INFORMATION: CMV IL-10 Amino Acid Sequence

<400> SEQUENCE: 5

Met Leu Ser Val Met Val Ser Ser Leu Val Leu Ile Val Phe Phe
1               5                   10                  15

Leu Gly Ala Ser Glu Glu Ala Lys Pro Ala Ala Thr Thr Thr Thr Ile
            20                  25                  30

Lys Asn Thr Lys Pro Gln Cys Arg Pro Glu Asp Tyr Ala Ser Arg Leu
        35                  40                  45

Gln Asp Leu Arg Val Thr Phe His Arg Val Lys Pro Thr Leu Gln Arg
    50                  55                  60

Glu Asp Asp Tyr Ser Val Trp Leu Asp Gly Thr Val Val Lys Gly Cys
65                  70                  75                  80

Trp Gly Cys Ser Val Met Asp Trp Leu Leu Arg Arg Tyr Leu Glu Ile
                85                  90                  95

Val Phe Pro Ala Gly Asp His Val Tyr Pro Gly Leu Lys Thr Glu Leu
            100                 105                 110

His Ser Met Arg Ser Thr Leu Glu Ser Ile Tyr Lys Asp Met Arg Gln
        115                 120                 125

Cys Pro Leu Leu Gly Cys Gly Asp Lys Ser Val Ile Ser Arg Leu Ser
    130                 135                 140

Gln Glu Ala Glu Arg Lys Ser Asp Asn Gly Thr Arg Lys Gly Leu Ser
145                 150                 155                 160

Glu Leu Asp Thr Leu Phe Ser Arg Leu Glu Glu Tyr Leu His Ser Arg
                165                 170                 175

Lys

<210> SEQ ID NO 6
```

<211> LENGTH: 693
<212> TYPE: DNA
<213> ORGANISM: Human betaherpesvirus 5
<220> FEATURE:
<223> OTHER INFORMATION: CMV IL-10 Nucleic Acid Sequence

<400> SEQUENCE: 6

```
atgctgtcgg tgatggtctc ttcctctctg gtcctgatcg tctttttct aggcgcttcc      60
gaggaggcga agccggcggc gacgacgacg acgataaaga atacaaagcc gcagtgtcgt    120
ccggaggatt acgcgagcag attgcaagat ctccgcgtca cctttcatcg agtaaaacct    180
acgttggtag tcatgtagg tacggtttat tgcgacggtc tttcttttcc gcgtgtcggg    240
tgacgtagtt ttcctcttgt agcaacgtga ggacgactac tccgtgtggc tcgacggtac    300
ggtggtcaaa ggctgttggg gatgcagcgt catggactgg ttgttgaggc ggtatctgga    360
gatcgtgttc cccgcaggcg accacgtcta tcctggactt aagacggaat tgcatagtat    420
gcgctcgacg ctagaatcca tctacaaaga catgcggcaa tgcgtaagtg tctctgtggc    480
ggcgctgtcc gcgcagaggt aacaacgtgt tcatagcacg ctgttttact tttgtcgggc    540
tcccagcctc tgttaggttg cggagataag tccgtgatta gtcggctgtc tcaggaggcg    600
gaaaggaaat cggataacgg cacgcggaaa ggtctcagcg agttggacac gttgtttagc    660
cgtctcgaag agtatctgca ctcgagaaag tag                                 693
```

<210> SEQ ID NO 7
<211> LENGTH: 178
<212> TYPE: PRT
<213> ORGANISM: Mus musculus
<220> FEATURE:
<223> OTHER INFORMATION: Mouse IL-10 Amino Acid Sequence

<400> SEQUENCE: 7

Met Pro Gly Ser Ala Leu Leu Cys Cys Leu Leu Leu Leu Thr Gly Met
1               5                   10                  15

Arg Ile Ser Arg Gly Gln Tyr Ser Arg Glu Asp Asn Asn Cys Thr His
            20                  25                  30

Phe Pro Val Gly Gln Ser His Met Leu Leu Glu Leu Arg Thr Ala Phe
        35                  40                  45

Ser Gln Val Lys Thr Phe Phe Gln Thr Lys Asp Gln Leu Asp Asn Ile
    50                  55                  60

Leu Leu Thr Asp Ser Leu Met Gln Asp Phe Lys Gly Tyr Leu Gly Cys
65                  70                  75                  80

Gln Ala Leu Ser Glu Met Ile Gln Phe Tyr Leu Val Glu Val Met Pro
                85                  90                  95

Gln Ala Glu Lys His Gly Pro Glu Ile Lys Glu His Leu Asn Ser Leu
            100                 105                 110

Gly Glu Lys Leu Lys Thr Leu Arg Met Arg Leu Arg Arg Cys His Arg
        115                 120                 125

Phe Leu Pro Cys Glu Asn Lys Ser Lys Ala Val Glu Gln Val Lys Ser
    130                 135                 140

Asp Phe Asn Lys Leu Gln Asp Gln Gly Val Tyr Lys Ala Met Asn Glu
145                 150                 155                 160

Phe Asp Ile Phe Ile Asn Cys Ile Glu Ala Tyr Met Met Ile Lys Met
                165                 170                 175

Lys Ser

<210> SEQ ID NO 8

```
<211> LENGTH: 1314
<212> TYPE: DNA
<213> ORGANISM: Mus musculus
<220> FEATURE:
<223> OTHER INFORMATION: Mouse IL-10 Nucleic Acid Sequence

<400> SEQUENCE: 8
gggggggggg atttagagac ttgctcttgc actaccaaag ccacaaagca gccttgcaga      60
aaagagagct ccatcatgcc tggctcagca ctgctatgct gcctgctctt actgactggc     120
atgaggatca gcaggggcca gtacagccgg gaagacaata actgcaccca cttcccagtc     180
ggccagagcc acatgctcct agagctgcgg actgccttca gccaggtgaa gactttcttt     240
caaacaaagg accagctgga acatactg ctaaccgact ccttaatgca ggactttaag      300
ggttacttgg gttgccaagc cttatcggaa atgatccagt tttacctggt agaagtgatg     360
ccccaggcag agaagcatgg cccagaaatc aaggagcatt tgaattccct gggtgagaag     420
ctgaagaccc tcaggatgcg gctgaggcgc tgtcatcgat ttctcccctg tgaaaataag     480
agcaaggcag tggagcaggt gaagagtgat tttaataagc tccaagacca aggtgtctac     540
aaggccatga atgaatttga catcttcatc aactgcatag aagcatacat gatgatcaaa     600
atgaaaagct aaaacacctg cagtgtgtat tgagtctgct ggactccagg acctagacag     660
agctctctaa atctgatcca gggatcttag ctaacggaaa caactccttg aaaacctcg     720 tttgtacctc tctccgaaat atttattacc tctgatacct cagttcccat tctatttatt     780
cactgagctt ctctgtgaac tatttagaaa gaagcccaat attataattt tacagtattt     840
attattttta acctgtgttt aagctgtttc cattggggac actttatagt atttaaaggg     900
agattatatt atatgatggg aggggttctt ccttgggaag caattgaagc ttctattcta     960
aggctggcca cacttgagag ctgcagggcc ctttgctatg gtgtcctttc aattgctctc    1020
atccctgagt tcagagctcc taagagagtt gtgaagaaac tcatgggtct tgggaagaga    1080
aaccagggag atcctttgat gatcattcct gcagcagctc agagggttcc cctactgtca    1140
tcccccagcc gcttcatccc tgaaaactgt ggccagtttg ttatttataa ccacctaaaa    1200
ttagttctaa tagaactcat ttttaactag aagtaatgca attcctctgg gaatggtgta    1260
ttgtttgtct gcctttgtag cagcatctaa ttttgaataa atggatctta ttcg          1314

<210> SEQ ID NO 9
<211> LENGTH: 170
<212> TYPE: PRT
<213> ORGANISM: Artificial Sequence
<220> FEATURE:
<223> OTHER INFORMATION: Artificial Sequence DVLP5

<400> SEQUENCE: 9

Met Asp Met Arg Val Pro Ala Gln Leu Leu Gly Leu Leu Leu Leu Trp
  1               5                  10                  15

Leu Arg Gly Ala Arg Cys Gly Thr Asp Gln Cys Asp Asn Phe Pro Gln
                 20                  25                  30

Met Leu Arg Asp Leu Arg Asp Ala Phe Ser Arg Val Lys Thr Phe Phe
             35                  40                  45

Gln Thr Lys Asp Glu Leu Asp Asn Leu Leu Lys Glu Ser Leu Leu
         50                  55                  60

Glu Asp Phe Lys Gly Tyr Leu Gly Cys Gln Ala Leu Ser Glu Met Ile
 65                  70                  75                  80

Gln Phe Tyr Leu Glu Glu Val Met Pro Gln Ala Glu Asn Gln Asp Pro
                 85                  90                  95
```

Glu Ala Lys Asp His Val Asn Ser Leu Gly Glu Asn Leu Lys Thr Leu
            100                 105                 110

Arg Leu Arg Leu Arg Arg Cys His Arg Phe Leu Pro Cys Glu Asn Lys
        115                 120                 125

Ser Lys Ala Val Glu Gln Ile Lys Asn Ala Phe Asn Lys Leu Gln Glu
    130                 135                 140

Lys Gly Ile Tyr Lys Ala Met Ser Glu Phe Asp Ile Phe Ile Asn Tyr
145                 150                 155                 160

Ile Glu Ala Tyr Met Thr Ile Lys Ala Arg
                165                 170

<210> SEQ ID NO 10
<211> LENGTH: 170
<212> TYPE: PRT
<213> ORGANISM: Artificial Sequence
<220> FEATURE:
<223> OTHER INFORMATION: Artificial Sequence DVLP6

<400> SEQUENCE: 10

Met Asp Met Arg Val Pro Ala Gln Leu Leu Gly Leu Leu Leu Leu Trp
1               5                   10                  15

Leu Arg Gly Ala Arg Cys Gly Thr Asp Gln Cys Asp Asn Phe Pro Gln
            20                  25                  30

Met Leu Arg Asp Leu Arg Asp Ala Phe Ser Arg Val Lys Thr Phe Phe
        35                  40                  45

Gln Thr Lys Asp Glu Val Asp Asn Leu Leu Leu Lys Glu Ser Leu Leu
    50                  55                  60

Glu Asp Phe Lys Gly Tyr Leu Gly Cys Gln Ala Leu Ser Glu Met Ile
65                  70                  75                  80

Gln Phe Tyr Leu Glu Glu Val Met Pro Gln Ala Glu Asn Gln Asp Pro
                85                  90                  95

Glu Ile Lys Asp His Val Asn Ser Leu Gly Glu Asn Leu Lys Thr Leu
            100                 105                 110

Arg Leu Arg Leu Arg Arg Cys His Arg Phe Leu Pro Cys Glu Asn Lys
        115                 120                 125

Ser Lys Ala Val Glu Gln Ile Lys Asn Ala Phe Asn Lys Leu Gln Glu
    130                 135                 140

Lys Gly Ile Tyr Lys Ala Met Ser Glu Phe Asp Ile Phe Ile Asn Tyr
145                 150                 155                 160

Ile Glu Ala Tyr Met Thr Ile Lys Ala Arg
                165                 170

<210> SEQ ID NO 11
<211> LENGTH: 170
<212> TYPE: PRT
<213> ORGANISM: Artificial Sequence
<220> FEATURE:
<223> OTHER INFORMATION: Artificial Sequence DVLP7

<400> SEQUENCE: 11

Met Asp Met Arg Val Pro Ala Gln Leu Leu Gly Leu Leu Leu Leu Trp
1               5                   10                  15

Leu Arg Gly Ala Arg Cys Gly Thr Asp Gln Cys Asp Asn Phe Pro Gln
            20                  25                  30

Met Leu Arg Asp Leu Arg Asp Ala Phe Ser Arg Val Lys Thr Phe Phe
        35                  40                  45

```
Gln Thr Lys Asp Glu Leu Asp Asn Leu Leu Lys Glu Ser Leu Leu
     50                  55                  60

Glu Asp Phe Lys Gly Tyr Leu Gly Cys Gln Ala Leu Ser Glu Met Ile
 65                  70                  75                  80

Gln Phe Tyr Leu Glu Glu Val Met Pro Gln Ala Glu Asn Gln Asp Pro
                 85                  90                  95

Glu Ile Lys Asp His Val Asn Ser Leu Gly Glu Asn Leu Lys Thr Leu
            100                 105                 110

Arg Leu Arg Leu Arg Arg Cys His Arg Phe Leu Pro Cys Glu Asn Lys
        115                 120                 125

Ser Lys Ala Val Glu Gln Ile Lys Asn Ala Phe Asn Lys Leu Gln Glu
    130                 135                 140

Lys Gly Ile Tyr Lys Ala Met Ser Glu Phe Asp Ile Phe Ile Asn Tyr
145                 150                 155                 160

Ile Glu Ala Tyr Met Thr Ile Lys Ala Arg
                165                 170

<210> SEQ ID NO 12
<211> LENGTH: 147
<212> TYPE: PRT
<213> ORGANISM: Artificial Sequence
<220> FEATURE:
<223> OTHER INFORMATION: DV05 Amino Acid Sequence

<400> SEQUENCE: 12

Thr Asp Gln Cys Asp Asn Phe Pro Gln Met Leu Arg Asp Leu Arg Asp
  1               5                  10                  15

Ala Phe Ser Arg Val Lys Thr Phe Phe Gln Thr Lys Asp Glu Leu Asp
                 20                  25                  30

Asn Leu Leu Lys Glu Ser Leu Leu Glu Asp Phe Lys Gly Tyr Leu
             35                  40                  45

Gly Cys Gln Ala Leu Ser Glu Met Ile Gln Phe Tyr Leu Glu Glu Val
     50                  55                  60

Met Pro Gln Ala Glu Asn Gln Asp Pro Glu Ala Lys Asp His Val Asn
 65                  70                  75                  80

Ser Leu Gly Glu Asn Leu Lys Thr Leu Arg Leu Arg Leu Arg Arg Cys
                 85                  90                  95

His Arg Phe Leu Pro Cys Glu Asn Lys Ser Lys Ala Val Glu Gln Ile
            100                 105                 110

Lys Asn Ala Phe Asn Lys Leu Gln Glu Lys Gly Ile Tyr Lys Ala Met
        115                 120                 125

Ser Glu Phe Asp Ile Phe Ile Asn Tyr Ile Glu Ala Tyr Met Thr Ile
    130                 135                 140

Lys Ala Arg
145

<210> SEQ ID NO 13
<211> LENGTH: 441
<212> TYPE: DNA
<213> ORGANISM: Artificial Sequence
<220> FEATURE:
<223> OTHER INFORMATION: DV05 Nucleic Acid Sequence
<220> FEATURE:
<221> NAME/KEY: misc_feature
<222> LOCATION: (225)..(225)
<223> OTHER INFORMATION: n is a, c, g, or t
```

-continued

<400> SEQUENCE: 13

```
accgaccagt gcgacaactt ccctcagatg ctgcgggacc tgagagatgc cttctccaga    60
gtgaaaacat tcttccagac caaggacgag ctggacaacc tgctgctgaa agagtccctg   120
ctggaagatt tcaagggcta cctgggctgt caggccctgt ccgagatgat ccagttctac   180
ctggaagaag tgatgcccca ggccgagaat caggaccccg aggcnaagga ccacgtgaac   240
tccctgggcg agaacctgaa aaccctgcgg ctgagactgc ggcggtgcca cagatttctg   300
ccctgcgaga acaagtccaa ggccgtggaa cagatcaaga acgccttcaa caagctgcaa   360
gagaagggca tctacaaggc catgagcgag ttcgacatct tcatcaacta catcgaggcc   420
tacatgacca tcaaggccag a                                             441
```

<210> SEQ ID NO 14
<211> LENGTH: 147
<212> TYPE: PRT
<213> ORGANISM: Artificial Sequence
<220> FEATURE:
<223> OTHER INFORMATION: DV06 Amino Acid Sequence

<400> SEQUENCE: 14

```
Thr Asp Gln Cys Asp Asn Phe Pro Gln Met Leu Arg Asp Leu Arg Asp
1               5                   10                  15
Ala Phe Ser Arg Val Lys Thr Phe Phe Gln Thr Lys Asp Glu Val Asp
            20                  25                  30
Asn Leu Leu Leu Lys Glu Ser Leu Leu Glu Asp Phe Lys Gly Tyr Leu
        35                  40                  45
Gly Cys Gln Ala Leu Ser Glu Met Ile Gln Phe Tyr Leu Glu Glu Val
    50                  55                  60
Met Pro Gln Ala Glu Asn Gln Asp Pro Glu Ile Lys Asp His Val Asn
65                  70                  75                  80
Ser Leu Gly Glu Asn Leu Lys Thr Leu Arg Leu Arg Leu Arg Arg Cys
                85                  90                  95
His Arg Phe Leu Pro Cys Glu Asn Lys Ser Lys Ala Val Glu Gln Ile
            100                 105                 110
Lys Asn Ala Phe Asn Lys Leu Gln Glu Lys Gly Ile Tyr Lys Ala Met
        115                 120                 125
Ser Glu Phe Asp Ile Phe Ile Asn Tyr Ile Glu Ala Tyr Met Thr Ile
    130                 135                 140
Lys Ala Arg
145
```

<210> SEQ ID NO 15
<211> LENGTH: 441
<212> TYPE: DNA
<213> ORGANISM: Artificial Sequence
<220> FEATURE:
<223> OTHER INFORMATION: DV06 Nucleic Acid Sequence
<220> FEATURE:
<221> NAME/KEY: misc_feature
<222> LOCATION: (93)..(93)
<223> OTHER INFORMATION: n is a, c, g, or t

<400> SEQUENCE: 15

```
accgaccagt gcgacaactt ccctcagatg ctgcgggacc tgagagatgc cttctccaga    60
gtgaaaacat tcttccagac caaggacgag gtngacaacc tgctgctgaa agagtccctg   120
ctggaagatt tcaagggcta cctgggctgt caggccctgt ccgagatgat ccagttctac   180
```

```
ctggaagaag tgatgcccca ggccgagaat caggaccccg agatcaagga ccacgtgaac    240
tccctgggcg agaacctgaa aaccctgcgg ctgagactgc ggcggtgcca cagatttctg    300
ccctgcgaga acaagtccaa ggccgtggaa cagatcaaga acgccttcaa caagctgcaa    360
gagaagggca tctacaaggc catgagcgag ttcgacatct tcatcaacta catcgaggcc    420
tacatgacca tcaaggccag a                                              441
```

```
<210> SEQ ID NO 16
<211> LENGTH: 147
<212> TYPE: PRT
<213> ORGANISM: Artificial Sequence
<220> FEATURE:
<223> OTHER INFORMATION: DV07 Amino Acid Sequence

<400> SEQUENCE: 16
```

```
Thr Asp Gln Cys Asp Asn Phe Pro Gln Met Leu Arg Asp Leu Arg Asp
1               5                   10                  15

Ala Phe Ser Arg Val Lys Thr Phe Phe Gln Thr Lys Asp Glu Leu Asp
            20                  25                  30

Asn Leu Leu Leu Lys Glu Ser Leu Leu Glu Asp Phe Lys Gly Tyr Leu
        35                  40                  45

Gly Cys Gln Ala Leu Ser Glu Met Ile Gln Phe Tyr Leu Glu Glu Val
    50                  55                  60

Met Pro Gln Ala Glu Asn Gln Asp Pro Glu Ile Lys Asp His Val Asn
65                  70                  75                  80

Ser Leu Gly Glu Asn Leu Lys Thr Leu Arg Leu Arg Leu Arg Arg Cys
                85                  90                  95

His Arg Phe Leu Pro Cys Glu Asn Lys Ser Lys Ala Val Glu Gln Ile
            100                 105                 110

Lys Asn Ala Phe Asn Lys Leu Gln Glu Lys Gly Ile Tyr Lys Ala Met
        115                 120                 125

Ser Glu Phe Asp Ile Phe Ile Asn Tyr Ile Glu Ala Tyr Met Thr Ile
    130                 135                 140

Lys Ala Arg
145
```

```
<210> SEQ ID NO 17
<211> LENGTH: 441
<212> TYPE: DNA
<213> ORGANISM: Artificial Sequence
<220> FEATURE:
<223> OTHER INFORMATION: DV07 Nucleic Acid Sequence

<400> SEQUENCE: 17
```

```
accgaccagt gcgacaactt ccctcagatg ctgcgggacc tgagagatgc cttctccaga     60
gtgaaaacat tcttccagac caaggacgag ctggacaacc tgctgctgaa agagtccctg    120
ctggaagatt tcaagggcta cctgggctgt caggccctgt ccgagatgat ccagttctac    180
ctggaagaag tgatgcccca ggccgagaat caggaccccg agatcaagga ccacgtgaac    240
tccctgggcg agaacctgaa aaccctgcgg ctgagactgc ggcggtgcca cagatttctg    300
ccctgcgaga acaagtccaa ggccgtggaa cagatcaaga acgccttcaa caagctgcaa    360
gagaagggca tctacaaggc catgagcgag ttcgacatct tcatcaacta catcgaggcc    420
tacatgacca tcaaggccag a                                              441
```

```
<210> SEQ ID NO 18
<211> LENGTH: 567
```

<212> TYPE: PRT
<213> ORGANISM: Artificial Sequence
<220> FEATURE:
<223> OTHER INFORMATION: DV07 Ebo

<400> SEQUENCE: 18

Thr Asp Gln Cys Asp Asn Phe Pro Gln Met Leu Arg Asp Leu Arg Asp
1               5                   10                  15

Ala Phe Ser Arg Val Lys Thr Phe Phe Gln Thr Lys Asp Glu Leu Asp
            20                  25                  30

Asn Leu Leu Leu Lys Glu Ser Leu Leu Glu Asp Phe Lys Gly Tyr Leu
        35                  40                  45

Gly Cys Gln Ala Leu Ser Glu Met Ile Gln Phe Tyr Leu Glu Glu Val
50                  55                  60

Met Pro Gln Ala Glu Asn Gln Asp Pro Glu Ile Lys Asp His Val Asn
65                  70                  75                  80

Ser Leu Gly Glu Asn Leu Lys Thr Leu Arg Leu Arg Leu Arg Arg Cys
                85                  90                  95

His Arg Phe Leu Pro Cys Glu Asn Lys Ser Lys Ala Val Glu Gln Ile
            100                 105                 110

Lys Asn Ala Phe Asn Lys Leu Gln Glu Lys Gly Ile Tyr Lys Ala Met
        115                 120                 125

Ser Glu Phe Asp Ile Phe Ile Asn Tyr Ile Glu Ala Tyr Met Thr Ile
130                 135                 140

Lys Ala Arg Gly Gly Gly Gly Ser Gly Gly Gly Gly Ser Gly Gly Gly
145                 150                 155                 160

Gly Ser Gln Val Gln Leu Gln Gln Trp Gly Ala Gly Leu Leu Lys Pro
            165                 170                 175

Ser Glu Thr Leu Ser Leu Thr Cys Ala Val Tyr Gly Gly Ser Phe Thr
        180                 185                 190

Thr Thr Tyr Trp Asn Trp Ile Arg Gln Pro Pro Gly Lys Gly Leu Glu
195                 200                 205

Trp Ile Gly Glu Val Asn Tyr Ser Gly Asn Ala Asn Tyr Asn Pro Ser
210                 215                 220

Leu Lys Gly Arg Val Ala Ile Ser Val Asp Thr Ser Lys Asn Gln Phe
225                 230                 235                 240

Ser Leu Arg Leu Asn Ser Val Thr Ala Ala Asp Thr Ala Ile Tyr Tyr
            245                 250                 255

Cys Thr Ser Arg Ile Arg Ser His Ile Ala Tyr Ser Trp Lys Gly Asp
        260                 265                 270

Val Trp Gly Lys Gly Thr Thr Val Thr Val Gly Gly Gly Gly Ser Gly
            275                 280                 285

Gly Gly Gly Ser Gly Gly Gly Gly Ser Glu Ile Val Met Thr Gln Ser
290                 295                 300

Pro Gly Thr Leu Ser Leu Ser Pro Gly Glu Arg Ala Thr Leu Ser Cys
305                 310                 315                 320

Arg Ala Ser Gln Ser Val Pro Arg Asn Tyr Ile Gly Trp Phe Gln Gln
            325                 330                 335

Lys Pro Gly Gln Ala Pro Arg Leu Leu Ile Tyr Gly Ala Ser Ser Arg
        340                 345                 350

Ala Ala Gly Phe Pro Asp Arg Phe Ser Gly Ser Gly Ser Gly Thr Asp
            355                 360                 365

Phe Thr Leu Thr Ile Thr Arg Leu Glu Pro Glu Asp Phe Ala Met Tyr
370                 375                 380

```
Tyr Cys His Gln Tyr Asp Arg Leu Pro Tyr Thr Phe Gly Gln Gly Thr
385                 390                 395                 400

Lys Leu Glu Ile Lys Gly Gly Gly Ser Gly Gly Gly Gly Ser Gly
            405                 410                 415

Gly Gly Gly Ser Thr Asp Gln Cys Asp Asn Phe Pro Gln Met Leu Arg
            420                 425                 430

Asp Leu Arg Asp Ala Phe Ser Arg Val Lys Thr Phe Phe Gln Thr Lys
        435                 440                 445

Asp Glu Leu Asp Asn Leu Leu Lys Glu Ser Leu Leu Glu Asp Phe
    450                 455                 460

Lys Gly Tyr Leu Gly Cys Gln Ala Leu Ser Glu Met Ile Gln Phe Tyr
465                 470                 475                 480

Leu Glu Glu Val Met Pro Gln Ala Glu Asn Gln Asp Pro Glu Ile Lys
                485                 490                 495

Asp His Val Asn Ser Leu Gly Glu Asn Leu Lys Thr Leu Arg Leu Arg
            500                 505                 510

Leu Arg Arg Cys His Arg Phe Leu Pro Cys Glu Asn Lys Ser Lys Ala
        515                 520                 525

Val Glu Gln Ile Lys Asn Ala Phe Asn Lys Leu Gln Glu Lys Gly Ile
530                 535                 540

Tyr Lys Ala Met Ser Glu Phe Asp Ile Phe Ile Asn Tyr Ile Glu Ala
545                 550                 555                 560

Tyr Met Thr Ile Lys Ala Arg
                565

<210> SEQ ID NO 19
<211> LENGTH: 561
<212> TYPE: PRT
<213> ORGANISM: Artificial Sequence
<220> FEATURE:
<223> OTHER INFORMATION: DV07 Ebo EGF

<400> SEQUENCE: 19

Thr Asp Gln Cys Asp Asn Phe Pro Gln Met Leu Arg Asp Leu Arg Asp
1               5                   10                  15

Ala Phe Ser Arg Val Lys Thr Phe Phe Gln Thr Lys Asp Glu Leu Asp
            20                  25                  30

Asn Leu Leu Lys Glu Ser Leu Leu Glu Asp Phe Lys Gly Tyr Leu
        35                  40                  45

Gly Cys Gln Ala Leu Ser Glu Met Ile Gln Phe Tyr Leu Glu Glu Val
    50                  55                  60

Met Pro Gln Ala Glu Asn Gln Asp Pro Glu Ile Lys Asp His Val Asn
65                  70                  75                  80

Ser Leu Gly Glu Asn Leu Lys Thr Leu Arg Leu Arg Leu Arg Arg Cys
                85                  90                  95

His Arg Phe Leu Pro Cys Glu Asn Lys Ser Lys Ala Val Glu Gln Ile
            100                 105                 110

Lys Asn Ala Phe Asn Lys Leu Gln Glu Lys Gly Ile Tyr Lys Ala Met
        115                 120                 125

Ser Glu Phe Asp Ile Phe Ile Asn Tyr Ile Glu Ala Tyr Met Thr Ile
    130                 135                 140

Lys Ala Arg Gly Gly Gly Gly Ser Gly Gly Gly Gly Ser Gly Gly
145                 150                 155                 160

Gly Ser Gln Val Gln Leu Gln Gln Trp Gly Ala Gly Leu Leu Lys Pro
                165                 170                 175
```

-continued

```
Ser Glu Thr Leu Arg Leu Thr Cys Ala Val Tyr Gly Gly Ser Phe Thr
            180                 185                 190

Asn Tyr Gly Val His Trp Ile Arg Gln Pro Pro Gly Lys Gly Leu Glu
        195                 200                 205

Trp Ile Gly Val Ile Trp Ser Gly Gly Asn Thr Asp Tyr Asn Thr Pro
    210                 215                 220

Phe Thr Ser Arg Val Thr Ile Ser Val Asp Thr Ser Lys Asn Gln Phe
225                 230                 235                 240

Ser Leu Gln Leu Asn Ser Val Thr Ala Ala Asp Thr Ala Ile Tyr Tyr
                245                 250                 255

Cys Thr Ser Leu Thr Tyr Tyr Asp Tyr Glu Phe Ala Trp Gly Lys Gly
            260                 265                 270

Thr Thr Val Thr Val Gly Gly Gly Ser Gly Gly Gly Ser Gly
        275                 280                 285

Gly Gly Gly Ser Glu Ile Val Met Thr Gln Ser Pro Gly Thr Leu Ser
    290                 295                 300

Leu Ser Pro Gly Glu Arg Ala Thr Leu Ser Cys Arg Ala Ser Gln Ser
305                 310                 315                 320

Ile Gly Thr Asn Ile His Trp Phe Gln Gln Lys Pro Gly Gln Ala Pro
                325                 330                 335

Arg Leu Leu Ile Tyr Tyr Ala Ser Glu Ser Ile Ser Gly Phe Pro Asp
            340                 345                 350

Arg Phe Ser Gly Ser Gly Ser Gly Thr Asp Phe Thr Leu Thr Ile Thr
        355                 360                 365

Arg Leu Glu Pro Glu Asp Phe Ala Met Tyr Tyr Cys Gln Gln Asn Asn
    370                 375                 380

Asn Trp Pro Thr Thr Phe Gly Gln Gly Thr Lys Leu Glu Ile Lys Gly
385                 390                 395                 400

Gly Gly Gly Ser Gly Gly Gly Ser Gly Gly Gly Ser Thr Asp
                405                 410                 415

Gln Cys Asp Asn Phe Pro Gln Met Leu Arg Asp Leu Arg Asp Ala Phe
            420                 425                 430

Ser Arg Val Lys Thr Phe Phe Gln Thr Lys Asp Glu Leu Asp Asn Leu
        435                 440                 445

Leu Leu Lys Glu Ser Leu Leu Glu Asp Phe Lys Gly Tyr Leu Gly Cys
    450                 455                 460

Gln Ala Leu Ser Glu Met Ile Gln Phe Tyr Leu Glu Glu Val Met Pro
465                 470                 475                 480

Gln Ala Glu Asn Gln Asp Pro Glu Ile Lys Asp His Val Asn Ser Leu
                485                 490                 495

Gly Glu Asn Leu Lys Thr Leu Arg Leu Arg Leu Arg Arg Cys His Arg
            500                 505                 510

Phe Leu Pro Cys Glu Asn Lys Ser Lys Ala Val Glu Gln Ile Lys Asn
        515                 520                 525

Ala Phe Asn Lys Leu Gln Glu Lys Gly Ile Tyr Lys Ala Met Ser Glu
    530                 535                 540

Phe Asp Ile Phe Ile Asn Tyr Ile Glu Ala Tyr Met Thr Ile Lys Ala
545                 550                 555                 560

Arg
```

<210> SEQ ID NO 20
<211> LENGTH: 581
<212> TYPE: PRT
<213> ORGANISM: Artificial Sequence -continued

```
<220> FEATURE:
<223> OTHER INFORMATION: DV06 EboX
<220> FEATURE:
<221> NAME/KEY: MOD_RES
<222> LOCATION: (193)..(199)
<223> OTHER INFORMATION: Any amino acid
<220> FEATURE:
<221> NAME/KEY: MISC_FEATURE
<222> LOCATION: (193)..(199)
<223> OTHER INFORMATION: This region may encompass 3-7 residues
<220> FEATURE:
<221> NAME/KEY: MOD_RES
<222> LOCATION: (214)..(231)
<223> OTHER INFORMATION: Any amino acid
<220> FEATURE:
<221> NAME/KEY: MISC_FEATURE
<222> LOCATION: (214)..(231)
<223> OTHER INFORMATION: This region may encompass 14-18 residues
<220> FEATURE:
<221> NAME/KEY: MOD_RES
<222> LOCATION: (264)..(274)
<223> OTHER INFORMATION: Any amino acid
<220> FEATURE:
<221> NAME/KEY: MISC_FEATURE
<222> LOCATION: (264)..(274)
<223> OTHER INFORMATION: This region may encompass 7-11 residues
<220> FEATURE:
<221> NAME/KEY: MOD_RES
<222> LOCATION: (329)..(342)
<223> OTHER INFORMATION: Any amino acid
<220> FEATURE:
<221> NAME/KEY: MISC_FEATURE
<222> LOCATION: (329)..(342)
<223> OTHER INFORMATION: This region may encompass 9-14 residues
<220> FEATURE:
<221> NAME/KEY: MOD_RES
<222> LOCATION: (358)..(366)
<223> OTHER INFORMATION: Any amino acid
<220> FEATURE:
<221> NAME/KEY: MISC_FEATURE
<222> LOCATION: (358)..(366)
<223> OTHER INFORMATION: This region may encompass 5-9 residues
<220> FEATURE:
<221> NAME/KEY: MOD_RES
<222> LOCATION: (399)..(409)
<223> OTHER INFORMATION: Any amino acid
<220> FEATURE:
<221> NAME/KEY: MISC_FEATURE
<222> LOCATION: (399)..(409)
<223> OTHER INFORMATION: This region may encompass 7-11 residues
<220> FEATURE:
<223> OTHER INFORMATION: See specification as filed for detailed
      description of substitutions and preferred embodiments

<400> SEQUENCE: 20

Thr Asp Gln Cys Asp Asn Phe Pro Gln Met Leu Arg Asp Leu Arg Asp
1               5                   10                  15

Ala Phe Ser Arg Val Lys Thr Phe Phe Gln Thr Lys Asp Glu Val Asp
                20                  25                  30

Asn Leu Leu Leu Lys Glu Ser Leu Glu Asp Phe Lys Gly Tyr Leu
            35                  40                  45

Gly Cys Gln Ala Leu Ser Glu Met Ile Gln Phe Tyr Leu Glu Glu Val
        50                  55                  60

Met Pro Gln Ala Glu Asn Gln Asp Pro Glu Ile Lys Asp His Val Asn
65                  70                  75                  80

Ser Leu Gly Glu Asn Leu Lys Thr Leu Arg Leu Arg Leu Arg Arg Cys
                85                  90                  95

His Arg Phe Leu Pro Cys Glu Asn Lys Ser Lys Ala Val Glu Gln Ile
            100                 105                 110

Lys Asn Ala Phe Asn Lys Leu Gln Glu Lys Gly Ile Tyr Lys Ala Met
        115                 120                 125
```

```
Ser Glu Phe Asp Ile Phe Ile Asn Tyr Ile Glu Ala Tyr Met Thr Ile
130                 135                 140

Lys Ala Arg Gly Gly Gly Ser Gly Gly Gly Ser Gly Gly Gly
145                 150                 155                 160

Gly Ser Gln Val Gln Leu Gln Gln Trp Gly Ala Gly Leu Leu Lys Pro
            165                 170                 175

Ser Glu Thr Leu Ser Leu Thr Cys Ala Val Tyr Gly Gly Ser Phe Thr
                180                 185                 190

Xaa Xaa Xaa Xaa Xaa Xaa Xaa Trp Ile Arg Gln Pro Pro Gly Lys Gly
        195                 200                 205

Leu Glu Trp Ile Gly Xaa Xaa Xaa Xaa Xaa Xaa Xaa Xaa Xaa
210             215                 220

Xaa Xaa Xaa Xaa Xaa Xaa Xaa Arg Val Ala Ile Ser Val Asp Thr Ser
225                 230                 235                 240

Lys Asn Gln Phe Ser Leu Arg Leu Asn Ser Val Thr Ala Ala Asp Thr
                245                 250                 255

Ala Ile Tyr Tyr Cys Thr Ser Xaa Xaa Xaa Xaa Xaa Xaa Xaa Xaa
            260                 265                 270

Xaa Xaa Trp Lys Gly Asp Val Trp Gly Lys Gly Thr Thr Val Thr Val
        275                 280                 285

Ser Ser Gly Gly Gly Gly Ser Gly Gly Gly Ser Gly Gly Gly Gly
290                 295                 300

Ser Glu Ile Val Met Thr Gln Ser Pro Gly Thr Leu Ser Leu Ser Pro
305                 310                 315                 320

Gly Glu Arg Ala Thr Leu Ser Cys Xaa Xaa Xaa Xaa Xaa Xaa Xaa
                325                 330                 335

Xaa Xaa Xaa Xaa Xaa Xaa Trp Phe Gln Gln Lys Pro Gly Gln Ala Pro
        340                 345                 350

Arg Leu Leu Ile Tyr Xaa Xaa Xaa Xaa Xaa Xaa Xaa Xaa Gly Phe
            355                 360                 365

Pro Asp Arg Phe Ser Gly Ser Gly Ser Gly Thr Asp Phe Thr Leu Thr
370                 375                 380

Ile Thr Arg Leu Glu Pro Glu Asp Phe Ala Met Tyr Tyr Cys Xaa Xaa
385                 390                 395                 400

Xaa Xaa Xaa Xaa Xaa Xaa Xaa Xaa Xaa Phe Gly Gln Gly Thr Lys Leu
            405                 410                 415

Glu Ile Lys Gly Gly Gly Gly Ser Gly Gly Gly Gly Ser Gly Gly Gly
            420                 425                 430

Gly Ser Thr Asp Gln Cys Asp Asn Phe Pro Gln Met Leu Arg Asp Leu
        435                 440                 445

Arg Asp Ala Phe Ser Arg Val Lys Thr Phe Phe Gln Thr Lys Asp Glu
450                 455                 460

Val Asp Asn Leu Leu Leu Lys Glu Ser Leu Leu Glu Asp Phe Lys Gly
465                 470                 475                 480

Tyr Leu Gly Cys Gln Ala Leu Ser Glu Met Ile Gln Phe Tyr Leu Glu
            485                 490                 495

Glu Val Met Pro Gln Ala Glu Asn Gln Asp Pro Glu Ile Lys Asp His
            500                 505                 510

Val Asn Ser Leu Gly Glu Asn Leu Lys Thr Leu Arg Leu Arg Leu Arg
        515                 520                 525

Arg Cys His Arg Phe Leu Pro Cys Glu Asn Lys Ser Lys Ala Val Glu
530                 535                 540
```

-continued

```
Gln Ile Lys Asn Ala Phe Asn Lys Leu Gln Glu Lys Gly Ile Tyr Lys
545                 550                 555                 560

Ala Met Ser Glu Phe Asp Ile Phe Ile Asn Tyr Ile Glu Ala Tyr Met
            565                 570                 575

Thr Ile Lys Ala Arg
            580

<210> SEQ ID NO 21
<211> LENGTH: 569
<212> TYPE: PRT
<213> ORGANISM: Artificial Sequence
<220> FEATURE:
<223> OTHER INFORMATION: DV06 Ebo

<400> SEQUENCE: 21

Thr Asp Gln Cys Asp Asn Phe Pro Gln Met Leu Arg Asp Leu Arg Asp
1               5                  10                  15

Ala Phe Ser Arg Val Lys Thr Phe Phe Gln Thr Lys Asp Glu Val Asp
            20                  25                  30

Asn Leu Leu Leu Lys Glu Ser Leu Leu Glu Asp Phe Lys Gly Tyr Leu
        35                  40                  45

Gly Cys Gln Ala Leu Ser Glu Met Ile Gln Phe Tyr Leu Glu Glu Val
50                  55                  60

Met Pro Gln Ala Glu Asn Gln Asp Pro Glu Ile Lys Asp His Val Asn
65                  70                  75                  80

Ser Leu Gly Glu Asn Leu Lys Thr Leu Arg Leu Arg Leu Arg Arg Cys
                85                  90                  95

His Arg Phe Leu Pro Cys Glu Asn Lys Ser Lys Ala Val Glu Gln Ile
            100                 105                 110

Lys Asn Ala Phe Asn Lys Leu Gln Glu Lys Gly Ile Tyr Lys Ala Met
        115                 120                 125

Ser Glu Phe Asp Ile Phe Ile Asn Tyr Ile Glu Ala Tyr Met Thr Ile
130                 135                 140

Lys Ala Arg Gly Gly Gly Gly Ser Gly Gly Gly Gly Ser Gly Gly Gly
145                 150                 155                 160

Gly Ser Gln Val Gln Leu Gln Gln Trp Gly Ala Gly Leu Leu Lys Pro
                165                 170                 175

Ser Glu Thr Leu Ser Leu Thr Cys Ala Val Tyr Gly Gly Ser Phe Thr
            180                 185                 190

Thr Thr Tyr Trp Asn Trp Ile Arg Gln Pro Pro Gly Lys Gly Leu Glu
        195                 200                 205

Trp Ile Gly Glu Val Asn Tyr Ser Gly Asn Ala Asn Tyr Asn Pro Ser
210                 215                 220

Leu Lys Gly Arg Val Ala Ile Ser Val Asp Thr Ser Lys Asn Gln Phe
225                 230                 235                 240

Ser Leu Arg Leu Asn Ser Val Thr Ala Ala Asp Thr Ala Ile Tyr Tyr
                245                 250                 255

Cys Thr Ser Arg Ile Arg Ser His Ile Ala Tyr Ser Trp Lys Gly Asp
            260                 265                 270

Val Trp Gly Lys Gly Thr Thr Val Thr Val Ser Ser Gly Gly Gly Gly
        275                 280                 285

Ser Gly Gly Gly Gly Ser Gly Gly Gly Gly Ser Glu Ile Val Met Thr
290                 295                 300

Gln Ser Pro Gly Thr Leu Ser Leu Ser Pro Gly Glu Arg Ala Thr Leu
305                 310                 315                 320
```

Ser Cys Arg Ala Ser Gln Ser Val Pro Arg Asn Tyr Ile Gly Trp Phe
                325                 330                 335

Gln Gln Lys Pro Gly Gln Ala Pro Arg Leu Leu Ile Tyr Gly Ala Ser
            340                 345                 350

Ser Arg Ala Ala Gly Phe Pro Asp Arg Phe Ser Gly Ser Gly Ser Gly
            355                 360                 365

Thr Asp Phe Thr Leu Thr Ile Thr Arg Leu Glu Pro Glu Asp Phe Ala
    370                 375                 380

Met Tyr Tyr Cys His Gln Tyr Asp Arg Leu Pro Tyr Thr Phe Gly Gln
385                 390                 395                 400

Gly Thr Lys Leu Glu Ile Lys Gly Gly Gly Ser Gly Gly Gly Gly
                405                 410                 415

Ser Gly Gly Gly Gly Ser Thr Asp Gln Cys Asp Asn Phe Pro Gln Met
            420                 425                 430

Leu Arg Asp Leu Arg Asp Ala Phe Ser Arg Val Lys Thr Phe Phe Gln
        435                 440                 445

Thr Lys Asp Glu Val Asp Asn Leu Leu Leu Lys Glu Ser Leu Leu Glu
    450                 455                 460

Asp Phe Lys Gly Tyr Leu Gly Cys Gln Ala Leu Ser Glu Met Ile Gln
465                 470                 475                 480

Phe Tyr Leu Glu Glu Val Met Pro Gln Ala Glu Asn Gln Asp Pro Glu
                485                 490                 495

Ile Lys Asp His Val Asn Ser Leu Gly Glu Asn Leu Lys Thr Leu Arg
            500                 505                 510

Leu Arg Leu Arg Arg Cys His Arg Phe Leu Pro Cys Glu Asn Lys Ser
        515                 520                 525

Lys Ala Val Glu Gln Ile Lys Asn Ala Phe Asn Lys Leu Gln Glu Lys
    530                 535                 540

Gly Ile Tyr Lys Ala Met Ser Glu Phe Asp Ile Phe Ile Asn Tyr Ile
545                 550                 555                 560

Glu Ala Tyr Met Thr Ile Lys Ala Arg
                565

<210> SEQ ID NO 22
<211> LENGTH: 575
<212> TYPE: PRT
<213> ORGANISM: Artificial Sequence
<220> FEATURE:
<223> OTHER INFORMATION: DV06 MadCam

<400> SEQUENCE: 22

Thr Asp Gln Cys Asp Asn Phe Pro Gln Met Leu Arg Asp Leu Arg Asp
1               5                   10                  15

Ala Phe Ser Arg Val Lys Thr Phe Phe Gln Thr Lys Asp Glu Val Asp
            20                  25                  30

Asn Leu Leu Leu Lys Glu Ser Leu Leu Glu Asp Phe Lys Gly Tyr Leu
        35                  40                  45

Gly Cys Gln Ala Leu Ser Glu Met Ile Gln Phe Tyr Leu Glu Glu Val
    50                  55                  60

Met Pro Gln Ala Glu Asn Gln Asp Pro Glu Ile Lys Asp His Val Asn
65                  70                  75                  80

Ser Leu Gly Glu Asn Leu Lys Thr Leu Arg Leu Arg Leu Arg Arg Cys
                85                  90                  95

His Arg Phe Leu Pro Cys Glu Asn Lys Ser Lys Ala Val Glu Gln Ile
            100                 105                 110

```
Lys Asn Ala Phe Asn Lys Leu Gln Glu Lys Gly Ile Tyr Lys Ala Met
                115                 120                 125
Ser Glu Phe Asp Ile Phe Ile Asn Tyr Ile Glu Ala Tyr Met Thr Ile
            130                 135                 140
Lys Ala Arg Gly Gly Gly Ser Gly Gly Gly Ser Gly Gly Gly
145                 150                 155                 160
Gly Ser Gln Val Gln Leu Val Gln Ser Gly Ala Glu Val Lys Lys Pro
                165                 170                 175
Gly Ala Ser Val Lys Val Ser Cys Lys Ala Ser Gly Tyr Thr Phe Thr
                180                 185                 190
Ser Tyr Gly Ile Asn Trp Val Arg Gln Ala Pro Gly Gln Gly Leu Glu
            195                 200                 205
Trp Met Gly Trp Ile Ser Val Tyr Ser Gly Asn Thr Asn Tyr Ala Gln
210                 215                 220
Lys Val Gln Gly Arg Val Thr Met Thr Ala Asp Thr Ser Thr Ser Thr
225                 230                 235                 240
Ala Tyr Met Asp Leu Arg Ser Leu Arg Ser Asp Asp Thr Ala Val Tyr
                245                 250                 255
Tyr Cys Ala Arg Glu Gly Ser Ser Ser Gly Asp Tyr Tyr Tyr Gly
            260                 265                 270
Met Asp Val Trp Gly Gln Gly Thr Thr Val Thr Val Ser Ser Gly Gly
            275                 280                 285
Gly Gly Ser Gly Gly Gly Ser Gly Gly Gly Ser Asp Ile Val
                290                 295                 300
Met Thr Gln Thr Pro Leu Ser Leu Ser Val Thr Pro Gly Gln Pro Ala
305                 310                 315                 320
Ser Ile Ser Cys Lys Ser Ser Gln Ser Leu Leu His Thr Asp Gly Thr
                325                 330                 335
Thr Tyr Leu Tyr Trp Tyr Leu Gln Lys Pro Gly Gln Pro Gln Leu
            340                 345                 350
Leu Ile Tyr Glu Val Ser Asn Arg Phe Ser Gly Val Pro Asp Arg Phe
            355                 360                 365
Ser Gly Ser Gly Ser Gly Thr Asp Phe Thr Leu Lys Ile Ser Arg Val
            370                 375                 380
Glu Ala Glu Asp Val Gly Ile Tyr Tyr Cys Met Gln Asn Ile Gln Leu
385                 390                 395                 400
Pro Trp Thr Phe Gly Gln Gly Thr Lys Val Glu Ile Lys Gly Gly Gly
                405                 410                 415
Gly Ser Gly Gly Gly Gly Ser Gly Gly Gly Gly Ser Thr Asp Gln Cys
                420                 425                 430
Asp Asn Phe Pro Gln Met Leu Arg Asp Leu Arg Asp Ala Phe Ser Arg
                435                 440                 445
Val Lys Thr Phe Phe Gln Thr Lys Asp Glu Val Asp Asn Leu Leu Leu
                450                 455                 460
Lys Glu Ser Leu Leu Glu Asp Phe Lys Gly Tyr Leu Gly Cys Gln Ala
465                 470                 475                 480
Leu Ser Glu Met Ile Gln Phe Tyr Leu Glu Glu Val Met Pro Gln Ala
                485                 490                 495
Glu Asn Gln Asp Pro Glu Ile Lys Asp His Val Asn Ser Leu Gly Glu
                500                 505                 510
Asn Leu Lys Thr Leu Arg Leu Arg Leu Arg Arg Cys His Arg Phe Leu
            515                 520                 525
```

```
Pro Cys Glu Asn Lys Ser Lys Ala Val Glu Gln Ile Lys Asn Ala Phe
    530                 535                 540

Asn Lys Leu Gln Glu Lys Gly Ile Tyr Lys Ala Met Ser Glu Phe Asp
545                 550                 555                 560

Ile Phe Ile Asn Tyr Ile Glu Ala Tyr Met Thr Ile Lys Ala Arg
                565                 570                 575

<210> SEQ ID NO 23
<211> LENGTH: 573
<212> TYPE: PRT
<213> ORGANISM: Artificial Sequence
<220> FEATURE:
<223> OTHER INFORMATION: DV07 EboX
<220> FEATURE:
<221> NAME/KEY: MOD_RES
<222> LOCATION: (193)..(199)
<223> OTHER INFORMATION: Any amino acid
<220> F

```
Gly Cys Gln Ala Leu Ser Glu Met Ile Gln Phe Tyr Leu Glu Glu Val
 50                  55                  60

Met Pro Gln Ala Glu Asn Gln Asp Pro Glu Ile Lys Asp His Val Asn
 65                  70                  75                  80

Ser Leu Gly Glu Asn Leu Lys Thr Leu Arg Leu Arg Leu Arg Arg Cys
                 85                  90                  95

His Arg Phe Leu Pro Cys Glu Asn Lys Ser Lys Ala Val Glu Gln Ile
             100                 105                 110

Lys Asn Ala Phe Asn Lys Leu Gln Glu Lys Gly Ile Tyr Lys Ala Met
         115                 120                 125

Ser Glu Phe Asp Ile Phe Ile Asn Tyr Ile Glu Ala Tyr Met Thr Ile
         130                 135                 140

Lys Ala Arg Gly Gly Gly Ser Gly Gly Gly Ser Gly Gly Gly
145                 150                 155                 160

Gly Ser Gln Val Gln Leu Gln Gln Trp Gly Ala Gly Leu Leu Lys Pro
                 165                 170                 175

Ser Glu Thr Leu Arg Leu Thr Cys Ala Val Tyr Gly Ser Phe Thr
                 180                 185                 190

Xaa Xaa Xaa Xaa Xaa Xaa Xaa Trp Ile Arg Gln Pro Pro Gly Lys Gly
                 195                 200                 205

Leu Glu Trp Ile Xaa Xaa Xaa Xaa Xaa Xaa Xaa Xaa Xaa Xaa
             210                 215                 220

Xaa Xaa Xaa Xaa Xaa Xaa Arg Val Thr Ile Ser Val Asp Thr Ser Lys
225                 230                 235                 240

Asn Gln Phe Ser Leu Gln Leu Asn Ser Val Thr Ala Ala Asp Thr Ala
                 245                 250                 255

Ile Tyr Tyr Cys Thr Ser Xaa Xaa Xaa Xaa Xaa Xaa Xaa Xaa Xaa
             260                 265                 270

Xaa Trp Gly Lys Gly Thr Thr Val Thr Val Gly Gly Gly Gly Ser Gly
             275                 280                 285

Gly Gly Gly Ser Gly Gly Gly Gly Ser Glu Ile Val Met Thr Gln Ser
             290                 295                 300

Pro Gly Thr Leu Ser Leu Ser Pro Gly Glu Arg Ala Thr Leu Ser Cys
305                 310                 315                 320

Xaa Xaa Xaa Xaa Xaa Xaa Xaa Xaa Xaa Xaa Xaa Xaa Xaa Xaa Trp Phe
                 325                 330                 335

Gln Gln Lys Pro Gly Gln Ala Pro Arg Leu Leu Ile Tyr Xaa Xaa Xaa
             340                 345                 350

Xaa Xaa Xaa Xaa Xaa Xaa Gly Phe Pro Asp Arg Phe Ser Gly Ser Gly
             355                 360                 365

Ser Gly Thr Asp Phe Thr Leu Thr Ile Thr Arg Leu Glu Pro Glu Asp
             370                 375                 380

Phe Ala Met Tyr Tyr Cys Xaa Xaa Xaa Xaa Xaa Xaa Xaa Xaa Xaa
385                 390                 395                 400

Xaa Phe Gly Gln Gly Thr Lys Leu Glu Ile Lys Gly Gly Gly Gly Ser
                 405                 410                 415

Gly Gly Gly Gly Ser Gly Gly Gly Gly Ser Thr Asp Gln Cys Asp Asn
             420                 425                 430

Phe Pro Gln Met Leu Arg Asp Leu Arg Asp Ala Phe Ser Arg Val Lys
             435                 440                 445

Thr Phe Phe Gln Thr Lys Asp Glu Leu Asp Asn Leu Leu Leu Lys Glu
             450                 455                 460
```

```
Ser Leu Leu Glu Asp Phe Lys Gly Tyr Leu Gly Cys Gln Ala Leu Ser
465                 470                 475                 480

Glu Met Ile Gln Phe Tyr Leu Glu Glu Val Met Pro Gln Ala Glu Asn
                485                 490                 495

Gln Asp Pro Glu Ile Lys Asp His Val Asn Ser Leu Gly Glu Asn Leu
            500                 505                 510

Lys Thr Leu Arg Leu Arg Leu Arg Arg Cys His Arg Phe Leu Pro Cys
        515                 520                 525

Glu Asn Lys Ser Lys Ala Val Glu Gln Ile Lys Asn Ala Phe Asn Lys
    530                 535                 540

Leu Gln Glu Lys Gly Ile Tyr Lys Ala Met Ser Glu Phe Asp Ile Phe
545                 550                 555                 560

Ile Asn Tyr Ile Glu Ala Tyr Met Thr Ile Lys Ala Arg
                565                 570

<210> SEQ ID NO 24
<211> LENGTH: 573
<212> TYPE: PRT
<213> ORGANISM: Artificial Sequence
<220> FEATURE:
<223> OTHER INFORMATION: DV05 EboX
<220> FEATURE:
<221> NAME/KEY: MOD_RES
<222> LOCATION: (193)..(199)
<223> OTHER INFORMATION: Any amino acid
<220> FEATURE:
<221> NAME/KEY: MISC_FEATURE
<222> LOCATION: (193)..(199)
<223> OTHER INFORMATION: This region may encompass 3-7 residues
<220> FEATURE:
<221> NAME/KEY: MOD_RES
<222> LOCATION: (213)..(230)
<223> OTHER INFORMATION: Any amino acid
<220> FEATURE:
<221> NAME/KEY: MISC_FEATURE
<222> LOCATION: (213)..(230)
<223> OTHER INFORMATION: This region may encompass 14-18 residues
<220> FEATURE:
<221> NAME/KEY: MOD_RES
<222> LOCATION: (263)..(273)
<223> OTHER INFORMATION: Any amino acid
<220> FEATURE:
<221> NAME/KEY: MISC_FEATURE
<222> LOCATION: (263)..(273)
<223> OTHER INFORMATION: This region may encompass 7-11 residues
<220> FEATURE:
<221> NAME/KEY: MOD_RES
<222> LOCATION: (321)..(334)
<223> OTHER INFORMATION: Any amino acid
<220> FEATURE:
<221> NAME/KEY: MISC_FEATURE
<222> LOCATION: (321)..(334)
<223> OTHER INFORMATION: This region may encompass 9-14 residues
<220> FEATURE:
<221> NAME/KEY: MOD_RES
<222> LOCATION: (350)..(358)
<223> OTHER INFORMATION: Any amino acid
<220> FEATURE:
<221> NAME/KEY: MISC_FEATURE
<222> LOCATION: (350)..(358)
<223> OTHER INFORMATION: This region may encompass 5-9 residues
<220> FEATURE:
<221> NAME/KEY: MOD_RES
<222> LOCATION: (391)..(401)
<223> OTHER INFORMATION: Any amino acid
<220> FEATURE:
<221> NAME/KEY: MISC_FEATURE
<222> LOCATION: (391)..(401)
<223> OTHER INFORMATION: This region may encompass 7-11 residues
<220> FEATURE:
<223> OTHER INFORMATION: See specification as filed for detailed
      description of substitutions and preferred embodiments
```

<400> SEQUENCE: 24

```
Thr Asp Gln Cys Asp Asn Phe Pro Gln Met Leu Arg Asp Leu Arg Asp
1               5                   10                  15

Ala Phe Ser Arg Val Lys Thr Phe Phe Gln Thr Lys Asp Glu Leu Asp
            20                  25                  30

Asn Leu Leu Leu Lys Glu Ser Leu Glu Asp Phe Lys Gly Tyr Leu
        35                  40                  45

Gly Cys Gln Ala Leu Ser Glu Met Ile Gln Phe Tyr Leu Glu Glu Val
    50                  55                  60

Met Pro Gln Ala Glu Asn Gln Asp Pro Glu Ala Lys Asp His Val Asn
65                  70                  75                  80

Ser Leu Gly Glu Asn Leu Lys Thr Leu Arg Leu Arg Leu Arg Arg Cys
                85                  90                  95

His Arg Phe Leu Pro Cys Glu Asn Lys Ser Lys Ala Val Glu Gln Ile
            100                 105                 110

Lys Asn Ala Phe Asn Lys Leu Gln Glu Lys Gly Ile Tyr Lys Ala Met
        115                 120                 125

Ser Glu Phe Asp Ile Phe Ile Asn Tyr Ile Glu Ala Tyr Met Thr Ile
130                 135                 140

Lys Ala Arg Gly Gly Gly Ser Gly Gly Gly Ser Gly Gly Gly
145                 150                 155                 160

Gly Ser Gln Val Gln Leu Gln Trp Gly Ala Gly Leu Leu Lys Pro
            165                 170                 175

Ser Glu Thr Leu Arg Leu Thr Cys Ala Val Tyr Gly Gly Ser Phe Thr
            180                 185                 190

Xaa Xaa Xaa Xaa Xaa Xaa Trp Ile Arg Gln Pro Pro Gly Lys Gly
            195                 200                 205

Leu Glu Trp Ile Xaa Xaa Xaa Xaa Xaa Xaa Xaa Xaa Xaa Xaa Xaa
            210                 215                 220

Xaa Xaa Xaa Xaa Xaa Xaa Arg Val Thr Ile Ser Val Asp Thr Ser Lys
225                 230                 235                 240

Asn Gln Phe Ser Leu Gln Leu Asn Ser Val Thr Ala Ala Asp Thr Ala
            245                 250                 255

Ile Tyr Tyr Cys Thr Ser Xaa Xaa Xaa Xaa Xaa Xaa Xaa Xaa Xaa
            260                 265                 270

Xaa Trp Gly Lys Gly Thr Thr Val Thr Val Gly Gly Gly Ser Gly
            275                 280                 285

Gly Gly Gly Ser Gly Gly Gly Gly Ser Glu Ile Val Met Thr Gln Ser
290                 295                 300

Pro Gly Thr Leu Ser Leu Ser Pro Gly Glu Arg Ala Thr Leu Ser Cys
305                 310                 315                 320

Xaa Xaa Xaa Xaa Xaa Xaa Xaa Xaa Xaa Xaa Xaa Xaa Xaa Trp Phe
            325                 330                 335

Gln Gln Lys Pro Gly Gln Ala Pro Arg Leu Leu Ile Tyr Xaa Xaa Xaa
            340                 345                 350

Xaa Xaa Xaa Xaa Xaa Xaa Gly Phe Pro Asp Arg Phe Ser Gly Ser
            355                 360                 365

Ser Gly Thr Asp Phe Thr Leu Thr Ile Thr Arg Leu Glu Pro Glu Asp
    370                 375                 380

Phe Ala Met Tyr Tyr Cys Xaa Xaa Xaa Xaa Xaa Xaa Xaa Xaa Xaa
385                 390                 395                 400
```

```
Xaa Phe Gly Gln Gly Thr Lys Leu Glu Ile Lys Gly Gly Gly Ser
            405                 410                 415

Gly Gly Gly Gly Ser Gly Gly Gly Ser Thr Asp Gln Cys Asp Asn
            420                 425                 430

Phe Pro Gln Met Leu Arg Asp Leu Arg Asp Ala Phe Ser Arg Val Lys
            435                 440                 445

Thr Phe Phe Gln Thr Lys Asp Glu Leu Asp Asn Leu Leu Lys Glu
450                 455                 460

Ser Leu Leu Glu Asp Phe Lys Gly Tyr Leu Gly Cys Gln Ala Leu Ser
465                 470                 475                 480

Glu Met Ile Gln Phe Tyr Leu Glu Glu Val Met Pro Gln Ala Glu Asn
                485                 490                 495

Gln Asp Pro Glu Ala Lys Asp His Val Asn Ser Leu Gly Glu Asn Leu
            500                 505                 510

Lys Thr Leu Arg Leu Arg Leu Arg Arg Cys His Arg Phe Leu Pro Cys
            515                 520                 525

Glu Asn Lys Ser Lys Ala Val Glu Gln Ile Lys Asn Ala Phe Asn Lys
            530                 535                 540

Leu Gln Glu Lys Gly Ile Tyr Lys Ala Met Ser Glu Phe Asp Ile Phe
545                 550                 555                 560

Ile Asn Tyr Ile Glu Ala Tyr Met Thr Ile Lys Ala Arg
                565                 570

<210> SEQ ID NO 25
<211> LENGTH: 569
<212> TYPE: PRT
<213> ORGANISM: Artificial Sequence
<220> FEATURE:
<223> OTHER INFORMATION: DV07 EboL3

<400> SEQUENCE: 25

Thr Asp Gln Cys Asp Asn Phe Pro Gln Met Leu Arg Asp Leu Arg Asp
1               5                   10                  15

Ala Phe Ser Arg Val Lys Thr Phe Phe Gln Thr Lys Asp Glu Leu Asp
            20                  25                  30

Asn Leu Leu Lys Glu Ser Leu Leu Glu Asp Phe Lys Gly Tyr Leu
            35                  40                  45

Gly Cys Gln Ala Leu Ser Glu Met Ile Gln Phe Tyr Leu Glu Glu Val
50                  55                  60

Met Pro Gln Ala Glu Asn Gln Asp Pro Glu Ile Lys Asp His Val Asn
65                  70                  75                  80

Ser Leu Gly Glu Asn Leu Lys Thr Leu Arg Leu Arg Leu Arg Arg Cys
                85                  90                  95

His Arg Phe Leu Pro Cys Glu Asn Lys Ser Lys Ala Val Glu Gln Ile
            100                 105                 110

Lys Asn Ala Phe Asn Lys Leu Gln Glu Lys Gly Ile Tyr Lys Ala Met
            115                 120                 125

Ser Glu Phe Asp Ile Phe Ile Asn Tyr Ile Glu Ala Tyr Met Thr Ile
            130                 135                 140

Lys Ala Arg Gly Gly Gly Gly Ser Gly Gly Gly Gly Ser Gly Gly Gly
145                 150                 155                 160

Gly Ser Gln Val Gln Leu Gln Gln Trp Gly Ala Gly Leu Leu Lys Pro
                165                 170                 175

Ser Glu Thr Leu Ser Leu Thr Cys Ala Val Tyr Gly Gly Ser Phe Thr
            180                 185                 190
```

Thr Thr Tyr Trp Asn Trp Ile Arg Gln Pro Pro Gly Lys Gly Leu Glu
            195                 200                 205

Trp Ile Gly Glu Val Asn Tyr Ser Gly Asn Ala Asn Tyr Asn Pro Ser
    210                 215                 220

Leu Lys Gly Arg Val Ala Ile Ser Val Asp Thr Ser Lys Asn Gln Phe
225                 230                 235                 240

Ser Leu Arg Leu Asn Ser Val Thr Ala Ala Asp Thr Ala Ile Tyr Tyr
            245                 250                 255

Cys Thr Ser Arg Ile Arg Ser His Ile Ala Tyr Ser Trp Lys Gly Asp
            260                 265                 270

Val Trp Gly Lys Gly Thr Thr Val Thr Val Ser Ser Gly Gly Gly Gly
            275                 280                 285

Ser Gly Gly Gly Gly Ser Gly Gly Gly Gly Ser Glu Ile Val Met Thr
            290                 295                 300

Gln Ser Pro Gly Thr Leu Ser Leu Ser Pro Gly Glu Arg Ala Thr Leu
305                 310                 315                 320

Ser Cys Arg Ala Ser Gln Ser Val Pro Arg Asn Tyr Ile Gly Trp Phe
            325                 330                 335

Gln Gln Lys Pro Gly Gln Ala Pro Arg Leu Leu Ile Tyr Gly Ala Ser
            340                 345                 350

Ser Arg Ala Ala Gly Phe Pro Asp Arg Phe Ser Gly Ser Gly Ser Gly
            355                 360                 365

Thr Asp Phe Thr Leu Thr Ile Thr Arg Leu Glu Pro Glu Asp Phe Ala
            370                 375                 380

Met Tyr Tyr Cys His Gln Tyr Asp Arg Leu Pro Tyr Thr Phe Gly Gln
385                 390                 395                 400

Gly Thr Lys Leu Glu Ile Lys Gly Gly Gly Gly Ser Gly Gly Gly Gly
            405                 410                 415

Ser Gly Gly Gly Gly Ser Thr Asp Gln Cys Asp Asn Phe Pro Gln Met
            420                 425                 430

Leu Arg Asp Leu Arg Asp Ala Phe Ser Arg Val Lys Thr Phe Phe Gln
            435                 440                 445

Thr Lys Asp Glu Leu Asp Asn Leu Leu Leu Lys Glu Ser Leu Leu Glu
            450                 455                 460

Asp Phe Lys Gly Tyr Leu Gly Cys Gln Ala Leu Ser Glu Met Ile Gln
465                 470                 475                 480

Phe Tyr Leu Glu Glu Val Met Pro Gln Ala Glu Asn Gln Asp Pro Glu
            485                 490                 495

Ile Lys Asp His Val Asn Ser Leu Gly Glu Asn Leu Lys Thr Leu Arg
            500                 505                 510

Leu Arg Leu Arg Arg Cys His Arg Phe Leu Pro Cys Glu Asn Lys Ser
            515                 520                 525

Lys Ala Val Glu Gln Ile Lys Asn Ala Phe Asn Lys Leu Gln Glu Lys
            530                 535                 540

Gly Ile Tyr Lys Ala Met Ser Glu Phe Asp Ile Phe Ile Asn Tyr Ile
545                 550                 555                 560

Glu Ala Tyr Met Thr Ile Lys Ala Arg
            565

<210> SEQ ID NO 26
<211> LENGTH: 563
<212> TYPE: PRT
<213> ORGANISM: Artificial Sequence
<220> FEATURE:

<223> OTHER INFORMATION: DV07 EboEGFL3

<400> SEQUENCE: 26

```
Thr Asp Gln Cys As

Lys Gly Gly Gly Gly Ser Gly Gly Gly Ser Gly Gly Gly Ser
            405             410             415

Thr Asp Gln Cys Asp Asn Phe Pro Gln Met Leu Arg Asp Leu Arg Asp
            420             425             430

Ala Phe Ser Arg Val Lys Thr Phe Phe Gln Thr Lys Asp Glu Leu Asp
        435                 440             445

Asn Leu Leu Leu Lys Glu Ser Leu Leu Glu Asp Phe Lys Gly Tyr Leu
450                 455                 460

Gly Cys Gln Ala Leu Ser Glu Met Ile Gln Phe Tyr Leu Glu Glu Val
465                 470                 475                 480

Met Pro Gln Ala Glu Asn Gln Asp Pro Glu Ile Lys Asp His Val Asn
            485             490                 495

Ser Leu Gly Glu Asn Leu Lys Thr Leu Arg Leu Arg Leu Arg Arg Cys
            500             505             510

His Arg Phe Leu Pro Cys Glu Asn Lys Ser Lys Ala Val Glu Gln Ile
            515             520             525

Lys Asn Ala Phe Asn Lys Leu Gln Glu Lys Gly Ile Tyr Lys Ala Met
            530             535             540

Ser Glu Phe Asp Ile Phe Ile Asn Tyr Ile Glu Ala Tyr Met Thr Ile
545                 550             555                 560

Lys Ala Arg

<210> SEQ ID NO 27
<211> LENGTH: 565
<212> TYPE: PRT
<213> ORGANISM: Artificial Sequence
<220> FEATURE:
<223> OTHER INFORMATION: DEboegfrDV07 Variant 1 Amino Acid Sequence

<400> SEQUENCE: 27

Thr Asp Gln Cys Asp Asn Phe Pro Gln Met Leu Arg Asp Leu Arg Asp
1               5                   10                  15

Ala Phe Ser Arg Val Lys Thr Phe Phe Gln Thr Lys Asp Glu Leu Asp
            20                  25                  30

Asn Leu Leu Leu Lys Glu Ser Leu Leu Glu Asp Phe Lys Gly Tyr Leu
        35                  40                  45

Gly Cys Gln Ala Leu Ser Glu Met Ile Gln Phe Tyr Leu Glu Glu Val
    50                  55                  60

Met Pro Gln Ala Glu Asn Gln Asp Pro Glu Ile Lys Asp His Val Asn
65                  70                  75                  80

Ser Leu Gly Glu Asn Leu Lys Thr Leu Arg Leu Arg Leu Arg Arg Cys
                85                  90                  95

His Arg Phe Leu Pro Cys Glu Asn Lys Ser Lys Ala Val Glu Gln Ile
            100                 105                 110

Lys Asn Ala Phe Asn Lys Leu Gln Glu Lys Gly Ile Tyr Lys Ala Met
        115                 120                 125

Ser Glu Phe Asp Ile Phe Ile Asn Tyr Ile Glu Ala Tyr Met Thr Ile
    130                 135                 140

Lys Ala Arg Gly Gly Gly Ser Gly Gly Gly Gly Ser Gly Gly Gly Gly
145                 150                 155                 160

Gly Ser Gln Val Gln Leu Gln Gln Trp Gly Ala Gly Leu Leu Lys Pro
                165                 170                 175

Ser Glu Thr Leu Ser Leu Thr Cys Ala Val Ser Gly Phe Ser Leu Thr
            180                 185                 190

Asn Tyr Gly Val Asn Trp Ile Arg Gln Pro Pro Gly Lys Gly Leu Glu
            195                 200                 205

Trp Ile Gly Val Ile Trp Ser Gly Gly Asn Thr Asp Tyr Asn Pro Ser
    210                 215                 220

Leu Lys Gly Arg Val Ala Ile Ser Val Asp Thr Ser Lys Asn Gln Phe
225                 230                 235                 240

Ser Leu Arg Leu Asn Ser Val Thr Ala Ala Asp Thr Ala Ile Tyr Tyr
                245                 250                 255

Cys Ala Arg Ala Leu Thr Tyr Tyr Asp Tyr Glu Phe Ala Tyr Trp Gly
            260                 265                 270

Lys Gly Thr Thr Val Thr Val Ser Ser Gly Gly Gly Ser Gly Gly
            275                 280                 285

Gly Gly Ser Gly Gly Gly Ser Glu Ile Val Met Thr Gln Ser Pro
290                 295                 300

Gly Thr Leu Ser Leu Ser Pro Gly Glu Arg Ala Thr Leu Ser Cys Arg
305                 310                 315                 320

Ala Ser Gln Ser Ile Gly Thr Asn Ile Gly Trp Phe Gln Gln Lys Pro
                325                 330                 335

Gly Gln Ala Pro Arg Leu Leu Ile Lys Tyr Ala Ser Glu Arg Ala Ala
            340                 345                 350

Gly Phe Pro Asp Arg Phe Ser Gly Ser Gly Ser Gly Thr Asp Phe Thr
            355                 360                 365

Leu Thr Ile Thr Arg Leu Glu Pro Glu Asp Phe Ala Met Tyr Tyr Cys
    370                 375                 380

Gln Gln Asn Asn Asn Trp Pro Thr Thr Phe Gly Gln Gly Thr Lys Leu
385                 390                 395                 400

Glu Ile Lys Gly Gly Gly Gly Ser Gly Gly Gly Gly Ser Gly Gly Gly
                405                 410                 415

Gly Ser Thr Asp Gln Cys Asp Asn Phe Pro Gln Met Leu Arg Asp Leu
            420                 425                 430

Arg Asp Ala Phe Ser Arg Val Lys Thr Phe Phe Gln Thr Lys Asp Glu
            435                 440                 445

Leu Asp Asn Leu Leu Leu Lys Glu Ser Leu Leu Glu Asp Phe Lys Gly
    450                 455                 460

Tyr Leu Gly Cys Gln Ala Leu Ser Glu Met Ile Gln Phe Tyr Leu Glu
465                 470                 475                 480

Glu Val Met Pro Gln Ala Glu Asn Gln Asp Pro Glu Ile Lys Asp His
                485                 490                 495

Val Asn Ser Leu Gly Glu Asn Leu Lys Thr Leu Arg Leu Arg Leu Arg
            500                 505                 510

Arg Cys His Arg Phe Leu Pro Cys Glu Asn Lys Ser Lys Ala Val Glu
            515                 520                 525

Gln Ile Lys Asn Ala Phe Asn Lys Leu Gln Glu Lys Gly Ile Tyr Lys
    530                 535                 540

Ala Met Ser Glu Phe Asp Ile Phe Ile Asn Tyr Ile Glu Ala Tyr Met
545                 550                 555                 560

Thr Ile Lys Ala Arg
            565

<210> SEQ ID NO 28
<211> LENGTH: 1698
<212> TYPE: DNA
<213> ORGANISM: Artificial Sequence
<220> FEATURE:

<223> OTHER INFORMATION: DEboegfrDV07 Variant 1 Nucleic Acid Sequence

<400> SEQUENCE: 28

```
accgaccagt gcgacaactt ccctcagatg ctgcgggacc tgagagatgc cttctccaga    60
gtgaaaacat tcttccagac caaggacgag ctggacaacc tgctgctgaa agagtccctg   120
ctggaagatt tcaagggcta cctgggctgt caggccctgt ccgagatgat ccagttctac   180
ctggaagaag tgatgcccca ggccgagaat caggaccccg agatcaagga ccacgtgaac   240
tccctgggcg agaacctgaa aaccctgcgg ctgagactgc ggcggtgcca cagatttctg   300
ccctgcgaga caagtccaa ggccgtggaa cagatcaaga acgccttcaa caagctgcaa   360
gagaagggca tctacaaggc catgagcgag ttcgacatct tcatcaacta catcgaggcc   420
tacatgacca tcaaggccag aggcggcgga ggatctggcg aggtggaag cggaggcggt   480
ggatctcagg ttcagttgca gcaatggggc gctggcctgc tgaagccttc tgagacactg   540
tctctgacct gcgccgtgtc cggcttctct ctgaccaatt acggcgtgaa ctggattcgg   600
cagcctcctg gcaaaggcct ggaatggatc ggagtgattt ggagcggcgg caacaccgac   660
tacaaccccca gtctgaaggg cagagtggcc atctccgtgg acacctccaa gaaccagttc   720
tccctgagac tgaactccgt gaccgccgct gataccgcca tctactactg tgctagagcc   780
ctgacctact acgactacga gttcgcctat ggggcaaggg gcaccaccgt gactgttagt   840
agtggtggtg gcgtagtgg cggaggcggc tcaggcggtg gtggatctga atcgtgatg    900
acccagtctc ctggcactct gtctctgtct cccggcgaga gagctaccct gtcttgtaga   960
gcctctcagt ccatcggcac caacatcggc tggttccagc agaagcctgg acaggctccc  1020
cggctgctga ttaagtacgc ctctgagaga ccgctggct tccctgacag attctccggc  1080
tctggctctg gcaccgactt caccctgacc atcaccagac tggaacccga ggacttcgct  1140
atgtactact gccagcagaa caacaactgg cccaccacct ttggccaggg caccaagctg  1200
gaaatcaaag gtggcggtgg ttcaggtggc ggaggaagcg gcggaggcgg atctacagat  1260
cagtgtgaca ttttcccca aatgctgagg gatctgcggg acgccttcag ccgggtcaag  1320
acattttttc agacaaagga tgaactcgat aacctcttgc tcaaagagag cctgctcgag  1380
gactttaagg gatatctggg atgccaggct ctgagcgaaa tgattcagtt ttatctcgag  1440
gaagtcatgc ctcaagcaga gaaccaggat ccagagatta aggatcatgt gaatagcctc  1500
ggggagaacc tcaagacact gagactccgg ctgagaagat gccaccggtt tctgccttgt  1560
gaaaacaaaa gcaaggctgt cgagcagatt aagaatgctt ttaacaaact ccaagaaaaa  1620
gggatctata aggctatgtc tgagtttgat atctttatca attatatcga agcttatatg  1680
actattaagg cccggtag                                                1698
```

<210> SEQ ID NO 29
<211> LENGTH: 565
<212> TYPE: PRT
<213> ORGANISM: Artificial Sequence
<220> FEATURE:
<223> OTHER INFORMATION: DEboegfrDV07 Variant 2 Amino Acid Sequence

<400> SEQUENCE: 29

Thr Asp Gln Cys Asp Asn Phe Pro Gln Met Leu Arg Asp Leu Arg Asp
1               5                   10                  15

Ala Phe Ser Arg Val Lys Thr Phe Phe Gln Thr Lys Asp Glu Leu Asp
            20                  25                  30

Asn Leu Leu Leu Lys Glu Ser Leu Leu Glu Asp Phe Lys Gly Tyr Leu
          35                  40                  45

Gly Cys Gln Ala Leu Ser Glu Met Ile Gln Phe Tyr Leu Glu Glu Val
    50                  55                  60

Met Pro Gln Ala Glu Asn Gln Asp Pro Glu Ile Lys Asp His Val Asn
65                  70                  75                  80

Ser Leu Gly Glu Asn Leu Lys Thr Leu Arg Leu Arg Leu Arg Arg Cys
                85                  90                  95

His Arg Phe Leu Pro Cys Glu Asn Lys Ser Lys Ala Val Glu Gln Ile
            100                 105                 110

Lys Asn Ala Phe Asn Lys Leu Gln Glu Lys Gly Ile Tyr Lys Ala Met
            115                 120                 125

Ser Glu Phe Asp Ile Phe Ile Asn Tyr Ile Glu Ala Tyr Met Thr Ile
            130                 135                 140

Lys Ala Arg Gly Gly Gly Ser Gly Gly Gly Ser Gly Gly Gly
145                 150                 155                 160

Gly Ser Gln Val Gln Leu Gln Gln Trp Gly Ala Gly Leu Leu Lys Pro
                165                 170                 175

Ser Glu Thr Leu Ser Leu Thr Cys Ala Val Tyr Gly Phe Ser Leu Thr
            180                 185                 190

Asn Tyr Gly Val His Trp Ile Arg Gln Pro Pro Gly Lys Gly Leu Glu
            195                 200                 205

Trp Ile Gly Val Ile Trp Ser Gly Gly Asn Thr Asp Tyr Asn Thr Pro
210                 215                 220

Phe Thr Ser Arg Val Ala Ile Ser Val Asp Thr Ser Lys Asn Gln Phe
225                 230                 235                 240

Ser Leu Arg Leu Asn Ser Val Thr Ala Ala Asp Thr Ala Ile Tyr Tyr
            245                 250                 255

Cys Thr Ser Ala Leu Thr Tyr Tyr Asp Tyr Glu Phe Ala Tyr Trp Gly
            260                 265                 270

Lys Gly Thr Thr Val Thr Val Ser Ser Gly Gly Gly Ser Gly Gly
            275                 280                 285

Gly Gly Ser Gly Gly Gly Ser Glu Ile Val Met Thr Gln Ser Pro
290                 295                 300

Gly Thr Leu Ser Leu Ser Pro Gly Glu Arg Ala Thr Leu Ser Cys Arg
305                 310                 315                 320

Ala Ser Gln Ser Ile Gly Thr Asn Ile His Trp Phe Gln Gln Lys Pro
            325                 330                 335

Gly Gln Ala Pro Arg Leu Leu Ile Tyr Tyr Ala Ser Glu Ser Ile Ser
            340                 345                 350

Gly Phe Pro Asp Arg Phe Ser Gly Ser Gly Ser Gly Thr Asp Phe Thr
            355                 360                 365

Leu Thr Ile Thr Arg Leu Glu Pro Glu Asp Phe Ala Met Tyr Tyr Cys
    370                 375                 380

Gln Gln Asn Asn Asn Trp Pro Thr Thr Phe Gly Gln Gly Thr Lys Leu
385                 390                 395                 400

Glu Ile Lys Gly Gly Gly Gly Ser Gly Gly Gly Gly Ser Gly Gly Gly
            405                 410                 415

Gly Ser Thr Asp Gln Cys Asp Asn Phe Pro Gln Met Leu Arg Asp Leu
            420                 425                 430

Arg Asp Ala Phe Ser Arg Val Lys Thr Phe Phe Gln Thr Lys Asp Glu
            435                 440                 445

```
Leu Asp Asn Leu Leu Leu Lys Glu Ser Leu Leu Glu Asp Phe Lys Gly
    450                 455                 460

Tyr Leu Gly Cys Gln Ala Leu Ser Glu Met Ile Gln Phe Tyr Leu Glu
465                 470                 475                 480

Glu Val Met Pro Gln Ala Glu Asn Gln Asp Pro Glu Ile Lys Asp His
                485                 490                 495

Val Asn Ser Leu Gly Glu Asn Leu Lys Thr Leu Arg Leu Arg Leu Arg
            500                 505                 510

Arg Cys His Arg Phe Leu Pro Cys Glu Asn Lys Ser Lys Ala Val Glu
        515                 520                 525

Gln Ile Lys Asn Ala Phe Asn Lys Leu Gln Glu Lys Gly Ile Tyr Lys
    530                 535                 540

Ala Met Ser Glu Phe Asp Ile Phe Ile Asn Tyr Ile Glu Ala Tyr Met
545                 550                 555                 560

Thr Ile Lys Ala Arg
                565

<210> SEQ ID NO 30
<211> LENGTH: 1770
<212> TYPE: DNA
<213> ORGANISM: Artificial Sequence
<220> FEATURE:
<223> OTHER INFORMATION: DEboegfrDV07 Variant 2 Nucleic Acid Sequence

<400> SEQUENCE: 30
gctagcgccg ccaccatggg atggtctttg atcctgctgt tcctggtggc cgtggctacc      60
agagtgcatt ctaccgacca gtgcgacaac ttccctcaga tgctgcggga cctgagagat     120
gccttctcca gagtgaaaac attcttccag accaaggacg agctggacaa cctgctgctg     180
aaagagtccc tgctggaaga tttcaagggc tacctgggct gtcaggccct gtccgagatg     240
atccagttct acctggaaga agtgatgccc caggccgaga tcaggacccc gagatcaag     300
gaccacgtga actccctggg cgagaacctg aaaaccctgc ggctgagact gcggcggtgc     360
cacagatttc tgccctgcga gaacaagtcc aaggccgtgg aacagatcaa gaacgccttc     420
aacaagctgc aagagaaggg catctacaag gccatgagcg agttcgacat cttcatcaac     480
tacatcgagg cctacatgac catcaaggcc agaggcggcg aggatctgg cggaggtgga     540
agcggaggcg gtggatctca ggttcagttg cagcaatggg gcgctggcct gctgaagcct     600
tctgagacac tgtctctgac ctgcgccgtg tacggcttct ccctgaccaa ttatggcgtg     660
cactggatca gacagcctcc aggcaaaggc ctggaatgga tcggagtgat ttggagcggc     720
ggcaacaccg actacaacac ccctttcacc tctagagtgg ccatctccgt ggacacctcc     780
aagaaccagt tcagcctgag actgaactcc gtgaccgccg ctgataccgc catctactac     840
tgcaccctccg ctctgaccta ctacgactac gagttcgcct actggggcaa gggcaccaca     900
gtgactgtta gtagtggtgg cggaggtagc ggtggtggtg gtagtggcgg tggcggatct     960
gagatcgtga tgacccaatc tcctggcact ctgtctctgt ccccggcga gagagctacc    1020
ctgtcttgta gagcctctca gtccatcggc accaacatcc actggttcca gcagaagcct    1080
ggacaggccc ctagactgct gatctactac gcctccgaga gcatcagcgg cttccctgac    1140
agattctccg gctctggctc tggcaccgac ttcaccctga caatcacccg gctggaacct    1200
gaggacttcg ctatgtacta ctgccagcag aacaacaact ggcccaccac ctttggccag    1260
ggcaccaagc tggaaatcaa aggcggaggc ggcagtggcg cggtggctc cggcggaggc    1320
ggatctacag atcagtgtga caattttccc caaatgctga gggatctgcg ggacgccttc    1380
```

```
agccgggtca agacattttt tcagacaaag gatgaactcg ataacctctt gctcaaagag    1440
agcctgctcg aggacttcaa aggatatctg ggatgccagg ctctgagcga aatgattcag    1500
ttttatctcg aggaagtcat gccacaagca gagaaccagg atccagagat taaggatcat    1560
gtgaatagcc tcggggagaa cctcaagaca ctgagactcc ggctgagaag atgccaccgg    1620
tttctgcctt gtgaaaacaa aagcaaggct gtcgagcaga ttaagaatgc ttttaacaaa    1680
ctccaagaaa aagggatcta taaggctatg tctgagtttg atatctttat caattatatc    1740
gaagcttata tgactattaa ggcccggtag                                     1770
```

<210> SEQ ID NO 31
<211> LENGTH: 565
<212> TYPE: PRT
<213> ORGANISM: Artificial Sequence
<220> FEATURE:
<223> OTHER INFORMATION: DEboegfrDV07 Variant 3 (SLP) Amino Acid Sequence

<400> SEQUENCE: 31

```
Thr Asp Gln Cys Asp Asn Phe Pro Gln Met Leu Arg Asp Leu Arg Asp
1               5                  10                  15

Ala Phe Ser Arg Val Lys Thr Phe Phe Gln Thr Lys Asp Glu Leu Asp
            20                  25                  30

Asn Leu Leu Leu Lys Glu Ser Leu Leu Glu Asp Phe Lys Gly Tyr Leu
        35                  40                  45

Gly Cys Gln Ala Leu Ser Glu Met Ile Gln Phe Tyr Leu Glu Glu Val
    50                  55                  60

Met Pro Gln Ala Glu Asn Gln Asp Pro Glu Ile Lys Asp His Val Asn
65                  70                  75                  80

Ser Leu Gly Glu Asn Leu Lys Thr Leu Arg Leu Arg Leu Arg Arg Cys
                85                  90                  95

His Arg Phe Leu Pro Cys Glu Asn Lys Ser Lys Ala Val Glu Gln Ile
            100                 105                 110

Lys Asn Ala Phe Asn Lys Leu Gln Glu Lys Gly Ile Tyr Lys Ala Met
        115                 120                 125

Ser Glu Phe Asp Ile Phe Ile Asn Tyr Ile Glu Ala Tyr Met Thr Ile
    130                 135                 140

Lys Ala Arg Gly Gly Gly Ser Gly Gly Gly Ser Gly Gly Gly
145                 150                 155                 160

Gly Ser Gln Val Gln Leu Gln Gln Trp Gly Ala Gly Leu Leu Lys Pro
                165                 170                 175

Ser Glu Thr Leu Ser Leu Thr Cys Ala Val Tyr Gly Phe Ser Leu Thr
            180                 185                 190

Asn Tyr Gly Val His Trp Ile Arg Gln Pro Pro Gly Lys Gly Leu Glu
        195                 200                 205

Trp Leu Gly Val Ile Trp Ser Gly Gly Asn Thr Asp Tyr Asn Thr Pro
    210                 215                 220

Phe Thr Ser Arg Val Ala Ile Ser Lys Asp Asn Ser Lys Asn Gln Val
225                 230                 235                 240

Ser Leu Arg Leu Asn Ser Val Thr Ala Ala Asp Thr Ala Ile Tyr Tyr
                245                 250                 255

Cys Ala Arg Ala Leu Thr Tyr Tyr Asp Tyr Glu Phe Ala Tyr Trp Gly
            260                 265                 270

Lys Gly Thr Thr Val Thr Val Ser Ser Gly Gly Gly Gly Ser Gly Gly
        275                 280                 285
```

Gly Ser Gly Gly Gly Ser Glu Ile Val Leu Thr Gln Ser Pro
            290                 295                 300

Gly Thr Leu Ser Leu Ser Pro Gly Glu Arg Ala Thr Leu Ser Cys Arg
305                 310                 315                 320

Ala Ser Gln Ser Ile Gly Thr Asn Ile His Trp Tyr Gln Gln Lys Pro
                325                 330                 335

Gly Gln Ala Pro Arg Leu Leu Ile Lys Tyr Ala Ser Glu Ser Ile Ser
            340                 345                 350

Gly Phe Pro Asp Arg Phe Ser Gly Ser Gly Ser Gly Thr Asp Phe Thr
        355                 360                 365

Leu Thr Ile Thr Arg Leu Glu Pro Glu Asp Phe Ala Met Tyr Tyr Cys
370                 375                 380

Gln Gln Asn Asn Asn Trp Pro Thr Thr Phe Gly Gln Gly Thr Lys Leu
385                 390                 395                 400

Glu Ile Lys Gly Gly Gly Gly Ser Gly Gly Gly Gly Ser Gly Gly Gly
                405                 410                 415

Gly Ser Thr Asp Gln Cys Asp Asn Phe Pro Gln Met Leu Arg Asp Leu
            420                 425                 430

Arg Asp Ala Phe Ser Arg Val Lys Thr Phe Phe Gln Thr Lys Asp Glu
        435                 440                 445

Leu Asp Asn Leu Leu Leu Lys Glu Ser Leu Leu Glu Asp Phe Lys Gly
450                 455                 460

Tyr Leu Gly Cys Gln Ala Leu Ser Glu Met Ile Gln Phe Tyr Leu Glu
465                 470                 475                 480

Glu Val Met Pro Gln Ala Glu Asn Gln Asp Pro Glu Ile Lys Asp His
                485                 490                 495

Val Asn Ser Leu Gly Glu Asn Leu Lys Thr Leu Arg Leu Arg Leu Arg
            500                 505                 510

Arg Cys His Arg Phe Leu Pro Cys Glu Asn Lys Ser Lys Ala Val Glu
        515                 520                 525

Gln Ile Lys Asn Ala Phe Asn Lys Leu Gln Glu Lys Gly Ile Tyr Lys
530                 535                 540

Ala Met Ser Glu Phe Asp Ile Phe Ile Asn Tyr Ile Glu Ala Tyr Met
545                 550                 555                 560

Thr Ile Lys Ala Arg
                565

<210> SEQ ID NO 32
<211> LENGTH: 1698
<212> TYPE: DNA
<213> ORGANISM: Artificial Sequence
<220> FEATURE:
<223> OTHER INFORMATION: DEboegfrDV07 Variant 3 (SLP) Nucleic Acid
      Sequence

<400> SEQUENCE: 32
accgaccagt gcgacaactt ccctcagatg ctgcgggacc tgagagatgc cttctccaga     60
gtgaaaacat tcttccagac caaggacgag ctggacaacc tgctgctgaa agagtccctg    120
ctggaagatt tcaagggcta cctgggctgt caggccctgt ccgagatgat ccagttctac    180
ctggaagaag tgatgcccca ggccgagaat caggaccccg agatcaagga ccacgtgaac    240
tccctgggcg agaacctgaa aaccctgcgg ctgagactgc ggcggtgcca cagatttctg    300
ccctgcgaga caagtccaa ggccgtggaa cagatcaaga cgccttcaa caagctgcaa    360 gagaagggca tctacaaggc catgagcgag ttcgacatct catcaacta catcgaggcc    420

```
tacatgacca tcaaggccag aggcggcgga ggatctggcg gaggtggaag cggaggcggt      480
ggatctcagg ttcagttgca gcaatggggc gctggcctgc tgaagccttc tgagacactg      540
tctctgacct gcgccgtgta cggcttctcc ctgaccaatt atggcgtgca ctggatcaga      600
cagcctccag gcaaaggcct ggaatggctg ggagtgattt ggagcggcgg caacaccgac      660
tacaacaccc ctttcacctc tagagtggcc atctccaagg acaactccaa gaaccaggtg      720
tccctgagac tgaactccgt gaccgctgcc gataccgcca tctactactg tgctagagcc      780
ctgacctact acgactacga gttcgcctat ggggcaaggg caccaccgt gactgttagt      840 agtggtggtg gcgtagtgg cggaggcggc tcaggcggtg gtggatctga aattgtgctg      900
acccagtctc ctggcactct gtctttgagc cctggcgaga gctacccct gtcctgtaga      960 gcctctcagt ccatcggcac caacatccac tggtatcagc agaagcctgg acaggcccct     1020
cggctgctga ttaagtacgc ctccgagtcc atcagcggct ccctgacag attctccggc     1080 tctggctctg gcaccgactt cacccctgaca atcaccccgg ctggaacctga ggacttcgct     1140 atgtactact gccagcagaa caacaactgg cccaccacct ttggccaggg caccaagctg     1200
gaaatcaaag gtggcggtgg ttcaggtggc ggaggaagcg gcggaggcgg atctacagat     1260
cagtgtgaca attttccca atgctgagg gatctgcggg acgccttcag ccgggtcaag     1320 acatttttc agacaaagga tgaactcgat aacctcttgc tcaaagagag cctgctcgag     1380
gacttcaaag gatatctggg atgccaggct ctgagcgaaa tgattcagtt ttatctcgag     1440
gaagtcatgc ctcaagcaga gaaccaggat ccagagatta aggatcatgt gaatagcctc     1500
ggggagaacc tcaagacact gagactccgg ctgagaagat gccaccggtt tctgccttgt     1560
gaaaacaaaa gcaaggctgt cgagcagatt aagaatgctt taacaaatt gcaagaaaaa     1620 gggatctata aggctatgtc tgagtttgat atctttatca attatatcga agcttatatg     1680
actattaagg cccggtag                                                   1698
```

<210> SEQ ID NO 33
<211> LENGTH: 565
<212> TYPE: PRT
<213> ORGANISM: Artificial Sequence
<220> FEATURE:
<223> OTHER INFORMATION: DEboegfrDV07 Variant 4 Amino Acid Sequence

<400> SEQUENCE: 33

Thr Asp Gln Cys Asp Asn Phe Pro Gln Met Leu Arg Asp Leu Arg Asp
1               5                   10                  15

Ala Phe Ser Arg Val Lys Thr Phe Phe Gln Thr Lys Asp Glu Leu Asp
            20                  25                  30

Asn Leu Leu Leu Lys Glu Ser Leu Leu Glu Asp Phe Lys Gly Tyr Leu
        35                  40                  45

Gly Cys Gln Ala Leu Ser Glu Met Ile Gln Phe Tyr Leu Glu Glu Val
    50                  55                  60

Met Pro Gln Ala Glu Asn Gln Asp Pro Glu Ile Lys Asp His Val Asn
65                  70                  75                  80

Ser Leu Gly Glu Asn Leu Lys Thr Leu Arg Leu Arg Leu Arg Arg Cys
                85                  90                  95

His Arg Phe Leu Pro Cys Glu Asn Lys Ser Lys Ala Val Glu Gln Ile
            100                 105                 110

Lys Asn Ala Phe Asn Lys Leu Gln Glu Lys Gly Ile Tyr Lys Ala Met
        115                 120                 125

```
Ser Glu Phe Asp Ile Phe Ile Asn Tyr Ile Glu Ala Tyr Met Thr Ile
    130                 135                 140

Lys Ala Arg Gly Gly Gly Ser Gly Gly Gly Ser Gly Gly Gly
145                 150                 155                 160

Gly Ser Gln Val Gln Leu Gln Gln Trp Gly Ala Gly Leu Leu Lys Pro
                165                 170                 175

Ser Glu Thr Leu Ser Leu Thr Cys Thr Val Ser Gly Phe Ser Leu Thr
                180                 185                 190

Asn Tyr Gly Val His Trp Val Arg Gln Pro Pro Gly Lys Gly Leu Glu
        195                 200                 205

Trp Leu Gly Val Ile Trp Ser Gly Gly Asn Thr Asp Tyr Asn Thr Pro
    210                 215                 220

Phe Thr Ser Arg Val Ala Ile Ser Lys Asp Asn Ser Lys Asn Gln Val
225                 230                 235                 240

Ser Leu Arg Leu Asn Ser Val Thr Ala Ala Asp Thr Ala Ile Tyr Tyr
                245                 250                 255

Cys Ala Arg Ala Leu Thr Tyr Tyr Asp Tyr Glu Phe Ala Tyr Trp Gly
                260                 265                 270

Lys Gly Thr Thr Val Thr Val Ser Ser Gly Gly Gly Ser Gly Gly
                275                 280                 285

Gly Gly Ser Gly Gly Gly Ser Glu Ile Val Leu Thr Gln Ser Pro
    290                 295                 300

Gly Thr Leu Ser Leu Ser Pro Gly Glu Arg Ala Thr Leu Ser Cys Arg
305                 310                 315                 320

Ala Ser Gln Ser Ile Gly Thr Asn Ile His Trp Tyr Gln Gln Lys Pro
                325                 330                 335

Gly Gln Ala Pro Arg Leu Leu Ile Lys Tyr Ala Ser Glu Ser Ile Ser
                340                 345                 350

Gly Ile Pro Asp Arg Phe Ser Gly Ser Gly Ser Gly Thr Asp Phe Thr
                355                 360                 365

Leu Thr Ile Thr Arg Leu Glu Pro Glu Asp Phe Ala Asp Tyr Tyr Cys
    370                 375                 380

Gln Gln Asn Asn Asn Trp Pro Thr Thr Phe Gly Gln Gly Thr Lys Leu
385                 390                 395                 400

Glu Ile Lys Gly Gly Gly Gly Ser Gly Gly Gly Gly Ser Gly Gly Gly
                405                 410                 415

Gly Ser Thr Asp Gln Cys Asp Asn Phe Pro Gln Met Leu Arg Asp Leu
                420                 425                 430

Arg Asp Ala Phe Ser Arg Val Lys Thr Phe Phe Gln Thr Lys Asp Glu
                435                 440                 445

Leu Asp Asn Leu Leu Leu Lys Glu Ser Leu Leu Glu Asp Phe Lys Gly
                450                 455                 460

Tyr Leu Gly Cys Gln Ala Leu Ser Glu Met Ile Gln Phe Tyr Leu Glu
465                 470                 475                 480

Glu Val Met Pro Gln Ala Glu Asn Gln Asp Pro Glu Ile Lys Asp His
                485                 490                 495

Val Asn Ser Leu Gly Glu Asn Leu Lys Thr Leu Arg Leu Arg Leu Arg
                500                 505                 510

Arg Cys His Arg Phe Leu Pro Cys Glu Asn Lys Ser Lys Ala Val Glu
            515                 520                 525

Gln Ile Lys Asn Ala Phe Asn Lys Leu Gln Glu Lys Gly Ile Tyr Lys
                530                 535                 540
```

Ala Met Ser Glu Phe Asp Ile Phe Ile Asn Tyr Ile Glu Ala Tyr Met
545                 550                 555                 560

Thr Ile Lys Ala Arg
            565

<210> SEQ ID NO 34
<211> LENGTH: 1695
<212> TYPE: DNA
<213> ORGANISM: Artificial Sequence
<220> FEATURE:
<223> OTHER INFORMATION: DEboegfrDV07 Variant 4 Nucleic Acid Sequence

<400> SEQUENCE: 34

```
accgaccagt gcgacaactt ccctcagatg ctgcgggacc tgagagatgc cttctccaga     60
gtgaaaacat tcttccagac caaggacgag ctggacaacc tgctgctgaa agagtccctg    120
ctggaagatt tcaagggcta cctgggctgt caggccctgt ccgagatgat ccagttctac    180
ctggaagaag tgatgcccca ggccgagaat caggaccccg agatcaagga ccacgtgaac    240
tccctgggcg agaacctgaa acccctgcgg ctgagactgc ggcggtgcca cagatttctg    300
ccctgcgaga caagtccaa ggccgtggaa cagatcaaga cgccttcaa caagctgcaa    360
gagaagggca tctacaaggc catgagcgag ttcgacatct tcatcaacta catcgaggcc    420
tacatgacca tcaaggccag aggcggcgga ggatctggcg aggtggaag cggaggcggt    480
ggatctcagg ttcagttgca gcaatggggc gctggcctgc tgaagccttc tgagacactg    540
tctctgacct gcaccgtgtc cggcttctcc ctgaccaatt atggcgtgca ctgggtccga    600
cagcctccag gcaaaggatt ggaatggctg ggagtgattt ggagcggcgg caacaccgac    660
tacaacaccc ctttcacctc tagagtggcc atctccaagg acaactccaa gaaccaggtg    720
tccctgagac tgaactccgt gaccgctgcc gataccgcca tctactactg tgctagagcc    780
ctgacctact acgactacga gttcgcctat tgggggcaagg gcaccaccgt gactgttagt    840
agtggtggtg gcggtagtgg cggaggcggc tcaggcggtg gtggatctga aattgtgctg    900
acccagtctc ctggcactct gtctttgagc cctggcgaga gagctaccct gtcctgtaga    960
gcctctcagt ccatcggcac caacatccac tggtatcagc agaagcctgg acaggcccct   1020
cggctgctga ttaagtacgc ctccgagtcc atcagcggca tccctgacag attctccggc   1080
tctggctctg gcaccgactt caccctgaca atcacccggc tggaacctga ggacttcgcc   1140
gactactact gccagcagaa caacaactgg cccaccacct ttggccaggg caccaagctg   1200
gaaatcaaag gtggcggtgg ttcaggtggc ggaggaagcg gcggaggcgg atctacagat   1260
cagtgtgaca tttttcccca aatgctgagg gatctgcggg acgccttcag ccgggtcaag   1320
acatttttc agacaaagga tgaactcgat aacctcttgc tcaaagagag cctgctcgag   1380
gacttcaaag gatatctggg atgccaggct ctgagcgaaa tgattcagtt ttatctcgag   1440
gaagtcatgc ctcaagcaga gaccaggat ccagagatta aggatcatgt gaatagcctc   1500
ggggagaacc tcaagacact gagactccgg ctgagaagat gccaccggtt tctgccttgt   1560
gaaaacaaaa gcaaggctgt cgagcagatt aagaatgctt ttaacaaatt gcaagaaaaa   1620
gggatctata aggctatgtc tgagtttgat atctttatca attatatcga agcttatatg   1680
actattaagg cccgg                                                    1695
```

<210> SEQ ID NO 35
<211> LENGTH: 713
<212> TYPE: PRT

<213> ORGANISM: Artificial Sequence
<220> FEATURE:
<223> OTHER INFORMATION: DK210egfr Amino Acid Sequence

<400> SEQUENCE: 35

```
Thr Asp Gln Cys Asp Asn Phe Pro Gln Met Leu Arg Asp Leu Arg Asp
1               5                   10                  15

Ala Phe Ser Arg Val Lys Thr Phe Phe Gln Thr Lys Asp Glu Leu Asp
            20                  25                  30

Asn Leu Leu Leu Lys Glu Ser Leu Glu Asp Phe Lys Gly Tyr Leu
        35                  40                  45

Gly Cys Gln Ala Leu Ser Glu Met Ile Gln Phe Tyr Leu Glu Glu Val
    50                  55                  60

Met Pro Gln Ala Glu Asn Gln Asp Pro Glu Ile Lys Asp His Val Asn
65                  70                  75                  80

Ser Leu Gly Glu Asn Leu Lys Thr Leu Arg Leu Arg Leu Arg Arg Cys
                85                  90                  95

His Arg Phe Leu Pro Cys Glu Asn Lys Ser Lys Ala Val Glu Gln Ile
                100                 105                 110

Lys Asn Ala Phe Asn Lys Leu Gln Glu Lys Gly Ile Tyr Lys Ala Met
        115                 120                 125

Ser Glu Phe Asp Ile Phe Ile Asn Tyr Ile Glu Ala Tyr Met Thr Ile
130                 135                 140

Lys Ala Arg Gly Gly Gly Ser Gly Gly Gly Ser Gly Gly Gly
145                 150                 155                 160

Gly Ser Gln Val Gln Leu Gln Gln Trp Gly Ala Gly Leu Leu Lys Pro
                165                 170                 175

Ser Glu Thr Leu Ser Leu Thr Cys Ala Val Tyr Gly Phe Ser Leu Thr
            180                 185                 190

Asn Tyr Gly Val His Trp Ile Arg Gln Pro Pro Gly Lys Gly Leu Glu
        195                 200                 205

Trp Leu Gly Val Ile Trp Ser Gly Gly Asn Thr Asp Tyr Asn Thr Pro
    210                 215                 220

Phe Thr Ser Arg Val Ala Ile Ser Lys Asp Asn Ser Lys Asn Gln Val
225                 230                 235                 240

Ser Leu Arg Leu Asn Ser Val Thr Ala Ala Asp Thr Ala Ile Tyr Tyr
                245                 250                 255

Cys Ala Arg Ala Leu Thr Tyr Tyr Asp Tyr Glu Phe Ala Tyr Trp Gly
                260                 265                 270

Lys Gly Thr Thr Val Thr Val Ser Ser Gly Gly Gly Ser Gly Gly
        275                 280                 285

Gly Gly Ser Gly Gly Gly Ser Ala Pro Thr Ser Ser Ser Thr Lys
    290                 295                 300

Lys Thr Gln Leu Gln Leu Glu His Leu Leu Leu Asp Leu Gln Met Ile
305                 310                 315                 320

Leu Asn Gly Ile Asn Asn Tyr Lys Asn Pro Lys Leu Thr Arg Met Leu
                325                 330                 335

Thr Phe Lys Phe Tyr Met Pro Lys Lys Ala Thr Glu Leu Lys His Leu
            340                 345                 350

Gln Cys Leu Glu Glu Glu Leu Lys Pro Leu Glu Glu Val Leu Asn Leu
        355                 360                 365

Ala Gln Ser Lys Asn Phe His Leu Arg Pro Arg Asp Leu Ile Ser Asn
    370                 375                 380
```

Ile Asn Val Ile Val Leu Glu Leu Lys Gly Ser Glu Thr Thr Phe Met
385                 390                 395                 400

Cys Glu Tyr Ala Asp Glu Thr Ala Thr Ile Val Glu Phe Leu Asn Arg
                405                 410                 415

Trp Ile Thr Phe Cys Gln Ser Ile Ile Ser Thr Leu Thr Gly Gly Gly
            420                 425                 430

Gly Ser Gly Gly Gly Ser Gly Gly Gly Ser Glu Ile Val Leu
        435                 440                 445

Thr Gln Ser Pro Gly Thr Leu Ser Leu Ser Pro Gly Glu Arg Ala Thr
        450                 455                 460

Leu Ser Cys Arg Ala Ser Gln Ser Ile Gly Thr Asn Ile His Trp Tyr
465                 470                 475                 480

Gln Gln Lys Pro Gly Gln Ala Pro Arg Leu Leu Ile Lys Tyr Ala Ser
                485                 490                 495

Glu Ser Ile Ser Gly Phe Pro Asp Arg Phe Ser Gly Ser Gly Ser Gly
            500                 505                 510

Thr Asp Phe Thr Leu Thr Ile Thr Arg Leu Glu Pro Glu Asp Phe Ala
        515                 520                 525

Met Tyr Tyr Cys Gln Gln Asn Asn Asn Trp Pro Thr Thr Phe Gly Gln
530                 535                 540

Gly Thr Lys Leu Glu Ile Lys Gly Gly Gly Gly Ser Gly Gly Gly Gly
545                 550                 555                 560

Ser Gly Gly Gly Gly Ser Thr Asp Gln Cys Asp Asn Phe Pro Gln Met
                565                 570                 575

Leu Arg Asp Leu Arg Asp Ala Phe Ser Arg Val Lys Thr Phe Phe Gln
            580                 585                 590

Thr Lys Asp Glu Leu Asp Asn Leu Leu Leu Lys Glu Ser Leu Leu Glu
        595                 600                 605

Asp Phe Lys Gly Tyr Leu Gly Cys Gln Ala Leu Ser Glu Met Ile Gln
610                 615                 620

Phe Tyr Leu Glu Glu Val Met Pro Gln Ala Glu Asn Gln Asp Pro Glu
625                 630                 635                 640

Ile Lys Asp His Val Asn Ser Leu Gly Glu Asn Leu Lys Thr Leu Arg
                645                 650                 655

Leu Arg Leu Arg Arg Cys His Arg Phe Leu Pro Cys Glu Asn Lys Ser
            660                 665                 670

Lys Ala Val Glu Gln Ile Lys Asn Ala Phe Asn Lys Leu Gln Glu Lys
        675                 680                 685

Gly Ile Tyr Lys Ala Met Ser Glu Phe Asp Ile Phe Ile Asn Tyr Ile
        690                 695                 700

Glu Ala Tyr Met Thr Ile Lys Ala Arg
705                 710

<210> SEQ ID NO 36
<211> LENGTH: 133
<212> TYPE: PRT
<213> ORGANISM: Homo sapiens
<220> FEATURE:
<223> OTHER INFORMATION: Human IL-2 Amino Acid Sequence

<400> SEQUENCE: 36

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

```
Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
            130

<210> SEQ ID NO 37
<211> LENGTH: 119
<212> TYPE: PRT
<213> ORGANISM: Artificial Sequence
<220> FEATURE:
<223> OTHER INFORMATION: Modified VH region of anti-EGFR antibody

<400> SEQUENCE: 37

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Phe Ser Leu Thr Asn Tyr
            20                  25                  30

Gly Val His Trp Ile Arg Gln Pro Pro Gly Lys Gly Leu Glu Trp Leu
        35                  40                  45

Gly Val Ile Trp Ser Gly Gly Asn Thr Asp Tyr Asn Thr Pro Phe Thr
 50                  55                  60

Ser Arg Val Ala Ile Ser Lys Asp Asn Ser Lys Asn Gln Val Ser Leu
 65                  70                  75                  80

Arg Leu Asn Ser Val Thr Ala Ala Asp Thr Ala Ile Tyr Tyr Cys Ala
                 85                  90                  95

Arg Ala Leu Thr Tyr Tyr Asp Tyr Glu Phe Ala Tyr Trp Gly Lys Gly
                100                 105                 110

Thr Thr Val Thr Val Ser Ser
            115

<210> SEQ ID NO 38
<211> LENGTH: 107
<212> TYPE: PRT
<213> ORGANISM: Artificial Sequence
<220> FEATURE:
<223> OTHER INFORMATION: Modified VL region of anti-EGFR antibody

<400> SEQUENCE: 38

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Gly Thr Asn
            20                  25                  30

Ile His Trp Tyr Gln Gln Lys Pro Gly Gln Ala Pro Arg Leu Leu Ile
        35                  40                  45

Lys Tyr Ala Ser Glu Ser Ile Ser Gly Phe Pro Asp Arg Phe Ser Gly
 50                  55                  60
```

```
Ser Gly Ser Gly Thr Asp Phe Thr Leu Thr Ile Thr Arg Leu Glu Pro
 65                  70                  75                  80

Glu Asp Phe Ala Met Tyr Tyr Cys Gln Gln Asn Asn Asn Trp Pro Thr
                 85                  90                  95

Thr Phe Gly Gln Gly Thr Lys Leu Glu Ile Lys
            100                 105

<210> SEQ ID NO 39
<211> LENGTH: 7
<212> TYPE: PRT
<213> ORGANISM: Artificial Sequence
<220> FEATURE:
<223> OTHER INFORMATION: Artificial Sequence Linker 1

<400> SEQUENCE: 39

Ser Ser Gly Gly Gly Gly Ser
 1               5

<210> SEQ ID NO 40
<211> LENGTH: 15
<212> TYPE: PRT
<213> ORGANISM: Artificial Sequence
<220> FEATURE:
<223> OTHER INFORMATION: Artificial Sequence Linker 2

<400> SEQUENCE: 40

Gly Gly Gly Gly Ser Gly Gly Gly Gly Ser Gly Gly Gly Gly Ser
 1               5                  10                  15

<210> SEQ ID NO 41
<211> LENGTH: 17
<212> TYPE: PRT
<213> ORGANISM: Artificial Sequence
<220> FEATURE:
<223> OTHER INFORMATION: Artificial Sequence Linker 3

<400> SEQUENCE: 41

Ser Ser Gly Gly Gly Gly Ser Gly Gly Gly Gly Ser Gly Gly Gly Gly Ser
 1               5                  10                  15

<210> SEQ ID NO 42
<211> LENGTH: 6
<212> TYPE: PRT
<213> ORGANISM: Artificial Sequence
<220> FEATURE:
<223> OTHER INFORMATION: Artificial Sequence 6xHis tag

<400> SEQUENCE: 42

His His His His His His
 1               5

<210> SEQ ID NO 43
<211> LENGTH: 129
<212> TYPE: PRT
<213> ORGANISM: Homo sapiens
<220> FEATURE:
<223> OTHER INFORMATION: Human IL-4 Amino Acid Sequence

<400> SEQUENCE: 43

His Lys Cys Asp Ile Thr Leu Gln Glu Ile Ile Lys Thr Leu Asn Ser
 1               5                  10                  15

Leu Thr Glu Gln Lys Thr Leu Cys Thr Glu Leu Thr Val Thr Asp Ile
             20                  25                  30
```

```
Phe Ala Ala Ser Lys Asn Thr Thr Glu Lys Glu Thr Phe Cys Arg Ala
            35                  40                  45

Ala Thr Val Leu Arg Gln Phe Tyr Ser His His Glu Lys Asp Thr Arg
 50                  55                  60

Cys Leu Gly Ala Thr Ala Gln Gln Phe His Arg His Lys Gln Leu Ile
 65                  70                  75                  80

Arg Phe Leu Lys Arg Leu Asp Arg Asn Leu Trp Gly Leu Ala Gly Leu
                85                  90                  95

Asn Ser Cys Pro Val Lys Glu Ala Asn Gln Ser Thr Leu Glu Asn Phe
               100                 105                 110

Leu Glu Arg Leu Lys Thr Ile Met Arg Glu Lys Tyr Ser Lys Cys Ser
               115                 120                 125

Ser

<210> SEQ ID NO 44
<211> LENGTH: 129
<212> TYPE: PRT
<213> ORGANISM: Artificial Sequence
<220> FEATURE:
<223> OTHER INFORMATION: hIL4 (N38A)

<400> SEQUENCE: 44

His Lys Cys Asp Ile Thr Leu Gln Glu Ile Ile Lys Thr Leu Asn Ser
 1               5                  10                  15

Leu Thr Glu Gln Lys Thr Leu Cys Thr Glu Leu Thr Val Thr Asp Ile
                20                  25                  30

Phe Ala Ala Ser Lys Ala Thr Thr Glu Lys Glu Thr Phe Cys Arg Ala
            35                  40                  45

Ala Thr Val Leu Arg Gln Phe Tyr Ser His His Glu Lys Asp Thr Arg
 50                  55                  60

Cys Leu Gly Ala Thr Ala Gln Gln Phe His Arg His Lys Gln Leu Ile
 65                  70                  75                  80

Arg Phe Leu Lys Arg Leu Asp Arg Asn Leu Trp Gly Leu Ala Gly Leu
                85                  90                  95

Asn Ser Cys Pro Val Lys Glu Ala Asn Gln Ser Thr Leu Glu Asn Phe
               100                 105                 110

Leu Glu Arg Leu Lys Thr Ile Met Arg Glu Lys Tyr Ser Lys Cys Ser
               115                 120                 125

Ser

<210> SEQ ID NO 45
<211> LENGTH: 129
<212> TYPE: PRT
<213> ORGANISM: Artificial Sequence
<220> FEATURE:
<223> OTHER INFORMATION: hIL4 (T13D)

<400> SEQUENCE: 45

His Lys Cys Asp Ile Thr Leu Gln Glu Ile Ile Lys Asp Leu Asn Ser
 1               5                  10                  15

Leu Thr Glu Gln Lys Thr Leu Cys Thr Glu Leu Thr Val Thr Asp Ile
                20                  25                  30

Phe Ala Ala Ser Lys Ala Thr Thr Glu Lys Glu Thr Phe Cys Arg Ala
            35                  40                  45

Ala Thr Val Leu Arg Gln Phe Tyr Ser His His Glu Lys Asp Thr Arg
 50                  55                  60
```

```
Cys Leu Gly Ala Thr Ala Gln Gln Phe His Arg His Lys Gln Leu Ile
 65                  70                  75                  80

Arg Phe Leu Lys Arg Leu Asp Arg Asn Leu Trp Gly Leu Ala Gly Leu
                 85                  90                  95

Asn Ser Cys Pro Val Lys Glu Ala Asn Gln Ser Thr Leu Glu Asn Phe
            100                 105                 110

Leu Glu Arg Leu Lys Thr Ile Met Arg Glu Lys Tyr Ser Lys Cys Ser
        115                 120                 125

Ser

<210> SEQ ID NO 46
<211> LENGTH: 713
<212> TYPE: PRT
<213> ORGANISM: Artificial Sequence
<220> FEATURE:
<223> OTHER INFORMATION: DK410DV06 (non targeting)

<400> SEQUENCE: 46

Thr Asp Gln Cys Asp Asn Phe Pro Gln Met Leu Arg Asp Leu Arg Asp
  1               5                  10                  15

Ala Phe Ser Arg Val Lys Thr Phe Phe Gln Thr Lys Asp Glu Val Asp
                 20                  25                  30

Asn Leu Leu Leu Lys Glu Ser Leu Leu Glu Asp Phe Lys Gly Tyr Leu
             35                  40                  45

Gly Cys Gln Ala Leu Ser Glu Met Ile Gln Phe Tyr Leu Glu Glu Val
     50                  55                  60

Met Pro Gln Ala Glu Asn Gln Asp Pro Glu Ile Lys Asp His Val Asn
 65                  70                  75                  80

Ser Leu Gly Glu Asn Leu Lys Thr Leu Arg Leu Arg Leu Arg Arg Cys
                 85                  90                  95

His Arg Phe Leu Pro Cys Glu Asn Lys Ser Lys Ala Val Glu Gln Ile
            100                 105                 110

Lys Asn Ala Phe Asn Lys Leu Gln Glu Lys Gly Ile Tyr Lys Ala Met
        115                 120                 125

Ser Glu Phe Asp Ile Phe Ile Asn Tyr Ile Glu Ala Tyr Met Thr Ile
130                 135                 140

Lys Ala Arg Gly Gly Gly Gly Ser Gly Gly Gly Gly Ser Gly Gly Gly
145                 150                 155                 160

Gly Ser Gln Val Gln Leu Gln Gln Trp Gly Ala Gly Leu Leu Lys Pro
                165                 170                 175

Ser Glu Thr Leu Ser Leu Thr Cys Ala Val Tyr Gly Gly Ser Phe Thr
            180                 185                 190

Thr Thr Tyr Trp Asn Trp Ile Arg Gln Pro Pro Gly Lys Gly Leu Glu
        195                 200                 205

Trp Ile Gly Glu Val Asn Tyr Ser Gly Asn Ala Asn Tyr Asn Pro Ser
210                 215                 220

Leu Lys Gly Arg Val Ala Ile Ser Val Asp Thr Ser Lys Asn Gln Phe
225                 230                 235                 240

Ser Leu Arg Leu Asn Ser Val Thr Ala Ala Asp Thr Ala Ile Tyr Tyr
                245                 250                 255

Cys Thr Ser Arg Ile Arg Ser His Ile Ala Tyr Ser Trp Lys Gly Asp
            260                 265                 270

Val Trp Gly Lys Gly Thr Thr Val Thr Val Ser Ser Gly Gly Gly Gly
        275                 280                 285
```

```
Ser Gly Gly Gly Ser Gly Gly Gly Ser His Lys Cys Asp Ile
    290             295             300
Thr Leu Gln Glu Ile Ile Lys Thr Leu Asn Ser Leu Thr Glu Gln Lys
305                 310             315                 320
Thr Leu Cys Thr Glu Leu Thr Val Thr Asp Ile Phe Ala Ala Ser Lys
                325             330              335
Asn Thr Thr Glu Lys Glu Thr Phe Cys Arg Ala Ala Thr Val Leu Arg
                340             345             350
Gln Phe Tyr Ser His His Glu Lys Asp Thr Arg Cys Leu Gly Ala Thr
            355             360             365
Ala Gln Gln Phe His Arg His Lys Gln Leu Ile Arg Phe Leu Lys Arg
    370             375             380
Leu Asp Arg Asn Leu Trp Gly Leu Ala Gly Leu Asn Ser Cys Pro Val
385             390             395             400
Lys Glu Ala Asn Gln Ser Thr Leu Glu Asn Phe Leu Glu Arg Leu Lys
                405             410             415
Thr Ile Met Arg Glu Lys Tyr Ser Lys Cys Ser Ser Gly Gly Gly Gly
            420             425             430
Ser Gly Gly Gly Gly Ser Gly Gly Gly Gly Ser Glu Ile Val Met Thr
    435             440             445
Gln Ser Pro Gly Thr Leu Ser Leu Ser Pro Gly Glu Arg Ala Thr Leu
    450             455             460
Ser Cys Arg Ala Ser Gln Ser Val Pro Arg Asn Tyr Ile Gly Trp Phe
465             470             475             480
Gln Gln Lys Pro Gly Gln Ala Pro Arg Leu Leu Ile Tyr Gly Ala Ser
                485             490             495
Ser Arg Ala Ala Gly Phe Pro Asp Arg Phe Ser Gly Ser Gly Ser Gly
            500             505             510
Thr Asp Phe Thr Leu Thr Ile Thr Arg Leu Glu Pro Glu Asp Phe Ala
            515             520             525
Met Tyr Tyr Cys His Gln Tyr Asp Arg Leu Pro Tyr Thr Phe Gly Gln
    530             535             540
Gly Thr Lys Leu Glu Ile Lys Gly Gly Gly Gly Ser Gly Gly Gly Gly
545             550             555             560
Ser Gly Gly Gly Gly Ser Thr Asp Gln Cys Asp Asn Phe Pro Gln Met
            565             570             575
Leu Arg Asp Leu Arg Asp Ala Phe Ser Arg Val Lys Thr Phe Phe Gln
            580             585             590
Thr Lys Asp Glu Val Asp Asn Leu Leu Leu Lys Glu Ser Leu Leu Glu
            595             600             605
Asp Phe Lys Gly Tyr Leu Gly Cys Gln Ala Leu Ser Glu Met Ile Gln
            610             615             620
Phe Tyr Leu Glu Glu Val Met Pro Gln Ala Glu Asn Gln Asp Pro Glu
625             630             635             640
Ile Lys Asp His Val Asn Ser Leu Gly Glu Asn Leu Lys Thr Leu Arg
                645             650             655
Leu Arg Leu Arg Arg Cys His Arg Phe Leu Pro Cys Glu Asn Lys Ser
            660             665             670
Lys Ala Val Glu Gln Ile Lys Asn Ala Phe Asn Lys Leu Gln Glu Lys
            675             680             685
```

-continued

```
Gly Ile Tyr Lys Ala Met Ser Glu Phe Asp Ile Phe Ile Asn Tyr Ile
        690                 695                 700

Glu Ala Tyr Met Thr Ile Lys Ala Arg
705                 710

<210> SEQ ID NO 47
<211> LENGTH: 729
<212> TYPE: PRT
<213> ORGANISM: Artificial Sequence
<220> FEATURE:
<223> OTHER INFORMATION: DK410HADeglyDV06mCD14

<400> SEQUENCE: 47

Met Gly Trp Ser Leu Ile Leu Leu Phe Leu Val Ala Val Ala Thr Arg
1               5                   10                  15

Val His Ser Thr Asp Gln Cys Asp Asn Phe Pro Gln Met Leu Arg Asp
                20                  25                  30

Leu Arg Asp Ala Phe Ser Arg Val Lys Thr Phe Phe Gln Thr Lys Asp
            35                  40                  45

Glu Val Asp Asn Leu Leu Leu Lys Glu Ser Leu Leu Glu Asp Phe Lys
        50                  55                  60

Gly Tyr Leu Gly Cys Gln Ala Leu Ser Glu Met Ile Gln Phe Tyr Leu
65                  70                  75                  80

Glu Glu Val Met Pro Gln Ala Glu Asn Gln Asp Pro Glu Ile Lys Asp
                85                  90                  95

His Val Asn Ser Leu Gly Glu Asn Leu Lys Thr Leu Arg Leu Arg Leu
            100                 105                 110

Arg Arg Cys His Arg Phe Leu Pro Cys Glu Asn Lys Ser Lys Ala Val
        115                 120                 125

Glu Gln Ile Lys Asn Ala Phe Asn Lys Leu Gln Glu Lys Gly Ile Tyr
    130                 135                 140

Lys Ala Met Ser Glu Phe Asp Ile Phe Ile Asn Tyr Ile Glu Ala Tyr
145                 150                 155                 160

Met Thr Ile Lys Ala Arg Gly Gly Gly Gly Ser Gly Gly Gly Gly Ser
                165                 170                 175

Gly Gly Gly Gly Ser Gln Val Gln Leu Gln Gln Trp Gly Ala Gly Leu
            180                 185                 190

Leu Lys Pro Ser Glu Thr Leu Ser Leu Thr Cys Ala Val Ser Gly Phe
        195                 200                 205

Ser Leu Thr Thr Tyr Tyr Met Asn Trp Ile Arg Gln Pro Pro Gly Lys
    210                 215                 220

Gly Leu Glu Trp Ile Gly Phe Ile Arg Ser Gly Ser Thr Glu Tyr
225                 230                 235                 240

Asn Pro Ser Leu Lys Gly Arg Val Ala Ile Ser Val Asp Thr Ser Lys
                245                 250                 255

Asn Gln Phe Ser Leu Arg Leu Asn Ser Val Thr Ala Ala Asp Thr Ala
            260                 265                 270

Ile Tyr Tyr Cys Ala Arg Gly Asp Tyr Tyr Asn Phe Asp Tyr Trp Gly
        275                 280                 285

Lys Gly Thr Thr Val Thr Val Ser Ser Gly Gly Gly Ser Gly Gly
    290                 295                 300

Gly Gly Ser Gly Gly Gly Gly Ser His Lys Cys Asp Ile Thr Leu Gln
305                 310                 315                 320

Glu Ile Ile Lys Asp Leu Asn Ser Leu Thr Glu Gln Lys Thr Leu Cys
                325                 330                 335
```

```
Thr Glu Leu Thr Val Thr Asp Ile Phe Ala Ala Ser Lys Ala Thr Thr
                340                 345                 350

Glu Lys Glu Thr Phe Cys Arg Ala Thr Val Leu Arg Gln Phe Tyr
            355                 360                 365

Ser His His Glu Lys Asp Thr Arg Cys Leu Gly Ala Thr Ala Gln Gln
    370                 375                 380

Phe His Arg His Lys Gln Leu Ile Arg Phe Leu Lys Arg Leu Asp Arg
385                 390                 395                 400

Asn Leu Trp Gly Leu Ala Gly Leu Asn Ser Cys Pro Val Lys Glu Ala
                405                 410                 415

Asn Gln Ser Thr Leu Glu Asn Phe Leu Glu Arg Leu Lys Thr Ile Met
            420                 425                 430

Arg Glu Lys Tyr Ser Lys Cys Ser Ser Gly Gly Gly Ser Gly Gly
                435                 440                 445

Gly Gly Ser Gly Gly Gly Ser Glu Ile Val Met Thr Gln Ser Pro
    450                 455                 460

Gly Thr Leu Ser Leu Ser Pro Gly Glu Arg Ala Thr Leu Ser Cys Arg
465                 470                 475                 480

Ala Ser Gln Ser Leu Val His Ser Asn Gly Lys Thr Tyr Val Gly Trp
                485                 490                 495

Phe Gln Gln Lys Pro Gly Gln Ala Pro Arg Leu Leu Ile Tyr Arg Val
            500                 505                 510

Ser Asn Arg Ala Ala Gly Phe Pro Asp Arg Phe Ser Gly Ser Gly Ser
                515                 520                 525

Gly Thr Asp Phe Thr Leu Thr Ile Thr Arg Leu Glu Pro Glu Asp Phe
    530                 535                 540

Ala Met Tyr Tyr Cys Leu Gln Ser Thr His Phe Pro Arg Thr Phe Gly
545                 550                 555                 560

Gln Gly Thr Lys Leu Glu Ile Lys Gly Gly Gly Ser Gly Gly Gly
                565                 570                 575

Gly Ser Gly Gly Gly Gly Ser Thr Asp Gln Cys Asp Asn Phe Pro Gln
            580                 585                 590

Met Leu Arg Asp Leu Arg Asp Ala Phe Ser Arg Val Lys Thr Phe Phe
                595                 600                 605

Gln Thr Lys Asp Glu Val Asn Leu Leu Leu Lys Glu Ser Leu Leu Glu
            610                 615                 620

Asp Phe Lys Gly Tyr Leu Gly Cys Gln Ala Leu Ser Glu Met Ile Gln
625                 630                 635                 640

Phe Tyr Leu Glu Glu Val Met Pro Gln Ala Glu Asn Gln Asp Pro Glu
                645                 650                 655

Ile Lys Asp His Val Asn Ser Leu Gly Glu Asn Leu Lys Thr Leu Arg
            660                 665                 670

Leu Arg Leu Arg Arg Cys His Arg Phe Leu Pro Cys Glu Asn Lys Ser
            675                 680                 685

Lys Ala Val Glu Gln Ile Lys Asn Ala Phe Asn Lys Leu Gln Glu Lys
        690                 695                 700

Gly Ile Tyr Lys Ala Met Ser Glu Phe Asp Ile Phe Ile Asn Tyr Ile
705                 710                 715                 720

Glu Ala Tyr Met Thr Ile Lys Ala Arg
                725

<210> SEQ ID NO 48
<211> LENGTH: 729
```

```
<212> TYPE: PRT
<213> ORGANISM: Artificial Sequence
<220> FEATURE:
<223> OTHER INFORMATION: DK410HADeglyDV07mCD14

<400> SEQUENCE: 48

Met Gly Trp Ser Leu Ile Leu Leu Phe Leu Val Ala Val Ala Thr Arg
1               5                   10                  15

Val His Ser Thr Asp Gln Cys Asp Asn Phe Pro Gln Met Leu Arg Asp
            20                  25                  30

Leu Arg Asp Ala Phe Ser Arg Val Lys Thr Phe Phe Gln Thr Lys Asp
        35                  40                  45

Glu Leu Asp Asn Leu Leu Lys Glu Ser Leu Leu Glu Asp Phe Lys
50                  55                  60

Gly Tyr Leu Gly Cys Gln Ala Leu Ser Glu Met Ile Gln Phe Tyr Leu
65                  70                  75                  80

Glu Glu Val Met Pro Gln Ala Glu Asn Gln Asp Pro Glu Ile Lys Asp
                85                  90                  95

His Val Asn Ser Leu Gly Glu Asn Leu Lys Thr Leu Arg Leu Arg Leu
            100                 105                 110

Arg Arg Cys His Arg Phe Leu Pro Cys Glu Asn Lys Ser Lys Ala Val
        115                 120                 125

Glu Gln Ile Lys Asn Ala Phe Asn Lys Leu Gln Glu Lys Gly Ile Tyr
    130                 135                 140

Lys Ala Met Ser Glu Phe Asp Ile Phe Ile Asn Tyr Ile Glu Ala Tyr
145                 150                 155                 160

Met Thr Ile Lys Ala Arg Gly Gly Gly Gly Ser Gly Gly Gly Gly Ser
                165                 170                 175

Gly Gly Gly Gly Ser Gln Val Gln Leu Gln Gln Trp Gly Ala Gly Leu
            180                 185                 190

Leu Lys Pro Ser Glu Thr Leu Ser Leu Thr Cys Ala Val Ser Gly Phe
        195                 200                 205

Ser Leu Thr Thr Tyr Tyr Met Asn Trp Ile Arg Gln Pro Pro Gly Lys
    210                 215                 220

Gly Leu Glu Trp Ile Gly Phe Ile Arg Ser Gly Gly Ser Thr Glu Tyr
225                 230                 235                 240

Asn Pro Ser Leu Lys Gly Arg Val Ala Ile Ser Val Asp Thr Ser Lys
                245                 250                 255

Asn Gln Phe Ser Leu Arg Leu Asn Ser Val Thr Ala Ala Asp Thr Ala
            260                 265                 270

Ile Tyr Tyr Cys Ala Arg Gly Asp Tyr Tyr Asn Phe Asp Tyr Trp Gly
        275                 280                 285

Lys Gly Thr Thr Val Thr Val Ser Ser Gly Gly Gly Ser Gly Gly
    290                 295                 300

Gly Gly Ser Gly Gly Gly Gly Ser His Lys Cys Asp Ile Thr Leu Gln
305                 310                 315                 320

Glu Ile Ile Lys Asp Leu Asn Ser Leu Thr Glu Gln Lys Thr Leu Cys
                325                 330                 335

Thr Glu Leu Thr Val Thr Asp Ile Phe Ala Ala Ser Lys Ala Thr Thr
            340                 345                 350

Glu Lys Glu Thr Phe Cys Arg Ala Ala Thr Val Leu Arg Gln Phe Tyr
        355                 360                 365

Ser His His Glu Lys Asp Thr Arg Cys Leu Gly Ala Thr Ala Gln Gln
    370                 375                 380
```

Phe His Arg His Lys Gln Leu Ile Arg Phe Leu Lys Arg Leu Asp Arg
385                 390                 395                 400

Asn Leu Trp Gly Leu Ala Gly Leu Asn Ser Cys Pro Val Lys Glu Ala
            405                 410                 415

Asn Gln Ser Thr Leu Glu Asn Phe Leu Glu Arg Leu Lys Thr Ile Met
            420                 425                 430

Arg Glu Lys Tyr Ser Lys Cys Ser Ser Gly Gly Gly Ser Gly Gly
        435                 440                 445

Gly Gly Ser Gly Gly Gly Ser Glu Ile Val Met Thr Gln Ser Pro
    450                 455                 460

Gly Thr Leu Ser Leu Ser Pro Gly Glu Arg Ala Thr Leu Ser Cys Arg
465                 470                 475                 480

Ala Ser Gln Ser Leu Val His Ser Asn Gly Lys Thr Tyr Val Gly Trp
                485                 490                 495

Phe Gln Gln Lys Pro Gly Gln Ala Pro Arg Leu Leu Ile Tyr Arg Val
            500                 505                 510

Ser Asn Arg Ala Ala Gly Phe Pro Asp Arg Phe Ser Gly Ser Gly Ser
            515                 520                 525

Gly Thr Asp Phe Thr Leu Thr Ile Thr Arg Leu Glu Pro Glu Asp Phe
    530                 535                 540

Ala Met Tyr Tyr Cys Leu Gln Ser Thr His Phe Pro Arg Thr Phe Gly
545                 550                 555                 560

Gln Gly Thr Lys Leu Glu Ile Lys Gly Gly Gly Ser Gly Gly Gly
            565                 570                 575

Gly Ser Gly Gly Gly Ser Thr Asp Gln Cys Asp Asn Phe Pro Gln
    580                 585                 590

Met Leu Arg Asp Leu Arg Asp Ala Phe Ser Arg Val Lys Thr Phe Phe
            595                 600                 605

Gln Thr Lys Asp Glu Leu Asn Leu Leu Lys Glu Ser Leu Leu Glu
    610                 615                 620

Asp Phe Lys Gly Tyr Leu Gly Cys Gln Ala Leu Ser Glu Met Ile Gln
625                 630                 635                 640

Phe Tyr Leu Glu Glu Val Met Pro Gln Ala Glu Asn Gln Asp Pro Glu
            645                 650                 655

Ile Lys Asp His Val Asn Ser Leu Gly Glu Asn Leu Lys Thr Leu Arg
            660                 665                 670

Leu Arg Leu Arg Arg Cys His Arg Phe Leu Pro Cys Glu Asn Lys Ser
        675                 680                 685

Lys Ala Val Glu Gln Ile Lys Asn Ala Phe Asn Lys Leu Gln Glu Lys
690                 695                 700

Gly Ile Tyr Lys Ala Met Ser Glu Phe Asp Ile Phe Ile Asn Tyr Ile
705                 710                 715                 720

Glu Ala Tyr Met Thr Ile Lys Ala Arg
                725

<210> SEQ ID NO 49
<211> LENGTH: 729
<212> TYPE: PRT
<213> ORGANISM: Artificial Sequence
<220> FEATURE:
<223> OTHER INFORMATION: DK410ngDV06CmD14

<400> SEQUENCE: 49

Met Gly Trp Ser Leu Ile Leu Leu Phe Leu Val Ala Val Ala Thr Arg
1               5                   10                  15

-continued

```
Val His Ser Thr Asp Gln Cys Asp Asn Phe Pro Gln Met Leu Arg Asp
                 20                  25                  30

Leu Arg Asp Ala Phe Ser Arg Val Lys Thr Phe Gln Thr Lys Asp
         35                  40                  45

Glu Val Asp Asn Leu Leu Lys Glu Ser Leu Leu Glu Asp Phe Lys
 50                  55                  60

Gly Tyr Leu Gly Cys Gln Ala Leu Ser Glu Met Ile Gln Phe Tyr Leu
 65                  70                  75                  80

Glu Glu Val Met Pro Gln Ala Glu Asn Gln Asp Pro Glu Ile Lys Asp
                 85                  90                  95

His Val Asn Ser Leu Gly Glu Asn Leu Lys Thr Leu Arg Leu Arg Leu
                100                 105                 110

Arg Arg Cys His Arg Phe Leu Pro Cys Glu Asn Lys Ser Lys Ala Val
            115                 120                 125

Glu Gln Ile Lys Asn Ala Phe Asn Lys Leu Gln Glu Lys Gly Ile Tyr
        130                 135                 140

Lys Ala Met Ser Glu Phe Asp Ile Phe Ile Asn Tyr Ile Glu Ala Tyr
145                 150                 155                 160

Met Thr Ile Lys Ala Arg Gly Gly Gly Ser Gly Gly Gly Ser
                165                 170                 175

Gly Gly Gly Gly Ser Gln Val Gln Leu Gln Gln Trp Gly Ala Gly Leu
            180                 185                 190

Leu Lys Pro Ser Glu Thr Leu Ser Leu Thr Cys Ala Val Ser Gly Phe
        195                 200                 205

Ser Leu Thr Thr Tyr Tyr Met Asn Trp Ile Arg Gln Pro Pro Gly Lys
    210                 215                 220

Gly Leu Glu Trp Ile Gly Phe Ile Arg Ser Gly Gly Ser Thr Glu Tyr
225                 230                 235                 240

Asn Pro Ser Leu Lys Gly Arg Val Ala Ile Ser Val Asp Thr Ser Lys
                245                 250                 255

Asn Gln Phe Ser Leu Arg Leu Asn Ser Val Thr Ala Ala Asp Thr Ala
            260                 265                 270

Ile Tyr Tyr Cys Ala Arg Gly Asp Tyr Tyr Asn Phe Asp Tyr Trp Gly
        275                 280                 285

Lys Gly Thr Thr Val Thr Val Ser Ser Gly Gly Gly Ser Gly Gly
    290                 295                 300

Gly Gly Ser Gly Gly Gly Ser His Lys Cys Asp Ile Thr Leu Gln
305                 310                 315                 320

Glu Ile Ile Lys Thr Leu Asn Ser Leu Thr Glu Gln Lys Thr Leu Cys
                325                 330                 335

Thr Glu Leu Thr Val Thr Asp Ile Phe Ala Ala Ser Lys Ala Thr Thr
            340                 345                 350

Glu Lys Glu Thr Phe Cys Arg Ala Ala Thr Val Leu Arg Gln Phe Tyr
        355                 360                 365

Ser His His Glu Lys Asp Thr Arg Cys Leu Gly Ala Thr Ala Gln Gln
    370                 375                 380

Phe His Arg His Lys Gln Leu Ile Arg Phe Leu Lys Arg Leu Asp Arg
385                 390                 395                 400

Asn Leu Trp Gly Leu Ala Gly Leu Asn Ser Cys Pro Val Lys Glu Ala
                405                 410                 415

Asn Gln Ser Thr Leu Glu Asn Phe Leu Glu Arg Leu Lys Thr Ile Met
            420                 425                 430
```

```
Arg Glu Lys Tyr Ser Lys Cys Ser Gly Gly Gly Ser Gly Gly
        435                 440                 445

Gly Gly Ser Gly Gly Gly Ser Glu Ile Val Met Thr Gln Ser Pro
    450                 455                 460

Gly Thr Leu Ser Leu Ser Pro Gly Glu Arg Ala Thr Leu Ser Cys Arg
465                 470                 475                 480

Ala Ser Gln Ser Leu Val His Ser Asn Gly Lys Thr Tyr Val Gly Trp
                485                 490                 495

Phe Gln Gln Lys Pro Gly Gln Ala Pro Arg Leu Leu Ile Tyr Arg Val
            500                 505                 510

Ser Asn Arg Ala Ala Gly Phe Pro Asp Arg Phe Ser Gly Ser Gly Ser
        515                 520                 525

Gly Thr Asp Phe Thr Leu Thr Ile Thr Arg Leu Glu Pro Glu Asp Phe
    530                 535                 540

Ala Met Tyr Tyr Cys Leu Gln Ser Thr His Phe Pro Arg Thr Phe Gly
545                 550                 555                 560

Gln Gly Thr Lys Leu Glu Ile Lys Gly Gly Gly Ser Gly Gly Gly
                565                 570                 575

Gly Ser Gly Gly Gly Ser Thr Asp Gln Cys Asp Asn Phe Pro Gln
            580                 585                 590

Met Leu Arg Asp Leu Arg Asp Ala Phe Ser Arg Val Lys Thr Phe Phe
            595                 600                 605

Gln Thr Lys Asp Glu Val Asn Leu Leu Leu Lys Glu Ser Leu Leu Glu
        610                 615                 620

Asp Phe Lys Gly Tyr Leu Gly Cys Gln Ala Leu Ser Glu Met Ile Gln
625                 630                 635                 640

Phe Tyr Leu Glu Glu Val Met Pro Gln Ala Glu Asn Gln Asp Pro Glu
                645                 650                 655

Ile Lys Asp His Val Asn Ser Leu Gly Glu Asn Leu Lys Thr Leu Arg
            660                 665                 670

Leu Arg Leu Arg Arg Cys His Arg Phe Leu Pro Cys Glu Asn Lys Ser
        675                 680                 685

Lys Ala Val Glu Gln Ile Lys Asn Ala Phe Asn Lys Leu Gln Glu Lys
    690                 695                 700

Gly Ile Tyr Lys Ala Met Ser Glu Phe Asp Ile Phe Ile Asn Tyr Ile
705                 710                 715                 720

Glu Ala Tyr Met Thr Ile Lys Ala Arg
                725

<210> SEQ ID NO 50
<211> LENGTH: 729
<212> TYPE: PRT
<213> ORGANISM: Artificial Sequence
<220> FEATURE:
<223> OTHER INFORMATION: DK410ngDV07CmD14

<400> SEQUENCE: 50

Met Gly Trp Ser Leu Ile Leu Leu Phe Leu Val Ala Val Ala Thr Arg
1               5                   10                  15

Val His Ser Thr Asp Gln Cys Asp Asn Phe Pro Gln Met Leu Arg Asp
            20                  25                  30

Leu Arg Asp Ala Phe Ser Arg Val Lys Thr Phe Phe Gln Thr Lys Asp
        35                  40                  45

Glu Leu Asp Asn Leu Leu Leu Lys Glu Ser Leu Leu Glu Asp Phe Lys
    50                  55                  60
```

```
Gly Tyr Leu Gly Cys Gln Ala Leu Ser Glu Met Ile Gln Phe Tyr Leu
 65                  70                  75                  80

Glu Glu Val Met Pro Gln Ala Glu Asn Gln Asp Pro Glu Ile Lys Asp
                 85                  90                  95

His Val Asn Ser Leu Gly Glu Asn Leu Lys Thr Leu Arg Leu Arg Leu
            100                 105                 110

Arg Arg Cys His Arg Phe Leu Pro Cys Glu Asn Lys Ser Lys Ala Val
        115                 120                 125

Glu Gln Ile Lys Asn Ala Phe Asn Lys Leu Gln Glu Lys Gly Ile Tyr
    130                 135                 140

Lys Ala Met Ser Glu Phe Asp Ile Phe Ile Asn Tyr Ile Glu Ala Tyr
145                 150                 155                 160

Met Thr Ile Lys Ala Arg Gly Gly Gly Ser Gly Gly Gly Gly Gly Ser
                165                 170                 175

Gly Gly Gly Gly Ser Gln Val Gln Leu Gln Gln Trp Gly Ala Gly Leu
            180                 185                 190

Leu Lys Pro Ser Glu Thr Leu Ser Leu Thr Cys Ala Val Ser Gly Phe
        195                 200                 205

Ser Leu Thr Thr Tyr Tyr Met Asn Trp Ile Arg Gln Pro Pro Gly Lys
    210                 215                 220

Gly Leu Glu Trp Ile Gly Phe Ile Arg Ser Gly Ser Thr Glu Tyr
225                 230                 235                 240

Asn Pro Ser Leu Lys Gly Arg Val Ala Ile Ser Val Asp Thr Ser Lys
                245                 250                 255

Asn Gln Phe Ser Leu Arg Leu Asn Ser Val Thr Ala Ala Asp Thr Ala
            260                 265                 270

Ile Tyr Tyr Cys Ala Arg Gly Asp Tyr Tyr Asn Phe Asp Tyr Trp Gly
        275                 280                 285

Lys Gly Thr Thr Val Thr Val Ser Ser Gly Gly Gly Ser Gly Gly
    290                 295                 300

Gly Gly Ser Gly Gly Gly Gly Ser His Lys Cys Asp Ile Thr Leu Gln
305                 310                 315                 320

Glu Ile Ile Lys Thr Leu Asn Ser Leu Thr Glu Gln Lys Thr Leu Cys
                325                 330                 335

Thr Glu Leu Thr Val Thr Asp Ile Phe Ala Ala Ser Lys Ala Thr Thr
            340                 345                 350

Glu Lys Glu Thr Phe Cys Arg Ala Ala Thr Val Leu Arg Gln Phe Tyr
        355                 360                 365

Ser His His Glu Lys Asp Thr Arg Cys Leu Gly Ala Thr Ala Gln Gln
    370                 375                 380

Phe His Arg His Lys Gln Leu Ile Arg Phe Leu Lys Arg Leu Asp Arg
385                 390                 395                 400

Asn Leu Trp Gly Leu Ala Gly Leu Asn Ser Cys Pro Val Lys Glu Ala
                405                 410                 415

Asn Gln Ser Thr Leu Glu Asn Phe Leu Glu Arg Leu Lys Thr Ile Met
            420                 425                 430

Arg Glu Lys Tyr Ser Lys Cys Ser Ser Gly Gly Gly Ser Gly Gly
        435                 440                 445

Gly Gly Ser Gly Gly Gly Ser Glu Ile Val Met Thr Gln Ser Pro
    450                 455                 460

Gly Thr Leu Ser Leu Ser Pro Gly Glu Arg Ala Thr Leu Ser Cys Arg
465                 470                 475                 480
```

Ala Ser Gln Ser Leu Val His Ser Asn Gly Lys Thr Tyr Val Gly Trp
              485                 490                 495

Phe Gln Gln Lys Pro Gly Gln Ala Pro Arg Leu Leu Ile Tyr Arg Val
        500                 505                 510

Ser Asn Arg Ala Ala Gly Phe Pro Asp Arg Phe Ser Gly Ser Gly Ser
        515                 520                 525

Gly Thr Asp Phe Thr Leu Thr Ile Thr Arg Leu Glu Pro Glu Asp Phe
    530                 535                 540

Ala Met Tyr Tyr Cys Leu Gln Ser Thr His Phe Pro Arg Thr Phe Gly
545                 550                 555                 560

Gln Gly Thr Lys Leu Glu Ile Lys Gly Gly Gly Ser Gly Gly Gly
            565                 570                 575

Gly Ser Gly Gly Gly Ser Thr Asp Gln Cys Asp Asn Phe Pro Gln
        580                 585                 590

Met Leu Arg Asp Leu Arg Asp Ala Phe Ser Arg Val Lys Thr Phe Phe
            595                 600                 605

Gln Thr Lys Asp Glu Leu Asn Leu Leu Lys Glu Ser Leu Leu Glu
        610                 615                 620

Asp Phe Lys Gly Tyr Leu Gly Cys Gln Ala Leu Ser Glu Met Ile Gln
625                 630                 635                 640

Phe Tyr Leu Glu Glu Val Met Pro Gln Ala Glu Asn Gln Asp Pro Glu
            645                 650                 655

Ile Lys Asp His Val Asn Ser Leu Gly Glu Asn Leu Lys Thr Leu Arg
                660                 665                 670

Leu Arg Leu Arg Arg Cys His Arg Phe Leu Pro Cys Glu Asn Lys Ser
        675                 680                 685

Lys Ala Val Glu Gln Ile Lys Asn Ala Phe Asn Lys Leu Gln Glu Lys
    690                 695                 700

Gly Ile Tyr Lys Ala Met Ser Glu Phe Asp Ile Phe Ile Asn Tyr Ile
705                 710                 715                 720

Glu Ala Tyr Met Thr Ile Lys Ala Arg
                725

<210> SEQ ID NO 51
<211> LENGTH: 729
<212> TYPE: PRT
<213> ORGANISM: Artificial Sequence
<220> FEATURE:
<223> OTHER INFORMATION: DK410ngDV06mMAdCAM

<400> SEQUENCE: 51

Met Gly Trp Ser Leu Ile Leu Leu Phe Leu Val Ala Val Ala Thr Arg
1               5                  10                  15

Val His Ser Thr Asp Gln Cys Asp Asn Phe Pro Gln Met Leu Arg Asp
            20                  25                  30

Leu Arg Asp Ala Phe Ser Arg Val Lys Thr Phe Phe Gln Thr Lys Asp
        35                  40                  45

Glu Val Asp Asn Leu Leu Leu Lys Glu Ser Leu Leu Glu Asp Phe Lys
    50                  55                  60

Gly Tyr Leu Gly Cys Gln Ala Leu Ser Glu Met Ile Gln Phe Tyr Leu
65                  70                  75                  80

Glu Glu Val Met Pro Gln Ala Glu Asn Gln Asp Pro Glu Ile Lys Asp
                85                  90                  95

His Val Asn Ser Leu Gly Glu Asn Leu Lys Thr Leu Arg Leu Arg Leu
            100                 105                 110

Arg Arg Cys His Arg Phe Leu Pro Cys Glu Asn Lys Ser Lys Ala Val
            115                 120                 125

Glu Gln Ile Lys Asn Ala Phe Asn Lys Leu Gln Glu Lys Gly Ile Tyr
        130                 135                 140

Lys Ala Met Ser Glu Phe Asp Ile Phe Ile Asn Tyr Ile Glu Ala Tyr
145                 150                 155                 160

Met Thr Ile Lys Ala Arg Gly Gly Gly Ser Gly Gly Gly Gly Ser
                165                 170                 175

Gly Gly Gly Gly Ser Gln Val Gln Leu Gln Gln Trp Gly Ala Gly Leu
            180                 185                 190

Leu Lys Pro Ser Glu Thr Leu Ser Leu Thr Cys Ala Val Tyr Gly Phe
        195                 200                 205

Thr Phe Thr Asp Phe Tyr Met Asn Trp Ile Arg Gln Pro Pro Gly Lys
        210                 215                 220

Gly Leu Glu Trp Ile Gly Leu Ile Arg Asn Lys Ala Asn Ala Tyr Thr
225                 230                 235                 240

Thr Glu Tyr Asn Pro Ser Val Lys Gly Arg Val Ala Ile Ser Val Asp
                245                 250                 255

Thr Ser Lys Asn Gln Phe Ser Leu Arg Leu Asn Ser Val Thr Ala Ala
            260                 265                 270

Asp Thr Ala Ile Tyr Tyr Cys Thr Ser Asp Asp His Trp Gly Lys Gly
        275                 280                 285

Thr Thr Val Thr Val Ser Ser Gly Gly Gly Ser Gly Gly Gly Gly
        290                 295                 300

Ser Gly Gly Gly Gly Ser His Lys Cys Asp Ile Thr Leu Gln Glu Ile
305                 310                 315                 320

Ile Lys Thr Leu Asn Ser Leu Thr Glu Gln Lys Thr Leu Cys Thr Glu
                325                 330                 335

Leu Thr Val Thr Asp Ile Phe Ala Ala Ser Lys Ala Thr Thr Glu Lys
            340                 345                 350

Glu Thr Phe Cys Arg Ala Ala Thr Val Leu Arg Gln Phe Tyr Ser His
        355                 360                 365

His Glu Lys Asp Thr Arg Cys Leu Gly Ala Thr Ala Gln Gln Phe His
        370                 375                 380

Arg His Lys Gln Leu Ile Arg Phe Leu Lys Arg Leu Asp Arg Asn Leu
385                 390                 395                 400

Trp Gly Leu Ala Gly Leu Asn Ser Cys Pro Val Lys Glu Ala Asn Gln
                405                 410                 415

Ser Thr Leu Glu Asn Phe Leu Glu Arg Leu Lys Thr Ile Met Arg Glu
            420                 425                 430

Lys Tyr Ser Lys Cys Ser Ser Gly Gly Gly Ser Gly Gly Gly Gly
        435                 440                 445

Ser Gly Gly Gly Gly Ser Glu Ile Val Met Thr Gln Ser Pro Gly Thr
        450                 455                 460

Leu Ser Leu Ser Pro Gly Glu Arg Ala Thr Leu Ser Cys Lys Ser Ser
465                 470                 475                 480

Gln Ser Leu Leu Tyr Asn Glu Asn Lys Lys Asn Tyr Leu Ala Trp Phe
                485                 490                 495

Gln Gln Lys Pro Gly Gln Ala Pro Arg Leu Leu Ile Tyr Trp Ala Ser
            500                 505                 510

Thr Arg Glu Ser Gly Phe Pro Asp Arg Phe Ser Gly Ser Gly Ser Gly
        515                 520                 525

```
Thr Asp Phe Thr Leu Thr Ile Thr Arg Leu Glu Pro Glu Asp Phe Ala
        530                 535                 540

Met Tyr Tyr Cys Gln Gln Tyr Tyr Asn Phe Pro Tyr Thr Phe Gly Gln
545                 550                 555                 560

Gly Thr Lys Leu Glu Ile Lys Gly Gly Gly Ser Gly Gly Gly Gly
            565                 570                 575

Ser Gly Gly Gly Ser Thr Asp Gln Cys Asp Asn Phe Pro Gln Met
        580                 585                 590

Leu Arg Asp Leu Arg Asp Ala Phe Ser Arg Val Lys Thr Phe Phe Gln
            595                 600                 605

Thr Lys Asp Glu Val Asp Asn Leu Leu Leu Lys Glu Ser Leu Leu Glu
        610                 615                 620

Asp Phe Lys Gly Tyr Leu Gly Cys Gln Ala Leu Ser Glu Met Ile Gln
625                 630                 635                 640

Phe Tyr Leu Glu Glu Val Met Pro Gln Ala Glu Asn Gln Asp Pro Glu
            645                 650                 655

Ile Lys Asp His Val Asn Ser Leu Gly Glu Asn Leu Lys Thr Leu Arg
        660                 665                 670

Leu Arg Leu Arg Arg Cys His Arg Phe Leu Pro Cys Glu Asn Lys Ser
            675                 680                 685

Lys Ala Val Glu Gln Ile Lys Asn Ala Phe Asn Lys Leu Gln Glu Lys
        690                 695                 700

Gly Ile Tyr Lys Ala Met Ser Glu Phe Asp Ile Phe Ile Asn Tyr Ile
705                 710                 715                 720

Glu Ala Tyr Met Thr Ile Lys Ala Arg
                725

<210> SEQ ID NO 52
<211> LENGTH: 733
<212> TYPE: PRT
<213> ORGANISM: Artificial Sequence
<220> FEATURE:
<223> OTHER INFORMATION: DK210her2 (Variant 2)

<400> SEQUENCE: 52

Met Gly Trp Ser Leu Ile Leu Leu Phe Leu Val Ala Val Ala Thr Arg
1               5                   10                  15

Val His Ser Thr Asp Gln Cys Asp Asn Phe Pro Gln Met Leu Arg Asp
            20                  25                  30

Leu Arg Asp Ala Phe Ser Arg Val Lys Thr Phe Phe Gln Thr Lys Asp
        35                  40                  45

Glu Leu Asp Asn Leu Leu Leu Lys Glu Ser Leu Leu Glu Asp Phe Lys
    50                  55                  60

Gly Tyr Leu Gly Cys Gln Ala Leu Ser Glu Met Ile Gln Phe Tyr Leu
65                  70                  75                  80

Glu Glu Val Met Pro Gln Ala Glu Asn Gln Asp Pro Glu Ile Lys Asp
                85                  90                  95

His Val Asn Ser Leu Gly Glu Asn Leu Lys Thr Leu Arg Leu Arg Leu
            100                 105                 110

Arg Arg Cys His Arg Phe Leu Pro Cys Glu Asn Lys Ser Lys Ala Val
        115                 120                 125

Glu Gln Ile Lys Asn Ala Phe Asn Lys Leu Gln Glu Lys Gly Ile Tyr
    130                 135                 140

Lys Ala Met Ser Glu Phe Asp Ile Phe Ile Asn Tyr Ile Glu Ala Tyr
145                 150                 155                 160
```

```
Met Thr Ile Lys Ala Arg Gly Gly Gly Ser Gly Gly Gly Ser
                165                 170             175

Gly Gly Gly Gly Ser Gln Val Gln Leu Gln Gln Trp Gly Ala Gly Leu
            180                 185                 190

Leu Lys Pro Ser Glu Thr Leu Ser Leu Thr Cys Ala Val Tyr Gly Phe
        195                 200                 205

Asn Ile Lys Asp Thr Tyr Ile His Trp Ile Arg Gln Pro Pro Gly Lys
    210                 215                 220

Gly Leu Glu Trp Ile Gly Arg Ile Tyr Pro Thr Asn Gly Tyr Thr Arg
225                 230                 235                 240

Tyr Ala Asp Ser Val Lys Gly Arg Val Ala Ile Ser Val Asp Thr Ser
            245                 250                 255

Lys Asn Gln Phe Ser Leu Arg Leu Asn Ser Val Thr Ala Ala Asp Thr
        260                 265                 270

Ala Ile Tyr Tyr Cys Thr Ser Trp Gly Gly Asp Gly Phe Tyr Ala Met
    275                 280                 285

Asp Tyr Trp Gly Lys Gly Thr Thr Val Thr Val Ser Ser Gly Gly Gly
        290                 295                 300

Gly Ser Gly Gly Gly Gly Ser Gly Gly Gly Gly Ser Ala Pro Thr Ser
305                 310                 315                 320

Ser Ser Thr Lys Lys Thr Gln Leu Gln Leu Glu His Leu Leu Leu Asp
            325                 330                 335

Leu Gln Met Ile Leu Asn Gly Ile Asn Asn Tyr Lys Asn Pro Lys Leu
        340                 345                 350

Thr Arg Met Leu Thr Phe Lys Phe Tyr Met Pro Lys Lys Ala Thr Glu
    355                 360                 365

Leu Lys His Leu Gln Cys Leu Glu Glu Leu Lys Pro Leu Glu Glu
        370                 375                 380

Val Leu Asn Leu Ala Gln Ser Lys Asn Phe His Leu Arg Pro Arg Asp
385                 390                 395                 400

Leu Ile Ser Asn Ile Asn Val Ile Val Leu Glu Leu Lys Gly Ser Glu
            405                 410                 415

Thr Thr Phe Met Cys Glu Tyr Ala Asp Glu Thr Ala Thr Ile Val Glu
        420                 425                 430

Phe Leu Asn Arg Trp Ile Thr Phe Cys Gln Ser Ile Ile Ser Thr Leu
    435                 440                 445

Thr Gly Gly Gly Gly Ser Gly Gly Gly Gly Ser Gly Gly Gly Gly Ser
450                 455                 460

Glu Ile Val Met Thr Gln Ser Pro Gly Thr Leu Ser Leu Ser Pro Gly
465                 470                 475                 480

Glu Arg Ala Thr Leu Ser Cys Arg Ala Ser Gln Asp Val Asn Thr Ala
            485                 490                 495

Val Ala Trp Phe Gln Gln Lys Pro Gly Gln Ala Pro Arg Leu Leu Ile
        500                 505                 510

Tyr Ser Ala Ser Phe Leu Tyr Ser Gly Phe Pro Asp Arg Phe Ser Gly
    515                 520                 525

Ser Gly Ser Gly Thr Asp Phe Thr Leu Thr Ile Thr Arg Leu Glu Pro
530                 535                 540

Glu Asp Phe Ala Met Tyr Tyr Cys Gln Gln His Tyr Thr Thr Pro Pro
545                 550                 555                 560

Thr Phe Gly Gln Gly Thr Lys Leu Glu Ile Lys Gly Gly Gly Gly Ser
            565                 570                 575
```

```
Gly Gly Gly Gly Ser Gly Gly Gly Ser Thr Asp Gln Cys Asp Asn
            580             585                 590

Phe Pro Gln Met Leu Arg Asp Leu Arg Asp Ala Phe Ser Arg Val Lys
        595                 600                 605

Thr Phe Phe Gln Thr Lys Asp Glu Leu Asp Asn Leu Leu Leu Lys Glu
    610                 615                 620

Ser Leu Leu Glu Asp Phe Lys Gly Tyr Leu Gly Cys Gln Ala Leu Ser
625                 630                 635                 640

Glu Met Ile Gln Phe Tyr Leu Glu Glu Val Met Pro Gln Ala Glu Asn
                645                 650                 655

Gln Asp Pro Glu Ile Lys Asp His Val Asn Ser Leu Gly Glu Asn Leu
            660                 665                 670

Lys Thr Leu Arg Leu Arg Leu Arg Arg Cys His Arg Phe Leu Pro Cys
        675                 680                 685

Glu Asn Lys Ser Lys Ala Val Glu Gln Ile Lys Asn Ala Phe Asn Lys
    690                 695                 700

Leu Gln Glu Lys Gly Ile Tyr Lys Ala Met Ser Glu Phe Asp Ile Phe
705                 710                 715                 720

Ile Asn Tyr Ile Glu Ala Tyr Met Thr Ile Lys Ala Arg
                725                 730

<210> SEQ ID NO 53
<211> LENGTH: 733
<212> TYPE: PRT
<213> ORGANISM: Artificial Sequence
<220> FEATURE:
<223> OTHER INFORMATION: DK210her2 (Variant 3)

<400> SEQUENCE: 53

Met Gly Trp Ser Leu Ile Leu Leu Phe Leu Val Ala Val Ala Thr Arg
1               5                   10                  15

Val His Ser Thr Asp Gln Cys Asp Asn Phe Pro Gln Met Leu Arg Asp
                20                  25                  30

Leu Arg Asp Ala Phe Ser Arg Val Lys Thr Phe Phe Gln Thr Lys Asp
            35                  40                  45

Glu Leu Asp Asn Leu Leu Leu Lys Glu Ser Leu Leu Glu Asp Phe Lys
    50                  55                  60

Gly Tyr Leu Gly Cys Gln Ala Leu Ser Glu Met Ile Gln Phe Tyr Leu
65                  70                  75                  80

Glu Glu Val Met Pro Gln Ala Glu Asn Gln Asp Pro Glu Ile Lys Asp
                85                  90                  95

His Val Asn Ser Leu Gly Glu Asn Leu Lys Thr Leu Arg Leu Arg Leu
            100                 105                 110

Arg Arg Cys His Arg Phe Leu Pro Cys Glu Asn Lys Ser Lys Ala Val
        115                 120                 125

Glu Gln Ile Lys Asn Ala Phe Asn Lys Leu Gln Glu Lys Gly Ile Tyr
    130                 135                 140

Lys Ala Met Ser Glu Phe Asp Ile Phe Ile Asn Tyr Ile Glu Ala Tyr
145                 150                 155                 160

Met Thr Ile Lys Ala Arg Gly Gly Gly Ser Gly Gly Gly Gly Ser
                165                 170                 175

Gly Gly Gly Gly Ser Gln Val Gln Leu Gln Gln Trp Gly Ala Gly Leu
            180                 185                 190

Leu Lys Pro Ser Glu Thr Leu Ser Leu Thr Cys Ala Val Tyr Gly Phe
        195                 200                 205
```

```
Asn Ile Lys Asp Thr Tyr Ile His Trp Ile Arg Gln Pro Pro Gly Lys
210                 215                 220

Gly Leu Glu Trp Val Ala Arg Ile Tyr Pro Thr Asn Gly Tyr Thr Arg
225                 230                 235                 240

Tyr Ala Asp Ser Val Lys Gly Arg Phe Ala Ile Ser Ala Asp Thr Ser
            245                 250                 255

Lys Asn Gln Ala Ser Leu Arg Leu Asn Ser Val Thr Ala Ala Asp Thr
        260                 265                 270

Ala Ile Tyr Tyr Cys Ser Arg Trp Gly Asp Gly Phe Tyr Ala Met
    275                 280                 285

Asp Tyr Trp Gly Lys Gly Thr Thr Val Thr Val Ser Ser Gly Gly Gly
290                 295                 300

Gly Ser Gly Gly Gly Gly Ser Gly Gly Gly Ser Ala Pro Thr Ser
305                 310                 315                 320

Ser Ser Thr Lys Lys Thr Gln Leu Gln Leu Glu His Leu Leu Leu Asp
            325                 330                 335

Leu Gln Met Ile Leu Asn Gly Ile Asn Asn Tyr Lys Asn Pro Lys Leu
        340                 345                 350

Thr Arg Met Leu Thr Phe Lys Phe Tyr Met Pro Lys Lys Ala Thr Glu
        355                 360                 365

Leu Lys His Leu Gln Cys Leu Glu Glu Glu Leu Lys Pro Leu Glu Glu
    370                 375                 380

Val Leu Asn Leu Ala Gln Ser Lys Asn Phe His Leu Arg Pro Arg Asp
385                 390                 395                 400

Leu Ile Ser Asn Ile Asn Val Ile Val Leu Glu Leu Lys Gly Ser Glu
            405                 410                 415

Thr Thr Phe Met Cys Glu Tyr Ala Asp Glu Thr Ala Thr Ile Val Glu
        420                 425                 430

Phe Leu Asn Arg Trp Ile Thr Phe Cys Gln Ser Ile Ile Ser Thr Leu
        435                 440                 445

Thr Gly Gly Gly Gly Ser Gly Gly Gly Gly Ser Gly Gly Gly Gly Ser
    450                 455                 460

Glu Ile Val Met Thr Gln Ser Pro Gly Thr Leu Ser Leu Ser Pro Gly
465                 470                 475                 480

Glu Arg Ala Thr Leu Ser Cys Arg Ala Ser Gln Asp Val Asn Thr Ala
            485                 490                 495

Val Ala Trp Tyr Gln Gln Lys Pro Gly Gln Ala Pro Arg Leu Leu Ile
        500                 505                 510

Tyr Ser Ala Ser Phe Leu Tyr Ser Gly Phe Pro Asp Arg Phe Ser Gly
        515                 520                 525

Ser Arg Ser Gly Thr Asp Phe Thr Leu Thr Ile Thr Arg Leu Glu Pro
530                 535                 540

Glu Asp Phe Ala Met Tyr Tyr Cys Gln Gln His Tyr Thr Thr Pro Pro
545                 550                 555                 560

Thr Phe Gly Gln Gly Thr Lys Leu Glu Ile Lys Gly Gly Gly Gly Ser
            565                 570                 575

Gly Gly Gly Gly Ser Gly Gly Gly Ser Thr Asp Gln Cys Asp Asn
        580                 585                 590

Phe Pro Gln Met Leu Arg Asp Leu Arg Asp Ala Phe Ser Arg Val Lys
        595                 600                 605

Thr Phe Phe Gln Thr Lys Asp Glu Leu Asp Asn Leu Leu Leu Lys Glu
610                 615                 620
```

-continued

Ser Leu Leu Glu Asp Phe Lys Gly Tyr Leu Gly Cys Gln Ala Leu Ser
625                 630                 635                 640

Glu Met Ile Gln Phe Tyr Leu Glu Val Met Pro Gln Ala Glu Asn
            645                 650                 655

Gln Asp Pro Glu Ile Lys Asp His Val Asn Ser Leu Gly Glu Asn Leu
        660                 665                 670

Lys Thr Leu Arg Leu Arg Leu Arg Cys His Arg Phe Leu Pro Cys
            675                 680                 685

Glu Asn Lys Ser Lys Ala Val Glu Gln Ile Lys Asn Ala Phe Asn Lys
        690                 695                 700

Leu Gln Glu Lys Gly Ile Tyr Lys Ala Met Ser Glu Phe Asp Ile Phe
705                 710                 715                 720

Ile Asn Tyr Ile Glu Ala Tyr Met Thr Ile Lys Ala Arg
                725                 730

<210> SEQ ID NO 54
<211> LENGTH: 733
<212> TYPE: PRT
<213> ORGANISM: Artificial Sequence
<220> FEATURE:
<223> OTHER INFORMATION: DK210her2 (Variant 4)

<400> SEQUENCE: 54

Met Gly Trp Ser Leu Ile Leu Leu Phe Leu Val Ala Val Ala Thr Arg
1               5                   10                  15

Val His Ser Thr Asp Gln Cys Asp Asn Phe Pro Gln Met Leu Arg Asp
            20                  25                  30

Leu Arg Asp Ala Phe Ser Arg Val Lys Thr Phe Phe Gln Thr Lys Asp
        35                  40                  45

Glu Leu Asp Asn Leu Leu Leu Lys Glu Ser Leu Leu Glu Asp Phe Lys
    50                  55                  60

Gly Tyr Leu Gly Cys Gln Ala Leu Ser Glu Met Ile Gln Phe Tyr Leu
65                  70                  75                  80

Glu Glu Val Met Pro Gln Ala Glu Asn Gln Asp Pro Glu Ile Lys Asp
                85                  90                  95

His Val Asn Ser Leu Gly Glu Asn Leu Lys Thr Leu Arg Leu Arg Leu
            100                 105                 110

Arg Arg Cys His Arg Phe Leu Pro Cys Glu Asn Lys Ser Lys Ala Val
        115                 120                 125

Glu Gln Ile Lys Asn Ala Phe Asn Lys Leu Gln Glu Lys Gly Ile Tyr
    130                 135                 140

Lys Ala Met Ser Glu Phe Asp Ile Phe Ile Asn Tyr Ile Glu Ala Tyr
145                 150                 155                 160

Met Thr Ile Lys Ala Arg Gly Gly Gly Ser Gly Gly Gly Ser
                165                 170                 175

Gly Gly Gly Gly Ser Gln Val Gln Leu Gln Glu Trp Gly Ala Gly Leu
            180                 185                 190

Leu Lys Pro Ser Glu Thr Leu Ser Leu Thr Cys Ala Ala Ser Gly Phe
        195                 200                 205

Asn Ile Lys Asp Thr Tyr Ile His Trp Val Arg Gln Pro Pro Gly Lys
    210                 215                 220

Gly Leu Glu Trp Val Ala Arg Ile Tyr Pro Thr Asn Gly Tyr Thr Arg
225                 230                 235                 240

Tyr Ala Asp Ser Val Lys Gly Arg Phe Ala Ile Ser Ala Asp Thr Ser
                245                 250                 255

```
Lys Asn Gln Ala Ser Leu Arg Leu Asn Ser Val Thr Ala Ala Asp Thr
                260                 265                 270

Ala Val Tyr Tyr Cys Ser Arg Trp Gly Gly Asp Gly Phe Tyr Ala Met
            275                 280                 285

Asp Tyr Trp Gly Lys Gly Thr Thr Val Thr Val Ser Ser Gly Gly Gly
290                 295                 300

Gly Ser Gly Gly Gly Gly Ser Gly Gly Gly Gly Ser Ala Pro Thr Ser
305                 310                 315                 320

Ser Ser Thr Lys Lys Thr Gln Leu Gln Leu Glu His Leu Leu Leu Asp
                325                 330                 335

Leu Gln Met Ile Leu Asn Gly Ile Asn Asn Tyr Lys Asn Pro Lys Leu
            340                 345                 350

Thr Arg Met Leu Thr Phe Lys Phe Tyr Met Pro Lys Lys Ala Thr Glu
            355                 360                 365

Leu Lys His Leu Gln Cys Leu Glu Glu Glu Leu Lys Pro Leu Glu Glu
        370                 375                 380

Val Leu Asn Leu Ala Gln Ser Lys Asn Phe His Leu Arg Pro Arg Asp
385                 390                 395                 400

Leu Ile Ser Asn Ile Asn Val Ile Val Leu Glu Leu Lys Gly Ser Glu
                405                 410                 415

Thr Thr Phe Met Cys Glu Tyr Ala Asp Glu Thr Ala Thr Ile Val Glu
            420                 425                 430

Phe Leu Asn Arg Trp Ile Thr Phe Cys Gln Ser Ile Ile Ser Thr Leu
            435                 440                 445

Thr Gly Gly Gly Gly Ser Gly Gly Gly Ser Gly Gly Gly Gly Ser
    450                 455                 460

Glu Ile Val Met Thr Gln Ser Pro Gly Thr Leu Ser Leu Ser Pro Gly
465                 470                 475                 480

Glu Arg Ala Thr Leu Ser Cys Arg Ala Ser Gln Asp Val Asn Thr Ala
            485                 490                 495

Val Ala Trp Tyr Gln Gln Lys Pro Gly Gln Ala Pro Arg Leu Leu Ile
            500                 505                 510

Tyr Ser Ala Ser Phe Leu Tyr Ser Gly Val Pro Asp Arg Phe Ser Gly
        515                 520                 525

Ser Arg Ser Gly Thr Asp Phe Thr Leu Thr Ile Thr Arg Leu Glu Pro
530                 535                 540

Glu Asp Phe Ala Thr Tyr Tyr Cys Gln Gln His Tyr Thr Thr Pro Pro
545                 550                 555                 560

Thr Phe Gly Gln Gly Thr Lys Leu Glu Ile Lys Gly Gly Gly Gly Ser
                565                 570                 575

Gly Gly Gly Gly Ser Gly Gly Gly Ser Thr Asp Gln Cys Asp Asn
            580                 585                 590

Phe Pro Gln Met Leu Arg Asp Leu Arg Asp Ala Phe Ser Arg Val Lys
            595                 600                 605

Thr Phe Phe Gln Thr Lys Asp Glu Leu Asp Asn Leu Leu Leu Lys Glu
            610                 615                 620

Ser Leu Leu Glu Asp Phe Lys Gly Tyr Leu Gly Cys Gln Ala Leu Ser
625                 630                 635                 640

Glu Met Ile Gln Phe Tyr Leu Glu Glu Val Met Pro Gln Ala Glu Asn
                645                 650                 655

Gln Asp Pro Glu Ile Lys Asp His Val Asn Ser Leu Gly Glu Asn Leu
            660                 665                 670
```

```
Lys Thr Leu Arg Leu Arg Leu Arg Arg Cys His Arg Phe Leu Pro Cys
            675                 680                 685

Glu Asn Lys Ser Lys Ala Val Glu Gln Ile Lys Asn Ala Phe Asn Lys
        690                 695                 700

Leu Gln Glu Lys Gly Ile Tyr Lys Ala Met Ser Glu Phe Asp Ile Phe
705                 710                 715                 720

Ile Asn Tyr Ile Glu Ala Tyr Met Thr Ile Lys Ala Arg
                725                 730

<210> SEQ ID NO 55
<211> LENGTH: 733
<212> TYPE: PRT
<213> ORGANISM: Artificial Sequence
<220> FEATURE:
<223> OTHER INFORMATION: DK210her2 (Variant 5)

<400> SEQUENCE: 55

Met Gly Trp Ser Leu Ile Leu Leu Phe Leu Val Ala Val Ala Thr Arg
1               5                   10                  15

Val His Ser Thr Asp Gln Cys Asp Asn Phe Pro Gln Met Leu Arg Asp
            20                  25                  30

Leu Arg Asp Ala Phe Ser Arg Val Lys Thr Phe Phe Gln Thr Lys Asp
        35                  40                  45

Glu Leu Asp Asn Leu Leu Leu Lys Glu Ser Leu Leu Glu Asp Phe Lys
50                  55                  60

Gly Tyr Leu Gly Cys Gln Ala Leu Ser Glu Met Ile Gln Phe Tyr Leu
65                  70                  75                  80

Glu Glu Val Met Pro Gln Ala Glu Asn Gln Asp Pro Glu Ile Lys Asp
                85                  90                  95

His Val Asn Ser Leu Gly Glu Asn Leu Lys Thr Leu Arg Leu Arg Leu
            100                 105                 110

Arg Arg Cys His Arg Phe Leu Pro Cys Glu Asn Lys Ser Lys Ala Val
        115                 120                 125

Glu Gln Ile Lys Asn Ala Phe Asn Lys Leu Gln Glu Lys Gly Ile Tyr
130                 135                 140

Lys Ala Met Ser Glu Phe Asp Ile Phe Ile Asn Tyr Ile Glu Ala Tyr
145                 150                 155                 160

Met Thr Ile Lys Ala Arg Gly Gly Gly Ser Gly Gly Gly Gly Ser
                165                 170                 175

Gly Gly Gly Gly Ser Gln Val Gln Leu Gln Glu Trp Gly Ala Gly Leu
            180                 185                 190

Leu Lys Pro Ser Glu Thr Leu Ser Leu Thr Cys Ala Ala Ser Gly Phe
        195                 200                 205

Asn Ile Lys Asp Thr Tyr Ile His Trp Val Arg Gln Pro Pro Gly Lys
210                 215                 220

Gly Leu Glu Trp Val Ala Arg Ile Tyr Pro Thr Asn Gly Tyr Thr Arg
225                 230                 235                 240

Tyr Ala Asp Ser Val Lys Gly Arg Phe Ala Ile Ser Ala Asp Thr Ser
                245                 250                 255

Lys Asn Gln Ala Ser Leu Gln Met Asn Ser Leu Arg Ala Glu Asp Thr
            260                 265                 270

Ala Val Tyr Tyr Cys Ser Arg Trp Gly Gly Asp Gly Phe Tyr Ala Met
        275                 280                 285

Asp Tyr Trp Gly Lys Gly Thr Thr Val Thr Val Ser Ser Gly Gly Gly
290                 295                 300
```

```
Gly Ser Gly Gly Gly Ser Gly Gly Gly Ser Ala Pro Thr Ser
305                 310                 315                 320

Ser Ser Thr Lys Lys Thr Gln Leu Gln Leu Glu His Leu Leu Leu Asp
            325                 330                 335

Leu Gln Met Ile Leu Asn Gly Ile Asn Asn Tyr Lys Asn Pro Lys Leu
                340                 345                 350

Thr Arg Met Leu Thr Phe Lys Phe Tyr Met Pro Lys Lys Ala Thr Glu
                355                 360                 365

Leu Lys His Leu Gln Cys Leu Glu Glu Glu Leu Lys Pro Leu Glu Glu
        370                 375                 380

Val Leu Asn Leu Ala Gln Ser Lys Asn Phe His Leu Arg Pro Arg Asp
385                 390                 395                 400

Leu Ile Ser Asn Ile Asn Val Ile Val Leu Glu Leu Lys Gly Ser Glu
                405                 410                 415

Thr Thr Phe Met Cys Glu Tyr Ala Asp Glu Thr Ala Thr Ile Val Glu
                420                 425                 430

Phe Leu Asn Arg Trp Ile Thr Phe Cys Gln Ser Ile Ile Ser Thr Leu
            435                 440                 445

Thr Gly Gly Gly Gly Ser Gly Gly Gly Gly Ser Gly Gly Gly Gly Ser
        450                 455                 460

Glu Ile Gln Met Thr Gln Ser Pro Ser Ser Leu Ser Leu Ser Pro Gly
465                 470                 475                 480

Glu Arg Ala Thr Leu Ser Cys Arg Ala Ser Gln Asp Val Asn Thr Ala
                485                 490                 495

Val Ala Trp Tyr Gln Gln Lys Pro Gly Gln Ala Pro Arg Leu Leu Ile
                500                 505                 510

Tyr Ser Ala Ser Phe Leu Tyr Ser Gly Val Pro Asp Arg Phe Ser Gly
        515                 520                 525

Ser Arg Ser Gly Thr Asp Phe Thr Leu Thr Ile Ser Ser Leu Gln Pro
530                 535                 540

Glu Asp Phe Ala Thr Tyr Tyr Cys Gln Gln His Tyr Thr Thr Pro Pro
545                 550                 555                 560

Thr Phe Gly Gln Gly Thr Lys Leu Glu Ile Lys Gly Gly Gly Gly Ser
                565                 570                 575

Gly Gly Gly Gly Ser Gly Gly Gly Gly Ser Thr Asp Gln Cys Asp Asn
        580                 585                 590

Phe Pro Gln Met Leu Arg Asp Leu Arg Asp Ala Phe Ser Arg Val Lys
        595                 600                 605

Thr Phe Phe Gln Thr Lys Asp Glu Leu Asp Asn Leu Leu Leu Lys Glu
        610                 615                 620

Ser Leu Leu Glu Asp Phe Lys Gly Tyr Leu Gly Cys Gln Ala Leu Ser
625                 630                 635                 640

Glu Met Ile Gln Phe Tyr Leu Glu Glu Val Met Pro Gln Ala Glu Asn
                645                 650                 655

Gln Asp Pro Glu Ile Lys Asp His Val Asn Ser Leu Gly Glu Asn Leu
            660                 665                 670

Lys Thr Leu Arg Leu Arg Leu Arg Arg Cys His Arg Phe Leu Pro Cys
        675                 680                 685

Glu Asn Lys Ser Lys Ala Val Glu Gln Ile Lys Asn Ala Phe Asn Lys
        690                 695                 700

Leu Gln Glu Lys Gly Ile Tyr Lys Ala Met Ser Glu Phe Asp Ile Phe
705                 710                 715                 720
```

Ile Asn Tyr Ile Glu Ala Tyr Met Thr Ile Lys Ala Arg
            725                 730

<210> SEQ ID NO 56
<211> LENGTH: 728
<212> TYPE: PRT
<213> ORGANISM: Artificial Sequence
<220> FEATURE:
<223> OTHER INFORMATION: DK410ngDV06CD14 (Variant 2)

<400> SEQUENCE: 56

Met Gly Trp Ser Leu Ile Leu Leu Phe Leu Val Ala Val Ala Thr Arg
1               5                   10                  15

Val His Ser Thr Asp Gln Cys Asp Asn Phe Pro Gln Met Leu Arg Asp
            20                  25                  30

Leu Arg Asp Ala Phe Ser Arg Val Lys Thr Phe Phe Gln Thr Lys Asp
        35                  40                  45

Glu Val Asp Asn Leu Leu Leu Lys Glu Ser Leu Leu Glu Asp Phe Lys
    50                  55                  60

Gly Tyr Leu Gly Cys Gln Ala Leu Ser Glu Met Ile Gln Phe Tyr Leu
65                  70                  75                  80

Glu Glu Val Met Pro Gln Ala Glu Asn Gln Asp Pro Glu Ile Lys Asp
                85                  90                  95

His Val Asn Ser Leu Gly Glu Asn Leu Lys Thr Leu Arg Leu Arg Leu
            100                 105                 110

Arg Arg Cys His Arg Phe Leu Pro Cys Glu Asn Lys Ser Lys Ala Val
        115                 120                 125

Glu Gln Ile Lys Asn Ala Phe Asn Lys Leu Gln Glu Lys Gly Ile Tyr
    130                 135                 140

Lys Ala Met Ser Glu Phe Asp Ile Phe Ile Asn Tyr Ile Glu Ala Tyr
145                 150                 155                 160

Met Thr Ile Lys Ala Arg Gly Gly Gly Ser Gly Gly Gly Gly Ser
                165                 170                 175

Gly Gly Gly Gly Ser Gln Val Gln Leu Gln Gln Trp Gly Ala Gly Leu
            180                 185                 190

Leu Lys Pro Ser Glu Thr Leu Ser Leu Thr Cys Ala Val Tyr Gly Tyr
        195                 200                 205

Ser Ile Thr Ser Asp Ser Ala Trp Asn Trp Ile Arg Gln Pro Pro Gly
    210                 215                 220

Lys Gly Leu Glu Trp Ile Gly Tyr Ile Ser Tyr Ser Gly Ser Thr Ser
225                 230                 235                 240

Tyr Asn Pro Ser Leu Lys Ser Arg Val Ala Ile Ser Val Asp Thr Ser
                245                 250                 255

Lys Asn Gln Phe Ser Leu Arg Leu Asn Ser Val Thr Ala Ala Asp Thr
            260                 265                 270

Ala Ile Tyr Tyr Cys Thr Ser Gly Leu Arg Phe Ala Tyr Trp Gly Lys
        275                 280                 285

Gly Thr Thr Val Thr Val Ser Ser Gly Gly Gly Ser Gly Gly Gly
    290                 295                 300

Gly Ser Gly Gly Gly Gly Ser His Lys Cys Asp Ile Thr Leu Gln Glu
305                 310                 315                 320

Ile Ile Lys Thr Leu Asn Ser Leu Thr Glu Gln Lys Thr Leu Cys Thr
                325                 330                 335

Glu Leu Thr Val Thr Asp Ile Phe Ala Ala Ser Lys Ala Thr Thr Glu
            340                 345                 350

```
Lys Glu Thr Phe Cys Arg Ala Ala Thr Val Leu Arg Gln Phe Tyr Ser
            355                 360                 365

His His Glu Lys Asp Thr Arg Cys Leu Gly Ala Thr Ala Gln Gln Phe
    370                 375                 380

His Arg His Lys Gln Leu Ile Arg Phe Leu Lys Arg Leu Asp Arg Asn
385                 390                 395                 400

Leu Trp Gly Leu Ala Gly Leu Asn Ser Cys Pro Val Lys Glu Ala Asn
                405                 410                 415

Gln Ser Thr Leu Glu Asn Phe Leu Glu Arg Leu Lys Thr Ile Met Arg
            420                 425                 430

Glu Lys Tyr Ser Lys Cys Ser Ser Gly Gly Gly Ser Gly Gly Gly
            435                 440                 445

Gly Ser Gly Gly Gly Ser Glu Ile Val Met Thr Gln Ser Pro Gly
        450                 455                 460

Thr Leu Ser Leu Ser Pro Gly Glu Arg Ala Thr Leu Ser Cys Arg Ala
465                 470                 475                 480

Ser Glu Ser Val Asp Ser Tyr Val Asn Ser Phe Leu His Trp Phe Gln
                485                 490                 495

Gln Lys Pro Gly Gln Ala Pro Arg Leu Leu Ile Tyr Arg Ala Ser Asn
            500                 505                 510

Leu Gln Ser Gly Phe Pro Asp Arg Phe Ser Gly Ser Gly Ser Gly Thr
        515                 520                 525

Asp Phe Thr Leu Thr Ile Thr Arg Leu Glu Pro Glu Asp Phe Ala Met
        530                 535                 540

Tyr Tyr Cys Gln Gln Ser Asn Glu Asp Pro Thr Phe Gly Gln Gly
545                 550                 555                 560

Thr Lys Leu Glu Ile Lys Gly Gly Gly Ser Gly Gly Gly Gly Ser
                565                 570                 575

Gly Gly Gly Gly Ser Thr Asp Gln Cys Asp Asn Phe Pro Gln Met Leu
            580                 585                 590

Arg Asp Leu Arg Asp Ala Phe Ser Arg Val Lys Thr Phe Phe Gln Thr
        595                 600                 605

Lys Asp Glu Val Asp Asn Leu Leu Leu Lys Glu Ser Leu Leu Glu Asp
        610                 615                 620

Phe Lys Gly Tyr Leu Gly Cys Gln Ala Leu Ser Glu Met Ile Gln Phe
625                 630                 635                 640

Tyr Leu Glu Glu Val Met Pro Gln Ala Glu Asn Gln Asp Pro Glu Ile
                645                 650                 655

Lys Asp His Val Asn Ser Leu Gly Glu Asn Leu Lys Thr Leu Arg Leu
            660                 665                 670

Arg Leu Arg Arg Cys His Arg Phe Leu Pro Cys Glu Asn Lys Ser Lys
        675                 680                 685

Ala Val Glu Gln Ile Lys Asn Ala Phe Asn Lys Leu Gln Glu Lys Gly
        690                 695                 700

Ile Tyr Lys Ala Met Ser Glu Phe Asp Ile Phe Ile Asn Tyr Ile Glu
705                 710                 715                 720

Ala Tyr Met Thr Ile Lys Ala Arg
                725

<210> SEQ ID NO 57
<211> LENGTH: 728
<212> TYPE: PRT
<213> ORGANISM: Artificial Sequence
<220> FEATURE:
```

<223> OTHER INFORMATION: DK410ngDV06CD14 (Variant 3)

<400> SEQUENCE: 57

```
Met Gly Trp Ser Leu Ile Leu Leu Phe Leu Val Ala Val Ala Thr Arg
1               5                   10                  15

Val His Ser Thr Asp Gln Cys Asp Asn Phe Pro Gln Met Leu Arg Asp
            20                  25                  30

Leu Arg Asp Ala Phe Ser Arg Val Lys Thr Phe Phe Gln Thr Lys Asp
        35                  40                  45

Glu Val Asp Asn Leu Leu Leu Lys Glu Ser Leu Leu Glu Asp Phe Lys
    50                  55                  60

Gly Tyr Leu Gly Cys Gln Ala Leu Ser Glu Met Ile Gln Phe Tyr Leu
65                  70                  75                  80

Glu Glu Val Met Pro Gln Ala Glu Asn Gln Asp Pro Glu Ile Lys Asp
                85                  90                  95

His Val Asn Ser Leu Gly Glu Asn Leu Lys Thr Leu Arg Leu Arg Leu
            100                 105                 110

Arg Arg Cys His Arg Phe Leu Pro Cys Glu Asn Lys Ser Lys Ala Val
        115                 120                 125

Glu Gln Ile Lys Asn Ala Phe Asn Lys Leu Gln Glu Lys Gly Ile Tyr
    130                 135                 140

Lys Ala Met Ser Glu Phe Asp Ile Phe Ile Asn Tyr Ile Glu Ala Tyr
145                 150                 155                 160

Met Thr Ile Lys Ala Arg Gly Gly Gly Ser Gly Gly Gly Ser
                165                 170                 175

Gly Gly Gly Gly Ser Gln Val Gln Leu Gln Gln Trp Gly Ala Gly Leu
            180                 185                 190

Leu Lys Pro Ser Glu Thr Leu Ser Leu Thr Cys Ala Val Tyr Gly Tyr
        195                 200                 205

Ser Ile Thr Ser Asp Ser Ala Trp Asn Trp Ile Arg Gln Pro Pro Gly
    210                 215                 220

Lys Gly Leu Glu Trp Met Gly Tyr Ile Ser Tyr Ser Gly Ser Thr Ser
225                 230                 235                 240

Tyr Asn Pro Ser Leu Lys Ser Arg Ile Ala Ile Ser Arg Asp Thr Ser
                245                 250                 255

Lys Asn Gln Phe Ser Leu Arg Leu Asn Ser Val Thr Ala Ala Asp Thr
            260                 265                 270

Ala Ile Tyr Tyr Cys Val Arg Gly Leu Arg Phe Ala Tyr Trp Gly Lys
        275                 280                 285

Gly Thr Thr Val Thr Val Ser Ser Gly Gly Gly Ser Gly Gly Gly
    290                 295                 300

Gly Ser Gly Gly Gly Ser His Lys Cys Asp Ile Thr Leu Gln Glu
305                 310                 315                 320

Ile Ile Lys Thr Leu Asn Ser Leu Thr Glu Gln Lys Thr Leu Cys Thr
                325                 330                 335

Glu Leu Thr Val Thr Asp Ile Phe Ala Ala Ser Lys Ala Thr Thr Glu
            340                 345                 350

Lys Glu Thr Phe Cys Arg Ala Ala Thr Val Leu Arg Gln Phe Tyr Ser
        355                 360                 365

His His Glu Lys Asp Thr Arg Cys Leu Gly Ala Thr Ala Gln Gln Phe
    370                 375                 380

His Arg His Lys Gln Leu Ile Arg Phe Leu Lys Arg Leu Asp Arg Asn
385                 390                 395                 400
```

```
Leu Trp Gly Leu Ala Gly Leu Asn Ser Cys Pro Val Lys Glu Ala Asn
                405                 410                 415

Gln Ser Thr Leu Glu Asn Phe Leu Glu Arg Leu Lys Thr Ile Met Arg
            420                 425                 430

Glu Lys Tyr Ser Lys Cys Ser Ser Gly Gly Gly Ser Gly Gly Gly
        435                 440                 445

Gly Ser Gly Gly Gly Ser Glu Ile Val Leu Thr Gln Ser Pro Gly
    450                 455                 460

Thr Leu Ser Leu Ser Pro Gly Glu Arg Ala Thr Leu Ser Cys Arg Ala
465                 470                 475                 480

Ser Glu Ser Val Asp Ser Tyr Val Asn Ser Phe Leu His Trp Tyr Gln
                485                 490                 495

Gln Lys Pro Gly Gln Ala Pro Arg Leu Leu Ile Tyr Arg Ala Ser Asn
            500                 505                 510

Leu Gln Ser Gly Phe Pro Asp Arg Phe Ser Gly Ser Gly Ser Arg Thr
        515                 520                 525

Asp Phe Thr Leu Thr Ile Thr Arg Leu Glu Pro Glu Asp Phe Ala Met
    530                 535                 540

Tyr Tyr Cys Gln Gln Ser Asn Glu Asp Pro Thr Thr Phe Gly Gln Gly
545                 550                 555                 560

Thr Lys Leu Glu Ile Lys Gly Gly Gly Ser Gly Gly Gly Ser
                565                 570                 575

Gly Gly Gly Gly Ser Thr Asp Gln Cys Asp Asn Phe Pro Gln Met Leu
            580                 585                 590

Arg Asp Leu Arg Asp Ala Phe Ser Arg Val Lys Thr Phe Phe Gln Thr
        595                 600                 605

Lys Asp Glu Val Asp Asn Leu Leu Leu Lys Glu Ser Leu Leu Glu Asp
    610                 615                 620

Phe Lys Gly Tyr Leu Gly Cys Gln Ala Leu Ser Glu Met Ile Gln Phe
625                 630                 635                 640

Tyr Leu Glu Glu Val Met Pro Gln Ala Glu Asn Gln Asp Pro Glu Ile
                645                 650                 655

Lys Asp His Val Asn Ser Leu Gly Glu Asn Leu Lys Thr Leu Arg Leu
            660                 665                 670

Arg Leu Arg Arg Cys His Arg Phe Leu Pro Cys Glu Asn Lys Ser Lys
        675                 680                 685

Ala Val Glu Gln Ile Lys Asn Ala Phe Asn Lys Leu Gln Glu Lys Gly
    690                 695                 700

Ile Tyr Lys Ala Met Ser Glu Phe Asp Ile Phe Ile Asn Tyr Ile Glu
705                 710                 715                 720

Ala Tyr Met Thr Ile Lys Ala Arg
                725

<210> SEQ ID NO 58
<211> LENGTH: 728
<212> TYPE: PRT
<213> ORGANISM: Artificial Sequence
<220> FEATURE:
<223> OTHER INFORMATION: DK410ngDV06CD14 (Variant 4)

<400> SEQUENCE: 58

Met Gly Trp Ser Leu Ile Leu Leu Phe Leu Val Ala Val Ala Thr Arg
1               5                   10                  15

Val His Ser Thr Asp Gln Cys Asp Asn Phe Pro Gln Met Leu Arg Asp
            20                  25                  30
```

```
Leu Arg Asp Ala Phe Ser Arg Val Lys Thr Phe Phe Gln Thr Lys Asp
        35                  40                  45

Glu Val Asp Asn Leu Leu Leu Lys Glu Ser Leu Leu Glu Asp Phe Lys
50                  55                  60

Gly Tyr Leu Gly Cys Gln Ala Leu Ser Glu Met Ile Gln Phe Tyr Leu
65                  70                  75                  80

Glu Glu Val Met Pro Gln Ala Glu Asn Gln Asp Pro Glu Ile Lys Asp
                85                  90                  95

His Val Asn Ser Leu Gly Glu Asn Leu Lys Thr Leu Arg Leu Arg Leu
            100                 105                 110

Arg Arg Cys His Arg Phe Leu Pro Cys Glu Asn Lys Ser Lys Ala Val
        115                 120                 125

Glu Gln Ile Lys Asn Ala Phe Asn Lys Leu Gln Glu Lys Gly Ile Tyr
    130                 135                 140

Lys Ala Met Ser Glu Phe Asp Ile Phe Ile Asn Tyr Ile Glu Ala Tyr
145                 150                 155                 160

Met Thr Ile Lys Ala Arg Gly Gly Gly Ser Gly Gly Gly Gly Ser
                165                 170                 175

Gly Gly Gly Gly Ser Gln Val Gln Leu Gln Gln Trp Gly Ala Gly Leu
            180                 185                 190

Leu Lys Pro Ser Glu Thr Leu Ser Leu Thr Cys Thr Val Thr Gly Tyr
        195                 200                 205

Ser Ile Thr Ser Asp Ser Ala Trp Asn Trp Ile Arg Gln Pro Pro Gly
    210                 215                 220

Lys Gly Leu Glu Trp Met Gly Tyr Ile Ser Tyr Ser Gly Ser Thr Ser
225                 230                 235                 240

Tyr Asn Pro Ser Leu Lys Ser Arg Ile Ala Ile Ser Arg Asp Thr Ser
                245                 250                 255

Lys Asn Gln Phe Ser Leu Arg Leu Asn Ser Val Thr Ala Ala Asp Thr
            260                 265                 270

Ala Thr Tyr Tyr Cys Val Arg Gly Leu Arg Phe Ala Tyr Trp Gly Lys
        275                 280                 285

Gly Thr Thr Val Thr Val Ser Ser Gly Gly Gly Ser Gly Gly Gly
    290                 295                 300

Gly Ser Gly Gly Gly Gly Ser His Lys Cys Asp Ile Thr Leu Gln Glu
305                 310                 315                 320

Ile Ile Lys Thr Leu Asn Ser Leu Thr Glu Gln Lys Thr Leu Cys Thr
                325                 330                 335

Glu Leu Thr Val Thr Asp Ile Phe Ala Ala Ser Lys Ala Thr Thr Glu
            340                 345                 350

Lys Glu Thr Phe Cys Arg Ala Ala Thr Val Leu Arg Gln Phe Tyr Ser
        355                 360                 365

His His Glu Lys Asp Thr Arg Cys Leu Gly Ala Thr Ala Gln Gln Phe
    370                 375                 380

His Arg His Lys Gln Leu Ile Arg Phe Leu Lys Arg Leu Asp Arg Asn
385                 390                 395                 400

Leu Trp Gly Leu Ala Gly Leu Asn Ser Cys Pro Val Lys Glu Ala Asn
                405                 410                 415

Gln Ser Thr Leu Glu Asn Phe Leu Glu Arg Leu Lys Thr Ile Met Arg
            420                 425                 430

Glu Lys Tyr Ser Lys Cys Ser Ser Gly Gly Gly Ser Gly Gly Gly
        435                 440                 445
```

```
Gly Ser Gly Gly Gly Ser Glu Ile Val Leu Thr Gln Ser Pro Gly
            450                 455                 460

Thr Leu Ser Leu Ser Pro Gly Glu Arg Ala Thr Leu Ser Cys Arg Ala
465                 470                 475                 480

Ser Glu Ser Val Asp Ser Tyr Val Asn Ser Phe Leu His Trp Tyr Gln
                485                 490                 495

Gln Lys Pro Gly Gln Ala Pro Arg Leu Leu Ile Tyr Arg Ala Ser Asn
            500                 505                 510

Leu Gln Ser Gly Ile Pro Asp Arg Phe Ser Gly Ser Gly Ser Arg Thr
            515                 520                 525

Asp Phe Thr Leu Thr Ile Thr Arg Leu Glu Pro Glu Asp Phe Ala Thr
530                 535                 540

Tyr Tyr Cys Gln Gln Ser Asn Glu Asp Pro Thr Thr Phe Gly Gln Gly
545                 550                 555                 560

Thr Lys Leu Glu Ile Lys Gly Gly Gly Ser Gly Gly Gly Gly Ser
                565                 570                 575

Gly Gly Gly Gly Ser Thr Asp Gln Cys Asp Asn Phe Pro Gln Met Leu
            580                 585                 590

Arg Asp Leu Arg Asp Ala Phe Ser Arg Val Lys Thr Phe Phe Gln Thr
            595                 600                 605

Lys Asp Glu Val Asp Asn Leu Leu Leu Lys Glu Ser Leu Leu Glu Asp
610                 615                 620

Phe Lys Gly Tyr Leu Gly Cys Gln Ala Leu Ser Glu Met Ile Gln Phe
625                 630                 635                 640

Tyr Leu Glu Glu Val Met Pro Gln Ala Glu Asn Gln Asp Pro Glu Ile
                645                 650                 655

Lys Asp His Val Asn Ser Leu Gly Glu Asn Leu Lys Thr Leu Arg Leu
            660                 665                 670

Arg Leu Arg Arg Cys His Arg Phe Leu Pro Cys Glu Asn Lys Ser Lys
            675                 680                 685

Ala Val Glu Gln Ile Lys Asn Ala Phe Asn Lys Leu Gln Glu Lys Gly
            690                 695                 700

Ile Tyr Lys Ala Met Ser Glu Phe Asp Ile Phe Ile Asn Tyr Ile Glu
705                 710                 715                 720

Ala Tyr Met Thr Ile Lys Ala Arg
                725
```

<210> SEQ ID NO 59
<211> LENGTH: 728
<212> TYPE: PRT
<213> ORGANISM: Artificial Sequence
<220> FEATURE:
<223> OTHER INFORMATION: DK410ngDV06CD14 (Variant 5)

<400> SEQUENCE: 59

```
Met Gly Trp Ser Leu Ile Leu Leu Phe Leu Val Ala Val Ala Thr Arg
1               5                   10                  15

Val His Ser Thr Asp Gln Cys Asp Asn Phe Pro Gln Met Leu Arg Asp
                20                  25                  30

Leu Arg Asp Ala Phe Ser Arg Val Lys Thr Phe Phe Gln Thr Lys Asp
            35                  40                  45

Glu Val Asp Asn Leu Leu Leu Lys Glu Ser Leu Leu Glu Asp Phe Lys
    50                  55                  60

Gly Tyr Leu Gly Cys Gln Ala Leu Ser Glu Met Ile Gln Phe Tyr Leu
65                  70                  75                  80
```

```
Glu Glu Val Met Pro Gln Ala Glu Asn Gln Asp Pro Glu Ile Lys Asp
                85                  90                  95
His Val Asn Ser Leu Gly Glu Asn Leu Lys Thr Leu Arg Leu Arg Leu
            100                 105                 110
Arg Arg Cys His Arg Phe Leu Pro Cys Glu Asn Lys Ser Lys Ala Val
        115                 120                 125
Glu Gln Ile Lys Asn Ala Phe Asn Lys Leu Gln Glu Lys Gly Ile Tyr
    130                 135                 140
Lys Ala Met Ser Glu Phe Asp Ile Phe Ile Asn Tyr Ile Glu Ala Tyr
145                 150                 155                 160
Met Thr Ile Lys Ala Arg Gly Gly Gly Ser Gly Gly Gly Gly Gly Ser
                165                 170                 175
Gly Gly Gly Gly Ser Gln Val Gln Leu Gln Gln Trp Gly Ala Gly Leu
            180                 185                 190
Leu Lys Pro Ser Glu Thr Leu Ser Leu Thr Cys Thr Val Thr Gly Tyr
        195                 200                 205
Ser Ile Thr Ser Asp Ser Ala Trp Asn Trp Ile Arg Gln Pro Pro Gly
    210                 215                 220
Lys Gly Leu Glu Trp Met Gly Tyr Ile Ser Tyr Ser Gly Ser Thr Ser
225                 230                 235                 240
Tyr Asn Pro Ser Leu Lys Ser Arg Ile Ala Ile Ser Arg Asp Thr Ser
                245                 250                 255
Lys Asn Gln Phe Ser Leu Gln Leu Asn Ser Val Thr Thr Glu Asp Thr
            260                 265                 270
Ala Thr Tyr Tyr Cys Val Arg Gly Leu Arg Phe Ala Tyr Trp Gly Lys
        275                 280                 285
Gly Thr Thr Val Thr Val Ser Ser Gly Gly Gly Ser Gly Gly Gly Gly
    290                 295                 300
Gly Ser Gly Gly Gly Gly Ser His Lys Cys Asp Ile Thr Leu Gln Glu
305                 310                 315                 320
Ile Ile Lys Thr Leu Asn Ser Leu Thr Glu Gln Lys Thr Leu Cys Thr
                325                 330                 335
Glu Leu Thr Val Thr Asp Ile Phe Ala Ala Ser Lys Ala Thr Thr Glu
            340                 345                 350
Lys Glu Thr Phe Cys Arg Ala Ala Thr Val Leu Arg Gln Phe Tyr Ser
        355                 360                 365
His His Glu Lys Asp Thr Arg Cys Leu Gly Ala Thr Ala Gln Gln Phe
    370                 375                 380
His Arg His Lys Gln Leu Ile Arg Phe Leu Lys Arg Leu Asp Arg Asn
385                 390                 395                 400
Leu Trp Gly Leu Ala Gly Leu Asn Ser Cys Pro Val Lys Glu Ala Asn
                405                 410                 415
Gln Ser Thr Leu Glu Asn Phe Leu Glu Arg Leu Lys Thr Ile Met Arg
            420                 425                 430
Glu Lys Tyr Ser Lys Cys Ser Ser Gly Gly Gly Ser Gly Gly Gly Gly
        435                 440                 445
Gly Ser Gly Gly Gly Gly Ser Glu Ile Val Leu Thr Gln Ser Pro Gly
    450                 455                 460
Thr Leu Ser Leu Ser Pro Gly Glu Arg Ala Thr Leu Ser Cys Arg Ala
465                 470                 475                 480
Ser Glu Ser Val Asp Ser Tyr Val Asn Ser Phe Leu His Trp Tyr Gln
                485                 490                 495
```

Gln Lys Pro Gly Gln Ala Pro Arg Leu Leu Ile Tyr Arg Ala Ser Asn
                500                 505                 510

Leu Gln Ser Gly Ile Pro Asp Arg Phe Ser Gly Ser Gly Ser Arg Thr
            515                 520                 525

Asp Phe Thr Leu Thr Ile Asn Arg Val Glu Pro Glu Asp Phe Ala Thr
        530                 535                 540

Tyr Tyr Cys Gln Gln Ser Asn Glu Asp Pro Thr Thr Phe Gly Gln Gly
545                 550                 555                 560

Thr Lys Leu Glu Ile Lys Gly Gly Gly Ser Gly Gly Gly Gly Ser
                565                 570                 575

Gly Gly Gly Gly Ser Thr Asp Gln Cys Asp Asn Phe Pro Gln Met Leu
            580                 585                 590

Arg Asp Leu Arg Asp Ala Phe Ser Arg Val Lys Thr Phe Phe Gln Thr
        595                 600                 605

Lys Asp Glu Val Asp Asn Leu Leu Leu Lys Glu Ser Leu Leu Glu Asp
610                 615                 620

Phe Lys Gly Tyr Leu Gly Cys Gln Ala Leu Ser Glu Met Ile Gln Phe
625                 630                 635                 640

Tyr Leu Glu Glu Val Met Pro Gln Ala Glu Asn Gln Asp Pro Glu Ile
                645                 650                 655

Lys Asp His Val Asn Ser Leu Gly Glu Asn Leu Lys Thr Leu Arg Leu
            660                 665                 670

Arg Leu Arg Arg Cys His Arg Phe Leu Pro Cys Glu Asn Lys Ser Lys
        675                 680                 685

Ala Val Glu Gln Ile Lys Asn Ala Phe Asn Lys Leu Gln Glu Lys Gly
690                 695                 700

Ile Tyr Lys Ala Met Ser Glu Phe Asp Ile Phe Ile Asn Tyr Ile Glu
705                 710                 715                 720

Ala Tyr Met Thr Ile Lys Ala Arg
                725

<210> SEQ ID NO 60
<211> LENGTH: 2208
<212> TYPE: DNA
<213> ORGANISM: Artificial Sequence
<220> FEATURE:
<223> OTHER INFORMATION: DK210egfr Nucleic Acid Sequence

<400> SEQUENCE: 60
gccgccacca tgggatggtc tttgatcctg ctgttcctgg tggccgtggc taccagagtg      60
cattctaccg accagtgcga caacttccct cagatgctgc gggacctgag ggacgccttc     120
tccagagtga aaacattctt ccagaccaag gacgagctgg acaacctgct gctgaaagag     180
tccctgctgg aagatttcaa gggctacctg gctgtcaggc cctgtccga gatgatccag     240 ttctacctgg aagaagtgat gccccaggcc gagaatcagg accctgagat caaggaccat     300
gtgaactccc tgggcgagaa cctgaaaacc ctgcggctga ctgcgcgcg tgtcacaga      360 tttctgccct gcgagaacaa gtccaaggcc gtggaacaga tcaagaacgc cttcaacaag     420
ctgcaagaga agggcatcta caaggccatg agcgagttcg acatcttcat caactacatc     480
gaggcctaca tgaccatcaa ggctagaggt ggcgaggat ctggcggtgg tggttctggc      540
ggaggcggat ctcaggttca gttgcaacaa tggggcgctg gcctgctgaa gccttctgag     600
acactgtctc tgacctgcgc cgtgtacggc ttctctctga ccaattacgg cgtgcactgg     660
atccggcagc cacctggaaa aggactggaa tggctgggag tgatttggag cggcggcaac     720

| | |
|---|---:|
| accgactaca acacccctt tacctctaga gtggccatct ccaaggacaa ctccaagaac | 780 |
| caggtgtccc tgagactgaa ctctgtgacc gccgctgata ccgccatcta ctactgtgct | 840 |
| agagccctga cctactacga ctacgagttc gcttattggg gcaagggcac caccgtgaca | 900 |
| gtttcatctg cggcggagg aagcggtggc ggcggtagcg gaggtggtgg atctgctcct | 960 |
| acctcctcca gcaccaagaa acccagctg cagttggagc atctgctgct ggacctccag | 1020 |
| atgatcctga acggcatcaa caactacaag aatcccaagc tgacccggat gctgaccttc | 1080 |
| aagttctaca tgcccaagaa ggccaccgag ctgaaacatc tgcagtgcct ggaagaggaa | 1140 |
| ctgaagcccc tcgaggaagt gctgaatctg gcccagtcca agaacttcca cctgaggcct | 1200 |
| agggacctga tctccaacat caacgtgatc gtgctcgagc tgaagggctc cgagacaacc | 1260 |
| tttatgtgcg agtacgccga cgagacagcc accatcgtgg aatttctgaa ccggtggatc | 1320 |
| accttctgcc agtccatcat ctctacattg accggtggtg gcggatcagg cggtggcgga | 1380 |
| agcggaggcg gaggttctga aattgtgctg acccagtctc ctggcactct gtctttgagt | 1440 |
| cctggcgaga gagctaccct gtcctgcaga gcttctcagt ccatcggcac caacatccac | 1500 |
| tggtatcagc agaagcctgg acaggcccct cggctgctga ttaagtacgc ctctgagtcc | 1560 |
| atcagcggct ccctgacag attctctggc tctggatctg gcaccgactt cacccctgacc | 1620 |
| atcaccagac tggaacccga ggacttcgct atgtactact gccagcagaa caacaactgg | 1680 |
| cccaccacct ttggccaggg caccaagttg gaaatcaaag gtggcggtgg aagtggcggc | 1740 |
| ggtggctcag cggcggtgg atctacagac cagtgtgata attttccaca gatgctcagg | 1800 |
| gatctccgcg acgcctttag ccgggtcaag acatttttc agacaaagga tgaactcgat | 1860 |
| aatctcctgc tcaaagagag cctgctcgag gactttaaag gatacctggg atgccaggct | 1920 |
| ctcagcgaaa tgattcagtt ttatttggag gaagtcatgc ctcaagctga aaaccaggat | 1980 |
| ccagagatta aggatcacgt caacagcctc ggcgagaatc tcaagacact gcgcctgagg | 2040 |
| ctgagaagat gccaccggtt tctgcctttgt gaaaacaaga gcaaggctgt cgagcagatt | 2100 |
| aagaatgctt ttaacaaatt gcaagaaaaa gggatctata aggctatgtc tgagtttgat | 2160 |
| atctttatca attatatcga agcttatatg actattaagg cccggtga | 2208 |

<210> SEQ ID NO 61
<211> LENGTH: 2288
<212> TYPE: DNA
<213> ORGANISM: Artificial Sequence
<220> FEATURE:
<223> OTHER INFORMATION: DK410ngDV06CD14 Variant 2 Nucleic Acid Sequence

<400> SEQUENCE: 61

| | |
|---|---:|
| atcgaaatta atacgactca ctatagggag acccaagctg gctagcgccg ccaccatggg | 60 |
| atggtctttg atcctgctgt tcctggtggc cgtggctacc agagtgcatt ctaccgacca | 120 |
| gtgcgacaac ttccctcaga tgctgcggga cctgagagat gccttctcca gagtgaaaac | 180 |
| attcttccag accaaggacg aggtggacaa cctgctgctg aaagagtccc tgctggaaga | 240 |
| tttcaagggc tacctgggct gtcaggccct gtccgagatg atccagttct acctggaaga | 300 |
| agtgatgccc caggccgaga tcaggaccc gagatcaag gaccacgtga actccctggg | 360 |
| cgagaacctg aaaaccctgc ggctgagact gcggcggtgc acagatttc tgccctgcga | 420 |
| gaacaagtcc aaggccgtgg aacagatcaa gaacgccttc aacaagctgc aagagaaggg | 480 |
| catctacaag gccatgagcg agttcgacat cttcatcaac tacatcgagg cctacatgac | 540 |
| catcaaggcc agaggcggcg aggatctgg cgaggtggga gcggaggcg gtggatctca | 600 |

```
ggttcagttg cagcaatggg gcgctggcct gctgaagcct tctgagacac tgtctctgac    660
ctgcgccgtg tacggctact ccatcacctc tgactctgcc tggaattgga tccggcagcc    720
tcctggcaaa ggactggaat ggatcggcta catctcctac tccggctcca ccagctacaa    780
ccccagcctg aagtctagag tggccatctc cgtggacacc tccaagaacc agttctccct    840
gagactgaac tccgtgaccg ccgctgatac cgccatctac tactgcacct ccggcctgag    900
atttgcctac tggggcaagg gcaccaccgt gactgttagt agtggtggtg gcggtagtgg    960
cggaggcggc tcaggcggtg gcggatctca taagtgcgac atcaccctgc aagaaatcat   1020
caagaccctg aacagcctga ccgagcagaa aactctgtgc accgagctga ccgtgaccga   1080
tatctttgcc gcctctaagg ccacaaccga aaagagaca ttctgcagag ccgccaccgt   1140
gctgcggcag ttttactctc accacgaaa ggacaccaga tgcctgggcg ctaccgctca   1200
gcagttccac agacacaagc agctgatccg gttcctgaag cggctggaca gaaacctgtg   1260
gggactcgcc ggcctgaact cttgcccctgt gaaagaggcc aaccagtcta ccctggaaaa   1320
cttcctggaa cggctcaaga ccatcatgcg cgagaagtac tccaagtgct ccagcggtgg   1380
cggtggttca ggtggcggtg gctctggcgg cggaggtagt gaaattgtga tgacccagtc   1440
tcctggcact ctgtctctgt ctcccggcga gagagctacc ctgtcttgta gagcctccga   1500
gtccgtggac tcctacgtga acagcttcct gcactggttc cagcagaagc ctggacaggc   1560
tcccagactg ctgatctaca gagcctccaa cctgcagagc ggcttccctg acagattttc   1620
cggctctggc tccggcaccg acttcaccct gacaatcacc agactggaac ccgaggactt   1680
cgctatgtac tactgccagc agtccaacga ggaccccacc catttggcc agggcaccaa   1740 gctggaaatc aaaggtggcg gaggaagtgg tggcggaggc tccggcggag cggttctac   1800 agatcagtgt gataatttc cacagatgct ccgcgatctg cgggacgcct ttagccgggt   1860
caagacattt tttcagacaa aggatgaagt cgataacctc ttgctcaaag agagcctgct   1920
cgaggacttt aagggatatc tgggatgcca ggctctgagc gaaatgattc agttttatct   1980
cgaggaagtc atgcctcaag cagagaacca ggatccagag attaaggatc atgtgaatag   2040 cctcgggag aacctcaaga cactgagact ccggctgaga agatgccacc ggtttctgcc   2100
ttgtgaaaac aaaagcaagg ctgtcgagca gattaagaat gcttttaaca aactccaaga   2160
aaaagggatc tataaggcta tgtctgagtt tgatatctt atcaattata tcgaagctta   2220
tatgactatt aaggctcgct aggggcccgt ttaaacccgc tgatcagcct cgactgtgcc   2280
ttctagtt                                                             2288
```

<210> SEQ ID NO 62
<211> LENGTH: 2303
<212> TYPE: DNA
<213> ORGANISM: Artificial Sequence
<220> FEATURE:
<223> OTHER INFORMATION: DK210her2 Variant 4 Nucleic Acid Sequence

<400> SEQUENCE: 62

```
atcgaaatta atacgactca ctataggag acccaagctg gctagcgccg ccaccatggg     60
atggtctttg atcctgctgt tcctggtggc cgtggctacc agagtgcatt ctaccgacca    120
gtgcgacaac ttccctcaga tgctgcggga cctgagagat gccttctcca gagtgaaaac    180
attcttccag accaaggacg agctggacaa cctgctgctg aaagagtccc tgctggaaga    240
tttcaagggc tacctgggct gtcaggccct gtccgagatg atccagttct acctggaaga    300
```

```
agtgatgccc caggccgaga atcaggaccc cgagatcaag gaccacgtga actccctggg    360
cgagaacctg aaaaccctgc ggctgagact gcggcggtgc cacagatttc tgccctgcga    420
gaacaagtcc aaggccgtgg aacagatcaa gaacgccttc aacaagctgc aagagaaggg    480
catctacaag gccatgagcg agttcgacat cttcatcaac tacatcgagg cctacatgac    540
catcaaggcc agaggcggcg gaggatctgg cggaggtgga agcggaggcg gtggatctca    600
ggtgcagttg caagaatggg gcgctggcct gctgaagcct tccgaaacac tgtctctgac    660
ctgcgccgcc agcggcttca acatcaagga cacctacatc cactgggtcc gacagcctcc    720
aggcaaagga ctggaatggg tcgccagaat ctaccccacc aacggctaca ccagatacgc    780
cgactctgtg aagggcagat tcgccatctc tgccgacacc tccaagaacc aggccagcct    840
gagactgaac tctgtgaccg ctgctgacac cgccgtgtac tactgctcta gatggggcgg    900
agatggcttc tacgccatgg actattgggg caagggcacc accgtgacag ttagtagtgg    960
tggtggcggt agtggcggag gcggctcagg cggtggtgga tctgctccta catcctccag   1020
caccaagaaa acccagctgc agttggagca tctgctgctg gacctccaga tgatcctgaa   1080
cggcatcaac aactacaaga accccaagct gacccggatg ctgaccttca gttctacat    1140
gcccaagaag gccaccgagc tgaaacatct gcagtgcctg gaagaggaac tgaagcccct   1200
cgaggaagtg ctgaatctgg cccagtccaa gaacttccac ctgaggccta gggacctgat   1260
ctccaacatc aacgtgatcg tgctcgagct gaagggctcc gagacaacct tcatgtgcga   1320
gtacgccgac gagacagcta ccatcgtgga atttctgaac cggtggatca ccttctgcca   1380
gtccatcatc tctaccctga ctggtggcgg aggaagcggc ggaggcggat ctggcggcgg   1440
aggctctgaa attgtgatga cccagtctcc tggcactctg tctctgtctc ccggcgagag   1500
agctaccctg tcttgtagag ccagccagga cgtgaacacc gctgtggctt ggtatcagca   1560
gaagcctgga caggcccctc ggctgctgat ctactctgcc tcctttctgt actccggcgt   1620
gcccgacaga ttctccggct ctagatctgg caccgacttc accctgacca tcaccagact   1680
ggaacccgag gacttcgcca cctactactg ccagcagcac tacaccacac acctaccttt   1740
tggccagggc accaagctgg aaatcaaagg tggtggcgga tcaggcggtg cggtagcgg    1800
tggcggaggt tctacagacc agtgtgataa ttttcccaa atgctgaggg atctgcggga   1860
cgccttctct agggtcaaga catttttttca gacaaaggat gaactcgata acctcttgct   1920
caaagagagc ctgctcgagg actttaaggg atatctggga tgccaggctc tgagcgaaat   1980
gattcagttt tatttggagg aagtcatgcc tcaagcagaa aaccaggatc cagagattaa    2040
ggatcatgtc aacagcctcg gcgagaatct caagacactg cgcctgaggc tgagaagatg   2100
ccaccggttt ctgccttgtg aaaacaaaag caaggctgtc gagcagatta agaatgcttt   2160
taacaaactc caagaaaaag ggatctataa ggctatgtct gagtttgata tctttatcaa   2220
ttatatcgaa gcttatatga ctattaaggc tcgctagggg cccgtttaaa cccgctgatc   2280
agcctcgact gtgccttcta gtt                                            2303
```

<210> SEQ ID NO 63
<211> LENGTH: 2303
<212> TYPE: DNA
<213> ORGANISM: Artificial Sequence
<220> FEATURE:
<223> OTHER INFORMATION: DK210her2 Variant 5 Nucleic Acid Sequence

<400> SEQUENCE: 63

```
atcgaaatta atacgactca ctatagggag acccaagctg gctagcgccg ccaccatggg      60
atggtctttg atcctgctgt tcctggtggc cgtggctacc agagtgcatt ctaccgacca     120
gtgcgacaac ttccctcaga tgctgcggga cctgagagat gccttctcca gagtgaaaac     180
attcttccag accaaggacg agctggacaa cctgctgctg aaagagtccc tgctggaaga     240
tttcaagggc tacctgggct gtcaggccct gtccagatgg atccagttct acctggaaga     300
agtgatgccc caggccgaga tcaggaccc cgagatcaag gaccacgtga actccctggg     360
cgagaacctg aaaaccctgc ggctgagact gcggcggtgc cacagatttc tgccctgcga     420
gaacaagtcc aaggccgtgg aacagatcaa gaacgccttc aacaagctgc aagagaaggg     480
catctacaag gccatgagcg agttcgacat cttcatcaac tacatcgagg cctacatgac     540
catcaaggcc agaggcggcg aggatctgg cggaggtgga agcggaggcg gtggatctca     600
ggtgcagttg caagaatggg gcgctggcct gctgaagcct tccgaaacac tgtctctgac     660
ctgcgccgcc agcggcttca acatcaagga cacctacatc cactgggtcc gacagcctcc     720
aggcaaagga ctggaatggg tcgccagaat ctaccccacc aacggctaca ccagatacgc     780
cgactctgtg aagggcagat tcgccatctc tgccgacacc tccaagaacc aggccagcct     840
gcagatgaac agcctgagag ctgaggacac cgccgtgtac tactgctcta tgatggggcgg     900
agatggcttc tacgccatgg actattgggg caagggcacc accgtgacag ttagtagtgg     960
tggtggcggt agtggcggag gcggctcagg cggtggtgga tctgctccta catcctccag    1020
caccaagaaa acccagctgc agttggagca tctgctgctg gacctccaga tgatcctgaa    1080
cggcatcaac aactacaaga accccaagct gacccggatg ctgaccttca agttctacat    1140
gcccaagaag gccaccgagc tgaaacatct gcagtgcctg gaagaggaac tgaagcccct    1200
cgaggaagtg ctgaatctgg cccagtccaa gaacttccac ctgaggccta gggacctgat    1260
ctccaacatc aacgtgatcg tgctcgagct gaagggctcc gagacaacct tcatgtgcga    1320
gtacgccgac gagacagcta ccatcgtgga atttctgaac cggtggatca ccttctgcca    1380
gtccatcatc tctaccctga ctggtggcgg aggaagcggc ggaggcggat ctggcggcgg    1440
aggctctgaa attcagatga cccagtctcc ttccagcctg tctctgtccc ctggcgagag    1500
agctacccctg tcttgtagag ccagccagga cgtgaacacc gctgtggctt ggtatcagca    1560
gaagcctgga caggcccctc ggctgctgat ctactctgcc tcctttctgt actccggcgt    1620
gcccgacaga ttctccggct ctagatctgg caccgacttt accctgacaa tcagctccct    1680
gcagcctgag gacttcgcca cctactactg ccagcagcac tacaccacac acctaccttt    1740
tggccagggc accaagctgg aaatcaaagg tggtggcgga tcaggcggtg gcggtagcgg    1800
tggcggaggt tctacagacc agtgtgataa ttttccccaa atgctgaggg atctgcggga    1860
cgccttctct agggtcaaga cattttttca gacaaaggat gaactcgata acctcttgct    1920
caaagagagc ctgctcgagg acttcaaagg atatctggga tgccaggctc tgagcgaaat    1980
gattcagttt tatttggagg aagtcatgcc tcaagcagaa accaggatc cagagattaa    2040
ggatcatgtc aacagcctcg gcgagaatct caagacactg agactgaggc tgcggagatg    2100
tcaccggttt ctgccttgtg aaaacaagag caaggctgtc gagcagatta agaatgcttt    2160
taacaaactc caagaaaaag ggatctataa ggctatgtct gagtttgata tctttatcaa    2220
```

```
ttatatcgaa gcttatatga ctattaaggc tcgctagggg cccgtttaaa cccgctgatc    2280
agcctcgact gtgccttcta gtt                                            2303
```

DUAL CYTOKINE FUSION PROTEINS COMPRISING IL-10

CROSS-REFERENCE TO RELATED APPLICATION

This application is a Divisional application of U.S. patent application Ser. No. 17/199,239 filed on Mar. 11, 2021, which is a Continuation application of U.S. patent application Ser. No. 17/110,104, entitled "Dual Cytokine Fusion Proteins Comprising IL-10," filed on Dec. 2, 2020, which claims priority to U.S. Provisional Application No. 63/054,208 filed Jul. 20, 2020, the disclosure of each is incorporated by reference in its entirety.

FIELD OF INVENTION

The present disclosure relates to the field of biotechnology, and more specifically, to a novel dual cytokine fusion protein comprising Interleukin-10 ("IL-10") in combination with other inflammatory and immune regulating cytokines, methods of treating inflammatory and immune disease or conditions, and/or methods of treating cancer.

INTRODUCTION

IL-10, originally named cytokine synthesis inhibitory factor (Malefyt, Interleukin 10 inhibits cytokine synthesis by human monocytes: An autoregulatory role of IL-10 produced by monocytes, 1991), is a pleiotropic cytokine known to both suppress inflammatory response (Fedorak, 2000), and more recently activate $CD8^+$ T cells to induce Interferon γ ("IFNγ") dependent anti-tumor immune responses (Mumm J., 2011). IL-10 is a non-covalent homo-dimeric cytokine with structural similarities to IFNγ. IL-10 binds to the IL-10 receptor, which consists of two subunits of the IL10 receptor 1 (IL10R1) and two subunits of the IL-10 receptor 2 (IL10R2) (Moore, 2001). The IL-10 receptor complex is expressed on the surface of most hematopoietic cells and most highly expressed on macrophages and T-cells. While IL-10 has been reported to be both an immunosuppressive (Schreiber, 2000) and an immunostimulatory cytokine (Mumm, 2011), clinical evaluation of IL-10 treatment of Crohn's patients resulted in an inverse dose response (Fedorak, 2000; Schreiber, 2000), whereas treatment of cancer patients with PEGylated IL-10 resulted in dose titratable potent anti-tumor responses (Naing, 2018). PEGylated IL-10 anti-tumor response requires endogenous CD8+ T cells and IFNγ (Mumm, 2011). Treatment of tumor bearing animals with PEGylated IL-10 results in increased intratumor CD8+ T cells and increased IFNγ on a per cell basis. Most recently, however, cancer patients treated with PEGylated IL-10 lead to evidence of immune stimulation, but no increase in anti-tumor responses (Spigel, 2020).

Interleukin-2 ("IL-2") is a four-helix bundle pleiotropic cytokine known to induce anti-tumor immune responses (Jiang, 2016), but also exhibiting high toxicity due to uncontrolled activation of and secretion of IFNγ by natural killer ("NK") cells and $CD4^+$ T cells and expansion of T regulatory cells (Chinen, 2016). For this reason, many groups have attempted to mutate IL-2 to reduce its binding to the high affinity receptor, in an effort to reduce the toxicity of IL-2 (Chen, 2018). These muteins have not generated substantial clinical success (Bentebibe, 2019). This suggests other mechanisms must be employed to reduce the potentially lethal toxicity of IL-2.

IL-10 has been reported to suppress IL-2 driven IFNγ production secreted by both NK and $CD4^+$ T cells (Scott, 2006), but it has also been reported to act as a cofactor for IL-2 induced $CD8^+$ T cell proliferation (Groux, 1998). It is therefore not known whether IL-2 and IL-10 will co-activate cells of the immune system or cancel each other out.

Interleukin-4 ("IL-4") is a four-helix bundle pleiotropic cytokine considered the quintessential Th2 driving cytokine (McGuirk, 2000), that is mostly associated with driving alternative activation by macrophages (Balce, 2011). IL-4 is predominantly associated with driving inflammation associated with allergic responses and asthma (Steinke, 2001; Ryan, 1997). Furthermore, cancer patients have been treated safely with IL-4 (Davis, 2009), due to IL-4's ability to suppress some cancer cell proliferation (Lee, 2016; Gooch, 1998). While IL-4 has been reported to suppress monocyte secretion of proinflammatory cytokines (Woodward, 2012), it is not considered a potent anti-inflammatory cytokine due to its ability to prime antigen presenting cells and drive proinflammatory cytokine secretion by monocytes exposed to bacteria (Varin, 2010).

It was surprisingly discovered that Epstein-Barr virus ("EBV") IL-10 variants with one or more amino acid substitutions (at amino acid position 31, 75, or both of the mature EBV IL-10 amino acid sequence of SEQ ID No. 3) in key IL-10 receptor binding domain regions, altered the ability of EBV IL-10 to bind to and activate the IL-10 receptor. These modifications included the ability to increase the affinity of EBV IL-10 for the IL-10 receptor. The inventor discovered that EBV IL-10 variant molecules act as IL-10 receptor agonists capable of treating immune diseases, inflammatory diseases or conditions, and in treating cancer. The inventor also discovered that by incorporating monomeric EBV IL-10 variants into a scaffolding system comprising non-immunogenic variable heavy ("VH") and variable light ("VL") regions, the resulting EBV IL-10 variant molecules were half-life extended, properly folded and functionally active. The EBV IL-10 variants incorporated into the scaffolding system showed enhanced IL-10 function on both inflammatory cells (e.g., monocytes/macrophages/dendritic cells) and immune cells (e.g., $CD8^+$ T-cells). See, U.S. Pat. No. 10,858,412; filed on Mar. 6, 2020 as U.S. application Ser. No. 16/811,718, incorporated by reference in its entirety. This application focuses on a modification to the previously described EBV IL-10 scaffolding system to deliver both IL-10 and another cytokine as part of a new fusion protein structure that additively or synergistically enhances IL-10 biology to treat inflammatory diseases, immune diseases, and/or cancer.

SUMMARY OF VARIOUS ASPECTS OF THE INVENTION

The present disclosure generally relates to a dual cytokine fusion protein.

Thus in a first aspect, the present disclosure relates to a dual cytokine fusion protein comprising IL-10 or IL-10 variants as the first cytokine that is fused to an antigen binding fragment or variable heavy ("VH") and variable light ("VL") regions of a monoclonal antibody, and a second cytokine, wherein the second cytokine is linked in between the VH and VL regions of the antigen binding fragment. In certain embodiments, the first cytokine is an IL-10, such as but not limited to human, mouse, cytomegalovirus, ("CMV"), or EBV IL-10 forms or IL-10 variant molecule, wherein the IL-10 variant has one or more amino acid substitution(s) that impact the IL-10 receptor binding domains. The fusion protein also includes a second cytokine, which is a cytokine that is different from the first cytokine, that works in tandem with the IL-10 or IL-10 variant molecule such that there is an additive or synergistic effect when the first and second cytokines are targeted to a specific antigen by the fusion protein or half-life extended by the VH and VL regions of the antigen binding fragment. The fusion protein also includes an antibody, antibody fragment, or antigen binding portion comprising a VH and VL region that directs the dual cytokine fusion protein to a target antigen recognized by the VH and VL region of the antibody, antibody fragment, or antigen binding portion thereof. In certain embodiments, the antigen binding fragment is a scFv.

In yet another aspect, the present disclosure relates to a dual cytokine fusion protein of formula (I):

$$NH_2\text{-}(IL10)\text{-}(X^1)\text{-}(Z_n)\text{-}(X^2)\text{-}(IL10)\text{-}COOH;$$

wherein

"IL10" is a monomer of IL-10, wherein the IL-10 is human, mouse, CMV, or EBV IL-10, or a variant thereof, more preferably a IL10 is monomer comprising a sequence selected from SEQ ID Nos: 1, 3, 9, 10, 11, 12, 14, or 16;

"$X^1$" is a VL or VH region obtained from a first monoclonal antibody; "$X^2$" is a VH or VL region obtained from the first monoclonal antibody; wherein when $X^1$ is a VL, $X^2$ is a VH or when $X^1$ is a VH, $X^2$ is a VL;

"Z" is a cytokine other than IL-10; and

"n" is an integer selected from 0-2.

In yet another aspect, the present disclosure relates to an IL-10 fusion protein of formula (II)

$$NH_2\text{-}(IL10)\text{-}(L)\text{-}(X^1)\text{-}(L)\text{-}(Z_n)\text{-}(L)\text{-}(X^2)\text{-}(L)\text{-}(IL10)\text{-}COOH;$$

wherein

"IL-10" is a monomer sequence selected from SEQ ID Nos: 1, 3, 9, 10, 11, 12, 14, or 16;

"L" is any linker, more preferably the linker is selected from SEQ ID No: 39, 40, or 41;

$X^1$" is a VL or VH region obtained from a first monoclonal antibody; "$X^2$" is a VH or VL region obtained from the first monoclonal antibody; wherein when $X^1$ is a VL, $X^2$ is a VH or when $X^1$ is a VH, $X^2$ is a VL;

"Z" is a cytokine selected from IL-6, IL-4, IL-1, IL-2, IL-3, IL-5, IL-7, IL-8, IL-9, IL-15, IL-21 IL-26, IL-27, IL-28, IL-29, GM-CSF, G-CSF, interferons-α, -β, -γ, TGF-β, or tumor necrosis factors-α, -β, basic FGF, EGF, PDGF, IL-4, IL-11, or IL-13; and "n" is an integer selected from 0-2.

In other aspects, the present disclosure relates to nucleic acid molecule that encodes the dual cytokine fusion protein.

In other aspects, the present disclosure relates to methods of making and purifying the dual cytokine fusion protein. In one embodiment, the method of making the dual cytokine fusion protein includes recombinantly expressing the nucleic acid encoding the dual cytokine fusion protein.

In other aspects, the present disclosure relates to a method of treating cancer comprising administering to a subject in need thereof, an effective amount of the dual cytokine fusion protein.

In other aspects, the present disclosure relates to a method of treating inflammatory diseases or conditions comprising administering to a subject in need thereof, an effective amount of the dual cytokine fusion protein. Preferably, the inflammatory disease is Crohn's disease, psoriasis, and/or rheumatoid arthritis.

In other aspects, the present disclosure relates to a method of treating immune diseases or conditions comprising administering to a subject in need thereof, an effective amount of the dual cytokine fusion protein.

In other aspects, the present disclosure relates to method of treating, inhibiting, and/or alleviating sepsis and/or septic shock and associated symptoms thereof.

The above simplified summary of representative aspects serves to provide a basic understanding of the present disclosure. This summary is not an extensive overview of all contemplated aspects, and is intended to neither identify key or critical elements of all aspects nor delineate the scope of any or all aspects of the present disclosure. Its sole purpose is to present one or more aspects in a simplified form as a prelude to the more detailed description of the disclosure that follows. To the accomplishment of the foregoing, the one or more aspects of the present disclosure include the features described and exemplarily pointed out in the claims.

BRIEF DESCRIPTION OF THE DRAWINGS

Figure 14:
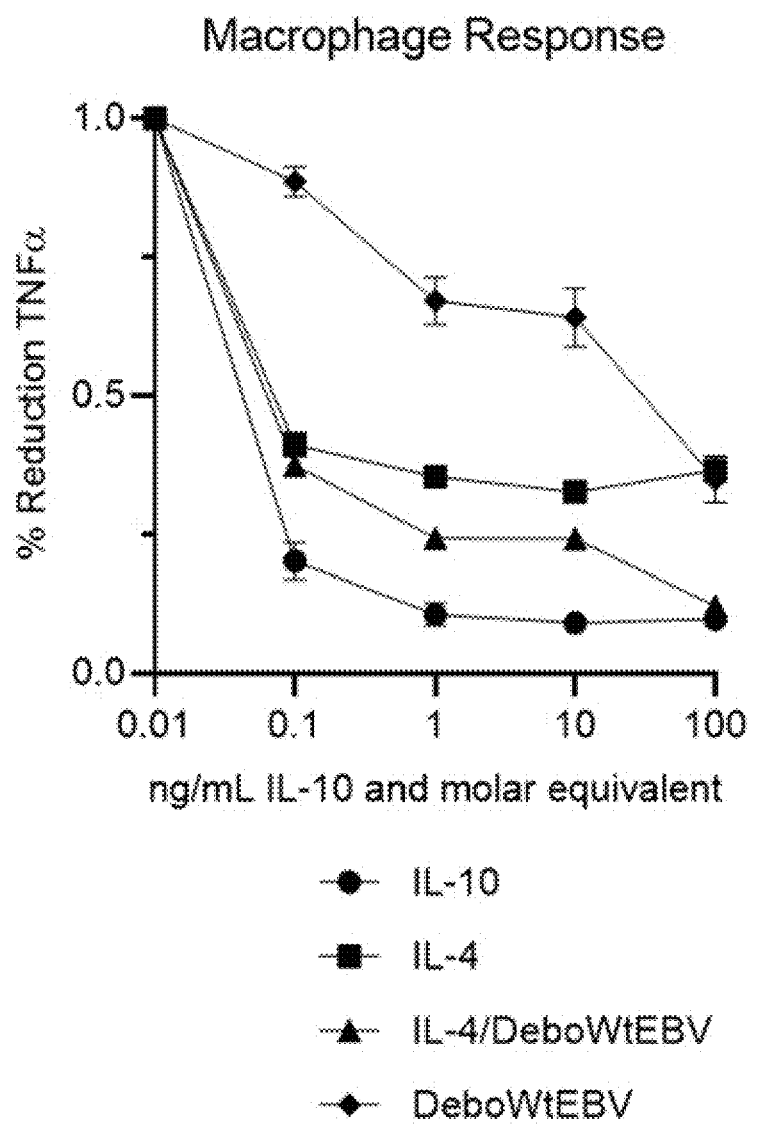

FIG. 14 is a titration study for IL-10, IL-4, IL-4 and DeboWtEBV, and DeboWtEBV alone on the percent reduction of TNFα secretion from monocytes.

Figure 15:
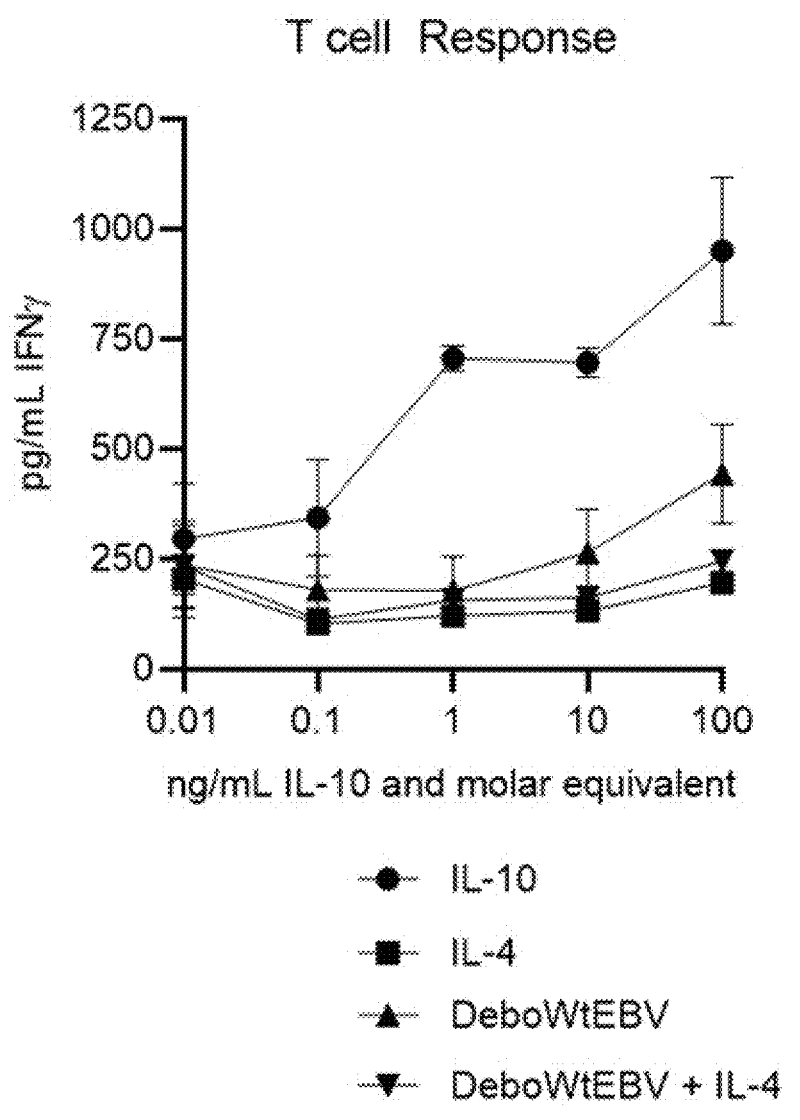

FIG. 15 is a T-cell IFNγ potentiation assay comparing DeboWtEBV and IL-4 against DeboWtEBV alone.

DETAILED DESCRIPTION

Figure 1:
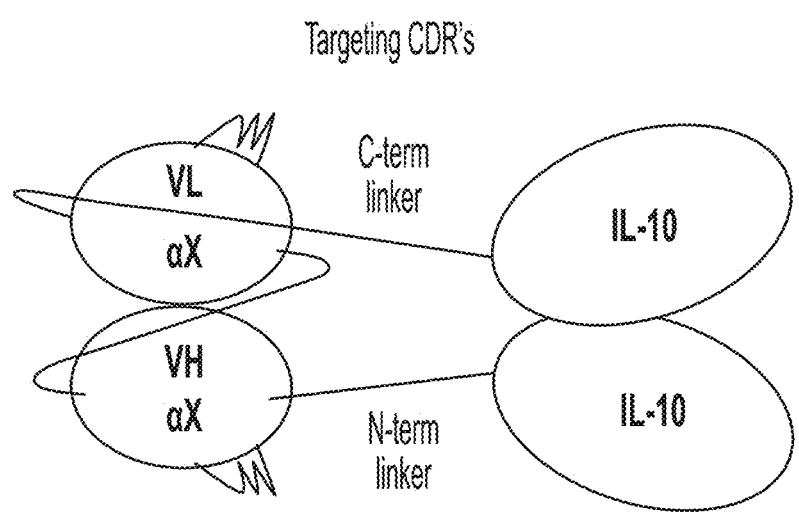
FIG. 1 is a schematic diagram of a IL-10 cytokine fusion protein described in U.S. Pat. No. 10,858,412.

Exemplary aspects are described herein in the context of a dual cytokine fusion protein comprising IL-10, methods of making the dual cytokine fusion protein comprising IL-10, and methods of using the dual cytokine fusion protein comprising IL-10 for treating inflammatory diseases or conditions, immune diseases or conditions, treating and/or preventing cancer. Those of ordinary skill in the art will realize that the following description is illustrative only and is not intended to be in any way limiting. Other aspects will readily suggest themselves to those skilled in the art having the benefit of this disclosure. Reference will now be made in detail to implementations of the exemplary aspects as illustrated in the accompanying drawings. The same reference indicators will be used to the extent possible throughout the drawings and the following description to refer to the same or like items.

Although a number of methods and materials similar or equivalent to those described herein can be used in the practice of the various described embodiments, the preferred materials and methods are described herein.

Unless otherwise indicated, the embodiments described herein employ conventional methods and techniques of molecular biology, biochemistry, pharmacology, chemistry, and immunology, well known to a person skilled in the art. Many of the general techniques for designing and fabricating the IL-10 variants, including but not limited to human, mouse, CMV and/or EBV forms of IL-10, as well as the assays for testing the IL-10 variants, are well known methods that are readily available and detailed in the art. See, e.g., Sambrook, et al., Molecular Cloning: A Laboratory Manual (2nd Edition, 1989); Methods In Enzymology (S. Colowick and N. Kaplan eds., Academic Press, Inc.); Handbook of Experimental Immunology, Vols. I-IV (D. M. Weir and C. C. Blackwell eds., Blackwell Scientific Publications); A. L. Lehninger, Biochemistry (Worth Publishers, Inc., current addition). N-terminal aldehyde based PEGylation chemistry is also well known in the art.

Definitions

The following terms will be used to describe the various embodiments discussed herein, and are intended to be defined as indicated below.

As used herein in describing the various embodiments, the singular forms "a", "an" and "the" include plural referents unless the content clearly dictates otherwise.

The term "about", refers to a deviance of between 0.0001-5% from the indicated number or range of numbers. In one embodiment, the term "about", refers to a deviance of between 1-10% from the indicated number or range of numbers. In one embodiment, the term "about", refers to a deviance of up to 25% from the indicated number or range of numbers. In a more specific embodiment, the term "about" refers to a difference of 1-25% in terms of nucleotide sequence homology or amino acid sequence homology when compared to a wild-type sequence.

The term "interleukin-10" or "IL-10" refers to a protein comprising two subunits non-covalently joined to form a homodimer, where IL-10 is an intercalated dimer of two six helix bundle (helix A-F). As used herein, unless otherwise indicated "interleukin-10" and "IL-10" refers to any form of IL-10, including but not limited to human IL-10 ("hIL-10"; Genbank Accession No. NP_000563; or U.S. Pat. No. 6,217,857) protein (SEQ ID No: 1) or nucleic acid (SEQ ID No: 2); mouse IL-10 ("mIL-10"; Genbank Accession No: M37897; or U.S. Pat. No. 6,217,857) protein (SEQ ID No: 7) or nucleic acid (SEQ ID No: 8); or viral IL-10, ("vIL-10"). Viral IL-10 homologs may be derived from EBV or CMV (Genbank Accession Nos. NC_007605 and DQ367962, respectively). The term EBV-IL10 refers to the EBV homolog of IL-10 protein (SEQ ID No: 3) or the nucleic acid (SEQ ID No: 4). The term CMV-IL10 refers to the CMV homolog of IL-10 protein (SEQ ID No: 5) or the nucleic acid (SEQ ID No: 6). The term "monomeric" or "monomer of" IL-10, as used herein, refers to the individual subunits of IL-10 or variant IL-10 that, when non-covalently joined, form a homodimer of IL-10 or variant IL-10. The terms "wild-type," "wt" and "native" are used interchangeably herein to refer to the sequence of the protein (e.g. IL-10, CMV-IL10 or EBV IL-10) as commonly found in nature in the species of origin of the specific IL-10 in question. For example, the term "wild-type" or "native" EBV IL-10 would thus correspond to an amino acid sequence that is most commonly found in nature.

The terms "variant," "analog" and "mutein" refer to biologically active derivatives of the reference molecule, that retain a desired activity, such as, for example, anti-inflammatory activity. Generally, the terms "variant," "variants," "analog" and "mutein" as it relates to a polypeptide refers to a compound or compounds having a native polypeptide sequence and structure with one or more amino acid additions, substitutions (which may be conservative in nature), and/or deletions, relative to the native molecule. As such, the terms "IL-10 variant", "variant IL-10," "IL-10 variant molecule," and grammatical variations and plural forms thereof are all intended to be equivalent terms that refer to an IL-10 amino acid (or nucleic acid) sequence that differs from wild-type IL-10 anywhere from 1-25% in sequence identity or homology. Thus, for example, an EBV IL-10 variant molecule is one that differs from wild-type EBV IL-10 by having one or more amino acid (or nucleotide sequence encoding the amino acid) additions, substitutions and/or deletions. Thus in one form, an EBV IL-10 variant is one that differs from the wild type sequence of SEQ ID No.:3 by having about 1% to 25% difference in sequence homology, which amounts to about 1-42 amino acid difference. In one embodiment, an IL-10 variant is an EBV IL-10 comprising a V31L amino acid mutation ("DV05"; SEQ ID No: 12), a A75I amino acid mutation ("DV06"; SEQ ID No: 14), or both V31L and a A75I amino acid mutations ("DV07"; SEQ ID No: 16).

The term "fusion protein" refers to a combination or conjugation of two or more proteins or polypeptides that results in a novel arrangement of proteins that do not normally exist naturally. The fusion protein is a result of covalent linkages of the two or more proteins or polypeptides. The two or more proteins that make up the fusion protein may be arranged in any configuration from amino-terminal end ("NH$_2$") to carboxy-terminal end ("COOH"). Thus for example, the carboxy-terminal end of one protein may be covalently linked to either the carboxy terminal end or the amino terminal end of another protein. Exemplary fusion proteins may include combining a monomeric IL-10 or a monomeric variant IL-10 molecule with one or more antibody variable domains (i.e., VH and/or VL) or single chain variable region ("scFv"). The fusion proteins may also form dimers or associated with other fusion proteins of the same type, which results in a fusion protein complex. The complexing of the fusion protein may in some cases activate or increase the functionality of a fusion protein when compared to a non-complexed fusion protein. For example, a monomeric IL-10 or monomeric variant IL-10 molecule with one or more antibody variable domains may have limited or decreased capacity to bind to an IL-10 receptor; however, when the fusion protein is complexed, the monomeric forms of IL-10 or variant IL-10 molecule become a homodimer and the variable domains associate into a functional diabody.

The term "homolog," "homology," "homologous" or "substantially homologous" refers to the percent identity between at least two polynucleotide sequences or at least two polypeptide sequences. Sequences are homologous to each other when the sequences exhibit at least about 50%, preferably at least about 75%, more preferably at least about 80%-85%, preferably at least about 90%, and most preferably at least about 95%-98% sequence identity over a defined length of the molecules.

The term "sequence identity" refers to an exact nucleotide-by-nucleotide or amino acid-by-amino acid correspondence. The sequence identity may range from 100% sequence identity to 50% sequence identity. A percent sequence identity can be determined using a variety of methods including but not limited to a direct comparison of the sequence information between two molecules (the reference sequence and a sequence with unknown percent identity to the reference sequence) by aligning the sequences, counting the exact number of matches between the two aligned sequences, dividing by the length of the reference sequence, and multiplying the result by 100. Readily available computer programs can be used to aid in the identification of percent identity.

The terms "subject," "individual" or "patient" are used interchangeably herein and refer to a vertebrate, preferably a mammal. Mammals include, but are not limited to, murine, rodent, simian, human, farm animals, sport animals, and certain pets.

The term "administering" includes routes of administration which allow the active ingredient of the application to perform their intended function.

A "therapeutically effective amount" as it relates to, for example, administering the EBV IL-10 variants or fusion proteins thereof described herein, refers to a sufficient amount of the EBV IL-10 variant or fusion proteins thereof to promote certain biological activities. These might include, for example, suppression of myeloid cell function, enhanced Kupffer cell activity, and/or lack of any effect on CD8$^+$ T cells or enhanced CD8$^+$ T-cell activity as well as blockade of mast cell upregulation of Fc receptor or prevention of degranulation. Thus, an "effective amount" will ameliorate or prevent a symptom or sign of the medical condition. Effective amount also means an amount sufficient to allow or facilitate diagnosis.

The term "treat" or "treatment" refers to a method of reducing the effects of a disease or condition. Treatment can also refer to a method of reducing the underlying cause of the disease or condition itself rather than just the symptoms. The treatment can be any reduction from native levels and can be, but is not limited to, the complete ablation of the disease, condition, or the symptoms of the disease or condition.

The following table provides definitions for the various IL-10 fusion proteins and dual cytokine fusions proteins comprising IL-10 referenced in the present disclosure:

| Term | Definition |
| --- | --- |
| "Debo" | Refers to the base half-life extended IL-10 scaffolding system schematically represented by FIG. 1, wherein monomers of IL-10 (e.g., SEQ ID No. 1, 3, or 5) or IL-10 variant molecules (e.g. SEQ ID No: 9-11, 12, 14, or 16) are linked to a scFv comprising VH and VL regions obtained from a human anti-ebola antibody. Without |

Figure 2:
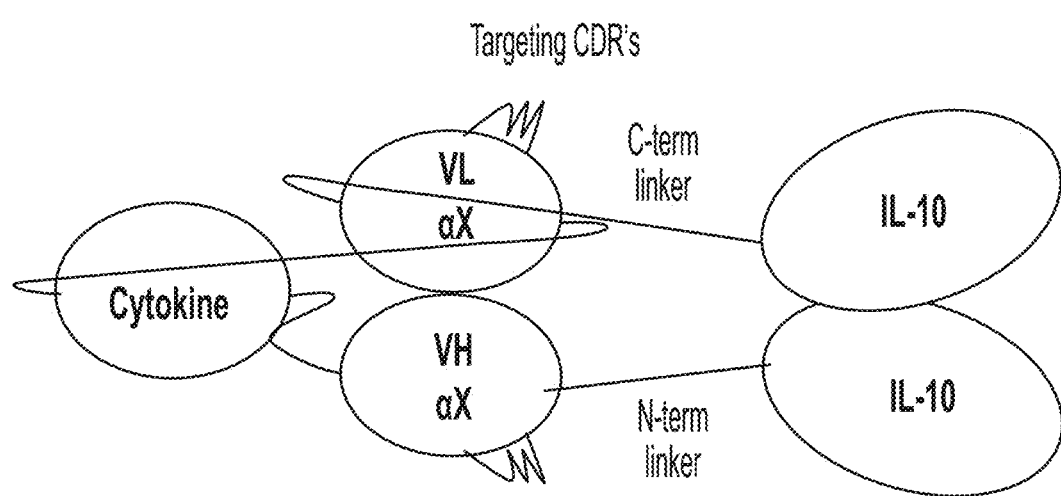
FIG. 2 is a schematic diagram of a dual cytokine fusion protein embodied in the present disclosure, wherein the dual cytokine fusion protein comprises terminally linked IL-10 monomers (or IL-10 variants), where a second cytokine is incorporated into the linker between the VH and VL of a scFv.
Figure 17:
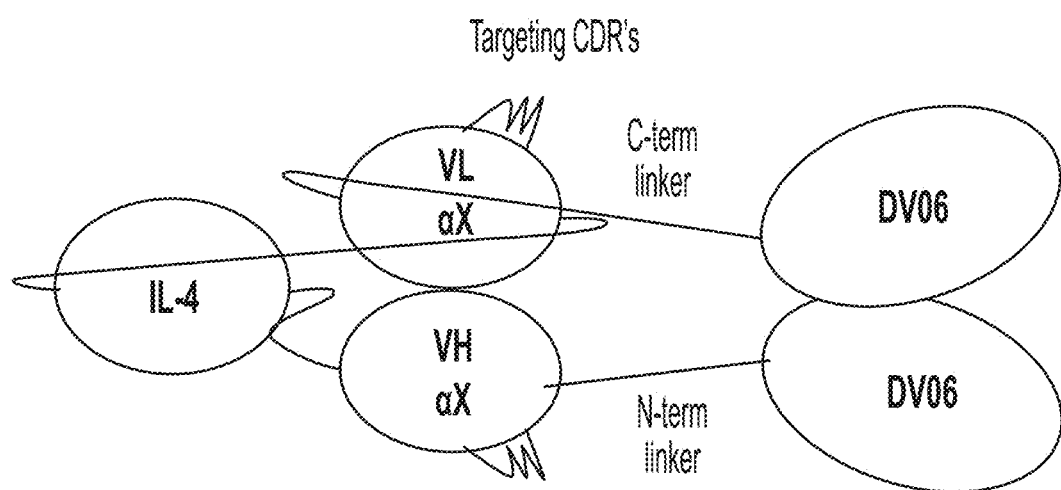
FIG. 17 is a schematic representation of the class of molecules designated as the $DK4^{10}$ form.
Figure 18:
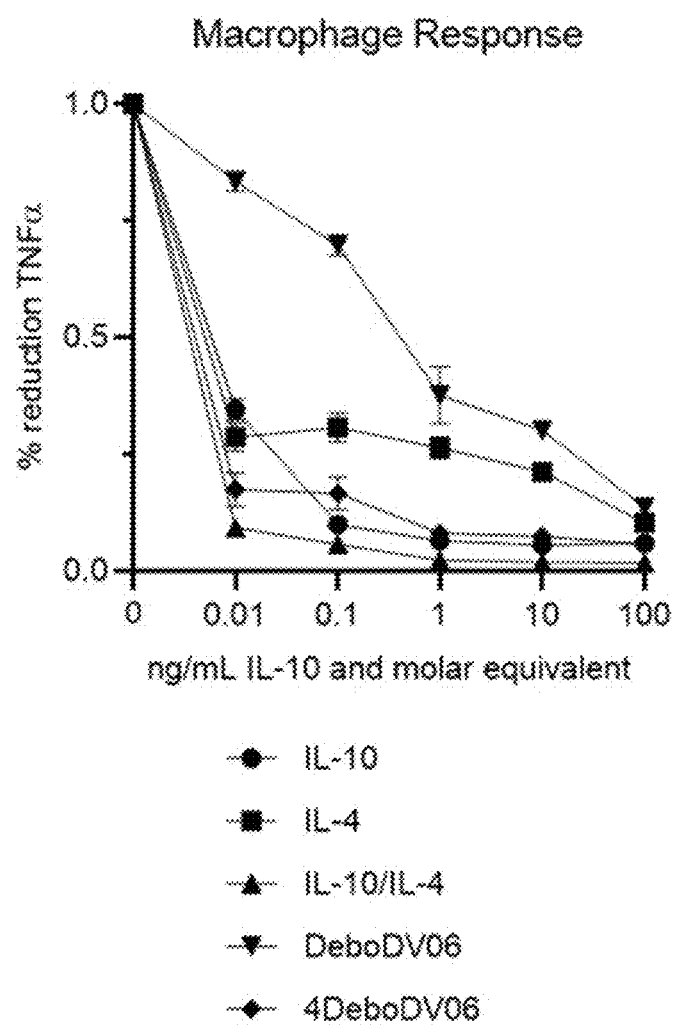
FIG. 18 is a titration study evaluating IL-4DeboDV06 in $DK4^{10}$ form (also known as "4DeboDV06") in comparison to IL-10, IL-4, DeboDV06, and IL-10 in combination with IL-4 on suppressing LPS induced TNFα secretion by monocytes/macrophages.

| Term | Definition |
|---|---|
| | being bound to any particular theory, the scaffolding system is capable of forming a stable complex due to VH and VL pair formation and the homodimerization of the IL-10 monomers. |
| "DeboWtEBV" or "DeboWt" | Refers to Debo schematically represented by FIG. 1, the molecule comprising monomers of wild type EBV IL-10 (SEQ ID No: 3) linked to a scFv comprising VH and VL regions obtained from a human anti-ebola antibody. |
| "DeboDV06" | Refers to Debo schematically represented by FIG. 1, the molecule comprising monomers of IL-10 variant DV06 (SEQ ID No: 14) linked to a scFv comprising VH and VL regions obtained from a human anti-ebola antibody. |
| "DeboDV07" | Refers to Debo schematically represented by FIG. 1, the molecule comprising monomers of IL-10 variant DV07 (SEQ ID No: 16) linked to a scFv comprising VH and VL regions obtained from a human anti-ebola antibody. |
| "DegfrDV07" | Refers to a Debo schematically represented by FIG. 1, the molecule comprising monomers of IL-10 variant DV07 and where the 3 CDRs in the VH and the 3 CDRs in the VL regions from the human anti-ebola scFv are replaced by 3 CDRs in the VH and 3 CDRs in the VL from an anti-EGFR antibody (Cetuximab). |
| "SLP" | Refers to an optimized variant form (variant #3) of DegfrDV07 that is SEQ ID No: 31. |
| "IL4DeboDV06" or "4DeboDV06" or "DK4$^{10}$DV06" | Refers to a dual cytokine fusion protein schematically represented by FIG. 17, where DeboDV06 includes a wild-type human IL-4 (SEQ ID No: 43) linked between the human anti-ebola derived scFv region. |
| "IL4DeboDV07" or "4DeboDV07" or "DK4$^{10}$DV07" | Refers to a dual cytokine fusion protein schematically represented by FIG. 2, where DeboDV07 includes a wild type human IL-4 (SEQ ID No: 43) linked between the human anti-ebola derived scFv region. |
| "DK2$^{10}$" or "DK2$^{10}$ form" | Refers to a class of dual cytokine fusion protein molecules schematically represented by FIG. 2, the molecule where DeboDV07 includes a human IL-2 (SEQ ID No: 36) linked between the human anti-ebola derived scFv region. DK2$^{10}$ may be made into a targeting molecule by optionally replacing the 6 CDR regions from the human anti-ebola derived scFv with 6 CDR regions (3 CDRs in the VH and 3 CDRs in the VL) from any monoclonal antibody. The nomenclature will follow the format of "DK2$^{10}$(protein target)". For example, if DK2$^{10}$ includes engraftment of 6 CDRs from a human anti-EGFR antibody (cetuximab), the molecule will be termed DK2$^{10}$egfr (SEQ ID No: 35) or if DK2$^{10}$ includes engraftment of the 6 CDRs from a human anti-HER2/Neu antibody (trastuzumab), the molecule will be termed DK2$^{10}$her2 (SEQ ID No: 52-54, or 55), respectively; or if DK2$^{10}$ includes engraftment of 6 CDRs from a human anti-VEGFR1 or anti-VEGFR2 antibody, the molecule will be termed DK2$^{10}$vegfr1 or DK2$^{10}$vegfr2, respectively; or if DK2$^{10}$ includes engraftment of 6 CDRs from a human anti-PDGFR antibody, the molecule will be termed DK2$^{10}$pdgfr. |
| "DK2$^{10}$egfr" | Refers to a DK2$^{10}$ molecule targeting EGFR, where the 6 CDR regions from the human anti-ebola derived scFv region are replaced by the 6 CDR regions (3 CDRs in the VH and 3 CDRs in the VL) from a human anti-EGFR antibody (cetuximab). The molecule is SEQ ID No: 35. The molecule may also include optimized VH (SEQ ID No: 37) and VL (SEQ ID No: 38) regions. |
| "DK2$^{10}$her2" | Refers to a DK2$^{10}$ molecule targeting HER2, where the 6 CDR regions from the human anti-ebola derived scFv region are replaced by the 6 CDR regions (3 CDRs in the VH and 3 CDRs in the VL) from a human anti-HER2 antibody (trastuzumab). The molecule is SEQ ID No: 52-54, or 55. |
| "DK2$^{10}$vegfr1" | Refers to a DK2$^{10}$ molecule targeting VEGFR1, where the 6 CDR regions from the human anti-ebola derived scFv region are replaced by the 6 CDR regions (3 CDRs in the VH and 3 CDRs in the VL) from a human anti-VEGFR1 antibody. |
| "DK2$^{10}$vegfr2" | Refers to a DK2$^{10}$ molecule targeting VEGFR2, where the 6 CDR regions from the human anti-ebola derived scFv region are replaced by the 6 CDR regions (3 CDRs in the VH and 3 CDRs in the VL) from a human anti-VEGFR2 antibody. |

-continued

| Term | Definition |
|---|---|
| "DK4$^{10}$" or "DK4$^{10}$ form" | Refers to a class of dual cytokine fusion protein molecules schematically represented by FIG. 2 or FIG. 17, the molecule comprising either DeboDV06 or DeboDV07 in combination with an IL-4 (SEQ ID No: 43) or IL- variants (SEQ ID No: 44 or 45) where the IL-4 or IL-4 variant is linked in the hinge region of a human anti-ebola derived scFv region. DK4$^{10}$ may be made into a targeting molecule by optionally replacing the 6 CDR regions from the human anti-ebola derived scFv with 6 CDR regions (3 CDRs in the VH and 3 CDRs in the VL) from any monoclonal antibody. For example, if DK4$^{10}$ includes engraftment of 6 CDRs from a mouse anti-CD14 antibody in combination with DV06 or DV07, the molecule will be termed DK4$^{10}$mCD14DV06 (SEQ ID No: 49) or DK4$^{10}$mCD14DV07 (SEQ ID No: 50), respectively; or if DK4$^{10}$ includes engraftment of 6 CDRs from a mouse anti-MAdCAM antibody in combination with DV06, the molecule will be termed DK4$^{10}$mMAdCAMDV06 or DK4$^{10}$mMAdCAM (SEQ ID No: 51); or if DK4$^{10}$ includes engraftment of 6 CDRs from a human anti-VEGFR1 or human anti-VEGFR2 antibody, the molecule will be termed DK4$^{10}$vegfr1 or DK4$^{10}$vegfr2, respectively, where the IL-4 moiety is the non-glycosylated form of IL-4 (a N38A IL-4 variant of SEQ ID Nos: 44) and DV06. |
| "DK4$^{10}$ngDV06mCD14" or "DK4$^{10}$mCD14DV06" | Refers to a DK4$^{10}$ molecule (schematically represented by FIG. 17) targeting mouse CD14, the molecule comprising DeboDV06 with an non-glycosylated form of IL-4 (a N38A IL-4 variant of SEQ ID Nos: 44) linked in the hinge region of the human anti-ebola derived scFv region. The 6 CDR regions from the human anti-ebola derived scFv are replaced by the 6 CDR regions (3 CDRs in the VH and 3 CDRs in the VL) from a mouse anti-CD14 antibody. This molecule is SEQ ID No: 49. |
| "DK4$^{10}$ngDV07mCD14" or "DK4$^{10}$mCD14DV07" | Refers to a DK4$^{10}$ molecule (schematically represented by FIG. 1) targeting mouse CD14, the molecule comprising DeboDV07 with a non-glycosylated form of IL-4 (a N38A IL-4 variant of SEQ ID Nos: 44) linked in the hinge region of the human anti-ebola derived scFv region. The 6 CDR regions from the human anti-ebola derived scFv are replaced by the 6 CDR regions (3 CDRs in the VH and 3 CDRs in the VL) from a mouse anti-CD14 antibody. The molecule is SEQ ID No: 50. |
| "DK4$^{10}$ngDV06mMAdCAM" or "DK4$^{10}$mMAdCAMDV06" or "DK4$^{10}$mMAdCAM" | Refers to a DK4$^{10}$ molecule (schematically represented by FIG. 17) targeting mouse MAdCAM, the molecule comprising DeboDV06 with a non-glycosylated form of IL-4 (a N38A IL-4 variant of SEQ ID Nos: 44) linked in the hinge region of the human anti-ebola derived scFv region. The 6 CDR regions from the human anti-ebola derived scFv are replaced by the 6 CDR regions (3 CDRs in the VH and 3 CDRs in the VL) from a mouse anti-CD14 antibody. The molecule is SEQ ID No: 51. |
| "DK4$^{10}$ngDV06CD14" or "DK4$^{10}$CD14DV06" | Refers to a DK4$^{10}$ molecule (schematically represented by FIG. 17) targeting human CD14, the molecule comprising DeboDV06 with an non-glycosylated form of IL-4 (a N38A IL-4 variant of SEQ ID Nos: 44) linked in the hinge region of the human anti-ebola derived scFv region. The 6 CDR regions from the human anti-ebola derived scFv are replaced by the 6 CDR regions (3 CDRs in the VH and 3 CDRs in the VL) from a human anti-CD14 antibody. This molecule is SEQ ID No: 56-58, or 59. |
| "DK4$^{10}$ngDV06vegfr1" or "DK4$^{10}$vegfr1 DV06" | Refers to a DK4$^{10}$ molecule (schematically represented by FIG. 17) targeting human VEGFR1, the molecule comprising DeboDV06 with an non-glycosylated form of IL-4 (a N38A IL-4 variant of SEQ ID Nos: 44) linked in the hinge region of the human anti-ebola derived scFv region. The 6 CDR regions from the human anti-ebola derived scFv are replaced by the 6 CDR regions (3 CDRs in the VH and 3 CDRs in the VL) from a human anti-VEGFR1 antibody. |
| "DK4$^{10}$ngDV06vegfr2" or "DK4$^{10}$vegfr2DV06" | Refers to a DK4$^{10}$ molecule (schematically represented by FIG. 17) targeting human VEGFR2, the molecule comprising DeboDV06 with an non-glycosylated form of IL-4 (a N38A IL-4 variant of SEQ ID Nos: 44) linked in the hinge region of the human anti-ebola derived scFv region. |

| Term | Definition |
| --- | --- |
| | The 6 CDR regions from the human anti-ebola derived scFv are replaced by the 6 CDR regions (3 CDRs in the VH and 3 CDRs in the VL) from a human anti-VEGFR2 antibody. |

Dual Cytokine Fusion Protein Structure

The present disclosure provides an improvement on an embodiment of an IL-10 fusion protein previously described in U.S. Pat. No. 10,858,412 (filed as U.S. application Ser. No. 16/811,718), which is incorporated by reference in its entirety. The improvement to the IL-10 fusion protein includes incorporating a second cytokine molecule into the previously described IL-10 fusion protein. FIG. 1 is a schematic diagram representing one of the previously disclosed IL-10 fusion protein constructs described in U.S. Pat. No. 10,858,412. This IL-10 fusion protein is constructed on a VH and VL scFv scaffolding featuring two monomers of IL-10 on each end (i.e., a first IL-10 monomer on the amino terminal end and a second IL-10 monomer on the carboxy terminal end). The primary scaffolding system comprises a scFv obtained from a human anti-ebola antibody. The IL-10 fusion protein described in U.S. Pat. No. 10,858,412 includes 6 complementarity-determining regions ("CDRs") having CDRs 1-3 in the VH and CDRs 1-3 in the VL. Optionally, the VH and VL regions are capable of targeting the IL-10 fusion protein to a specific antigen. This is accomplished by substituting the 6 CDR regions of the VH and VL pair (3 CDRs in the VH and 3 CDRs in the VL) with 6 CDR regions from a VH and VL of a receptor or antigen targeting antibody, or antigen binding fragment thereof. The ability to substitute and optimize the 6 CDR and framework regions and to engraft these CDRs into the scFv scaffolding described herein, is well known and practiced by those of skill in the art. These 6 CDR regions are substitutable with 6 CDRs from any monoclonal antibody, which any person of skill would be capable of determining based on the specific target of interest.

In a first aspect, the present application relates to a dual cytokine fusion protein comprising IL-10 and at least one other cytokine, whereby the dual cytokine fusion protein has a combined or synergistic functionality when compared to the IL-10 fusion protein previously described in U.S. Pat. No. 10,858,412. FIG. 2 is a representative diagram of the improved dual cytokine fusion protein comprising IL-10. In particular, the improved dual cytokine fusion protein adapts the same or substantially same scaffolding system made up of a VH and VL scFv whereby two monomers of IL-10 terminate the dual fusion protein at the amino and carboxy terminal ends. The second cytokine is conjugated to the IL-10 fusion protein by being fused between the VH and VL regions of the scFv, which is the hinge region of the scFv. The dual cytokine fusion protein is capable of forming a functional protein complex whereby the monomers of IL-10 homodimerize into a functional IL-10 molecule and the VH and VL regions form a pair that associate together to form a scFv complex that permits antigen binding and recognition.

In certain embodiments, the dual cytokine fusion protein comprising IL-10 is a structure having formula I $$NH_2\text{-}(IL10)\text{-}(X^1)\text{-}(Z_n)\text{-}(X^2)\text{-}(IL10)\text{-}COOH$$

wherein

"IL-10" is any IL-10 monomer, such as but not limited to human, mouse, CMV or EBV IL-10, or IL-10 variant molecules;

"$X^1$" is a VL or VH region obtained from a first monoclonal antibody;

"$X^2$" is a VH or VL region obtained from the first monoclonal antibody, wherein when $X^1$ is a VL, $X^2$ is a VH or when $X^1$ is a VH, $X^2$ is a VL;

"Z" is a second cytokine, wherein the second cytokine is a cytokine other than IL-10; and "n" is an integer selected from 0-2.

In another embodiment, the dual cytokine fusion protein comprising IL-10 is a structure having formula II $$NH_2\text{-}(IL10)\text{-}(L)\text{-}(X^1)\text{-}(L)\text{-}(Z_n)\text{-}(L)\text{-}(X^2)\text{-}(L)\text{-}(IL10)\text{-}COOH$$

wherein

"IL-10" is an IL-10 monomer;

"L" is a linker, preferably a linker of SEQ ID NO.: 39, 40, or 41;

"$X^1$" is a VL or VH region obtained from a first monoclonal antibody;

"$X^2$" is a VH or VL region obtained from the first monoclonal antibody; wherein when $X^1$ is a VL, $X^2$ is a VH or when $X^1$ is a VH, $X^2$ is a VL;

"Z" is a second cytokine; and

"n" is an integer selected from 0-2.

In one embodiment, the IL-10 monomer includes any form of IL-10 including human (SEQ ID NO.:1), CMV (SEQ ID NO.: 5), EBV (SEQ ID NO.:3), or mouse (SEQ ID No: 7). In another embodiment, the IL-10 monomer is a modified or variant form of EBV IL-10 (SEQ ID NO.: 3), including those that are described in U.S. Pat. No. 10,858,412. In a preferred embodiment, the EBV IL-10 comprises one or more substitutions in SEQ ID No. 3 at amino acid position 31 (herein termed "DV05"), 75 (herein termed "DV06"), or both (herein termed "DV07"). In yet another embodiment, the IL-10 monomer is a sequence of SEQ ID No: 9, 10, 11, 12, 14, or 16. The first and second monomers of IL-10 or IL-10 variant molecule are each located at the terminal ends of the fusion protein (i.e., the first monomer at the amino terminal end and the second monomer at the carboxy terminal end) as represented by FIG. 1.

In another embodiment, the VH and VL regions are from an antibody, antibody fragment, or antigen binding fragment thereof. The antigen binding fragment includes, but is not limited to, a scFv, Fab, F(ab')$_2$, V-NAR, diabody, or nanobody. Preferably the VH and VL, are from a single chain variable fragment ("scFv").

In another embodiment, the dual cytokine fusion protein comprising IL-10 includes a VH and VL pair from a single antibody. The VH and VL pair act as a scaffolding onto which monomers of IL-10 or variants thereof may be attached such that the monomers of IL-10 or variants thereof may be able to homodimerize into a functioning IL-10 molecule. A person of skill in the art will therefore appreciate that the VH and VL scaffolding used in the fusion protein may be selected based on the desired physical attributes needed for proper homodimerization of the IL-10 monomers or IL-10 monomer variants and/or the desire to maintain VH and VL targeting ability. Likewise, a person of skill will also understand that the 6 CDRs within the VH and VL pair (3 CDRs from the VH and 3 CDRs from VL) may also be substituted with 6 CDRs from other antibodies to obtain a specifically targeted fusion protein. In one embodiment, 3 CDRs from a VH and 3 CDRs from a VL (i.e., a VH and VL pair) of any monoclonal antibody may be engrafted into a scaffolding system comprising SEQ Nos: 18, 20, 21, 23, 24, or 25. It is also envisioned that if the fusion protein is not intended to target any specific antigen, a VH and VL pair may be selected as the scaffolding that does not target any particular antigen (or is an antigen in low abundance in vivo), such as the VH and VL pair from an anti-HIV and/or anti-Ebola antibody. Thus, in an embodiment, the IL-10 fusion protein of the present application may include a VH and VL pair from a human anti-ebola antibody, more preferably a sequence of SEQ ID No: 18, 21, or 25. The fusion protein may comprises a range of 1-4 variable regions. In another embodiment, the variable regions may be from the same antibody or from at least two different antibodies.

In another embodiment, the target specificity of the antibody variable chains or VH and VL pair or the 6 CDRs of the VH and VL pair may include, but not limited to those targeting proteins, cellular receptors, and/or tumor associated antigens. In another embodiment, the CDR regions from any VH and VL pair may be engrafted into the scaffolding system described above, such scaffolding preferably includes a system termed Debo (schematically represented by FIG. 1), whereby IL-10 monomers are linked to a scFv comprising VH and VL regions of a human anti-ebola antibody and the second cytokine is linked in the hinge region of the scFv (schematically represented by FIG. 2). More preferably engraftment into the Debo scaffolding system occurs in a scaffolding comprising a sequence of SEQ ID No: 18, 20, 21, 23, 24, or 25. In yet another embodiment, the variable regions or VH and VL pair or the 6 CDRs of the VH and VL pair are obtained from antibodies that target antigens associated with various diseases (e.g., cancer) or those that are not typically found or rarely found in the serum of a healthy subject, for example variable regions from antibodies directed to EGFR, PDGFR, VEGFR1, VEGFR2, Her2Neu, FGFR, GPC3, or other tumor associated antigens, MAdCam, ICAM, VCAM, CD14 or other inflammation associated cell surface proteins, HIV and/or Ebola. Thus, in one embodiment, the variable regions are obtained or derived from anti-EGFR, anti-MAdCam, anti-HIV (Chan et al, J. Virol, 2018, 92(18): e006411-19), anti-ICAM, anti-VCAM, anti-CD14, or anti-Ebola (US Published Application 2018/0180614, incorporated by reference in its entirety, especially mAbs described in Tables 2, 3, and 4) antibodies, for example. In another embodiment, the variable regions are obtained or derived from antibodies capable of enriching the concentration of cytokines, such as IL-10, to a specific target area so as to enable IL-10 to elicit its biological effect. Such an antibody might include those that target overexpressed or upregulated receptors or antigens in certain diseased regions or those that are specifically expressed in certain impacted areas. For example, the variable regions might be obtained from antibodies specific for epidermal growth factor receptor (EGFR); CD52; CD14; various immune check point targets, such as but not limited to PD-L1, PD-1, TIM3, BTLA, LAG3 or CTLA4; CD20; CD47; GD-2; VEGFR1; VEGFR2; HER2; PDGFR; EpCAM; ICAM (ICAM-1, -2, -3, -4, -5), VCAM, FAPα; 5T4; Trop2; EDB-FN; TGFβ Trap; MAdCam, β7 integrin subunit; α4β7 integrin; α4 integrin SR-A1; SR-A3; SR-A4; SR-A5; SR-A6; SR-B; dSR-C1; SR-D1; SR-E1; SR-F1; SR-F2; SR-G; SR-H1; SR-H2; SR-I1; and SR-J1 to name a few. A monomer of IL-10 (e.g., human, CMV, or EBV) or variant IL-10 molecule (described herein) is conjugated to either the amino terminal end or the carboxy terminal end of a variable region (VH or VL), such that the monomer IL-10 or variant IL-10 molecule is able to dimerize with one another. In a preferred embodiment, the monomers of IL-10 (or variant IL-10) are fused to the VH and VL pair in accordance to formula I or II, wherein the IL-10 monomer is an EBV IL-10, DV05, DV06, or DV07 form of IL-10.

The dual cytokine fusion protein or dual cytokine fusion protein complex may also have an antigen targeting functionality. The dual cytokine fusion protein or dual cytokine fusion protein complex will comprise a VH and VL pair that is able to associate together to form an antigen binding site or ABS. In some configurations, the IL-10 monomers or IL-10 variant monomers thereof will be covalently linked to the end comprising the antigen binding site. The variable regions may be further modified (e.g., by addition, subtraction, or substitution) by altering one or more amino acids that reduce antigenicity in a subject. Other modifications to the variable region may include amino acids substitutions, deletions, or additions that are found outside of the 6 CDR regions of the VH and VL regions and serve to increase stability and expression of the VH and VL regions of the scFv. For example, the modifications may include modifications that are described in SEQ ID No: 27, 29, 31, or 33 wherein the CDR regions are obtained from the VH and VL regions of an anti-EGFR antibody and the regions outside of the CDRs are optimized to stabilize the scFv and/or optimized to increase expression, which may be used as a basis for linking the second cytokine between the VH and VL regions of the scFv. To demonstrate that these types of modifications are within the purview of a skilled artisan, similar modifications to the CDR regions and regions outside of the CDRs were made to a molecule in $DK2^{10}$ form comprising DV07 and targeting human HER2 (i.e., $DK2^{10}$her2), such as those described in SEQ ID No: 52-54, or 55, more preferably SEQ ID No: 54 (variant 4) or 55 (variant 5). Moreover, modifications to the CDR regions and regions outside of the CDRs were made to a molecule in $DK4^{10}$ form comprising DV06 and targeting human CD14 (i.e., $DK4^{10}$CD14DV06), such as those described in SEQ ID No: 56-58, or 59, more preferably SEQ ID No: 56 (variant 2). These and other modifications may also be made to a molecule in $DK2^{10}$ form comprising DV07 and targeting human VEGFR1 or VEGFR2; or to a molecule in $DK4^{10}$ form comprising DV06 and targeting human VEGFR1 or VEGFR2. A person of skill in the art would be capable of determining other modifications that stabilize the scFv and/or to optimize the sequence for purposes of expression.

The VH and VL pair form a scaffolding onto which CDR regions obtained for a plurality of antibodies may be grafted or engrafted. Such antibody CDR regions include those antibodies known and described above. The CDR regions in the above described VH and VL scaffolding will include the following number of amino acid positions available for CDR engraftment/insertion:

| | |
|---|---|
| Heavy chain CDR1 | 3-7 amino acids |
| Heavy chain CDR2 | 7-11 amino acids |

| | |
|---|---|
| Heavy chain CDR3 | 7-11 amino acids |
| Light chain CDR1 | 9-14 amino acids |
| Light chain CDR2 | 5-9 amino acids |
| Light chain CDR3 | 7-11 amino acids |

In a preferred embodiment, the dual cytokine fusion protein comprising IL-10 will include the previously described scaffolding IL-10 fusion protein where the VH and VL pair is derived from an anti-ebola antibody (such as those described in SEQ ID No: 19, 27, 29, 31, and 33) whereby the 6 CDR regions from the anti-ebola antibody are removed and engrafted with a VH and VL pair of a specific targeting antibody, such as but not limited to EGFR; CD52; CD14; various immune check point targets, such as but not limited to PD-L1, PD-1, TIM3, BTLA, LAG3 or CTLA4; CD20; CD47; GD-2; VEGFR1; VEGFR2; HER2; PDGFR; EpCAM; ICAM (ICAM-1, -2, -3, -4, -5), VCAM, CD14, FAPα; 5T4; Trop2; EDB-FN; TGFβ Trap; MAdCam, β7 integrin subunit; α4β7 integrin; α4 integrin SR-A1; SR-A3; SR-A4; SR-A5; SR-A6; SR-B; dSR-C1; SR-D1; SR-E1; SR-F1; SR-F2; SR-G; SR-H1; SR-H2; SR-I1; and SR-J1. In an embodiment, the 6 anti-ebola CDR regions are substituted with 6 CDR regions from anti-EGFR, anti-MAdCAM, anti-VEGFR1, anti-VEGFR2, anti-PDGFR, or anti-CD14. In a preferred embodiment, the IL-10 fusion protein is a sequence of SEQ ID No: 18, 20, 21, 23, 24, or 25 to which any of the CDRs from the above described antibodies may be engrafted. In a more preferred embodiment, the IL-10 fusion protein is a sequence of SEQ ID No: 19, 22, or 26. In a preferred embodiment, a second cytokine, such as but not limited to IL-2, IL-4, IFNα, is linked in the hinge region between the VH and VL of the scFv obtained from a human anti-ebola antibody from an IL-10 fusion protein having a sequence of SEQ ID No: 18-27, 29, 31, or 33.

In yet another embodiment, the second cytokine, is fused between the VH and VL of a scFv, as depicted in FIG. 2. The second cytokine is conjugated between the VH or VL region such that the second cytokine retains its functional properties. In one embodiment, the second cytokine is different from the IL-10 monomer. In another aspect the second cytokine is IL-10. In one embodiment, the second cytokine is IL-6, IL-4, IL-1, IL-2, IL-3, IL-5, IL-7, IL-8, IL-9, IL-15, IL-21, IL-26, IL-27, IL-28, IL-29, GM-CSF, G-CSF, interferons-α, -β, -γ, TGF-β, or tumor necrosis factors-α, -β, basic FGF, EGF, PDGF, IL-4, IL-11, or IL-13. In a preferred embodiment, the second cytokine in the dual cytokine fusion protein comprising IL-10 and IL-2 or IL-4. In a more preferred embodiment, the dual cytokine fusion protein is a sequence of SEQ ID No: 35, 46-58 or 59. In yet another embodiment, the dual cytokine fusion protein will comprise an IL-10 variant molecule selected from DV05, DV06, or DV07; the IL-10 variant molecule linked to a scaffolding system comprising the VH and VL regions from a human anti-ebola antibody (i.e., Debo), wherein with the CDRs from an antibody selected from an anti-EGFR, anti-HER2, anti-CD14, anti-VEGFR1, anti-VEGFR2, anti-MAdCAM, or anti-PDGFR are engrafted into Debo; and a second cytokine selected from IL-2, IL-4, IFNα is linked in the hinge region of the VH and VL pair. In a most preferred embodiment, the dual cytokine is a fusion protein of SEQ ID No: 35, 46-58, or 59.

In still other embodiments, the dual cytokine fusion protein comprising IL-10 incorporates linkers. A person of skill in the art knows that linkers or spacers are used to achieve proper spatial configuration of the various fusion protein parts and therefore may select the appropriate linker to use in the formation of the dual cytokine fusion protein comprising IL-10. In a more preferred embodiment, the linker or spacer may be a random amino acid sequence (such as SSGGGGS (SEQ ID No.: 39), GGGGSGGGGSGGGGS (SEQ ID No.: 40) or SSGGGGSGGGGSGGGGS (SEQ ID No. 41)) a constant region of an antibody. The constant region can be derived from, but not limited to IgG1, IgG2, IgG3, IgG4, IgA, IgM, IgD, or IgE. In one embodiment, the linker or spacer is a constant heavy ("CH") region 1, CH2, or CH3. In a more preferred embodiment, the linker or spacer is a random amino acid sequence of SEQ ID No: 40. In another aspect, the linker or spacer may further comprise at least two interchain disulfide bonds.

In other aspects, the present disclosure relates to nucleic acid molecules that encode for the dual cytokine fusion protein comprising IL-10 and a second cytokine. One embodiment therefore includes a nucleic acid sequence that encodes the protein set forth in SEQ ID No: 35, 46-58, or 59. In a preferred embodiment, the nucleic acid sequence includes $DK2^{10}$egfr (SEQ ID No: 60), $DK2^{10}$her2 (SEQ ID No: 62 or 63), $DK4^{10}$CD14DV06 or $DK4^{10}$ngDV06CD14 (SEQ ID No: 61), or nucleic acid sequences that share 70% to 99% sequence homology thereof. In another embodiment, the nucleic acid sequence encodes a $DK2^{10}$ form comprising DV07 and targeting human VEGFR1 or VEGFR2; or to a molecule in $DK4^{10}$ form comprising DV06 and targeting human VEGFR1 or VEGFR2. The polynucleotide sequences that encode for the dual cytokine fusion protein comprising IL-10 and a second cytokine may also include modifications that do not alter the functional properties of the described dual cytokine fusion protein. Such modifications will employ conventional recombinant DNA techniques and methods. For example, the addition or substitution of specific amino acid sequences may be introduced into an IL-10 sequence at the nucleic acid (DNA) level using site-directed mutagenesis methods employing synthetic oligonucleotides, which methods are also well known in the art. In a preferred embodiment, the nucleic acid molecules encoding the dual cytokine fusion protein comprising IL-10 and a second cytokine may include insertions, deletions, or substitutions (e.g., degenerate code) that do not alter the functionality of the IL-10 variant molecule. The nucleotide sequences encoding the IL-10 variant and fusion proteins described herein may differ from the amino acid sequences due to the degeneracy of the genetic code and may be 70-99%, preferably 70%, 75%, 80%, 85%, 90%, 95%, 96%, 97%, 98%, or 99%, homologous to the aforementioned sequences. Accordingly, an embodiment of the present disclosure includes a nucleic acid sequence that encodes a protein of SEQ ID Nos: 35, 46-58, or 59 but differing by 70-99% due to the degeneracy of the genetic code.

The nucleotide sequences encoding the dual cytokine fusion proteins described herein may further comprise well known sequences that aid in, for example, the expression, production, or secretion of the proteins. Such sequences may include, for example a leader sequence, signal peptide, and/or translation initiation sites/sequence (e.g. Kozak consensus sequence). The nucleotide sequences described herein may also include one of more restriction enzyme sites that allow for insertion into various expression systems/vectors.

In another embodiment, the nucleotide sequences encoding the dual cytokine fusion protein may be used directly in gene therapy. In one embodiment, the variant IL-10 molecules or fusion protein of the present application can be delivered by any method know in the art, including direct administration of the mutant IL-10 protein and gene therapy with a vector encoding the mutant IL-10 protein. Gene therapy may be accomplished using plasmid DNA or a viral vector, such as an adeno-associated virus vector, an adenovirus vector, a retroviral vector, etc. In some embodiments, the viral vectors of the application are administered as virus particles, and in others they are administered as plasmids (e.g. as "naked" DNA).

Other methods for the delivery of the nucleotide sequences include those which are already known in the art. These would include the delivery of the nucleotide sequences, such as but not limited to DNA, RNA, siRNA, mRNA, oligonucleotides, or variants thereof, encoding the IL-10 or IL-10 variant molecules by a cell penetrating peptide, a hydrophobic moiety, an electrostatic complex, a liposome, a ligand, a liposomal nanoparticle, a lipoprotein (preferably HDL or LDL), a folate targeted liposome, an antibody (such as Folate receptor, transferrin receptor), a targeting peptide, or by an aptamer. The nucleotide sequences encoding IL-10 variant molecules may be delivered to a subject by direct injection, infusion, patches, bandages, mist or aerosol, or by thin film delivery. The nucleotide (or the protein) may be directed to any region that is desired for targeted delivery of a cytokine stimulus. These would include, for example, the lung, the GI tract, the skin, liver, brain though intracranial injection, deep seated metastatic tumor lesions via ultrasound guided injections.

In another aspect, the present disclosure relates to methods of preparing and purifying the dual cytokine fusion protein comprising IL-10. For example, nucleic acid sequences that encode the dual cytokine fusion protein described herein may be used to recombinantly produce the fusion proteins. For example, using conventional molecular biology and protein expression techniques, the dual cytokine fusion protein described herein may be expressed and purified from mammalian cell systems. These systems include well known eukaryotic cell expression vector systems and host cells. A variety of suitable expression vectors may be used and are well known to a person skilled in the art, which can be used for expression and introduction of the variant IL-10 molecules and fusion proteins. These vectors include, for example, pUC-type vectors, pBR-type vectors, pBI-type vectors, pGA-type, pBinI9, pBI121, pGreen series, pCAMBRIA series, pPZP series, pPCV001, pGA482, pCLD04541, pBIBAC series, pYLTAC series, pSB11, pSB1, pGPTV series, and viral vectors and the like can be used. Well known host cell systems include but not limited to expression in CHO cells.

The expression vectors harboring the dual cytokine fusion protein may also include other vector componentry required for vector functionality. For example, the vector may include signal sequences, tag sequences, protease identification sequences, selection markers and other sequences regulatory sequences, such as promoters, required for proper replication and expression of the dual cytokine fusion protein. The particular promoters utilized in the vector are not particularly limited as long as they can drive the expression of the dual cytokine fusion protein in a variety of host cell types. Likewise, the type of Tag promoters are not be limited as long as the Tag sequence makes for simplifier or easier purification of expressed variant IL-10 molecule easier. These might include, for example, 6-histidine, GST, MBP, HAT, HN, S, TF, Trx, Nus, biotin, FLAG, myc, RCFP, GFP and the like can be used. Protease recognition sequences are not particularly limited, for instance, recognition sequences such as Factor Xa, Thrombin, HRV, 3C protease can be used. Selected markers are not particularly limited as long as these can detect transformed rice plant cells, for example, neomycin-resistant genes, kanamycin-resistant genes, hygromycin-resistant genes and the like can be used.

The dual cytokine fusion protein described above may also include additional amino acid sequences that aid in the recovery or purification of the fusion proteins during the manufacturing process. These may include various sequence modifications or affinity tags, such as but not limited to protein A, albumin-binding protein, alkaline phosphatase, FLAG epitope, galactose-binding protein, histidine tags, and any other tags that are well known in the art. See, e.g., Kimple et al (Curr. Protoc. Protein Sci., 2013, 73: Unit 9.9, Table 9.91, incorporated by reference in its entirety). In one aspect, the affinity tag is an histidine tag having an amino acid sequence of HHHHHH (SEQ ID No.: 42). The histidine tag may be removed or left intact from the final product. In another embodiment, the affinity tag is a protein A modification that is incorporated into the fusion protein (e.g., into the VH region of the fusion proteins described herein). A person of skill in the art will understand that any dual cytokine fusion protein sequence described herein can be modified to incorporate a protein A modification by inserting amino acid point substitutions within the antibody framework regions as described in the art.

In another aspect, the protein and nucleic acid molecules encoding dual cytokine fusion protein may be formulated as a pharmaceutical composition comprising a therapeutically effective amount of the dual cytokine fusion protein and a pharmaceutical carrier and/or pharmaceutically acceptable excipients. The pharmaceutical composition may be formulated with commonly used buffers, excipients, preservatives, stabilizers. The pharmaceutical compositions comprising the dual cytokine fusion protein is mixed with a pharmaceutically acceptable carrier or excipient. Various pharmaceutical carriers are known in the art and may be used in the pharmaceutical composition. For example, the carrier can be any compatible, non-toxic substance suitable for delivering the dual cytokine fusion protein compositions of the application to a patient. Examples of suitable carriers include normal saline, Ringer's solution, dextrose solution, and Hank's solution. Carriers may also include any poloxamers generally known to those of skill in the art, including, but not limited to, those having molecular weights of 2900 (L64), 3400 (P65), 4200 (P84), 4600 (P85), 11,400 (F88), 4950 (P103), 5900 (P104), 6500 (P105), 14,600 (F108), 5750 (P123), and 12,600 (F127). Carriers may also include emulsifiers, including, but not limited to, polysorbate 20, polysorbate 40, polysorbate 60, and polysorbate 80, to name a few. Non-aqueous carriers such as fixed oils and ethyl oleate may also be used. The carrier may also include additives such as substances that enhance isotonicity and chemical stability, e.g., buffers and preservatives, see, e.g., Remington's Pharmaceutical Sciences and U.S. Pharmacopeia: National Formulary, Mack Publishing Company, Easton, Pa. (1984). Formulations of therapeutic and diagnostic agents may be prepared by mixing with physiologically acceptable carriers, excipients, or stabilizers in the form of lyophilized powders, slurries, aqueous solutions or suspensions, for example.

The pharmaceutical composition will be formulated for administration to a patient in a therapeutically effective amount sufficient to provide the desired therapeutic result. Preferably, such amount has minimal negative side effects. In one embodiment, the amount of dual cytokine fusion protein administered will be sufficient to treat or prevent inflammatory diseases or condition. In another embodiment, the amount of dual cytokine fusion protein administered will be sufficient to treat or prevent immune diseases or disorders. Instill another embodiment, the amount of dual cytokine fusion protein administered will be sufficient to treat or prevent cancer. The amount administered may vary from patient to patient and will need to be determined by considering the subject's or patient's disease or condition, the overall health of the patient, method of administration, the severity of side-effects, and the like.

An effective amount for a particular patient may vary depending on factors such as the condition being treated, the overall health of the patient, the method route and dose of administration and the severity of side effects. The appropriate dose administered to a patient is typically determined by a clinician using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

The method for determining the dosing of the presently described dual cytokine fusion protein will be substantially similar to that described in U.S. Pat. No. 10,858,412. Generally, the presently described dual cytokine fusion protein will have a dosing in the range of 0.5 microgram/kilogram to 100 micrograms/kilogram. The dual cytokine fusion protein may be administered daily, three times a week, twice a week, weekly, bimonthly, or monthly. An effective amount of therapeutic will impact the level of inflammation or disease or condition by relieving the symptom. For example, the impact might include a level of impact that is at least 10%; at least 20%; at least about 30%; at least 40%; at least 50%; or more such that the disease or condition is alleviated or fully treated.

Compositions of the application can be administered orally or injected into the body. Formulations for oral use can also include compounds to further protect the variant IL-10 molecules from proteases in the gastrointestinal tract. Injections are usually intramuscular, subcutaneous, intradermal or intravenous. Alternatively, intra-articular injection or other routes could be used in appropriate circumstances. Parenterally administered dual cytokine fusion protein are preferably formulated in a unit dosage injectable form (solution, suspension, emulsion) in association with a pharmaceutical carrier and/or pharmaceutically acceptable excipients. In other embodiments, compositions of the application may be introduced into a patient's body by implantable or injectable drug delivery system.

Testing the Dual Cytokine Fusion Protein

A plurality of screening assays are known and available to those of skill in the art to test for the desired biological function. In one embodiment, the desired biological function includes, but are not limited to, reduced anti-inflammatory response, reduce T-cell stimulation, enhanced T-cell function, enhanced Kupffer cell functionality and reduced mast cell degranulation.

For example, it is known that IL-10 exposure primes T cells to generate and secrete more IFNγ upon T cell receptor stimulation. Simultaneously, IL-10 exposure prevents the secretion of TNFα, IL-6 and other pro-inflammatory cytokines secreted from monocytes/macrophages in response to LPS. IL-10 also suppresses $FoxP3^{+}CD4^{+}$ $T_{reg}$ proliferation. In one embodiment, the dual cytokine fusion protein that maximize monocyte/macrophage suppression but lack T cell effects, including both stimulatory and suppressive responses, will be positively selected. In one embodiment, screening for dual cytokine fusion proteins that possess increased anti-inflammatory effects will be positively selected for the treatment of autoimmune, anti-inflammatory disease or both. In another embodiments, dual cytokine fusion proteins that enhance Kupffer cell scavenging and lack $T_{reg}$ suppression will also be selected to develop for treatment of Non-alcoholic Steatotic Hepatitis (NASH) and/or Non-alcoholic Fatty Liver Disease (NAFLD). In yet another embodiment, dual cytokine fusion proteins that maximize T cell biology, including both stimulatory and suppressive responses, and also possesses enhanced Kupffer cell scavenging, will be selected to develop for the treatment of cancer. Various assays and methods of screening the dual cytokine fusion proteins are previously described in co-pending U.S. Pat. No. 10,858,412, which is incorporated by reference in its entirety. See, U.S. application Ser. No. 16/811,718 Specification at pages 39-42.

Methods of Treating and/or Preventing Using the Dual Cytokine

In other aspects, the present disclosure relates to methods of treating and/or preventing malignant diseases or conditions or cancer comprising administering to a subject in need thereof a therapeutically effective amount of the dual cytokine fusion protein comprising IL-10 and a second cytokine. Such a protein will be in $DK2^{10}$ form, where the fusion protein will comprise monomers of DV07 linked to a VH and VL scaffolding system obtained from a human anti-ebola antibody which is engrafted with CDRs from any antibody targeting a tumor associated antigen ("TAA"); with a second cytokine, IL-2, linked between the hinge region of the VH and VL. In a preferred embodiment, the dual cytokine fusion protein comprises EBV IL-10 monomers of DV07. In a more preferred embodiment, the EBV IL-10 monomers include both substitutions at amino acid positions 31 (V31L) and 75 (A751) of EBV IL-10 of SEQ ID NO: 3. In a more preferred embodiment, the EBV IL-10 is SEQ ID Nos: 11 or 16. In a preferred embodiment, the dual cytokine fusion protein comprises a VH and VL pair from an anti-ebola antibody, wherein the CDRs are substituted with 6 CDRs from any TAA targeting antibody. In a preferred embodiment, the VH and VL regions of the dual cytokine fusion protein includes a VH of SEQ ID No: 37 and a VL of SEQ ID No: 38. In a more preferred embodiment, the dual cytokine fusion protein comprises a VH and VL pair from an anti-ebola antibody, wherein the CDRs are substituted with 6 CDRs from: an anti-EGFR antibody (SEQ ID Nos: 27, 29, 31, or 33), wherein the second cytokine is linked between the VH and VL regions of the scFv. In other embodiments, the 6 CDR regions are substituted with 6 CDRs from an anti-Her2 Neu; an anti-PDGFR; anti-VEGFR1 and anti-VEGFR2, an anti-FGFR; an anti-HER3; or an anti-GPC3. Preferably the 6 CDRs are obtained from anti-EGFR, or anti-HER2. In another preferred embodiment, the second cytokine is an IL-2. In a most preferred embodiment, a dual cytokine fusion protein of SEQ ID Nos: 35 (EGFR targeting) or 52-55 (HER2 targeting) is used to treat cancer.

In still other aspects, the present disclosure relates to methods of treating and/or preventing inflammatory diseases or conditions comprising administering to a subject in need thereof a therapeutically effective amount of the dual cytokine fusion protein comprising IL-10 (or variants thereof such as DV06) and a second cytokine (such as IL-4). In a preferred embodiment, the inflammatory diseases or disorders include, but are not limited to Crohn's disease, psoriasis, and rheumatoid arthritis ("RA"). Such a protein will be in $DK4^{10}$ form, where the fusion protein will comprise monomers of DV06 linked to a VH and VL scaffolding system obtained from a human anti-ebola antibody which is engrafted with CDRs from any antibody targeting various inflammatory/immune receptors or proteins (such as anti-CD14, anti-VEGFR2, anti-MAdCAM); with a second cytokine, IL-4 (SEQ ID No: 43) or a non-glycosylated form of IL-4 (SEQ ID No: 44), linked between the hinge region of the VH and VL. In an embodiment, the IL-10 monomer includes wild type EBV IL-10, an EBV IL-10 variant with a single amino acid substitution at position 75 of EBV IL-10 (DV06), or an EBV IL-10 variant with two amino acid substitutions at positions 31 and 75 of EBV IL-10 (DV07). In a preferred embodiment, the EBV IL-10 monomers is wild type EBV IL-10 or DV06. In a more preferred embodiment, the EBV IL-10 is SEQ ID Nos: 3, 9, 10, 11, 14 or 16. In a preferred embodiment, the dual cytokine fusion protein comprises a scaffolding system with a VH and VL pair from a human anti-ebola antibody. In a more preferred embodiment, the dual cytokine fusion protein used for treating inflammatory diseases or conditions comprises a VH and VL pair from a human anti-ebola antibody, wherein the CDRs are substituted with 6 CDRs from VH and VL of an anti-MAdCAM antibody (preferably a human anti-MAdCAM antibody) or an anti-CD14 antibody (preferably a human anti-CD14 antibody) or anti-VEGFR2 (preferably a human anti-VEGFR2 antibody). In another preferred embodiment, the second cytokine is an IL-4, preferably an IL-4 variant having a N38A substitution (SEQ ID No. 44). In a most preferred embodiment, the inflammatory disease includes sepsis and/or septic shock, which is treated with a dual cytokine fusion protein comprising DV06 or DV07 monomers and IL-4, wherein CDRs from an anti-CD14 antibody are engrafted into an anti-ebola VH and VL scFv scaffolding system. In a preferred embodiment, the dual cytokine fusion protein is in $DK4^{10}$ form of SEQ ID No: 56-58, or 59, more preferably SEQ ID No: 56. In another preferred embodiment, the inflammatory disease includes IBD, which is treated with a dual cytokine fusion protein comprising DV06 monomers and IL-4 wherein the CDRs from an anti-MAdCAM antibody are engrafted into an anti-ebola VH and VLscFv scaffolding system. In yet another preferred embodiment, the inflammatory disease includes psoriasis or RA, which is treated with a dual cytokine fusion protein comprising DV06 monomers and IL-4 wherein the CDRs from an anti-VEGFR2 antibody are engrafted into a human anti-ebola VH and VL scFv scaffolding system. In a most preferred embodiment, a dual cytokine fusion protein of SEQ ID No: 46-50, 56-58, or 59 (CD14 targeting) or 51 (MAdCAM targeting) is used to reduce inflammation or sepsis.

In yet another aspect, the present disclosure relates to methods of treating and/or preventing immune diseases or conditions comprising administering to a subject in need thereof a therapeutically effective amount of the dual cytokine fusion protein comprising IL-10.

In other embodiments, the present disclosure also contemplates methods of co-administration or treatment with a second therapeutic agent, e.g., a cytokine, steroid, chemotherapeutic agent, antibiotic, anti-inflammatory agents, or radiation, are well known in the art. These might include combination treatments with other therapeutic agents, such as but not limited to one or more the following: chemotherapeutics, interferon-β, for example, IFNβ-1α and IFN-β-1β; a protein that simulates myelin basic protein; corticosteroids; IL-1 inhibitors; TNF inhibitors; anti-TNFα antibodies, anti-IL-6 antibodies, IL-1br-Ig fusion, anti-IL-23 antibodies, antibodies to CD40 ligand and CD80; antagonists of IL-12 and IL-23, e.g., antagonists of a p40 subunit of IL-12 and IL-23 (e.g., inhibitory antibodies against the p40 subunit); IL-22 antagonists; small molecule inhibitors, e.g., methotrexate, leflunomide, sirolimus (rapamycin) and analogs thereof, e.g., CCI-779; Cox-2 and cPLA2 inhibitors; NSAIDs; p38 inhibitors; TPL-2; Mk-2; NFkβ inhibitors; RAGE or soluble RAGE; P-selectin or PSGL-1 inhibitors (e.g., small molecule inhibitors, antibodies thereto, e.g., antibodies to P-selectin); estrogen receptor beta (ERB) agonists or ERB-NFkβ antagonists.

Additionally, the combination treatment useful for administration with the dual cytokine fusion protein may include TNF inhibitors include, e.g., chimeric, humanized, effectively human, human or in vitro generated antibodies, or antigen-binding fragments thereof, that bind to TNF; soluble fragments of a TNF receptor, e.g., p55 or p75 human TNF receptor or derivatives thereof, e.g., 75 kdTNFR-IgG (75 kD TNF receptor-IgG fusion protein, ENBREL™), p55 kD TNF receptor-IgG fusion protein; and TNF enzyme antagonists, e.g., TNFα converting enzyme (TACE) inhibitors. Other combination treatment with anti-inflammatory agents/drugs that includes, but not limited to standard non-steroidal anti-inflammatory drugs (NSAIDs) and cyclo-oxygenase-2 inhibitors. NSAID may include aspirin, celecoxib, diclofenac, diflunisal, etodolac, ibuprofen, indomethacin, ketoprofen, ketorolac, nabumetone, naproxen, oxaprozin, piroxicam, salsalate, sulindac, and/or tolmetin. The cyclo-oxygenase-2 inhibitor employed in compositions according to the application could, for example, be celecoxib or rofecoxib.

Additional therapeutic agents that can be co-administered and/or co-formulated with the dual cytokine fusion protein include one or more of: interferon-β, for example, IFN β-1α and IFN β-1β; COPAXONE®; corticosteroids; IL-1 inhibitors; TNF antagonists (e.g., a soluble fragment of a TNF receptor, e.g., p55 or p75 human TNF receptor or derivatives thereof, e.g., 75 kdTNFR-IgG; antibodies to CD40 ligand and CD80; and antagonists of IL-12 and/or IL-23, e.g., antagonists of a p40 subunit of IL-12 and IL-23 (e.g., inhibitory antibodies that bind to the p40 subunit of IL-12 and IL-23); methotrexate, leflunomide, and a sirolimus (rapamycin) or an analog thereof, e.g., CCI-779. Other therapeutic agents may include Imfimzi or Atezolizumb.

For purposes of treating NASH, for example, the dual cytokine fusion protein may be combined with cholesterol lowering agents, such as statins and non-statin drugs. These agents include, but are not limited to simvastatin, atorvastatin, rosuvastatin, lovastatin, pravastatin, gemfibrozil, fluvastatin, cholestyramine, fenofibrate, cholesterol absorption inhibitors, bile acid-binding resins or sequestrants, and/or microsomal triglyceride transfer protein (MTP) inhibitors.

Representative chemotherapeutic agents that may be co-administered with the dual cytokine fusion protein described herein may include for following non-exhaustive list: include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime nitrogen mustards such as chiorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g. paclitaxel (TAXOL® Bristol-Myers Squibb Oncology, Princeton, N.J.) and doxetaxel (Taxotere™, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; Xeloda® Roche, Switzerland; ibandronate; CPT11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and antiandrogens such as flutamide, nilutamide, bicalutamide, leuprolide, and goserelin; and pharmaceutically acceptable salts, acids or derivatives of any of the above.

EXAMPLES

Example 1: IL-10 and IL-2 Dual Cytokine Fusion Protein In Vitro Study

To evaluate the in vitro effects of targeting two cytokines to a tumor, a dual cytokine fusion protein, termed DK2$^{10}$ (SEQ ID No: 35) (see FIG. 2 as a representative diagram of the structure), was constructed from the following components:
(a) two monomers of DV07 (which is a high affinity IL-10 receptor binding, EBV IL-10 variant) coupled to a scFv with a VH and VL pair targeting EGFR (the IL-10 fusion protein termed "SLP" of SEQ ID No. 31); and
(b) an IL-2 cytokine (SEQ ID No: 36);

where the IL-2 cytokine is conjugated or linked in the hinge (or linker) region between the VH (SEQ ID No: 37) and VL (SEQ ID No: 38) of the scFv targeting EGFR (the SLP variant of SEQ ID No:31).

This dual cytokine fusion protein was generated to evaluate the combined effects of these two cytokines on IL-2 induction of IFNγ from NK, CD4$^+$ and CD8$^+$ T cells. A comparative construct was also designed where the IL-2 was linked to the C-terminus of most C-terminal DV07 monomer of the SLP construct described above, creating a construct term "SLP-IL-2" (FIG. 3).

To test the effects of SLP-IL-2 (FIG. 3) and DK2$^{10}$ (SEQ ID No: 35, schematically represented in FIG. 2) on the immune system, peripheral blood monocytes were isolated by magnetic bead positive selection to evaluate the DV07 function, and then NK, CD4$^+$ and CD8$^+$ T cells were similarly isolated for in vitro testing. A series of cellular in vitro assays were set up to model immunological function at different time points in the exposure cycle of a molecule injected subcutaneously in the human body.

Figure 3:
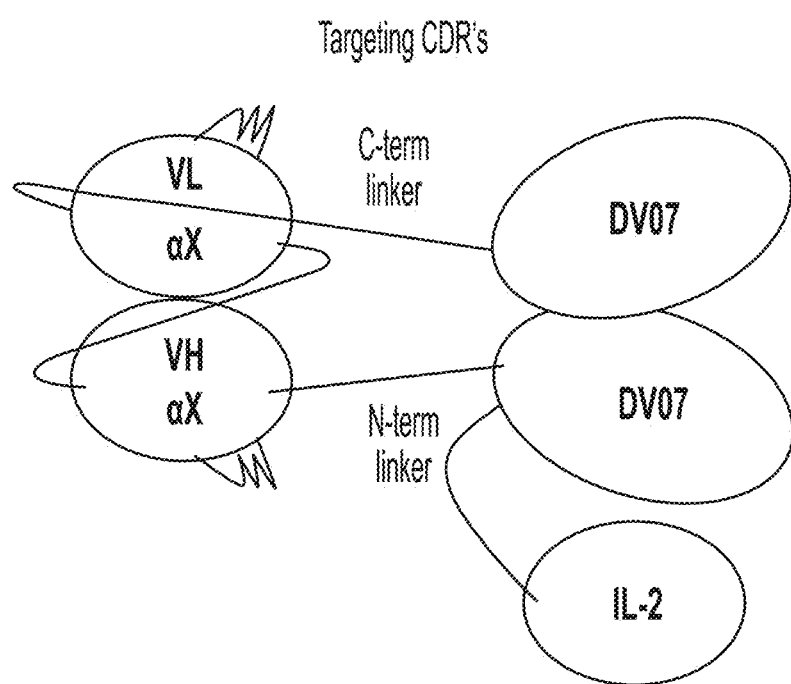
FIG. 3 is a schematic diagram of a fusion protein comprising two cytokines in an alternate form (termed "SLP-IL-2") comprising DV07 (a high IL-10 receptor affinity variant of EBV IL-10) linked to a VH and VL of a scFv and an IL-2, wherein the IL-2 is fused to the carboxy terminus of the most C-terminal IL-10 monomer.
Figure 4:
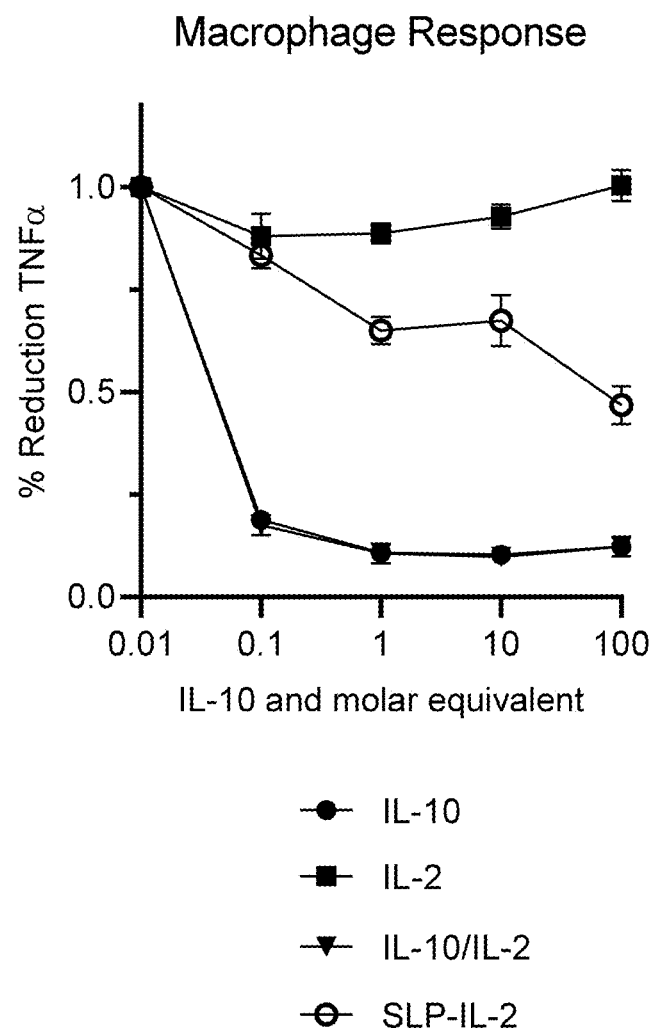
FIG. 4 is a titration study comparing SLP-IL-2 to IL-10, IL-2, and a combination of IL-10 and IL-2 on the percent reduction of TNFα secretion from monocytes/macrophages.

First, the effects of IL-10, IL-2, the combination of IL-10 and IL-2, and SLP-IL-2 were tested on monocytes/macrophages. This test shows that IL-2 alone does not suppress TNFα, a proinflammatory cytokine, secretion in response to LPS, whereas the SLP:IL-2 construct, which comprises DV07 was able to suppress proinflammatory cytokine secretion. A titration of IL-10, IL-2, the combination of IL-10 and IL-2, and SLP-IL-2 was performed (FIG. 4). Unexpectedly, these data also suggest that the function of a DV07 containing construct is compromised by the addition of the IL-2 cytokine to the C-terminus of the IL-10 monomer (i.e., SLP-IL-2; FIG. 3).

Figure 5:
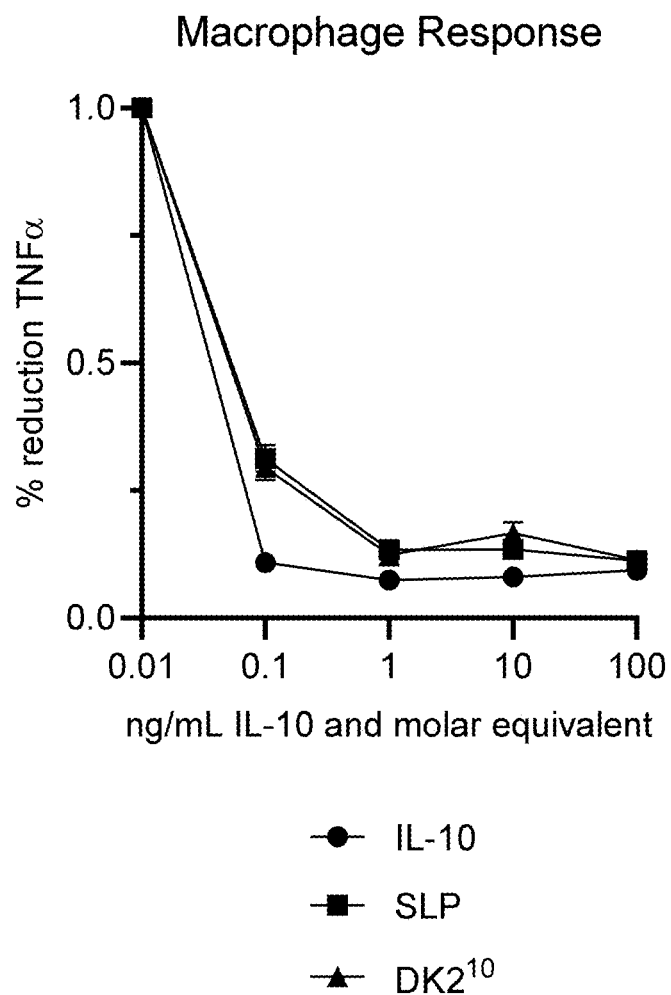
FIG. 5 is a titration study comparing DK2[10] to IL-10 and DegfrDV07 (SLP variant 3; SEQ ID No: 31) on the percent reduction of TNFα secretion from monocytes.

The effects of DK2$^{10}$, which was designed as a DV07 containing variant with IL-2 incorporated into the linker between the VH and VL of the scFv obtained from a human anti-ebola antibody, (schematically represented in FIG. 2), was also evaluated on monocytes/macrophages to determine whether the construct retains IL-10 function. A titration of IL-10, SLP (an optimized variant of DegfrDV07 of SEQ ID No: 31), and DK2$^{10}$egfr (SED ID No: 35) was performed (FIG. 5) and the data suggests that unlike linking IL-2 to the C-terminus of the most C-terminal IL-10 monomer (SLP-IL-2), the unexpected incorporation of IL-2 into the linker between the VH and VL of the scFv does not compromise the function of SLP (the DV07 containing IL-10 fusion protein of SEQ ID No: 31).

In order to assess the direct effects of DK2$^{10}$egfr on T cells, an assay that has been reported to directly elucidate the primary function of IL-10 on CD8$^+$ T cells, predominantly the potentiation of IFNγ that is only released upon T cell receptor engagement (Chan, 2015; Mumm J., 2011; Emmerich, 2012) was performed.

The necessary therapeutic concentration of PEG-rHuIL-10 was found to be 2-5 ng/mL, (Mumm J., 2011; Naing A., 2018; Naing A., 2016) in systemic circulation. The CD8$^+$ T cell IFNγ assay exhibits maximal T cell IFNγ potentiation at 1-10 ng/mL, suggesting this is an appropriate model assay system for evaluating the specific potency of IL-10 for cancer applications.

Figure 6:
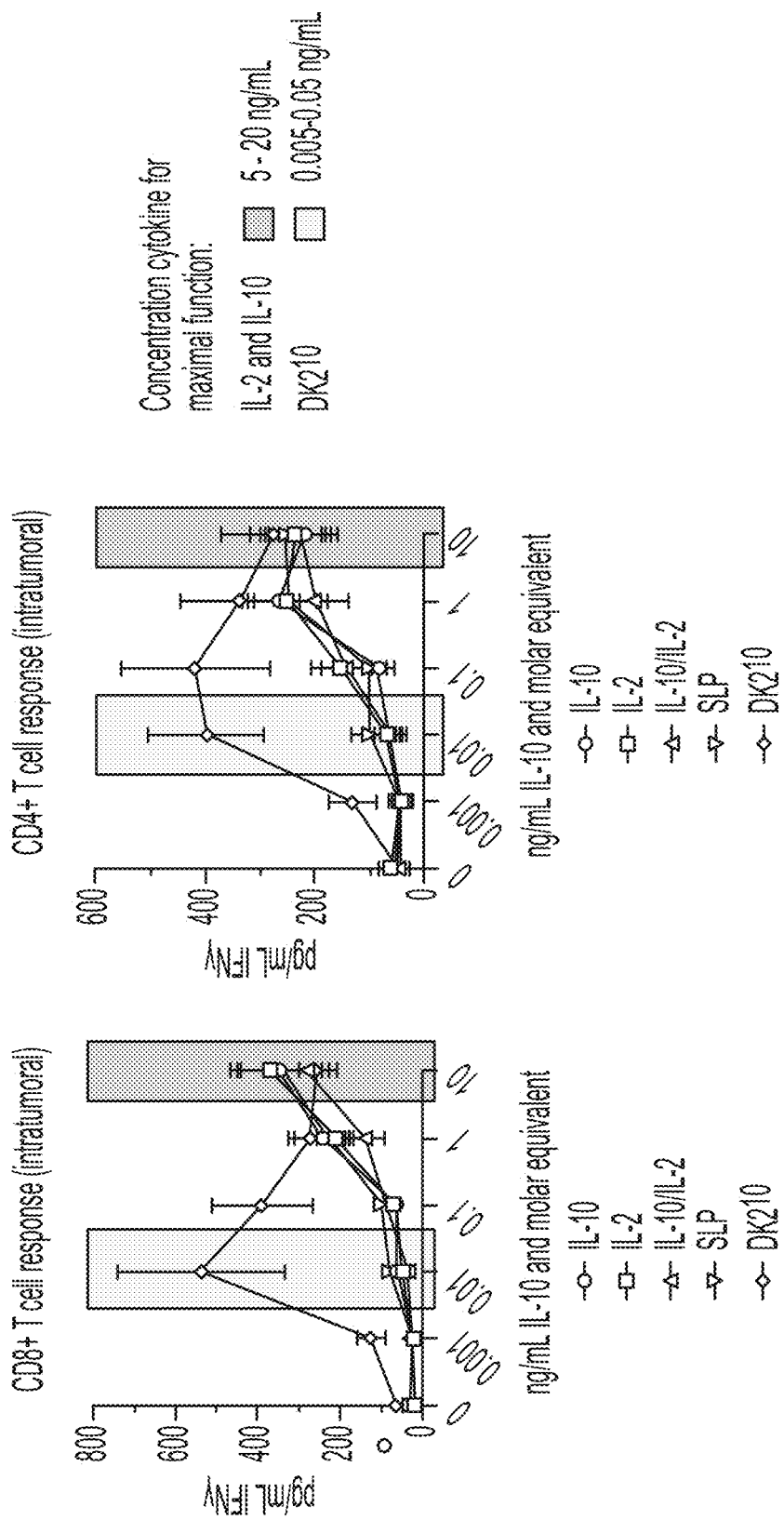
FIG. 6 is a T-cell IFNγ potentiation assay comparing SLP and DK2[10]. The dark gray bar denotes serum trough therapeutic concentrations of both cytokines, and the light gray bar denotes expected therapeutic concentration requirements for DK2[10].
Figure 7:
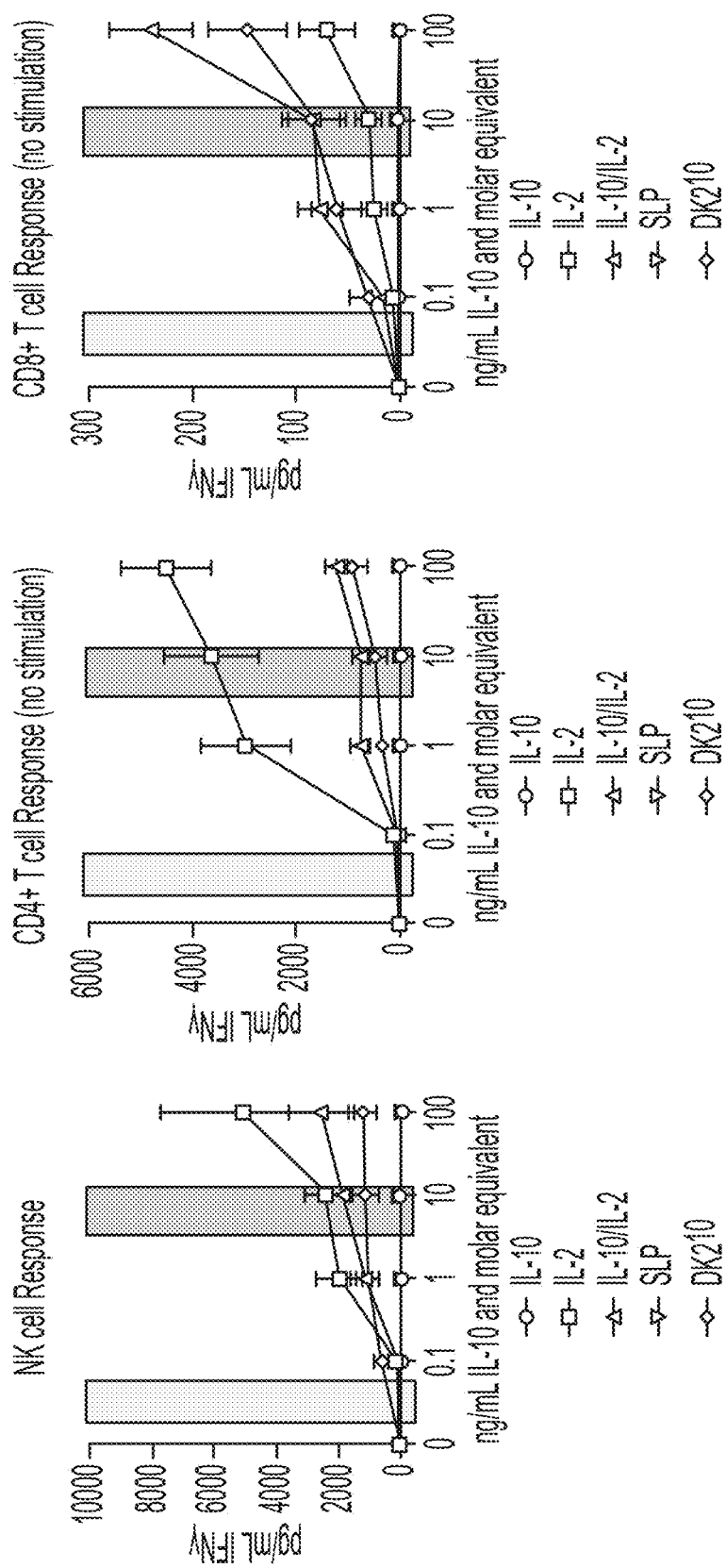
FIG. 7 is an assay to determine the effects of IL-10 on NK cells, CD4+ T-cells, and CD8+ T-cells on IL-2 mediated induction of IFNγ. The dark gray bar denotes serum trough therapeutic concentrations of both cytokines, and the light gray bar denotes expected therapeutic concentration requirements for DK2[10].
Figure 8:
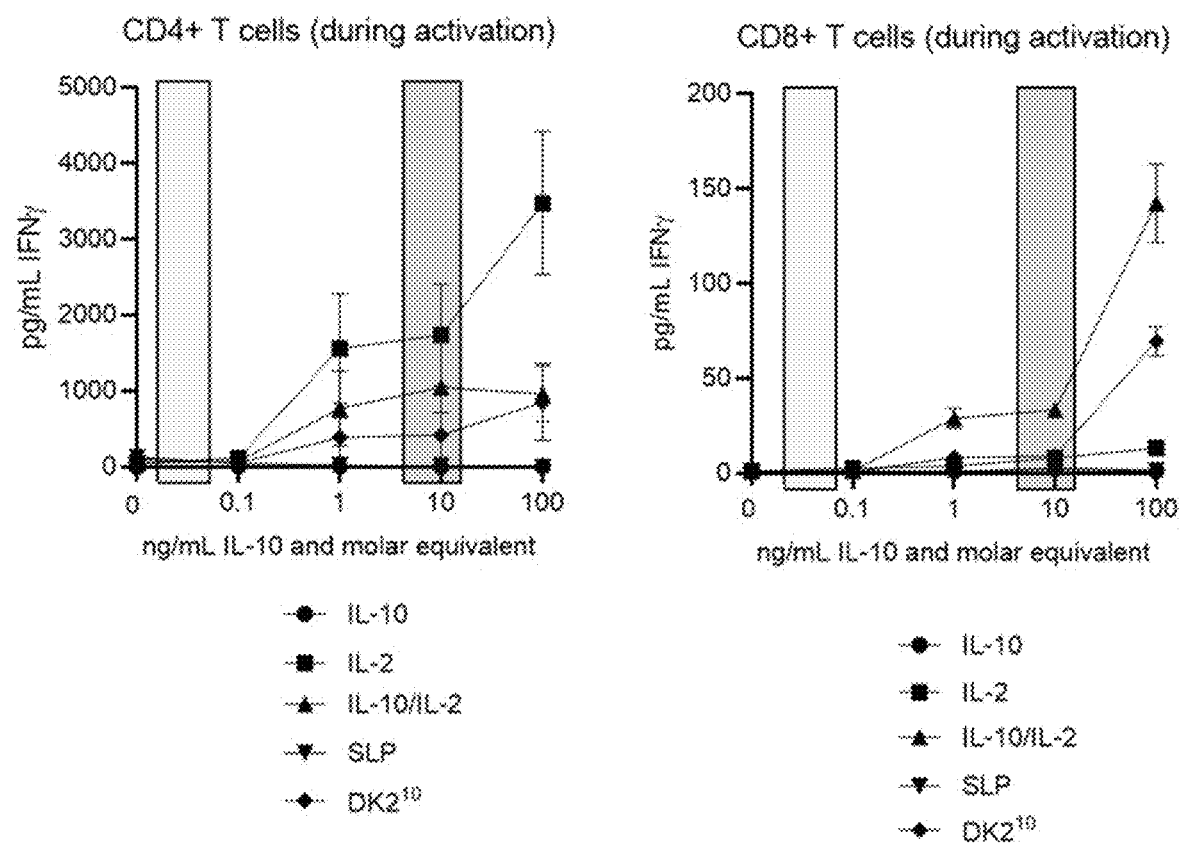
FIG. 8 is an assay measuring the effects of cytokines on model antigen presentation in T cells.
Figure 9:
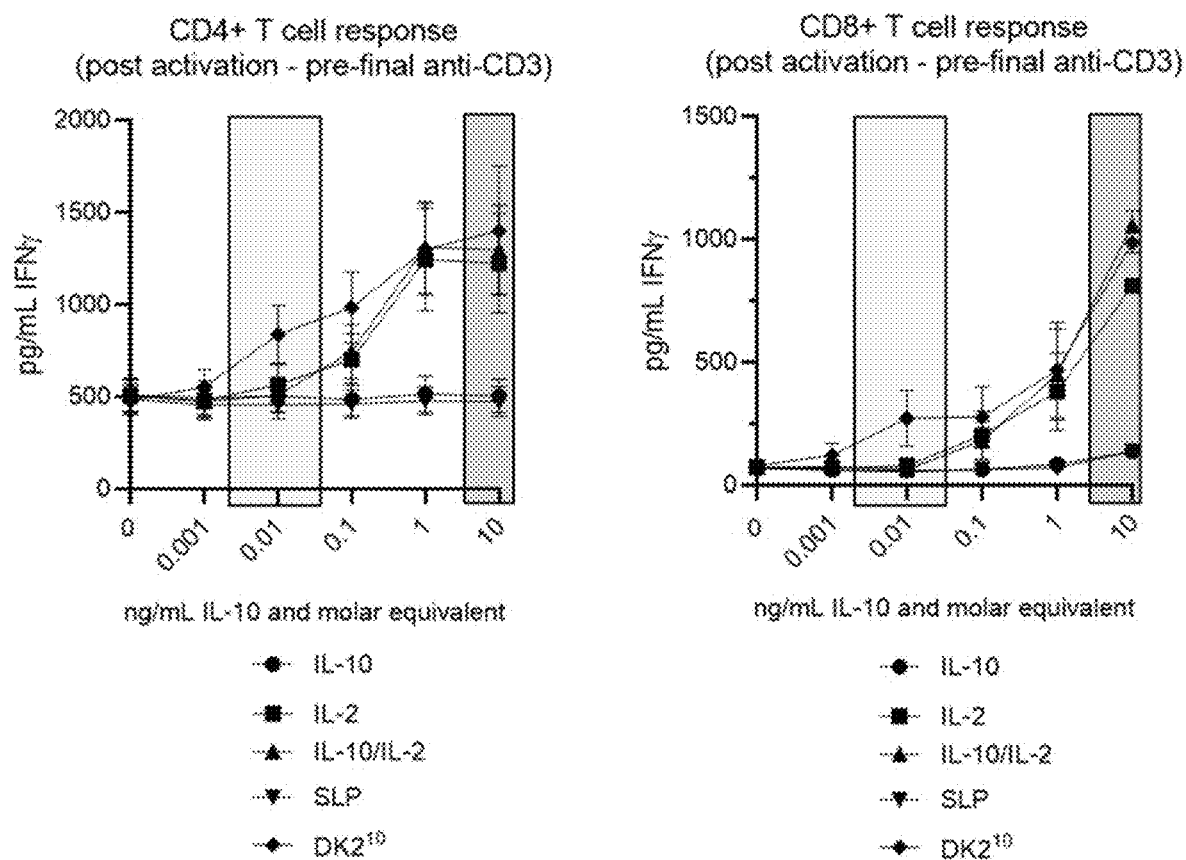
FIG. 9 is an assay measuring the induction of IFNγ in CD4+ and CD8+ T cells after antigen exposure.

High dose IL-2 therapy is the administration of between 600,000 to 720,000 U/kg IL-2 every 8 hours for 5 days (Buchbinder, 2019) which is the equivalent of 37-45 ug/kg, (1.1 mgs=18×106 IUs for IL-2). The $C_{max}$ concentration in systemic circulation for high dose IL-2 is between 37 to 45 ng/mL (Kirchner, 1998), where trough exposure is about 10 ng/ml. These data suggest that the use of this assay is also appropriate for evaluating T cell response to IL-2 as maximal IL-2 stimulation of antigen specific T cell function is approximately 10 ng/ml in vitro. We therefore assessed the response of CD8$^+$ and CD4$^+$ T-cells to IL-10, IL-2, the combination of IL-10 and IL-2, SLP and DK2$^{10}$ in this assay format (FIG. 6). Unexpectedly, the tethering of IL-2 and DV07 together (i.e., tethering IL-2 to SLP in the into the linker between the VH and VL of the scFv) increased the potency of either molecule alone by 100-fold (from ~1-10 ng/mL to 0.01 ng/mL). Unexpectedly, the addition of untethered IL-2 and IL-10 at these concentrations did not enhance IFNγ secretion, which suggests that the effect of tethering IL-2 and DV07 together leads to a significantly greater than additive or synergistic effect on T cell function.

IL-2 toxicity (vascular leak syndrome) is associated with NK (Assier, 2004), and $CD4^+$ T cell (Sivakumar, 2013), proinflammatory cytokine secretion (Guan, 2007; Baluna, 1997). We therefore assessed whether IL-10 could mute the proinflammatory effects of IL-2 on NK cells directly isolated from blood. $CD4^+$ and $CD8^+$ T cells (1) directly isolated from blood, (2) exposed to anti-CD3/anti-CD28 plus cytokines to model antigen priming, (3) exposed to cytokines after antigen priming to model exposure in the tumor and, (4) effect of exposure on antigen primed T cell function upon engagement with cognate antigen (FIG. 7). NK cells, $CD4^+$ and $CD8^+$ T cells directly isolated from peripheral blood were treated with a titration of IL-10, IL-2, combination of IL-10 and IL-2, SLP (an optimized variant of DegfrDV07 of SEQ ID No: 31), and $DK2^{10}$egfr for 4 days (FIG. 7). Expected dosing requirements for $DK2^{10}$egfr is once every 4 days suggesting this in vitro exposure models a high concentration of cytokines (up to 100 ng/mL) for 4 days, far exceeding the expected $C_{max}$ exposure. The data indicates that the addition of IL-10 to IL-2 as individual cytokines or tether together as $DK2^{10}$egfr suppresses IL-2 mediated induction of IFNγ secretion from NK, $CD4^+$ and $CD8^+$ T cells by ~50%, ~80% and ~50% respectively at 5-10 ng/mL. At the expected therapeutic dose of 0.01 ng/mL, little to no IFNγ is induced by the combined cytokines $DK2^{10}$egfr.

The effect of cytokine exposure during model antigen presentation (immobilized 10 ng/mL anti-CD3/2 ng/mL anti-CD28), (Chan, 2015) was also examined (FIG. 8). The data reveals that the addition of IL-10 to IL-2, and in particular the addition of tethered IL-2 and IL-10 via $DK2^{10}$egfr suppressed $CD4^+$ and $CD8^+$ IFNγ induction by ~75% and ~90% respectively at 10 ng/mL and exhibits no IFNγ induction of 0.01 ng/mL.

Finally, the induction of IFNγ in $CD4^+$ and $CD8^+$ T cells after antigen exposure to model T cells trafficking in tumors prior to engagement with cognate tumor antigen was examined (FIG. 9). Unexpectedly, the data reveals that the effects of IL-2, IL-10 and IL-2 individually applied versus $DK2^{10}$egfr exert different functions on antigen primed $CD4^+$ and $CD8^+$ T cells. At expected therapeutic concentrations of $DK2^{10}$egfr, $DK2^{10}$egfr potentiates IFNγ secretion more than IL-2 or IL-10 and IL-2 individually applied. At IL-10 and IL-2 expected therapeutic concentrations, $DK2^{10}$egfr, IL-2 and IL-10 and IL-2 individually applied equivalently induce IFNγ secretion from $CD4^+$ and $CD8^+$ T cells. These data collectively indicate the tethering of IL-2 and IL-10 (in the form of $DK2^{10}$) together potentiate antigen specific $CD4^+$ and $CD8^+$ T cell responses while suppressing pro-inflammatory cytokine secretion associated with IL-2 toxicity. Notably, these effects were not impacted by the engraftment of the anti-EGFR CDRs into the anti-ebola scFv scaffolding.

Example 2: IL-10 and IL-2 Dual Cytokine Fusion Protein In Vivo Study

Targeting DV07 via an anti-EGFR scFv (wherein DV07 is fused to a scFv comprising VH and VL obtained from a human anti-ebola ScFv scaffolding comprising 6 engrafted anti-EGFR CDRs; "Degfr:DV07" of SEQ ID No: 31) into the tumor microenvironment by virtue of generating a stably expressed human EGFR CT26 murine colorectal tumor cell line, was previously shown to exhibit superior anti-tumor function when compared with PEG-rHuIL-10. See, U.S. Pat. No. 10,858,412. Using the same in vivo tumor study, $DK2^{10}$egfr was evaluated and compared to Degfr:DV07 in human EGFR expressing CT26 cell murine tumor cell line.

CT26 ($hEGFR^+$) tumor bearing B cell k.o. Balb/C mice, with an average of 100 $mm^3$ tumors were treated with test articles, doses and frequencies as provided shown in Table 1. All test articles were administered subcutaneously in the scruff. All articles were dosed daily for 15 days.

TABLE 1

Test Articles, Doses and Frequencies

| No. | Test article | Dose | Frequency |
|---|---|---|---|
| 1 | Vehicle | 100 μl (control) | Daily |
| 2 | Degfr:DV07 | 1 mg/kg | Daily |
| 3 | $DK2^{10}$ | 1 mg/kg | Daily |
| 4 | $DK2^{10}$ | 2 mg/kg | Daily |
| 5 | $DK2^{10}$ | 4 mg/kg | Daily |

The length and width of tumors were measured every three days by electronic calipers and tumor volume was calculated $((L \times W^2)/2)$). In this example, the terms "Degfr:DV07" is human EGFR targeted DV07; $DK2^{10}$egfr is abbreviated as "$DK2^{10}$" and is human IL-2 coupled with DV07 via the Cetuximab CDR grafted anti-ebola scFv scaffold.

Methods

In vitro cell culture: $CT26^{(hEGFR+)}$ tumor cells (ATCC) were grown to 70% confluency in complete RPMI, 10% FCS, and 10 ug/mL puromycin. Cells were carried for no more than 3 passages in vitro prior to implantation. Cells were removed from cell culture plate using Accutase (Biolegend) and washed in complete RPMI spinning for 10 minutes at 400 g at 4° C.

Tumor Implantation: Tumor cells were implanted at $1 \times 10^5$ cells/mouse in 100 μL in 50% growth factor reduced Matrigel, 50% RPMI subcutaneous in the right flank of B cell knockout mice.

Results

Comparison of Degfr:DV07 and $DK2^{10}$ on tumor growth: Targeting DV07 to the tumor microenvironment via binding to the EGFR present on the stably transfected tumor cells was previously show to be effective. See U.S. Pat. No. 10,858,412. Using the same tumor system, Degfr5DV07 versus $DK2^{10}$ was compared.

Tumors were measured three times a week (Table 2). Female Balb/C B cell knockout mice with 75 $mm^3$ $CT26^{(hEGFR+)}$ tumors were treated subcutaneously with the test articles and dosing frequencies illustrated in Table 2.

TABLE 2

Raw Data

| Animal # | Ear Tag # | Group/Dosing Material | Day 0 TVM | Day 1 TVM | Day 3 TVM | Day 6 TVM | Day 8 TVM | Day 10 TVM | Day 13 TVM | Day 15 TVM | Day 17 TVM |
|---|---|---|---|---|---|---|---|---|---|---|---|
| D07-117-005 | 305 | 1. Vehicle | 57 | 107 | 379 | 921 | 1128 | 1664 | | | |
| D07-117-011 | 311 | | 52 | 75 | 194 | 373 | 651 | 1211 | | | |
| D07-117-012 | 312 | | 27 | 64 | 108 | 247 | 578 | 1230 | | | |
| D07-117-013 | 313 | | 33 | 152 | 407 | 542 | 725 | 1187 | | | |
| D07-117-014 | 314 | | 66 | 88 | 515 | 1274 | 1251 | 2461 | | | |
| | | | 47 | 97 | 321 | 671 | 867 | 1550 | | | |
| D07-117-003 | 303 | 2. DegfDV07 1 mg/kg | 48 | 90 | 81 | 84 | 90 | 130 | 508 | 672 | 573 |
| D07-117-006 | 306 | | 62 | 105 | 218 | 396 | 656 | 1195 | 1709 | 2291 | 3610 |
| D07-117-007 | 307 | | 56 | 80 | 122 | 131 | 215 | 333 | 595 | 776 | 1008 |
| D07-117-008 | 308 | | 37 | 84 | 145 | 420 | 775 | 1124 | 2293 | 2850 | 2781 |
| D07-117-017 | 317 | | 35 | 83 | 132 | 146 | 212 | 343 | 412 | 637 | 833 |
| | | | 48 | 89 | 140 | 235 | 390 | 625 | 1103 | 1445 | 1761 |
| D07-117-001 | 301 | 3. DK2$^{10}$ 1 mg/kg | 57 | 107 | 286 | 478 | 638 | 927 | 1565 | 2567 | 2584 |
| D07-117-004 | 304 | | 55 | 183 | 241 | 192 | 145 | 392 | 735 | 788 | 1320 |
| D07-117-015 | 315 | | 38 | 68 | 78 | 88 | 30 | 167 | 564 | 678 | 984 |
| D07-117-018 | 318 | | 54 | 103 | 77 | 41 | 9 | 21 | 26 | 49 | 24 |
| D07-117-020 | 320 | | 38 | 65 | 45 | 0 | 0 | 0 | 0 | 0 | 0 |
| | | | 48 | 105 | 145 | 160 | 164 | 302 | 578 | 816 | 982 |
| D07-117-024 | 324 | 4. DK2$^{10}$ 2 mg/kg | 69 | 116 | 57 | 9 | 0 | 0 | 0 | 0 | 0 |
| D07-117-029 | 329 | | 40 | 87 | 134 | 34 | 52 | 135 | 361 | 391 | 624 |
| D07-117-030 | 330 | | 32 | 37 | 141 | 96 | 118 | 339 | 641 | 912 | 1289 |
| D07-117-031 | 331 | | 66 | 83 | 68 | 0 | 0 | 0 | 0 | 0 | 0 |
| D07-117-039 | 339 | | 32 | 64 | 117 | 239 | 439 | 878 | 1394 | 1675 | 2233 |
| | | | 48 | 77 | 103 | 75 | 122 | 271 | 479 | 596 | 829 |
| D07-117-019 | 319 | 5. DK2$^{10}$ 4 mg/kg | 21 | 77 | 34 | 61 | 95 | 261 | 550 | 732 | 1127 |
| D07-117-032 | 332 | | 56 | 111 | 34 | 0 | 0 | 0 | 0 | 0 | 0 |
| D07-117-034 | 334 | | 50 | 49 | 125 | 49 | 27 | 0 | 0 | 0 | 0 |
| D07-117-037 | 337 | | 56 | 120 | 135 | 146 | 133 | 272 | 655 | 886 | 1413 |
| D07-117-038 | 338 | | 59 | 114 | 74 | 63 | 36 | 97 | 270 | 380 | 553 |
| | | | 48 | 94 | 80 | 64 | 58 | 126 | 295 | 400 | 618 |

For this experiment, the CT26$^{(hEGFR+)}$ cells were implanted at 1×10$^5$ cells in 50% growth factor reduced Matrigel to limit immunization of the mice against tumor antigens.

Figure 10:
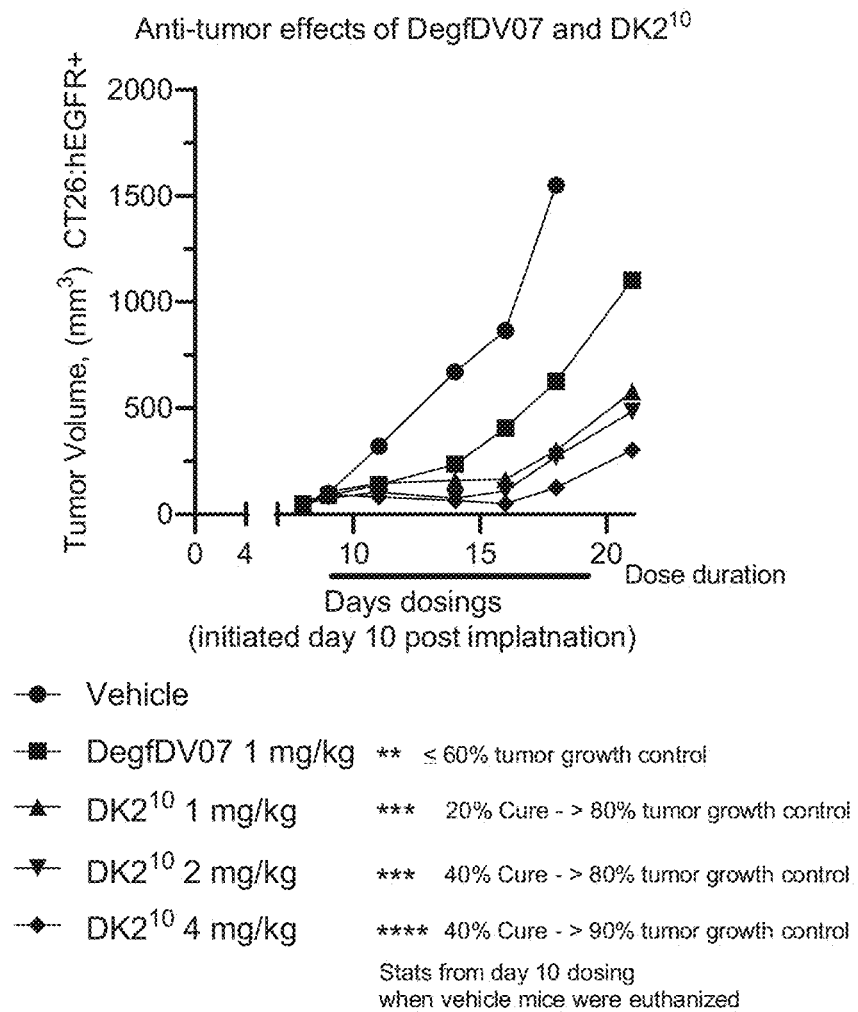
FIG. 10 is an in vivo CT26 (hEGFR+) tumor mouse model study comparing anti-tumor effects in mice treated with Degfr:DV07 or DK2[10].

The anti-tumor effect of Degfr:DV07 at 1 mg/kg was compared to the same dose of DK210 as well as 2 and 4 mg/kg doses (FIG. 10). 1 mg/kg daily dosing of DK2$^{10}$ exerts superior anti-tumor function compared to 1 mg/kg daily dosing of Degfr:DV07. 2 and 4 mg/kg doses of DK2$^{10}$ exert more anti-tumor function than 1 mg/kg.

Figure 11:
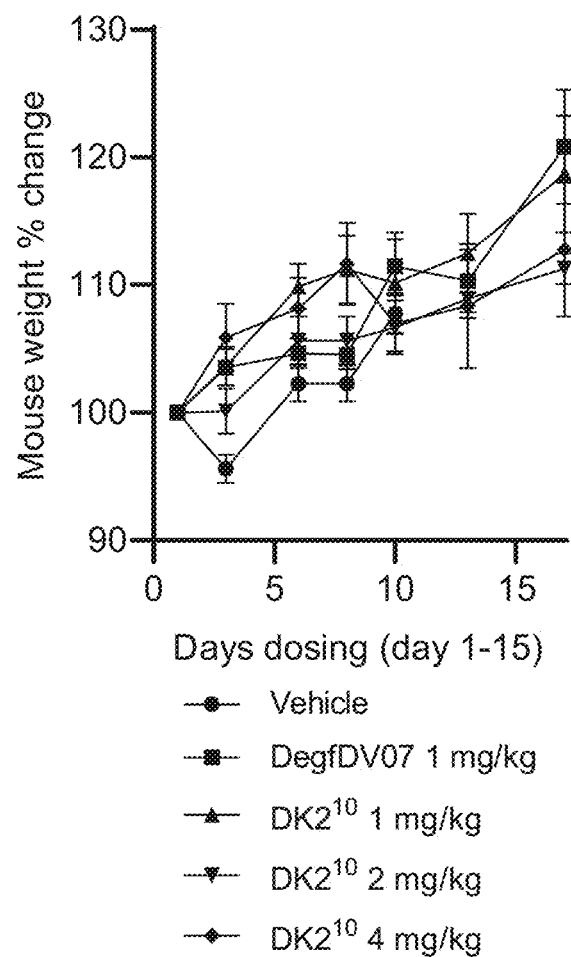
FIG. 11 is an in vivo CT 26 (hEGFR+) tumor mouse model study comparing the weight of mice treated with Degfr:DV07 or DK2[10].

Safety Assessment of DK2$^{10}$: To test the safety of DK2$^{10}$ dosing the weight of tumor bearing mice treated with Degfr:DV07 and DK2$^{10}$ was evaluated (FIG. 11). There are no apparent effects of dosing either Degfr:DV07 or DK2$^{10}$ on the weight of the mice.

Figure 12:
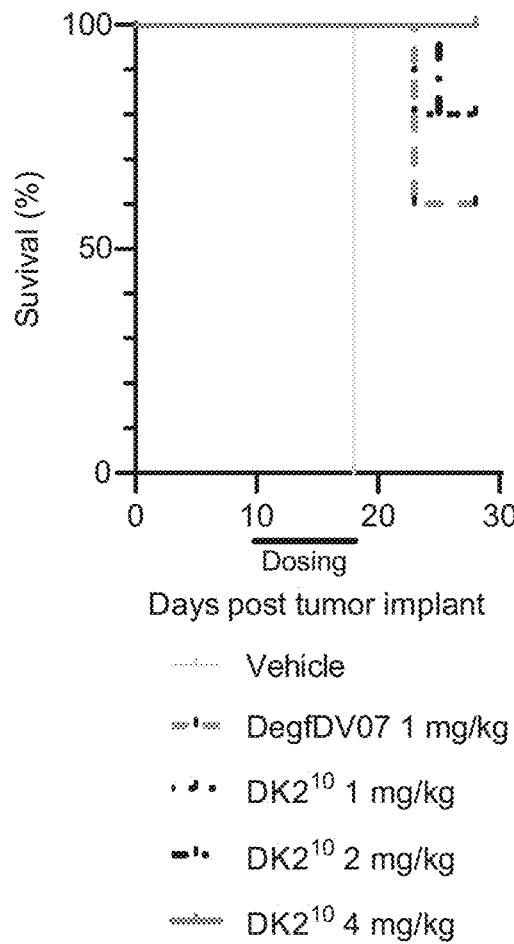
FIG. 12 is an in vivo CT26 (hEGFR+) tumor mouse model study comparing survival of mice treated Degfr:DV07 and DK2[10].
Figure 13:
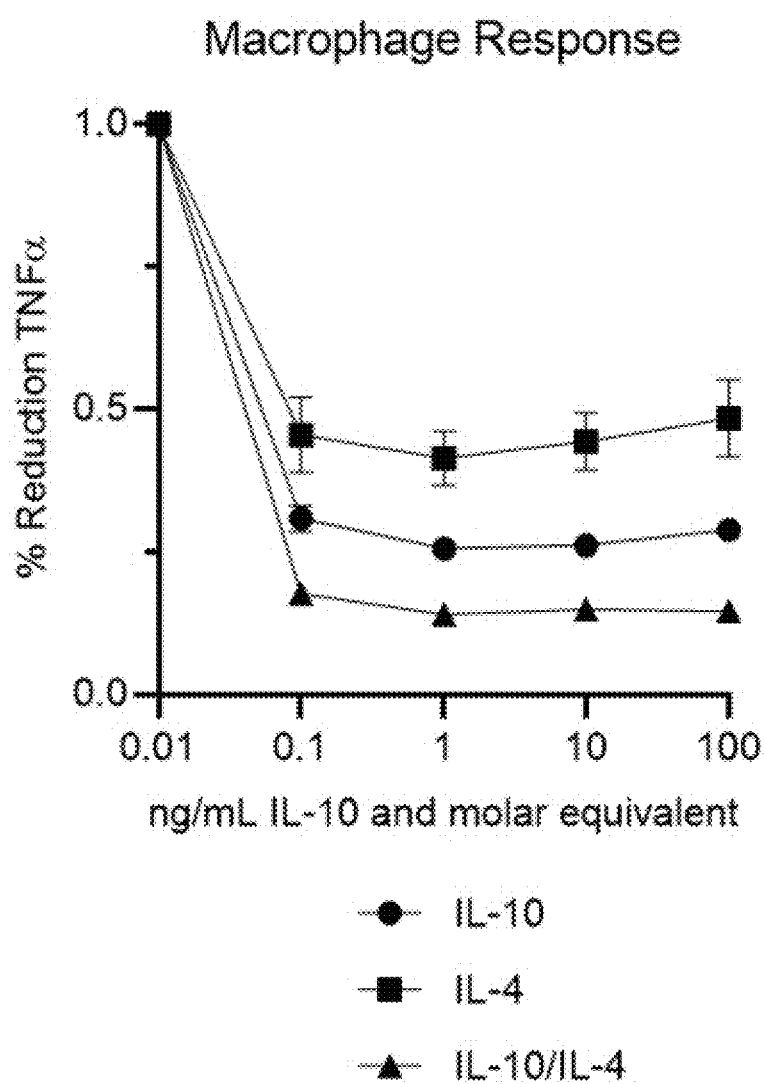
FIG. 13 is a titration study for IL-10, IL-4, and IL-10 and IL-4 on the percent reduction of TNFα secretion from monocytes.
Figure 16:
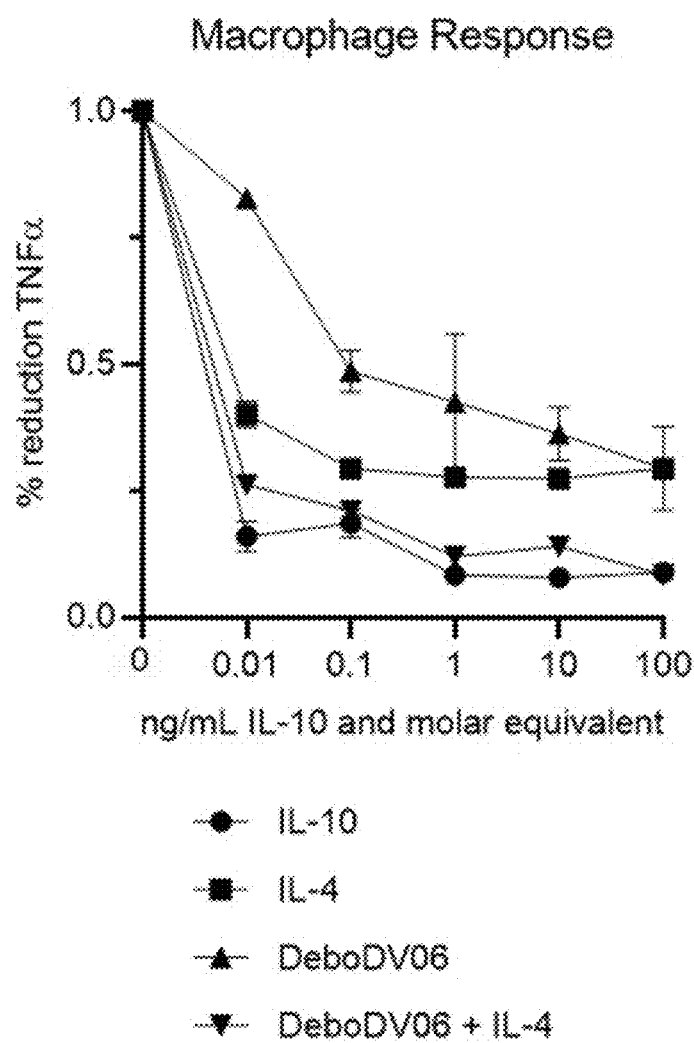
FIG. 16 is a titration study evaluating of IL-10, IL-4, DeboDV06, and DeboDV06 in combination with IL-4 on suppressing LPS induced TNFα secretion by monocytes/macrophages.

Effect of Degfr:DV07 and DK2$^{10}$ dosing on survival: The survivability of CT26$^{(hegfr+)}$ tumor bearing mice to DK2$^{10}$ was assessed (FIG. 12).

All tumors in the vehicle treatment mice were too large by IAACUC stipulation by day 17. 100%, 80%, 80% and 60% of mice were alive in the 4 mg/kg, 2 mg/kg and 1 mg/kg DK210 and Degfr:DV07 1 mg/kg treatment groups at day 30 respectively.

These data collectively suggest coupling a high affinity IL-10 variant (DV07) to IL-2 and targeting both molecules to the tumor microenvironment (via DK2$^{10}$egfr) prevents overt IL-2 mediated toxicity at therapeutically effective doses. Engrafting anti-EGFR CDRs into the scFv scaffolding comprising VH and VL regions obtained from a human anti-ebola scaffolding does not impact the combined effects of IL-10 and IL-2, rather the anti-EGFR CDRs act as a means to concentrate the DK2$^{10}$ molecule in the tumor microenvironment. We believe that engrafting CDRs from Methods PBMC and CD8+ T-cellisolation: Both macrophages and CD8+ T cells were isolated from PBMC or leukopak using anti-CD14 (monocytes) or anti-CD8 (CD8+ T cells) magnetic microbeads by magnet assisted cell sorting.

Cellular Assay—Monocyte/Macrophage cell response to cytokines and lipopolysaccharide (LPS): In this assay, PMBC derived monocytes are isolated with CD14 positive selection beads, plated at $2 \times 10^5$ cells/well and exposed to a titration cytokines and 10 ng/mL LPS. After 18 hours, supernatants are evaluated by ELISA for secreted proinflammatory cytokines. The percent reduction of TNFα is plotted to denote the effect the cytokine or test article exerts on LPS. This assay most appropriately mimics the response of monocytes to cytokines and bacterially derived proinflammatory products in peripheral blood.

Cellular Assay—CD8+ T cells: Multiple CD8+ T cells assays were used. Initially, CD8+ T cells were derived from PBMC using CD8+ positive magnetic selection beads, plated at $2 \times 10^5$ cells/well and were exposed to a titration of cytokines or test articles under the following conditions:
  (i) 4 days alone,
  (ii) 3 days to plate bound anti-CD3/anti-CD28 in the presence of cytokines to mimic how these molecules affect the cells response to cognate antigen presentation,
  (iii) post anti-CD3/anti-CD28 for 3 days to mimic how antigen stimulated cells respond to these cytokines and novel factors as the cells enter the tumors, and
  (iv) T cell receptor triggered IFNγ secretion was evaluated after 4 hours from the cells exposed in vitro to mimic how T cells in the tumor microenvironment respond to cognate antigen exposure.

Both monocyte/macrophage and CD8+ T cells were exposed to a titration of human IL-4, IL-10, DeboWtEBV, DeboDV06 and the various $DK4^{10}$ fusion molecules at 0.1, 1, 10, 100 ng/mL or 0.001, 0.01, 0.1, 1 and 10 ng/mL (or molar equivalent) for overnight or 3-4 days as stated, with all conditions run in duplicate. Anti-inflammatory (monocytes/macrophages) and stimulatory effects (CD8+ T cells) of these molecules were used to determine the most effective anti-inflammatory pair of cytokines.

Protein measurements: Macrophage cell culture media was assayed by ELISA for TNFα and CD8+ T cell culture media was assayed by ELISA for IFNγ. DeboDV06, 4DeboDV06 and the various $DK4^{10}$ fusion molecules were assessed by Nanodrop OD280 nM using each proteins' respective extinction coefficient and the concentration was corroborated by Coomassie stained SDS-PAGE gel band intensity.

Results

Development of Rational for IL-10 and IL-4 combination: IL-10 has been reported to suppress TNFα secretion by macrophages in response to LPS (Malefyt, Interleukin 10 Inhibits Cytokine Synthesis by Human Monocytes An Autoregulatory Role of IL-10 Produced by Monocytes, 1991; Moore, 2001). IL-4 has been reported to suppress LPS induced TNFα secretion from human monocytes (Hart, Potential antiinflammatory effects of interleukin 4: Suppression of human monocyte tumor necrosis factor ca, interleukin 1, and prostaglandin E2, 1989) and human peritoneal macrophages (Hart, 1991).

To determine the effects of combining IL-4 and IL-10 on the suppression of monocyte pro-inflammatory cytokine secretion in response to LPS as an inflammatory stimulus, peripheral blood monocytes were isolated from healthy donor PBMC by magnetic bead positive selection. The isolated monocytes were exposed to a titration of IL-10, IL-4, and a combination of IL-10 and IL-4 (FIG. 13). Assessment of healthy human macrophage response to the titration, (0.1, 1, 10, 100 ng/mL) of human IL-10, IL-4, and the combination of IL-10 and IL-4 demonstrates that both IL-10 alone and IL-4 alone are capable of suppressing LPS induced TNFα secretion. However, the combination of IL-10 and IL-4 together is superior in suppressing TNFα secretion to either cytokine alone.

Effect of IL-4 and DeboWtEBV on monocyte/macrophages: DeboWtEBV is comprised of the wild type EBV IL-10 coupled to the half-life extended VH and VL scaffolding system derived from a human anti-ebola antibody (previously described in U.S. Pat. No. 10,858,412). DeboWtEBV has been shown to suppress TNFα secretion. The isolated monocytes were exposed to a titration of IL-10, IL-4, DeboWtEBV, and DeboWtEBV in combination with IL-4 (FIG. 14). The combination of IL-4 with DeboWtEBV together suppress LPS induced TNFα secretion from monocytes in a manner that is superior to either IL-4 or DeboWtEBV alone.

Effect of IL-4 and DeboWtEBV on T cells: In addition to assessing combined suppressive effects of IL-10 and IL-4 on monocyte/macrophages, the combined effects of IL-4 and DeboWtEBV on T cells were also examined (FIG. 15). DeboWtEBV induces less IFNγ from CD8+ T cells compared to the same molar concentration of IL-10. The combination of IL-4 with DeboWtEBV reduce IFNγ more than that induced by DeboWtEBV alone at 100 ng/mL.

Effect of IL-4 and DeboDV06 on monocytes/macrophages: To determine if the suppressive effects of the IL-10 could be increased, a higher affinity variant of the EBV IL-10, denoted as DV06 was assessed. DV06 contains the point mutation (A75I) and is coupled to the half-life extended VH and VL scaffolding system derived from a human anti-ebola antibody (previously described in U.S. Pat. No. 10,858,412) by substituting wild type EBV IL-10 with DV06. Isolated monocytes were exposed to a titration of IL-10, IL-4, DeboDV06, and DeboDV06 in combination with IL-4 (FIG. 16). DeboDV06 exhibits increased suppressive function relative to DeboWtEBV (compared with FIG. 15), and the combination of DeboDV06 with IL-4 similarly increases the suppressive function on monocyte/macrophage response to LPS. The combination of IL-4 with DeboDV06 suppress LPS induced TNFα secretion from monocytes in a manner that is superior to either IL-4 or DeboDV06 alone.

Evaluation of IL-4 coupled with DeboDV06 (in $DK4^{10}$ form): The data suggest that combining IL-4 with the IL-10 variant, DV06 (which is an enhanced affinity variant of wild type EBV IL-10), suppress LPS mediated monocyte inflammatory responses in a manner superior to either molecule alone. Accordingly, IL-4 was coupled to the DeboDV06 molecule by expressing IL-4 in the linker between the VH and VL of the half-life extended scaffold molecule (FIG. 17), creating the first member of the $DK4^{10}$ class of molecules denoted as "IL-4DeboDV06" or "4DeboDV06", which are non-targeting forms of the dual cytokine fusion protein (i.e. comprising the 6 CDR regions from the anti-ebola antibody).

Effect of IL-4DeboDV06 (in $DK4^{10}$ form) on monocyte/macrophages: To determine whether IL-4DeboDV06, in $DK4^{10}$ form, suppresses LPS induced inflammatory responses, isolated monocytes were exposed to a titration of IL-10, IL-4, DeboDV06, IL-10 in combination with IL-4, and IL-4DeboDV06 (FIG. 18). IL-4DeboDV06 in $DK4^{10}$ form suppresses LPS induced TNFα secretion from monocytes in a manner that is superior to either IL-4 or DeboDV06 alone, but not quite as well as IL-4 plus IL-10, especially at lower concentrations.

Figure 19:
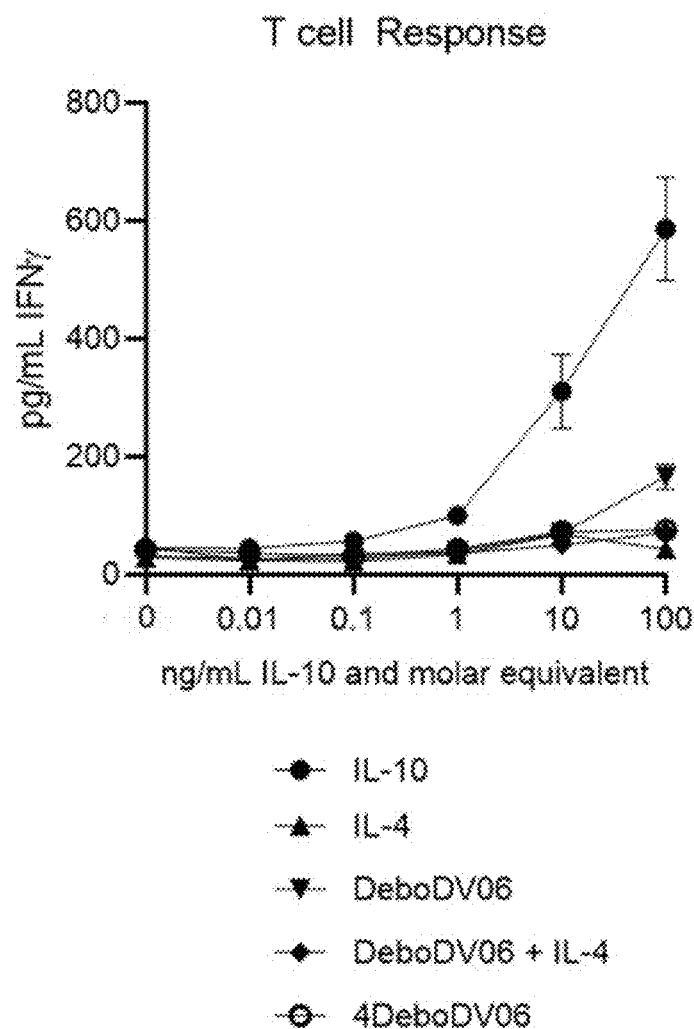
FIG. 19 is a titration study evaluating IL-4DeboDV06 in $DK4^{10}$ form (also known as "4DeboDV06") in comparison to IL-10, IL-4, DeboDV06, and DeboDV06 in combination with IL-4 on CD8+ T cells.

Effect of IL-4DeboDV06 (in DK4$^{10}$ form) on CD8+ T cells: The ability of IL-4DeboDV06 to potentiate and induce IFNγ from CD8+ T cells was examined and compared to IL-10, IL-4, DeboDV06, and DeboDV06 in combination with IL-4 (FIG. 19). IL-4DeboDV06 in DK4$^{10}$ form suppresses IFNγ secretion from CD8+ T cells similarly to the combination of DeboDV06 plus IL-4.

Figure 20:
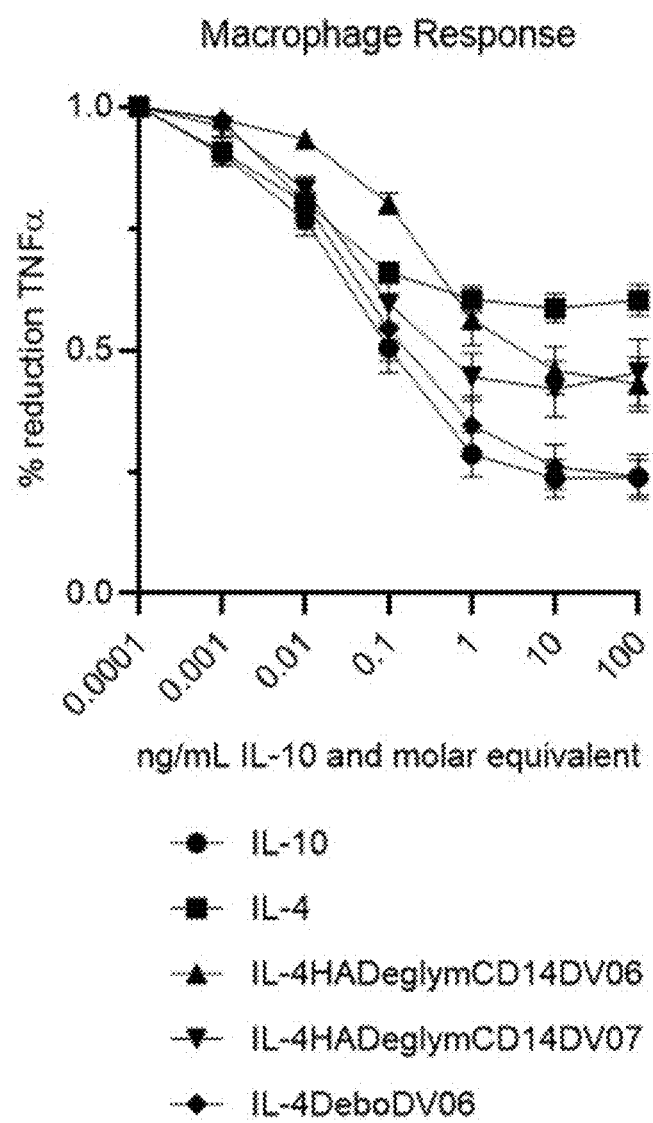
FIG. 20 is a titration study evaluating IL-4HADeglymCD14DV06 and IL-4HADeglymCD14DV07, which are members of the $DK4^{10}$ class of molecules comprising a non-glycosylated (N38A) and high affinity (T13D) form of human IL-4, and compared to IL-10, IL-4, and IL-4DeboDV06 (also known as "4DeboDV06") in $DK4^{10}$ form on suppressing LPS induced TNFα secretion by macrophage/monocytes.

Effect of IL-4HADeglyDmCD14DV06 and IL-4HADeglyDmCD14DV07 (in DK4$^{10}$ form) on monocyte/macrophages: It was determined that the IL-4 amino acid sequence used in manufacturing IL-4DeboDV06 in DK4$^{10}$ form appeared to be glycosylated. Sequence analysis confirmed that a putative N-linked glycosylation variant exists at amino acid position N38 but that glycosylation is not required for function (Li, 2013). Further research suggested that substituting amino acid T13 with an aspartate (D) generated a high affinity IL-4 variant (U.S. Pat. No. 6,028, 176). Both point mutations with substitutions at N38A and T13D were introduced into IL-4 and linked and incorporated into the Debo scaffolding engrafted with 6 CDRs from murine CD14 (FIG. 20). The data suggests that the high affinity, non-glycosylated IL-4 variant (i.e., comprising both the N38A and T13D point mutations) exhibits inferior function in the DK4$^{10}$ coupled format when compared to wild type IL-4 in the same format.

Figure 21:
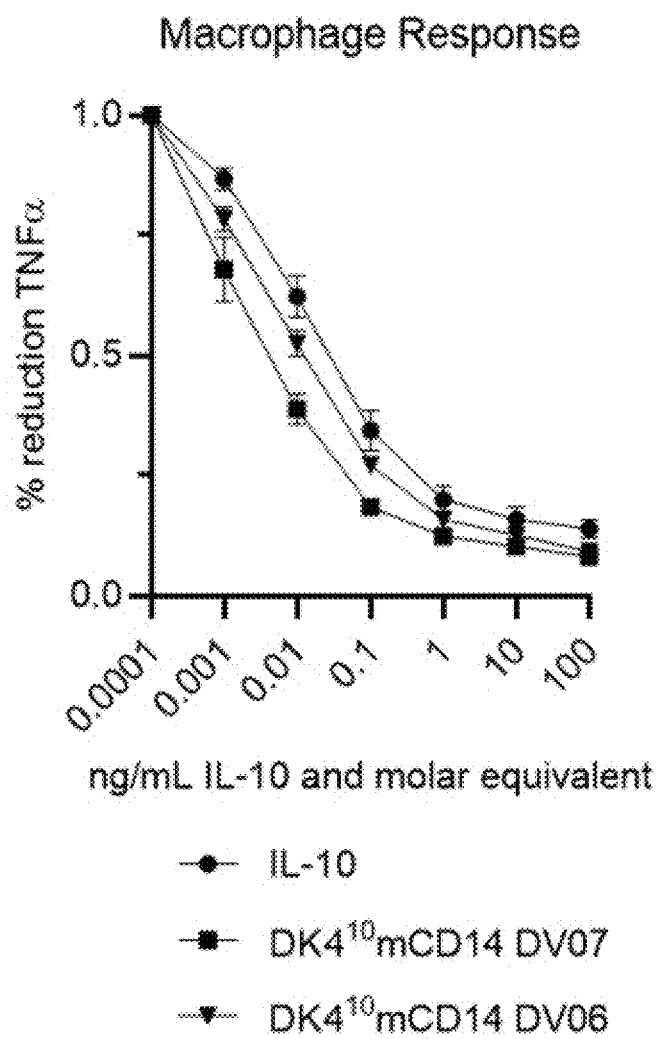
FIG. 21 is a titration study evaluating IL-4ngDmCD14DV06 and IL-4ngDmCD14DV07, which are members of the $DK4^{10}$ class of molecules comprising a single substitution at N38A resulting in a non-glycosylated form of IL4, and compared to IL-10 on suppressing LPS induced TNFα secretion by monocytes/macrophages.

Effect of IL-4ngDmCD14DV06 and IL-4ngDmCD14DV07 (in DK4$^{10}$ form) on monocyte/macrophages: The effects of IL-4ngDmCD14DV06 and IL-4ngDmCD14DV07 in DK4$^{10}$ form, which includes an IL-4 variant comprising the N38A substitution, were assessed by assaying for the suppression of LPS induced inflammatory responses by exposing the isolated monocytes to a titration of IL-10, IL-4ngDmCD14DV06 (also known as "DK4$^{10}$mCD14DV06") and IL-4ngDmCD14DV07 (also known as "DK4$^{10}$mCD14DV07") (FIG. 21). An IL-4 variant termed "IL-4ng" is the non-glycosylated form of IL-4 (comprising the N38A substitution, SEQ ID No: 44) that we introduced to improve manufacturability and "mCD14" represents the engraftment of the 6 CDRs from an anti-mCD14 antibody into the Debo scaffolding. Both DK4$^{10}$ (comprising the IL-10 variants of DV06 and DV07) molecules suppress LPS induced TNFα secretion.

Figure 22:
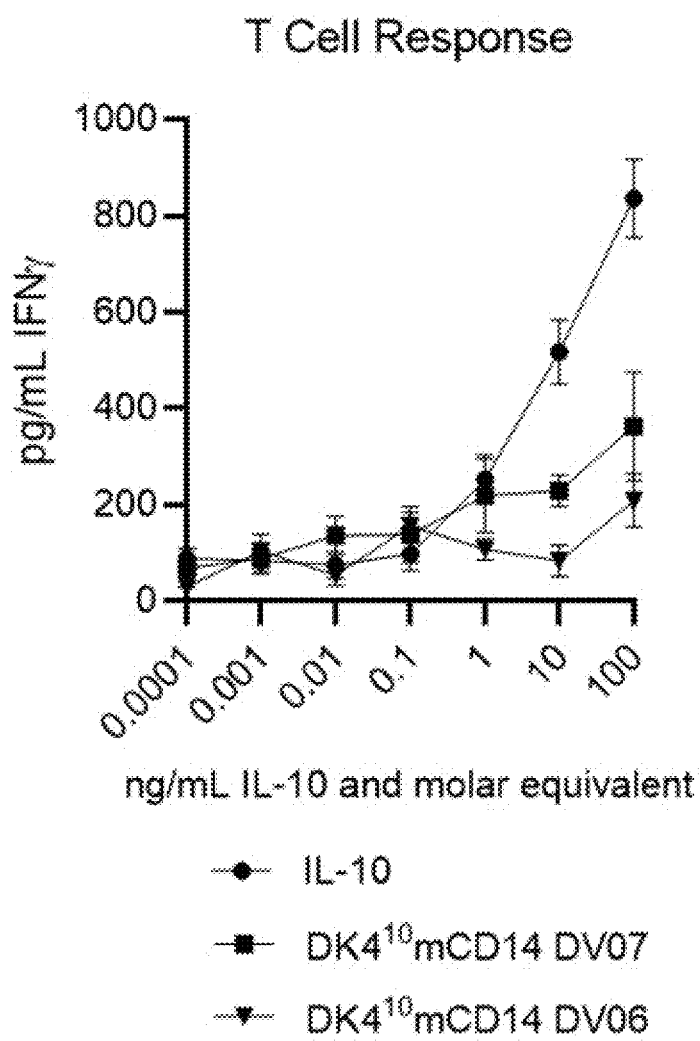
FIG. 22 is a titration study evaluating IL-4ngDmCD14DV06 and IL-4ngDmCD14DV07, which are members of the $DK4^{10}$ class of molecules comprising a single substitution at N38A resulting in a non-glycosylated form of IL4, and compared to IL-10 on mediating IFNγ induction by CD8+ T cells.

Effect of IL-4ngDmCD14DV06 and IL-4ngDmCD14DV07 (in DK4$^{10}$ form) on T cells: The stimulatory effects of IL-10, IL-4ngDmCD14DV06 and IL-4ngDmCD14DV07 in DK4$^{10}$ form (as described above) were assessed on T cells (FIG. 22). Both DK4$^{10}$ (comprising the IL-10 variants of DV06 and DV07) molecules do not induce as much IFNγ secretion as IL-10 from CD8+ T cells. IL-4ngDmCD14DV06 induces slightly less IFNγ secretion at 1-100 ng equivalent molar exposure in comparison to IL-4ngDmCD14DV07.

Figure 23:
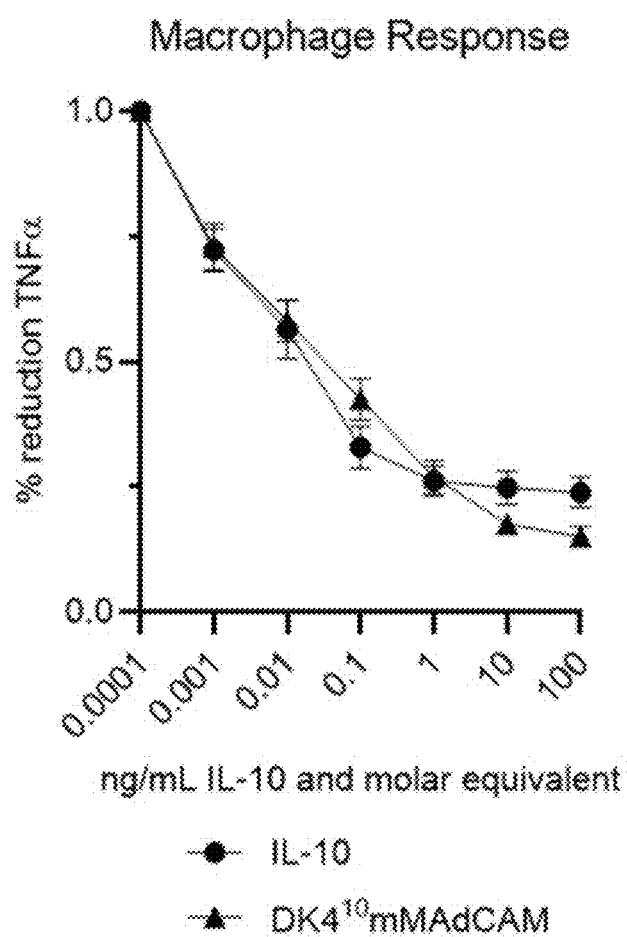
FIG. 23 is a titration study evaluating IL-4ngDmMAdCAMDV06, which are members of the $DK4^{10}$ class of molecules comprising a single substitution at N38A resulting in a non-glycosylated form of IL4, and compared to IL-10 on suppressing LPS induced TNFα secretion by monocytes/macrophage.

Effect of IL-4ngDmDMAdCAMDV06 (in DK4$^{10}$ form) on monocyte/macrophages: The effects of IL-4ngDmMAdCAMDV06 in DK4$^{10}$ form were assessed by assaying the suppression of LPS induced inflammatory response on monocytes/macrophages. IL-4ngDmMAdCAMDV06 is a dual cytokine fusion in DK4$^{10}$ form comprising: (1) an IL-4ng variant that is non-glycosylated (comprising the N38A substitution); (2) the engraftment of the 6 CDRs from a mouse anti-MAdCAM antibody into the Debo scaffolding; and (3) the IL-10 variant DV06. Isolated monocytes/macrophages were titrated with IL-10 or IL-4ngDmMAd-CAMDV06 (FIG. 23). IL-4ngDmMAdCAMDV06 suppresses LPS induced TNFα secretion in monocytes/macrophages.

Figure 24:
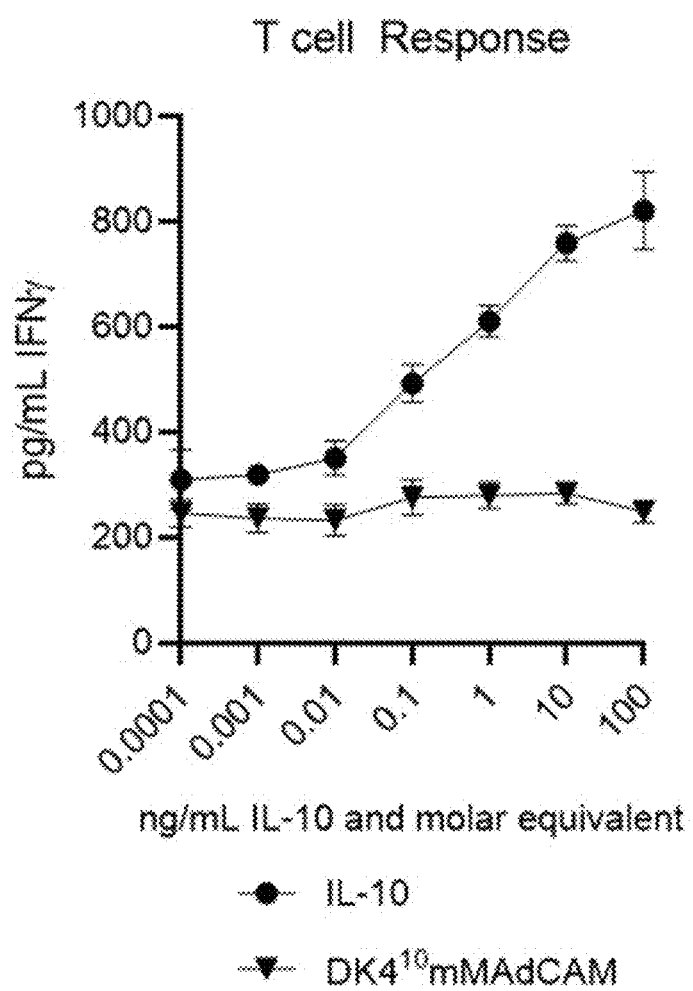
FIG. 24 is a titration study evaluating IL-4ngDmMAdCAMDV06, which are members of the $DK4^{10}$ class of molecules comprising a single substitution at N38A resulting in a non-glycosylated form of IL4, and compared to IL-10 on mediating IFNγ induction by CD8+ T cells.

Effect of IL-4ngDmMAdCAMDV06 (DK4$^{10}$ format) on T cells: We also evaluated the stimulatory effects of IL-10 and IL-4ngDmMAdCAMDV06 (DK4$^{10}$ format) on T cells (FIG. 24). IL-4ngDmMAdCAMDV06 does not induce IFNγ secretion from CD8+ T cells unlike IL-10.

Conclusion

These data suggest that IL-4 variants and IL-10 variants can be co-expressed via coupling these two cytokines to a human anti-ebola derived VH/VL scaffold system (i.e., in DK4$^{10}$ form). The combination of IL-4 and IL-10 variants suppresses LPS induced inflammatory responses by monocyte/macrophages while also inhibiting the induction of IFNγ from CD8+ T cells, regardless of the targeting CDR present within the VH and VL scaffolding system (compare 4DeboDV06 to engrafted versions of DK4$^{10}$ comprising CDRs from anti-mCD14 and anti-mMAdCAM).

The anti-ebola derived VH and VL scaffold couples IL-4 and IL-10 variant cytokines effectively and can accept multiple targeting CDR's grafts. The combination of IL-4ng (the IL-4 variant resulting in non-glycosylated IL-4 due to the N38A substitution) with DV06 suppresses LPS mediated TNFα secretion effectively from 0.1-100 ngs/mL and does not induce significant IFNγ from CD8+ T cells in the same dose range.

Example 4: DK4$^{10}$ in the Treatment of Sepsis

Having determined that IL-4ngDmCD14DV06 (also known as "DK4$^{10}$mCD14DV06") was capable of suppressing LPS induced TNFα secretion and tamped down the induction of IFNγ from CD8+ T-cells (see, FIG. 21 and FIG. 22), this molecule was examined in a well-known and conventional sepsis model.

Briefly, wild type Balb/C mice were obtained and acclimated, pursuant standard IACUCU protocols. The mice were maintained on standard chow and water ad libitum with a 12 hour light/dark cycle.

Vehicle, DK4$^{10}$mCD14DV06, was dosed subcutaneously in the animal at the stated dose in 100 milliliters of vehicle buffer at the stated time points either before ("pre") or after ("post") intraperitoneal LPS administration (350 mg/mouse).

Figure 25:
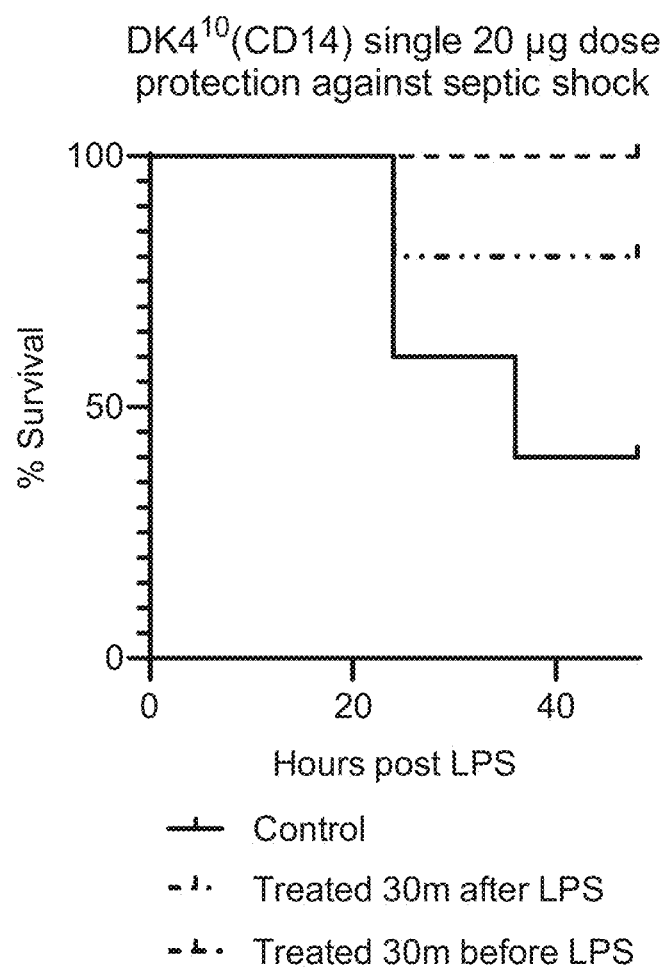
FIG. 25 is an in vivo sepsis mouse model study comparing survival of mice treated with IL-4ngDmMAdCAMDV06 before and after LPS administration.

After 4 days of acclimation, five (5) mice per group were treated with the following:
(1) 1 mg/kg DK410mCD14DV06 30 minutes before LPS administration; and
(2) 1 mg/kg DK410mCD14DV06 30 minutes after LPS administration The mice were evaluated for survival 48 hours after LPS administration. Treatment of mice with DK410mCD14DV06 30 minutes before LPS administration resulted in 100% survivor rate, whereas treatment with DK410mCD14DV06 30 minutes after LPS administration demonstrated protective effects against septic shock (FIG. 25).

The data suggests that coupling an IL-10 variant to an IL-4 variant (IL-4ng) and targeting the two molecules via a Debo scaffolding system with 6 CDRs from a mouse anti-CD14 antibody (e.g., using DK4$^{10}$mCD14DV06) significantly attenuates the inflammatory response and treats septic shock.

This written description uses examples to disclose aspects of the present disclosure, including the preferred embodiments, and also to enable any person skilled in the art to practice the aspects thereof, including making and using any devices or systems and performing any incorporated methods. The patentable scope of these aspects is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims. Aspects from the various embodiments described, as well as other known equivalents for each such aspect, can be mixed and matched by one of ordinary skill in the art to construct additional embodiments and techniques in accordance with principles of this application.

REFERENCES

Assier, E. (2004). NK Cells and Polymorphonuclear Neutrophils Are Both Critical for IL-2-Induced Pulmonary Vascular Leak Sydrome. *Journal of Immunology*.

Balce, D. R. (2011). Alternative activation of macrophages by IL-4 enhances the proteolytic capacity of their phagosomes through synergistic mechanisms. *Blood*.

Baluna, R. (1997). Vascular leak syndrome a side effect of immunotherapy. *Immunopharmacology*.

Bentebibe, S.-E. (2019). A First-in-Human Study and Biomarker Analysis of NKTR-214, a Novel IL2Raf Biased Cytokine, in Patients with Advanced or Metastatic Solid Tumors. *Cancer Discovery*.

Buchbinder, E. I. (2019). Therapy with high-dose Interleukin-2 (HD IL-2) in metastatic melanoma and renal cell carcinoma following PD1 or PDL1 inhibition. *Journal of Immunotherapy for Cancer*.

Chan, I. H. (2015). The Potentiation of IFNg and Induction of Cytotoxic Proteins by Pegylated IL-10 in Human CD8 T cells. *Journal of Interferon and Cytokine Research*.

Chen, X. (2018). A novel human IL-2 mutein with minimal systemic toxicity exerts greater antitumor efficacy than wild-type IL-2. *Cell Death and Disease*.

Chinen, T. (2016). An essential role for IL-2 receptor in regulatory T cell function. *Nature Immunology*.

Davis, I. D. (2009). A Phase I and Pharmacokinetic Study of Subcutaneously-Administered Recombinant Human Interleukin-4 (rhuIL-4) in Patients with Advanced Cancer. *Growth Factors*.

Emmerich, J. (2012). IL-10 Directly Activates and Expands Tumor-Resident CD8ϕ TCellswithoutDeNovoInfiltrationfromSecondaryLymphoid Organs. *Cancer Research*, 3570-3581.

Fedorak, R. (2000). Recombinant Human Interleukin 10 in the Treatment of Patients with Mild to Moderately Active Crohn's Disease. *Gastroenterology*, 1473-1482.

Gooch, J. L. (1998). Interleukin 4 Inhibits Growth and Induces Apoptosis in Human Breast Cancer Cells. *Cancer Research*.

Greve, J. M. (2000). U.S. Pat. No. 6,028,176.

Groux, H. (1998). Inhibitory and Stimulatory Effects of IL-10 on Human CD8+ T cells. *The Journal of Immunology*.

Guan, H. (2007). Blockade of Hyaluronan Inhibits IL-2 Induced Vascular Leak Syndrome and Maintains Effectiveness of IL-2 Treatment in Metastatic Melanoma. *Journal of Immunology*.

Hart, P. H. (1989). Potential antiinflammatory effects of interleukin 4: Suppression of human monocyte tumor necrosis factor ca, interleukin 1, and prostaglandin E2. *PNAS*.

Hart, P. H. (1991). IL-4 suppresses IL-1, TNF-a and PGE2 production by human peritoneal macrophages. *Immunology*.

Jiang, T. (2016). Role of IL-2 in cancer immunotherapy. *Oncoimmunology*.

Kirchner, G. I. (1998). Pharmacokinetics of human Interleukin-2 in advanced renal cell carcinoma patients following subcutaneous application. *British Journal Clinical Pharmacology*.

Lee, H. L. (2016). Tumor growth suppressive effect of IL-4 through p21-mediated activation of STAT6 in IL-4Rα overexpressed melanoma models. *Oncotarget*.

Li, R. (2013). Expression of recombinant human IL-4 in *Pichia pastoris* and relationship between its glycosylation and biological function. *Protein Expression and Purification*.

Malefyt, R. d. (1991). Interleukin 10 inhibits cytokine synthesis by human monocytes: An autoregulatory role of IL-10 produced by monocytes. *JEM*.

Malefyt, R. d. (1991). Interleukin 10 Inhibits Cytokine Synthesis by Human Monocytes An Autoregulatory Role of IL-10 Produced by Monocytes. *Journal of Experimental Medicine*, 1209-1220.

McGuirk, P. (2000). A Regulatory Role for Interleukin 4 in Differential Inflammatory Responses in the Lung following Infection of Mice Primed with Th1- or Th2-Inducing Pertussis Vaccines. *Infection and Immunity*.

Moore, K. W. (2001). Interleukin 10 and the Interleukin 10 Receptor. *Annual Reviews Immunology*.

Mumm, J. (2011). IL-10 induces IFNg-Mediated Tumor Immunity. *Cancer Cell*.

Mumm, J. B. (2011). IL-10 Elicits IFNg-Dependent Tumor Immune Surveillance. *Cancer Cell*.

Naing, A. (2016). Safety, Antitumor Activity, and Immune Activation of Pegylated Recombinant Human Interleukin-10 (AM0010) in Patients With Advanced Solid Tumors. *Journal of Clinical Oncology*.

Naing, A. (2018). PEGylated IL-10 (Pegilodecakin) Induces Systemic Immune Activation, CD8+ T cell Invigoration and Polyclonal T cell Expansion in Cancer Patients. *Cancer Cell*.

Ryan, J. J. (1997). Interleukin-4 and its receptor: Essential mediators of the allergic response. *The Journal of Allergy and Clinical Immunology*.

Schreiber, S. (2000). Safety and Efficacy of Recombinant Human Interleukin 10 in Chronic Active Crohn's Disease. *Gastroenterology*, 1461-1472.

Scott, M. J. (2006). Interleukin-10 suppresses natural killer cell but not natural killer T cell activation during bacterial infection. *Cytokine*.

Sivakumar, P. V. (2013). Comparison of Vascular Leak Syndrome in Mice Treated with IL21 or IL2. *Comparative Medicine*.

Spigel, D. R. (2020). Randomized phase II study of pembrolizumab (P) alone versus pegilodecakin (PEG) in combination with P as first-line (1 L) therapy in patients (pts) with stage IV non-small cell lung cancer (NSCLC) with high PD-L1 expression (CYPRESS 1). *ASCO*, (p. 9563).

Steinke, J. W. (2001). Th2 cytokines and asthma Interleukin-4: its role in the pathogenesis of asthma, and targeting it for asthma treatment with interleukin-4 receptor antagonists. *Respiratory Research*.

Varin, A. (2010). Alternative activation of macrophages by IL-4 impairs phagocytosis of pathogens but potentiates microbial-induced signalling and cytokine secretion. *Blood*.

Woodward, E. A. (2012). The anti-inflammatory actions of IL-4 in human monocytes are not mediated by IL-10, RP105 or the kinase activity of RIPK2. *Cytokine*.

---

The invention claimed is:

1. A dual cytokine fusion protein of formula (I)

$$NH_2\text{-(IL-10)-}(X^1)\text{-}(Z_n)\text{-}(X^2)\text{-(IL-10)-COOH} \quad \text{(Formula I)};$$

wherein
- "IL-10" is a monomer;
- "$X^1$" is a VL or VH region from a first monoclonal antibody;
- "$X^2$" is a VH or VL region from the first monoclonal antibody;
- wherein when $X^1$ is a VL, $X^2$ is a VH or when $X^1$ is a VH, $X^2$ is a VL;
- wherein the first monoclonal antibody is an anti Ebola antibody;
- wherein the VL and VH from the anti Ebola antibody include 3 light chain CDRs and 3 heavy chain CDRs that are engrafted with 3 light chain CDRs and 3 heavy chain CDRs from a second monoclonal antibody;
- "Z" is a cytokine other than IL-10;
- "n" is an integer of 1; and wherein:
- lvi. the IL-10 is SEQ ID No: 16, the second antibody is an anti-HER2 monoclonal antibody, and Z is IL-2.

2. The dual cytokine fusion protein according to claim 1, wherein lvi. is a fusion protein of SEQ ID No: 52, 53, 54, or 55.

3. A pharmaceutical composition comprising the dual cytokine fusion protein according to claim 1, pharmaceutically acceptable buffers, and pharmaceutically acceptable excipients.

4. The fusion protein according to claim 1, wherein the VH and VL regions comprise a framework region obtained from a human anti-Ebola antibody.

5. The fusion protein according to claim 4, wherein the framework region from the anti-Ebola antibody is engrafted with the three VH CDRs and three VL CDRs from an anti-HER2 monoclonal antibody.

6. The fusion protein according to claim 2, wherein the fusion protein is at least 95% identical to SEQ ID No: 52, 53, 54, or 55.

* * * * *